(12) United States Patent
Alonso-Alija et al.

(10) Patent No.: US 7,674,825 B2
(45) Date of Patent: *Mar. 9, 2010

(54) DICARBOXYLIC ACID DERIVATIVES WITH PHARMACEUTICAL PROPERTIES

(75) Inventors: Cristina Alonso-Alija, Haan (DE); Markus Heil, Leichlingen (DE); Dietmar Flubacher, Breisach (DE); Paul Naab, Wuppertal (DE); Johannes-Peter Stasch, Solingen (DE); Frank Wunder, Wuppertal (DE); Klaus Dembowsky, Boston, MA (US); Elisabeth Perzborn, Wuppertal (DE); Elke Stahl, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/823,462

(22) Filed: Jun. 27, 2007

(65) Prior Publication Data

US 2008/0058314 A1   Mar. 6, 2008

Related U.S. Application Data

(63) Continuation of application No. 10/070,039, filed on Oct. 22, 2002, now abandoned.

(51) Int. Cl.
*C07C 65/28* (2006.01)
*C07C 69/76* (2006.01)
(52) U.S. Cl. .................. 514/522; 514/533; 514/568
(58) Field of Classification Search ............ None
See application file for complete search history.

(56) References Cited

U.S. PATENT DOCUMENTS

| 6,166,027 | A | * | 12/2000 | Straub et al. ........... 514/269 |
| 6,180,656 | B1 | | 1/2001 | Furstner et al. |
| 6,451,805 | B1 | | 9/2002 | Straub et al. |

FOREIGN PATENT DOCUMENTS

| EP | 0341551 | 11/1989 |
| EP | 0410241 | 1/1991 |
| EP | 0341551 | 4/1992 |
| EP | 0494621 | 7/1992 |
| EP | 0791576 | 8/1997 |
| WO | WO 9816223 | 4/1998 |
| WO | WO 9816507 | 4/1998 |
| WO | WO 9823619 | 6/1998 |

OTHER PUBLICATIONS

Ko.F., Wu,C., Kuo, S., Lee, F., Teng, C., "YC-1, A Novel Activator of Platelet Guanylate Cyclase", Blood, 84: 4226-4233 (Dec. 1994).
Mulsch, A., Bauersachs, J., Schafer, A., Stasch,J., Kast, R., Busse, R., "Effect of YC-1, An NO-independent, Superoxide-sensitive Stimulator of Soluble Guanylyl Cydase, on Smooth Muscle Responsiveness to Nitrovasodilators", Br. J. Of Pharm., 120: 681-689 (1997).
Glass, D., Frey, W., Carr, D., Goldberg, N., "Stimulation of Human Platelet Guanylate Cyclase by Fatty Acids", J. Biol. Chem., 252: 1279-1285 (Feb. 1977).
Pettibone, D., Sweet,C., Risley, E., Kennedy, T., "A Structurally Novel Stimulator of Guanylate Cyclase with Long-lasting Hypotensive Activity in the Dog", Eu. J. of Pharm., 116: 307-312 (1985).
Yu, S., Kuo, S., "Vasorelaxant Effect of Isoliquiritigenin, A Novel Soluble Guanylate Cyclase Activator, in Rat Aorta", Br. J. of Pharm., 114: 1587-1594 (1995).
Gerzer, R., Bohme, E., Hofmann, F., Schultz, G., "Soluble Guanylate Cyclase Purified From Bovine Lung Contains Heme and Copper", Febs Letts., 132: 71-74 (Sep. 1981).
Hoenicka, M., Becker, E., Apeler, H., Sirichoke, T., Schroder, H., Gerzer, R., Stasch, J., "Purified Soluble Guanylyl Cyclase Expressed in a Baculovirus/Sf9 System: Stimulation byYC-1, Nitric Oxide, and Carbon Monoxide", J. Mol. Med., 77: 14-23 (1999).
Ignarro, L., "Regulation of Cytosolic Guanylyl Cylase by Porphyrins and Metalloporphyrins", Advances in Pharmacology, 26: 35-65 (1994).
Mulsch, A., Bauersachs, J., Stasch, J., Busse, R., "Potentiation of Vascular Responses to No-Donors by an No-Independent Activator of Soluble Gualylyl Cyclase", Naunyn Schmiedebergs Arch. Pharmacol., 355: R47.
Jones et al., Canadian Journal of Chemistry (1979), 57(9), 1025-32.

* cited by examiner

*Primary Examiner*—Karl J Puttlitz
(74) *Attorney, Agent, or Firm*—Edwards Angell Palmer & Dodge LLP; Nicholas J. DiCeglie, Jr.; Mark D. Russett

(57) ABSTRACT

The present invention relates to the use of compounds of the formula (I)

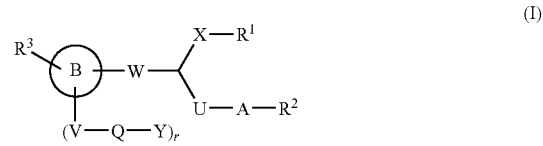

and to their salts and stereoisomers, for the preparation of medicaments for the treatment of cardiovascular disorders.

4 Claims, No Drawings

DICARBOXYLIC ACID DERIVATIVES WITH PHARMACEUTICAL PROPERTIES

The present invention relates to novel chemical compounds which stimulate soluble guanylate cyclase also via a novel mechanism of action which proceeds without participation of the heme group of the enzyme, to their preparation and to their use as medicaments, in particular as medicaments for treating cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyze the biosynthesis of cGMP from guanosine triphosphate (GTP). The hitherto known representatives of this family can be classified both according to structural features and according to the type of ligands into two groups: the particular guanylate cyclases, which can be stimulated by natriuretic peptides, and the soluble guanylate cyclases, which can be stimulated by NO. The soluble guanylate cyclases consist of two subunits and, most likely, contain one heme per heterodimer, which is part of the regulatory center. It is of central importance for the activation mechanism. NO can bind to the iron atom of the heme and thus increase the activity of the enzyme considerably. In contrast, heme-free preparations cannot be stimulated by NO, CO, too, is capable of attacking the central iron atom of heme, but the stimulation by CO is considerably lower than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disturbance of the abovementioned processes. Under pathophysiological conditions, the NO/cGMP system can be suppressed, which may lead, for example, to hypertension, platelet activation, increased cell proliferation, endothelial dysfunction, atherosclerosis, angina pectoris, cardiac insufficiency, thromboses, stroke and myocardial infarct.

Owing to the expected high efficiency and few side effects, a treatment of such disorders which targets the influence of the cGMP signal path in organisms and is NO-independent is a promising approach.

Hitherto, for the therapeutic stimulation of soluble guanylate cyclase use has exclusively been made of compounds such as organic nitrates whose effect is based on NO. This is formed by bioconversion and activates soluble guanylate cyclase by attacks at the central iron atom of heme. In addition to the side effects, the development of tolerance is one of the decisive disadvantages of this treatment.

Within the last few years, some substances have been described which stimulate soluble guanylate cyclase directly, i.e. without prior release of NO, such as, for example, 3-(5'-hydroxymethyl-2'-furyl)-1-benzylindazole (YC-1, Wu et al., Blood 84 (1994), 4226; Mülsch et al., Br. J. Pharmacol. 120 (1997), 681), fatty acids (Goldberg et al, J. Biol. Chem. 252 (1977), 1279), diphenyliodonium hexafluorophosphate (Pettibone et al., Eur. J. Pharmacol. 116 (1985), 307), isoliquiritigenin (Yu et al., Brit. J. Pharmacol. 114 (1995), 1587), and various substituted pyrazole derivatives (WO 98/16223, WO 98/16507 and WO 98/23619).

The known stimulators of soluble guanylate cyclase stimulate the enzyme either directly via the heme group (carbon monoxide, nitrogen monoxide or diphenyliodonium hexafluorophosphate) by interaction with the iron center of the heme group and a resulting change in conformation which leads to an increase in enzyme activity (Gerzer et al., FEBS Lett. 132(1981), 71), or via a heme-dependent mechanism which is independent of NO but leads to a potentiation of the stimulating effect of NO or CO (for example YC-1, Hoenicka et al., J. Mol. Med. (1999) 14; or the pyrazole derivatives described in WO 98/16223, WO 98/16507 and WO 98/23619).

The stimulating effect, asserted in the literature, of isoliquiritigenin and of fatty acids, such as, for example, arachidonic acid, prostaglandin endoperoxides and fatty acid hydroperoxides, on soluble guanylate cyclase could not be confirmed (cf., for example, Hoenicka et al., J. Mol. Med. 77 (1999), 14).

If the heme group of soluble guanylate cyclase is removed, the enzyme still shows a detectable catalytic basal activity, i.e., as before, cGMP is formed. The remaining catalytic basal activity of the heme-free enzyme cannot be stimulated by any of the abovementioned known stimulators.

Stimulation of heme-free soluble guanylate cyclase by protoporphyrin IX has been described (Ignarro et al., Adv. Pharmacol. 26 (1994), 35). However, protoporphyrin IX can be considered to be a mimic of the NO-heme adduct, owing to which the addition of protoporphyrin IX to heme-free soluble guanylate cyclase should result in the formation of an enzyme structure which corresponds to the heme-containing soluble guanylate cyclase which is stimulated by NO. This is also confirmed by the fact that the stimulating effect of protoporphyrin IX is increased by the NO-independent, but heme-dependent, stimulator YC-I described above (Mülsch et al., Naunyn Schmiedebergs Arch. Pharmacol. 355, R47).

Thus, hitherto no compounds have been described which are capable of stimulating soluble guanylate cyclase independently of the heme group present in the enzyme.

It was an object of the present invention to develop medicaments for the treatment of cardiovascular disorders or other disorders which can be treated by influencing the cGMP signal path in organisms.

The abovementioned object is achieved by using, for the preparation of medicaments, compounds which are capable of stimulating soluble guanylate cyclase also independently of NO and the heme group present in the enzyme.

Surprisingly, it has been found that there are compounds which are capable of stimulating soluble guanylate cyclase also independently of the heme group present in the enzyme. The biological activity of these stimulators is based on an entirely novel mechanism for stimulating soluble guanylate cyclase. In contrast to the above-described compounds which are known from the prior art as stimulators of soluble guanylate cyclase, the compounds according to the invention are capable of stimulating both the heme-containing and the heme-free form of soluble guanylate cyclase. In the case of these novel stimulators, the stimulation of the enzyme is therefore effected via a heme-independent route, which is also confirmed by the fact that, on the one hand, the novel stimulators do not show any synergistic action with NO at the heme-containing enzyme and, on the other hand, the action of these novel stimulators cannot be blocked by the heme-dependent inhibitor of soluble guanylate cyclase, 1H-1,2,4-oxadiazol-(4,3a)-quinoxalin-1-one (ODQ).

This is a novel therapeutic approach for the treatment of cardiovascular disorders and other disorders which can be treated by influencing the cGMP signal path in organisms.

EP-A-0 341 551 describes alkanoic and alkenoic acid derivatives such as, for example, (1) which are potent leukotriene antagonists and are therefore suitable, for example, for use as medicaments for the treatment of asthma or circulatory disorders p. 18, 1. 56-58). However, a stimulating action of these compounds on soluble guanylate cyclase and the resulting use of these compounds for preparing medicaments which are capable of influencing the cGMP signal path have not been described.

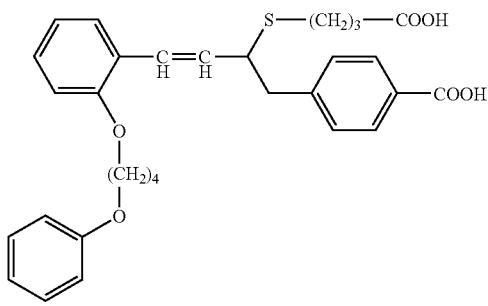
(1)

EP-A-0 410 241 describes further alkanoic and alkenoic acid derivatives such as, for example, (2) having $LTD_4$-, $LTC_4$- or $LTD_4$-antagonistic action.

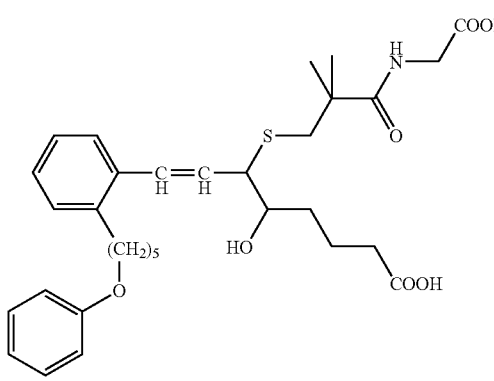
(2)

EP-A-0 494 621 describes sulfur-containing alkenoic acid derivatives such as, for example, (3) which can be used for allergic diseases, inflammations and cardiovascular disorders.

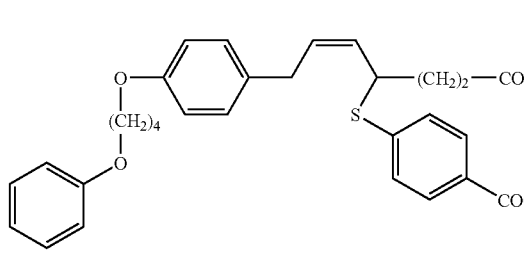
(3)

EP-A-0 791 576 describes benzoic acid derivatives such as, for example, (4) which can be used for treating respiratory disorders.

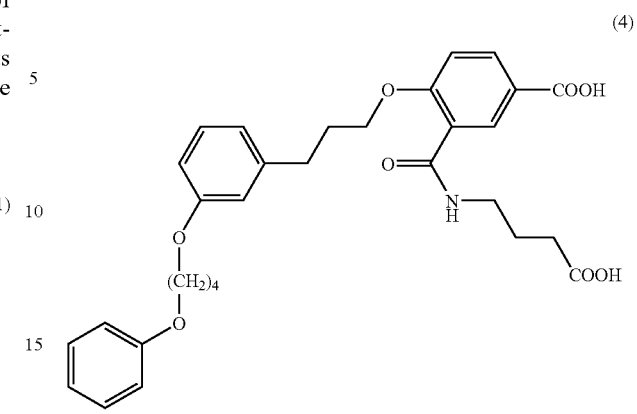
(4)

However, it has not been described that any of the above-mentioned prior-art compounds have stimulating action on soluble guanylate cyclase and can therefore be used for treating disorders which can be treated by influencing the cGMP level.

In a preferred embodiment, the present invention relates to compounds of the general formula (I)

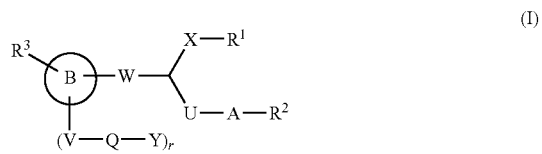
(I)

in which

B represents aryl having 6 to 10 carbon atoms or an aromatic heterocycle having 1 to 9 carbon atoms and up to 3 heteroatoms from the group consisting of S, N and O, r represents 0 or 1, V is absent or represents O, $NR^4$, $NR^4CONR^4$, $NR^4CO$, $NR^4SO_2$, COO, $CONR^4$ or $S(O)_o$, in which $R^4$ independently of any other radical $R^4$ which may be present, represents hydrogen, straight-chain or branched alkyl having up to 8 carbon atoms, cycloalkyl having 3 to 8 carbon atoms, aryl having 6 to 10 carbon atoms or arylalkyl having 7 to 18 carbon atoms, where the aryl radical for its part may be mono- or polysubstituted by halogen, alkyl, alkoxy having up to 6 carbon atoms, o represents 0, 1 or 2, Q is absent or represents straight-chain or branched alkylene, straight-chain or branched alkenediyl or straight-chain or branched alkinediyl having in each case up to 15 carbon atoms, which may contain one or more groups from the group consisting of O, $S(O)_p$, $NR^5$, CO, OCO, S—CO—, $CONR^5$ and $NR^5SO_2$ and which may be mono- or polysubstituted by halogen, hydroxyl or alkoxy having up to 4 carbon atoms, where, if appropriate, any two atoms of the chain above may be attached to one another forming a three- to eight-membered ring, or represents $CONR^5$, in which $R^5$ represents hydrogen, straight-chain or branched alkyl having up to 8 carbon atoms or cycloalkyl having 3 to 8 carbon atoms, which may be substituted by halogen or alkoxy having up to 4 carbon atoms, p represents 0, 1 or 2, Y represents hydrogen, $NR^6R^7$, aryl having 6 to 10 carbon atoms, an aromatic or saturated heterocycle having 1 to 9 carbon atoms and up to 3 heteroatoms from the group consisting of S, N and O or straight-chain or branched cycloalkyl having 3 to 8 carbon atoms, which may also be attached via N, where the cyclic radicals may in each case be mono- to trisubstituted by straight-chain or branched alkyl, straight-chain or branched alkenyl, straight-chain or branched alkinyl, straight-chain or branched alkoxy, straight-chain or branched halogenoalkyl, straight-chain or branched halogenoalkoxy having in each case up to 8 carbon atoms, straight-chain or branched cycloalkyl having 3 to 8 carbon atoms, halogen, hydroxyl, $COR^8$, CN, $SR^8$, $NO_2$, $NR^{10}R^{11}$, $NR^9COR^{12}$, $NR^9CONR^9R^{12}$ or $CONR^{13}R^{14}$, in which $R^6$ and $R^7$ in each case independently of one another represent hydrogen, straight-chain or branched alkyl, straight-chain or branched alkoxy, straight-chain or branched alkyloxyalkyl having up to 8 carbon atoms or cycloalkyl having 3 to 8 carbon atoms or aryl having 6 to 10 carbon atoms, which is optionally mono- or polysubstituted by aryl having 6 to 10 carbon atoms or by an aromatic heterocycle having 1 to 9 carbon atoms and up to 3 heteroatoms from the group consisting of S, N and O, $R^8$ represents hydrogen, straight-chain or branched alkyl having up to 8 carbon atoms, straight-chain or branched halogenoalkyl having up to 8 carbon atoms or cycloalkyl having 3 to 8 carbon atoms, $R^9$ represents hydrogen, straight-chain or branched alkyl having up to 8 carbon atoms or cycloalkyl having 3 to 8 carbon atoms, $R^{10}$, $R^{11}$, $R^{13}$ and $R^{14}$ independently of one another represent hydrogen, straight-chain or branched alkyl, straight-chain or branched alkenyl having up to 8 carbon atoms, aryl having 6 to 10 carbon atoms, an aromatic heterocycle having 1 to 9 carbon atoms and up to 3 heteroatoms from the group consisting of S, N and O, arylalkyl having 8 to 18 carbon atoms, cycloalkyl having 3 to 8 carbon atoms or a radical of the formula $SO_2R^{15}$, where the aryl radical for its part may be mono- or polysubstituted by halogen, hydroxyl, CN, $NO_2$, $NH_2$, $NHCOR^9$, alkyl, alkoxy, halogenoalkyl or halogenoalkoxy having up to 6 carbon atoms, or two substituents $R^{10}$ and $R^{11}$ or $R^{13}$ and $R^{14}$ may be attached to one another forming a five- or six-membered ring which may contain O or N, in which $R^{15}$ represents straight-chain or branched alkyl having up to 4 carbon atoms or aryl having 6 to 10 carbon atoms, where the aryl radical for its part may be mono- or polysubstituted by halogen, CN, $NO_2$, alkyl, alkoxy, halogenoalkyl or halogenoalkoxy having up to 6 carbon atoms, $R^{12}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by halogen, hydroxyl, CN, $NO_2$, $NH_2$, $NHCOR^9$, alkyl, alkoxy, halogenoalkyl or halogenoalkoxy having up to 6 carbon atoms;

and/or the cyclic radicals may in each case be mono- to trisubstituted by aryl having 6 to 10 carbon atoms, an aromatic or saturated heterocycle having 1 to 9 carbon atoms and up to 3 heteroatoms from the group consisting of S, N and O, which may also be attached via N, which may be attached directly or via a group selected from O, S, SO, $SO_2$, $NR^9$, $CONR^9$, $SO_2NR^9$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 8 carbon atoms and may be mono- to trisubstituted by straight-chain or branched alkyl, straight-chain or branched alkoxy, straight-chain or branched halogenoalkyl, straight-chain or branched halogenoalkoxy, carbonylalkyl or straight-chain or branched alkenyl having in each case up to 6 carbon atoms, aryl or aralkyl having 6 to 10 carbon atoms, halogen, $SR^8$, CN, $NO_2$, $NR^{17}R^{18}$, $CONR^{17}R^{18}$ or $NR^{16}COR^{19}$, in which $R^{16}$ represents hydrogen, straight-chain or branched alkyl having up to 8 carbon atoms or cycloalkyl having 3 to 8 carbon atoms, $R^{17}$, $R^{18}$ independently of one another represent hydrogen, straight-chain or branched alkyl having up to 8 carbon atoms, cycloalkyl having 3 to 8 carbon atoms, aryl having 6 to 10 carbon atoms or a radical of the formula $SO_2R^{20}$, where the aryl radical for its part may be mono- or polysubstituted by halogen, hydroxyl, CN, $NO_2$, $NH_2$, $NHCOR^9$, alkyl, alkoxy, halogenoalkyl or halogenoalkoxy having up to 6 carbon atoms, in which $R^{20}$ represents straight-chain or branched alkyl having up to 4 carbon atoms or aryl having 6 to 10 carbon atoms, where the aryl radical for its part may be mono- or polysubstituted by halogen, hydroxyl, CN, $NO_2$, $NH_2$, $NHCOR^9$, alkyl, alkoxy, halogenoalkyl or halogenoalkoxy having up to 6 carbon atoms, and $R^{19}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by halogen, hydroxyl, CN, $NO_2$, $NH_2$, $NHCOR^9$, alkyl, alkoxy, halogenoalkyl or halogenoalkoxy having up to 6 carbon atoms;

and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O, $R^3$ represents hydrogen, halogen, straight-chain or branched alkyl, straight-chain or branched halogenoalkyl, straight-chain or branched alkoxy or straight-chain or branched halogenoalkoxy having in each case up to 4 carbon atoms, OH, CN, $NO_2$ or $NR^{21}R^{22}$,
in which
$R^{21}$ and $R^{22}$ independently of one another represent hydrogen, straight-chain or branched alkyl having up to 8 carbon atoms, cycloalkyl having 3 to 8 carbon atoms or aryl having 6 to 10 carbon atoms, W represents straight-chain or branched alkylene, straight-chain or branched alkenediyl having in each case up to 6 carbon atoms, which may contain a group selected from O, $S(O)_q$, $NR^{23}$, CO and $CONR^{23}$, or represents O or S,
in which
q represents 0, 1 or 2,
$R^{23}$ represents hydrogen, straight-chain or branched alkyl having up to 8 carbon atoms or cycloalkyl having 3 to 8 carbon atoms, U represents straight-chain or branched alkylene having up to 4 carbon atoms, O, NH, S, SO or $SO_2$, A is absent or represents aryl having 6 to 10 carbon atoms or an aromatic heterocycle having 1 to 9 carbon atoms and up to 3 heteroatoms from the group consisting of S, N and O,
which may optionally be mono- to trisubstituted by halogen, straight-chain or branched alkyl, straight-chain or branched halogenoalkyl, straight-chain or branched alkoxy, halogenoalkoxy or alkoxycarbonyl having in each case up to 4 carbon atoms, CN, $NO_2$ or $NR^{24}R^{25}$,
in which
$R^{24}$ and $R^{25}$ in each case independently of one another represent hydrogen, straight-chain or branched alkyl having up to 8 carbon atoms or cycloalkyl having 3 to 8 carbon atoms, carbonylalkyl or sulfonylalkyl, $R^2$ represents CN, tetrazolyl, $COOR^{26}$ or $CONR^{27}R^{28}$,
in which
$R^{26}$ represents hydrogen or straight-chain or branched alkyl having up to 8 carbon atoms or cycloalkyl having 3 to 8 carbon atoms;
$R^{27}$ and $R^{28}$ in each case independently of one another represent hydrogen, straight-chain or branched alkyl having up to 8 carbon atoms, cycloalkyl having 3 to 8 carbon atoms or a radical of the formula $SO_2R^{29}$,
or $R^{27}$ and $R^{28}$ together form a five- or six-membered ring which may contain N or O,
in which
$R^{29}$ represents straight-chain or branched alkyl having up to 4 carbon atoms or aryl having 6 to 10 carbon atoms,
where the aryl radical for its part may be mono- or polysubstituted by halogen, CN, $NO_2$, alkyl, alkoxy, halogenoalkyl or halogenoalkoxy having up to 6 carbon atoms, X represents straight-chain or branched alkylene, straight-chain or branched alkenediyl having in each case up to 12 carbon atoms, which may contain a group selected from O, $S(O)_r$, $NR^{30}$, CO or $CONR^{31}$, or a three- to eight-membered saturated or unsaturated carbocycle having optionally one or two heteroatoms from the group consisting of $S(O)_r$, $NR^{32}$ and O and optionally one or more substituents,
in which
r represents 0, 1 or 2,
$R^{30}$ represents hydrogen, straight-chain or branched alkyl having up to 8 carbon atoms, cycloalkyl having 3 to 8 carbon atoms, aryl having 6 to 10 carbon atoms or straight-chain or branched arylalkyl having 7 to 15 carbon atoms,
$R^{31}$ represents hydrogen, halogen, straight-chain or branched alkyl, straight-chain or branched halogenoalkyl or straight-chain or branched alkoxy having in each case up to 4 carbon atoms, CN, $NO_2$ or $NR^{33}R^{34}$,
in which
$R^{33}$ and $R^{34}$ independently of one another represent hydrogen, straight-chain or branched alkyl having up to 8 carbon atoms, cycloalkyl having 3 to 8 carbon atoms or aryl having 6 to 10 carbon atoms,
$R^{32}$ represents hydrogen, straight-chain or branched alkyl having up to 8 carbon atoms, cycloalkyl having 3 to 8 carbon atoms or aryl having 6 to 10 carbon atoms, $R^1$ represents CN, tetrazolyl, $COOR^{35}$ or $CONR^{36}R^{37}$,
in which
$R^{35}$ represents hydrogen or straight-chain or branched alkyl having up to 8 carbon atoms or cycloalkyl having 3 to 8 carbon atoms;
$R^{36}$ and $R^{37}$ in each case independently of one another represent hydrogen, straight-chain or branched alkyl having up to 8 carbon atoms, cycloalkyl having 3 to 8 carbon atoms or a radical of the formula $SO_2R^{38}$,
in which
$R^{38}$ represents straight-chain or branched alkyl having up to 4 carbon atoms or aryl having 6 to 10 carbon atoms,
where the aryl radical for its part may be mono- or polysubstituted by halogen, CN, $NO_2$, alkyl, alkoxy, halogenoalkyl or halogenoalkoxy having up to 6 carbon atoms, with the proviso that Y may not be phenyl or phenyl substituted exclusively by one or two radicals from the group consisting of straight-chain or branched alkyl, straight-chain or branched alkoxy having in each case up to 12 carbon atoms, halogen, $CF_3$, $OCF_3$ and CN, if simultaneously B is phenyl, V is absent or represents O, Q represents straight-chain alkylene having 1 to 10 carbon atoms and is optionally attached to Y via an oxygen atom, W represents an alkylene group or an alkenediyl group having in each case 1 to 6 carbon atoms, U represents an alkylene group having up to 4 carbon atoms, O, S, SO or $SO_2$, A represents phenyl and X represents straight-chain alkylene having 1 to 11 carbon atoms and is optionally attached directly via O, S, SO or $SO_2$ to the carbon atom which carries the groups W and U;
and their stereoisomers and salts.

Preference according to the invention is given here to compounds of the formula (I) in which
B represents aryl having 6 to 10 carbon atoms,
and the other substituents are as defined above.

Particular preference is given here to compounds of the formula (I) in which
B represents aryl having 6 to 10 carbon atoms,
r represents 0 or 1,
V is absent or represents O, $NR^4$, $NR^4CONR^4$, $NR^4CO$, $NR^4SO_2$, COO, $CONR^4$ or $S(O)_o$,
in which
$R^4$ independently of any other radical $R^4$ which may be present, represents hydrogen, straight-chain or branched alkyl having up to 8 carbon atoms, cycloalkyl having 3 to 8 carbon atoms, aryl having 6 to 10 carbon atoms or arylalkyl having 7 to 18 carbon atoms, where the aryl radical for its part may be mono- or polysubstituted by halogen, alkyl, alkoxy having up to 6 carbon atoms,
o represents 0, 1 or 2, Q is absent or represents straight-chain or branched alkylene, straight-chain or branched alkenediyl or straight-chain or branched alkinediyl having in each case up to 15 carbon atoms, which may contain one or more groups from the group consisting of O, $S(O)_p$, $NR^5$, CO, OCO, S—CO—, $CONR^5$ and $NR^5SO_2$, or one or more alkene or alkine groups, and which may be mono- or polysubstituted by halogen, hydroxyl or alkoxy having up to 4 carbon atoms, where, if appropriate, any two atoms of the chain above may be attached to one another forming a three- to eight-membered ring, or represents $CONR^5$,
in which
$R^5$ represents hydrogen, straight-chain or branched alkyl having up to 8 carbon atoms or cycloalkyl having 3 to 8 carbon atoms, which may be substituted by halogen or alkoxy having up to 4 carbon atoms,
p represents 0, 1 or 2,
Y represents hydrogen, $NR^6R^7$, aryl having 6 to 10 carbon atoms, an aromatic or saturated heterocycle having 1 to 9 carbon atoms and up to 3 heteroatoms from the group consisting of S, N and O or straight-chain or branched cycloalkyl having 3 to 8 carbon atoms, which may also be attached via N,
where the cyclic radicals may in each case be mono- to trisubstituted by straight-chain or branched alkyl, straight-chain or branched alkenyl, straight-chain or branched alkinyl, straight-chain or branched alkoxy, straight-chain or branched halogenoalkyl, straight-chain or branched halogenoalkoxy having in each case up to 8 carbon atoms, straight-chain or branched cycloalkyl having 3 to 8 carbon atoms, halogen, hydroxyl, $COR^8$, CN, $SR^8$, $NO_2$, $NR^{10}R^{11}$, $NR^9COR^{12}$, $NR^9CONR^9R^{12}$ or $CONR^{13}R^{14}$,
in which
$R^6$ and $R^7$ in each case independently of one another represent hydrogen, straight-chain or branched alkyl, straight-chain or branched alkoxy, straight-chain or branched alkyloxyalkyl having up to 8 carbon atoms or cycloalkyl having 3 to 8 carbon atoms or aryl having 6 to 10 carbon atoms, which is optionally mono- or polysubstituted by aryl having 6 to 10 carbon atoms or by an aromatic heterocycle having 1 to 9 carbon atoms and up to 3 heteroatoms from the group consisting of S, N and O,
$R^8$ represents hydrogen, straight-chain or branched alkyl having up to 8 carbon atoms, straight-chain or branched halogenoalkyl having up to 8 carbon atoms or cycloalkyl having 3 to 8 carbon atoms,
$R^9$ represents hydrogen, straight-chain or branched alkyl having up to 8 carbon atoms or cycloalkyl having 3 to 8 carbon atoms,
$R^{10}$, $R^{11}$, $R^{13}$ and $R^{14}$ independently of one another represent hydrogen, straight-chain or branched alkyl, straight-chain or branched alkenyl having up to 8 carbon atoms, aryl having 6 to 10 carbon atoms, an aromatic heterocycle having 1 to 9 carbon atoms and up to 3 heteroatoms from the group consisting of S, N and O, arylalkyl having 8 to 18 carbon atoms, cycloalkyl having 3 to 8 carbon atoms or a radical of the formula $SO_2R^{15}$,
where the aryl radical for its part may be mono- or polysubstituted by halogen, hydroxyl, CN, $NO_2$, $NH_2$, $NHCOR^9$, alkyl, alkoxy, halogenoalkyl or halogenoalkoxy having up to 6 carbon atoms,
or two substituents $R^{10}$ and $R^{11}$ or $R^{13}$ and $R^{14}$ may be attached to one another forming a five- or six-membered ring which may contain O or N,
in which
$R^{15}$ represents straight-chain or branched alkyl having up to 4 carbon atoms or aryl having 6 to 10 carbon atoms,
where the aryl radical for its part may be mono- or polysubstituted by halogen, CN, $NO_2$, alkyl, alkoxy, halogenoalkyl or halogenoalkoxy having up to 6 carbon atoms,
$R^{12}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by halogen, hydroxyl, CN, $NO_2$, $NH_2$, $NHCOR^9$, alkyl, alkoxy, halogenoalkyl or halogenoalkoxy having up to 6 carbon atoms;
and/or the cyclic radicals may in each case be mono- to trisubstituted by aryl having 6 to 10 carbon atoms, an aromatic or saturated heterocycle having 1 to 9 carbon atoms and up to 3 heteroatoms from the group consisting of S, N and O, which may also be attached via N,
which may be attached directly or via a group selected from O, S, SO, $SO_2$, $NR^9$, $CONR^9$, $SO_2NR^9$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 8 carbon atoms and may be mono- to trisubstituted by straight-chain or branched alkyl, straight-chain or branched alkoxy, straight-chain or branched halogenoalkyl, straight-chain or branched halogenoalkoxy, carbonylalkyl or straight-chain or branched alkenyl having in each case up to 6 carbon atoms, phenyl, benzyl, halogen, $SR^8$, CN, $NO_2$, $NR^{17}R^{18}$, $CONR^{17}R^{18}$ or $NR^{16}COR^{19}$,
in which
$R^{16}$ represents hydrogen, straight-chain or branched alkyl having up to 8 carbon atoms or cycloalkyl having 3 to 8 carbon atoms,
$R^{17}$, $R^{18}$ independently of one another represent hydrogen, straight-chain or branched alkyl having up to 8 carbon atoms, cycloalkyl having 3 to 8 carbon atoms, aryl having 6 to 10 carbon atoms or a radical of the formula $SO_2R^{20}$, where the aryl radical for its part may be mono- or polysubstituted by halogen, hydroxyl, CN, $NO_2$, $NH_2$, $NHCOR^9$, alkyl, alkoxy, halogenoalkyl or halogenoalkoxy having up to 6 carbon atoms,
in which
$R^{20}$ represents straight-chain or branched alkyl having up to 4 carbon atoms or aryl having 6 to 10 carbon atoms,
where the aryl radical for its part may be mono- or polysubstituted by halogen, hydroxyl, CN, $NO_2$, $NH_2$, $NHCOR^9$, alkyl, alkoxy, halogenoalkyl or halogenoalkoxy having up to 6 carbon atoms,
and
$R^{19}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by halogen, hydroxyl, CN, $NO_2$, $NH_2$, $NHCOR^9$, alkyl, alkoxy, halogenoalkyl or halogenoalkoxy having up to 6 carbon atoms;
and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O, $R^3$ represents hydrogen, OH, halogen, straight-chain or branched alkyl, straight-chain or branched halogenoalkyl, straight-chain or branched alkoxy or straight-chain or branched halogenoalkoxy having in each case up to 4 carbon atoms, W represents straight-chain or branched alkylene, straight-chain or branched alkenediyl having in each case up to 4 carbon atoms, which may contain a group selected from O and $NR^{23}$,
in which
$R^{23}$ represents hydrogen, straight-chain or branched alkyl having up to 8 carbon atoms or cycloalkyl having 3 to 8 carbon atoms, U represents straight-chain or branched alkylene having up to 4 carbon atoms, O, NH, S, SO or $SO_2$, A is absent or represents phenyl or an aromatic heterocycle having 1 to 9 carbon atoms and up to 3 heteroatoms from the group consisting of S, N and O,
which may optionally be mono- to trisubstituted by halogen, straight-chain or branched alkyl, straight-chain or branched halogenoalkyl or straight-chain or branched alkoxy having in each case up to 4 carbon atoms, $R^2$ represents $COOR^{26}$ or CN,
in which
$R^{26}$ represents hydrogen or straight-chain or branched alkyl having up to 8 carbon atoms;

X represents straight-chain or branched alkylene, straight-chain or branched alkenediyl having in each case up to 8 carbon atoms, which may contain a group selected from O, $S(O)_r$, $NR^{30}$, one or more alkene groups, or a three- to six-membered saturated or unsaturated carbocycle which optionally has one or more straight-chain or branched alkyl radicals having 1 to 6 carbon atoms and optionally one or two heteroatoms from the group consisting of $S(O)_r$, $NR^{32}$ and O,
in which
r represents 0, 1 or 2,
$R^{30}$ represents hydrogen, straight-chain or branched alkyl having up to 6 carbon atoms, phenyl or arylalkyl having 7 to 12 carbon atoms,
$R^{32}$ represents hydrogen, straight-chain or branched alkyl having up to 6 carbon atoms, cycloalkyl having 3 to 6 carbon atoms or phenyl, $R^1$ represents CN or $COOR^{35}$,
in which
$R^{35}$ represents hydrogen or straight-chain or branched alkyl having up to 6 carbon atoms;

with the proviso that Y may not be phenyl or phenyl substituted exclusively by one or two radicals from the group consisting of straight-chain or branched alkyl, straight-chain or branched alkoxy having in each case up to 8 carbon atoms, halogen, $CF_3$, $OCF_3$ and CN, if simultaneously B is phenyl, V is absent or represents O, Q represents straight-chain alkylene having 1 to 10 carbon atoms and is optionally attached to Y via an oxygen atom, W represents an alkylene group or an alkenediyl group having in each case 1 to 4 carbon atoms, U represents an alkylene group having up to 4 carbon atoms, O, S, SO or $SO_2$, A represents phenyl and X represents straight-chain alkylene having 1 to 8 carbon atoms and is optionally attached directly via O, S, SO or $SO_2$ to the carbon atom which carries the groups W and U;

Especially preferred here are compounds of the formula (I) in which
B represents phenyl or naphthyl
r represents 0 or 1,
V is absent or represents O, $NR^4$ or $S(O)_n$
in which
$R^4$ represents hydrogen,
n represents 0, Q is absent or represents straight-chain or branched alkylene, straight-chain or branched alkenediyl having in each case up to 15 carbon atoms, which may contain one or more groups selected from O, $S(O)_p$, $NR^5$, $CONR^5$, S—CO— and OCO and which may be mono- or disubstituted by halogen or hydroxyl, or represents $CONR^5$,
in which
$R^5$ represents hydrogen,
p represents 0 or 1, Y represents hydrogen, $NR^6R^7$, phenyl, napthyl or a heterocycle from the group

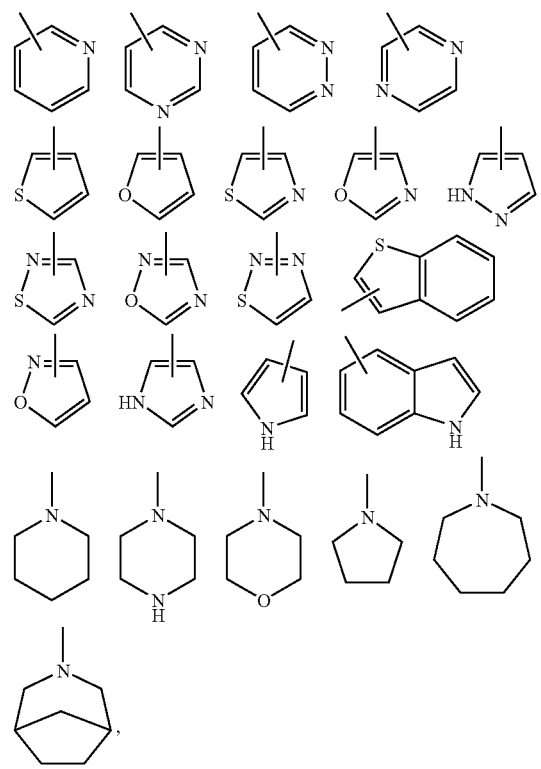

where the cyclic radicals may in each case be mono- to trisubstituted by straight-chain or branched alkyl, straight-chain or branched alkenyl, straight-chain or branched alkinyl, straight-chain or branched alkoxy, straight-chain or branched halogenoalkyl, straight-chain or branched halogenoalkoxy having in each case up to 4 carbon atoms, straight-chain or branched cycloalkyl having 3 to 7 carbon atoms, F, Cl, Br, I, $NO_2$, $COR^8$, $SR^8$, $NR^{10}R^{11}$, $NR^9COR^{12}$ or $CONR^{13}R^{14}$, in which
R⁶ and R⁷ in each case independently of one another represent hydrogen, straight-chain or branched alkyl, straight-chain or branched alkoxy or straight-chain or branched alkyloxyalkyl having in each case up to 4 carbon atoms or cycloalkyl having 3 to 8 carbon atoms or aryl having 6 to 10 carbon atoms, which is optionally mono- or polysubstituted by aryl having 6 to 10 carbon atoms or an aromatic heterocycle having 1 to 9 carbon atoms and up to 3 heteroatoms from the group consisting of S, N and O,
R⁸ represents hydrogen, straight-chain or branched alkyl having up to 4 carbon atoms, or straight-chain or branched halogenoalkyl having up to 4 carbon atoms,
R⁹ represents hydrogen, or straight-chain or branched alkyl having up to 4 carbon atoms,
R¹⁰, R¹¹, R¹³ and R¹⁴ independently of one another represent hydrogen, straight-chain or branched alkyl having up to 4 carbon atoms, or phenyl,
where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, NO₂, CF₃, OCF₃ or CN,
or two substituents R¹⁰ and R¹¹ or R¹³ and R¹⁴ may be attached to one another forming a five- or six-membered ring which may be interrupted by O or N,
R¹² represents hydrogen, straight-chain or branched alkyl having up to 4 carbon atoms, or phenyl,
where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, NO₂, CF₃, OCF₃ or CN;
and/or the cyclic radicals may in each case be mono- to trisubstituted by phenyl or a heterocycle from the group consisting of

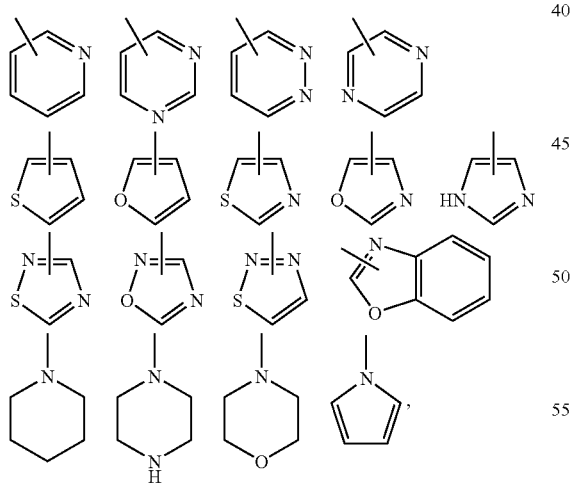

which are attached directly or via a group selected from O, S, SO, SO₂, CONR⁹, SO₂NR⁹, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 4 carbon atoms and may be mono- to trisubstituted by straight-chain or branched alkyl, straight-chain or branched alkoxy, straight-chain or branched halogenoalkyl or straight-chain or branched alkenyl having in each case up to 4 carbon atoms, phenyl, benzyl, F, Cl, Br, I, CN, NO₂, NR¹⁷R¹⁸ or NR¹⁶COR¹⁹,
in which
R¹⁶ represents hydrogen, straight-chain or branched alkyl having up to 8 carbon atoms or cycloalkyl having 3 to 8 carbon atoms,
R¹⁷, R¹⁸ independently of one another represent hydrogen, straight-chain or branched alkyl having up to 8 carbon atoms, cycloalkyl having 3 to 8 carbon atoms, phenyl, where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, NO₂, CF₃, OCF₃ or CN or represent a radical of the formula SO₂R²⁰,
in which
R²⁰ represents straight-chain or branched alkyl having up to 4 carbon atoms or phenyl,
and
R¹⁹ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by F, Cl Br, hydroxyl, methyl, ethyl, n-propyl, i-propyl, n-butyl, s-butyl, i-butyl, t-butyl, methoxy, ethoxy, amino, acetylamino, NO₂, CF₃, OCF₃ or CN;
and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O,
R³ represents hydrogen, OH, F, Cl, Br, straight-chain or branched alkyl, straight-chain or branched halogenoalkyl, straight-chain or branched alkoxy or straight-chain or branched halogenoalkoxy having in each case up to 4 carbon atoms,
W represents CH₂CH₂, CH=CH, CH₂O, OCH₂, CH₂OCH₂, CH₂NH, NHCH₂ or CH₂NHCH₂,
U represents straight-chain alkylene having up to 4 carbon atoms, O, NH, S, SO or SO₂,
A is absent or represents phenyl, pyridyl, thienyl or thiazolyl, which may optionally be mono- to trisubstituted by methyl, ethyl, n-propyl, i-propyl, n-butyl, i-butyl, s-butyl, t-butyl, CF₃, methoxy, ethoxy, F, Cl, Br,
R² represents COOR²⁶ or CN,
in which
R²⁶ represents hydrogen or straight-chain or branched alkyl having up to 4 carbon atoms;
X represents straight-chain or branched alkylene having up to 4 carbon atoms, which may contain a group selected from O, S(O)ᵣ, NR³⁰, or a three- to six-membered saturated or unsaturated carbocycle having optionally one or more straight-chain or branched alkyl radicals having 1 to 4 carbon atoms and having optionally one or two heteroatoms from the group consisting of S(O)ᵣ, NR³² and O,
in which
r represents 0, 1 or 2,
R³⁰ represents hydrogen, straight-chain or branched alkyl having up to 6 carbon atoms, phenyl or benzyl, $R^{32}$ represents hydrogen, straight-chain or branched alkyl having up to 6 carbon atoms, cycloalkyl having 3 to 6 carbon atoms or phenyl, $R^1$ represents CN or COOR$^{35}$, in which $R^{35}$ represents hydrogen or straight-chain or branched alkyl having up to 6 carbon atoms;

with the proviso that Y may not be phenyl or phenyl substituted exclusively by one or two radicals from the group consisting of straight-chain or branched alkyl, straight-chain or branched alkoxy having in each case up to 4 carbon atoms, halogen, CF$_3$, and OCF$_3$, if simultaneously V is absent or represents O, Q represents straight-chain-alkylene having 1 to 10 carbon atoms and is optionally attached to Y via an oxygen atom, W is an ethylene group or an ethanediyl group, having in each case 1 to 6 carbon atoms. U represents an alkylene group having up to 4 carbon atoms, O, S, SO or SO$_2$. A represents phenyl and X represents straight-chain alkylene having 1 to 4 carbon atoms and is optionally attached directly via O, S, SO or SO$_2$ to the carbon atom which carries the groups W and U;

Preference according to the invention is also given to compounds of the formula (I) in which B represents an aromatic heterocycle having 1 to 9 carbon atoms and up to 3 heteroatoms from the group consisting of S, N and O, and the other substituents are as defined above.

Particular preference is given here to compounds of the formula (I) in which

B represents an aromatic heterocycle having 1 to 9 carbon atoms and up to 3 heteroatoms from the group consisting of S, N and O, r represents 0 or 1, V is absent or represents O, NR$^4$, NR$^4$CONR$^4$, NR$^4$CO, NR$^4$SO$_2$, COO, CONR$^4$ or S(O)$_o$, in which $R^4$ independently of any other radical R$^4$ which may be present, represents hydrogen, straight-chain or branched alkyl having up to 8 carbon atoms, cycloalkyl having 3 to 8 carbon atoms, aryl having 6 to 10 carbon atoms or arylalkyl having 7 to 18 carbon atoms, where the aryl radical for its part may be mono- or polysubstituted by halogen, alkyl, alkoxy having up to 6 carbon atoms, o represents 0, 1 or 2, Q is absent or represents straight-chain or branched alkylene, straight-chain or branched alkenediyl or straight-chain or branched alkinediyl having in each case up to 15 carbon atoms, which may contain one or more groups from the group consisting of O, S(O)$_p$, NR$^5$, CO, OCO, S—CO—, CONR$^5$ and NR$^5$SO$_2$ and which may be mono- or polysubstituted by halogen, hydroxyl or alkoxy having up to 4 carbon atoms, where, if appropriate, any two atoms of the chain above may be attached to one another forming a three- to eight-membered ring, or represents CONR$^5$, in which $R^5$ represents hydrogen, straight-chain or branched alkyl having up to 8 carbon atoms or cycloalkyl having 3 to 8 carbon atoms, which may be substituted by halogen or alkoxy having up to 4 carbon atoms, p represents 0, 1 or 2, Y represents hydrogen, NR$^6$R$^7$, aryl having 6 to 10 carbon atoms, an aromatic or saturated heterocycle having 1 to 9 carbon atoms and up to 3 heteroatoms from the group consisting of S, N and O or straight-chain or branched cycloalkyl having 3 to 8 carbon atoms, which may also be attached via N, where the cyclic radicals may in each case be mono- to trisubstituted by straight-chain or branched alkyl, straight-chain or branched alkenyl, straight-chain or branched alkinyl, straight-chain or branched alkoxy, straight-chain or branched halogenoalkyl, straight-chain or branched halogenoalkoxy having in each case up to 8 carbon atoms, straight-chain or branched cycloalkyl having 3 to 8 carbon atoms, halogen, hydroxyl, COR$^8$, CN, SR$^8$, NO$_2$, NR$^{10}$R$^{11}$, NR$^9$COR$^{12}$, NR$^9$CONR$^9$R$^{12}$ or CONR$^{13}$R$^{14}$, in which $R^6$ and $R^7$ in each case independently of one another represent hydrogen, straight-chain or branched alkyl, straight-chain or branched alkoxy, straight-chain or branched alkyloxyalkyl having up to 8 carbon atoms or cycloalkyl having 3 to 8 carbon atoms or aryl having 6 to 10 carbon atoms, which is optionally mono- or polysubstituted by aryl having 6 to 10 carbon atoms or by an aromatic heterocycle having 1 to 9 carbon atoms and up to 3 heteroatoms from the group consisting of S, N and O, $R^8$ represents hydrogen, straight-chain or branched alkyl having up to 8 carbon atoms, straight-chain or branched halogenoalkyl having up to 8 carbon atoms or cycloalkyl having 3 to 8 carbon atoms, $R^9$ represents hydrogen, straight-chain or branched alkyl having up to 8 carbon atoms or cycloalkyl having 3 to 8 carbon atoms, $R^{10}$, $R^{11}$, $R^{13}$ and $R^{14}$ independently of one another represent hydrogen, straight-chain or branched alkyl, straight-chain or branched alkenyl having up to 8 carbon atoms, aryl having 6 to 10 carbon atoms, an aromatic heterocycle having 1 to 9 carbon atoms and up to 3 heteroatoms from the group consisting of S, N and O, arylalkyl having 8 to 18 carbon atoms, cycloalkyl having 3 to 8 carbon atoms or a radical of the formula SO$_2$R$^{15}$, where the aryl radical for its part may be mono- or polysubstituted by halogen, hydroxyl, CN, NO$_2$, NH$_2$, NHCOR$^9$, alkyl, alkoxy, halogenoalkyl or halogenoalkoxy having up to 6 carbon atoms, or two substituents R$^{10}$ and R$^{11}$ or R$^{13}$ and R$^{14}$ may be attached to one another forming a five- or six-membered ring which may contain O or N, in which $R^{15}$ represents straight-chain or branched alkyl having up to 4 carbon atoms or aryl having 6 to 10 carbon atoms, where the aryl radical for its part may be mono- or polysubstituted by halogen, CN, NO$_2$, alkyl, alkoxy, halogenoalkyl or halogenoalkoxy having up to 6 carbon atoms, $R^{12}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by halogen, hydroxyl, CN, NO$_2$, NH$_2$, NHCOR$^9$, alkyl, alkoxy, halogenoalkyl or halogenoalkoxy having up to 6 carbon atoms, and/or the cyclic radicals may in each case be mono- to trisubstituted by aryl having 6 to 10 carbon atoms, an aromatic or saturated heterocycle having 1 to 9 carbon atoms and up to 3 heteroatoms from the group consisting of S, N and O, which may also be attached via N, which may be attached directly or via a group selected from O, S, SO, $SO_2$, $NR^9$, $CONR^9$, $SO_2NR^9$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 8 carbon atoms and may be mono- to trisubstituted by straight-chain or branched alkyl, straight-chain or branched alkoxy, straight-chain or branched halogenoalkyl, straight-chain or branched halogenoalkoxy, carbonylalkyl or straight-chain or branched alkenyl having in each case up to 6 carbon atoms, phenyl, benzyl, halogen, $SR^8$, CN, $NO_2$, $NR^{17}R^{18}$, $CONR^{17}R^{18}$ or $NR^{16}COR^{19}$, in which $R^{16}$ represents hydrogen, straight-chain or branched alkyl having up to 8 carbon atoms or cycloalkyl having 3 to 8 carbon atoms, $R^{17}$, $R^{18}$ independently of one another represent hydrogen, straight-chain or branched alkyl having up to 8 carbon atoms, cycloalkyl having 3 to 8 carbon atoms, aryl having 6 to 10 carbon atoms or a radical of the formula $SO_2R^{20}$, where the aryl radical for its part may be mono- or polysubstituted by halogen, hydroxyl, CN, $NO_2$, $NH_2$, $NHCOR^9$, alkyl, alkoxy, halogenoalkyl or halogenoalkoxy having up to 6 carbon atoms, in which $R^{20}$ represents straight-chain or branched alkyl having up to 4 carbon atoms or aryl having 6 to 10 carbon atoms, where the aryl radical for its part may be mono- or polysubstituted by halogen, hydroxyl, CN, $NO_2$, $NH_2$, $NHCOR^9$, alkyl, alkoxy, halogenoalkyl or halogenoalkoxy having up to 6 carbon atoms, and $R^{19}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by halogen, hydroxyl, CN, $NO_2$, $NH_2$, $NHCOR^9$, alkyl, alkoxy, halogenoalkyl or halogenoalkoxy having up to 6 carbon atoms, and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O, $R^3$ represents hydrogen, halogen, straight-chain or branched alkyl, straight-chain or branched halogenoalkyl, straight-chain or branched alkoxy or straight-chain or branched halogenoalkoxy having in each case up to 4 carbon atoms, W represents straight-chain or branched alkylene, straight-chain or branched alkenediyl having in each case up to 4 carbon atoms, which may contain a group selected from O and $NR^{23}$, in which $R^{23}$ represents hydrogen, straight-chain or branched alkyl having up to 8 carbon atoms or cycloalkyl having 3 to 8 carbon atoms, U represents straight-chain or branched alkylene having up to 4 carbon atoms, O, NH, S, SO or $SO_2$, A is absent or represents phenyl or an aromatic heterocycle having 1 to 9 carbon atoms and up to 3 heteroatoms from the group consisting of S, N and O, which may optionally be mono- to trisubstituted by halogen, straight-chain or branched alkyl, straight-chain or branched halogenoalkyl or straight-chain or branched alkoxy having in each case up to 4 carbon atoms.

$R^2$ represents $COOR^{26}$ or CN, in which $R^{26}$ represents hydrogen or straight-chain or branched alkyl having up to 8 carbon atoms;

X represents straight-chain or branched alkylene, straight-chain or branched alkenediyl having in each case up to 8 carbon atoms, which may contain a group selected from O, $S(O)_r$, $NR^{30}$, or a three- to six-membered saturated or unsaturated carbocycle which optionally has one or more straight-chain or branched alkyl radicals having 1 to 6 carbon atoms and optionally one or two heteroatoms from the group consisting of $S(O)_r$, $NR^{32}$ and O, in which r represents 0, 1 or 2, $R^{30}$ represents hydrogen, straight-chain or branched alkyl having up to 6 carbon atoms, phenyl or arylalkyl having 7 to 12 carbon atoms, $R^{32}$ represents hydrogen, straight-chain or branched alkyl having up to 6 carbon atoms, cycloalkyl having 3 to 6 carbon atoms or phenyl, $R^1$ represents CN or $COOR^{35}$, in which $R^{35}$ represents hydrogen or straight-chain or branched alkyl having up to 6 carbon atoms.

Especially preferred here are compounds of the formula (I) in which

B represents a heterocycle from the group consisting of

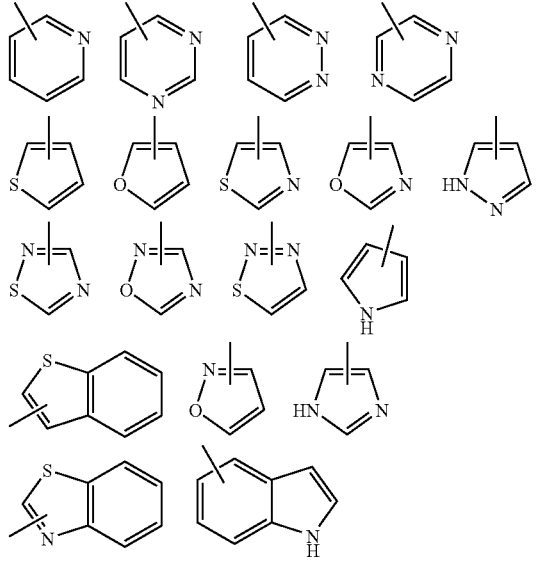

r represents 0 or 1,

V is absent or represents O, $NR^4$ or $S(O)_n$ in which
R⁴ represents hydrogen,
n represents 0,
Q is absent or represents straight-chain or branched alkylene, straight-chain or branched alkenediyl having in each case up to 15 carbon atoms, which may contain one or more groups selected from O, $S(O)_p$, $NR^5$, $CONR^5$, S—CO— and OCO and which may be mono- or disubstituted by halogen or hydroxyl, or represents $CONR^5$, in which
R⁵ represents hydrogen,
p represents 0 or 1,
Y represents hydrogen, $NR^6R^7$, phenyl, napthyl or a heterocycle from the group

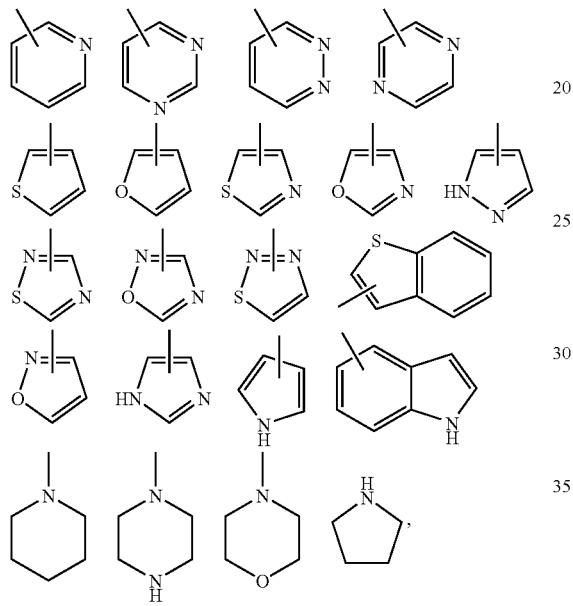

where the cyclic radicals may in each case be mono- to trisubstituted by straight-chain or branched alkyl, straight-chain or branched alkenyl, straight-chain or branched alkinyl, straight-chain or branched alkoxy, straight-chain or branched halogenoalkyl, straight-chain or branched halogenoalkoxy having in each case up to 4 carbon atoms, straight-chain or branched cycloalkyl having 3 to 7 carbon atoms, F, Cl, Br, I, $NO_2$, $COR^8$, $SR^8$, $NR^{10}R^{11}$, $NR^9COR^{12}$ or $CONR^{13}R^{14}$,
in which
R⁶ and R⁷ in each case independently of one another represent hydrogen, straight-chain or branched alkyl, straight-chain or branched alkoxy or straight-chain or branched alkyloxyalkyl having in each case up to 4 carbon atoms or cycloalkyl having 3 to 8 carbon atoms or aryl having 6 to 10 carbon atoms, which is optionally mono- or polysubstituted by aryl having 6 to 10 carbon atoms or an aromatic heterocycle having 1 to 9 carbon atoms and up to 3 heteroatoms from the group consisting of S, N and O,
R⁸ represents hydrogen, straight-chain or branched alkyl having up to 4 carbon atoms, or straight-chain or branched halogenoalkyl having up to 4 carbon atoms,
R⁹ represents hydrogen, or straight-chain or branched alkyl having up to 4 carbon atoms, $R^{10}$, $R^{11}$, $R^{13}$ and $R^{14}$ independently of one another represent hydrogen, straight-chain or branched alkyl having up to 4 carbon atoms, or phenyl,
where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN,
or two substituents $R^{10}$ and $R^{11}$ or $R^{13}$ and $R^{14}$ may be attached to one another forming a five- or six-membered ring which may be interrupted by O or N,
$R^{12}$ represents hydrogen, straight-chain or branched alkyl having up to 4 carbon atoms, or phenyl,
where the phenyl radical may be mono- to trisubstituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN:
and/or the cyclic radicals may in each case be mono- to trisubstituted by phenyl or a heterocycle from the group consisting of

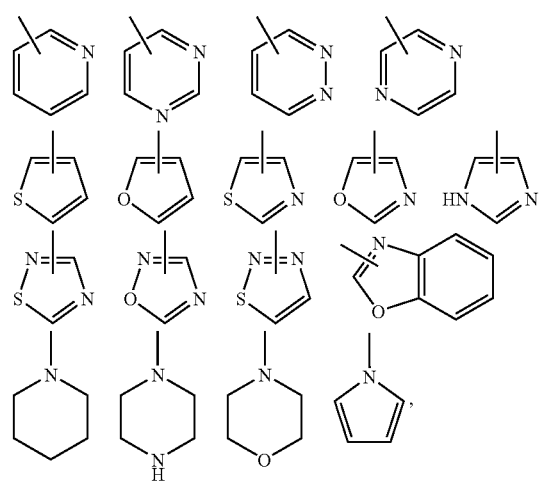

which are attached directly or via a group selected from O, S, SO, $SO_2$, $CONR^9$, $SO_2NR^9$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 4 carbon atoms and may be mono- to trisubstituted by straight-chain or branched alkyl, straight-chain or branched alkoxy, straight-chain or branched halogenoalkyl or straight-chain or branched alkenyl having in each case up to 4 carbon atoms, phenyl, benzyl, F, Cl, Br, I, CN, $NO_2$, $NR^{17}R^{18}$ or $NR^{16}COR^{19}$,
in which
$R^{16}$ represents hydrogen, straight-chain or branched alkyl having up to 8 carbon atoms or cycloalkyl having 3 to 8 carbon atoms,
$R^{17}$, $R^{18}$ independently of one another represent hydrogen, straight-chain or branched alkyl having up to 8 carbon atoms, cycloalkyl having 3 to 8 carbon atoms, phenyl, where the phenyl radical may be mono- to trisubstituted by F, Cl, Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN or represent a radical of the formula $SO_2R^{20}$,
in which
$R^{20}$ represents straight-chain or branched alkyl having up to 4 carbon atoms or phenyl,
and
$R^{19}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by F, Cl Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;
and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O,
$R^3$ represents hydrogen, F, Cl, Br, straight-chain or branched alkyl, straight-chain or branched halogenoalkyl, straight-chain or branched alkoxy or straight-chain or branched halogenoalkoxy having in each case up to 4 carbon atoms,
W represents $CH_2CH_2$, $CH=CH$, $CH_2O$, $OCH_2$, $CH_2OCH_2$, $CH_2NH$, $NHCH_2$ or $CH_2NHCH_2$,
U represents straight-chain alkylene having up to 4 carbon atoms, O, NH, S, SO or $SO_2$,
A is absent or represents phenyl, pyridyl, thienyl or thiazolyl, which may optionally be mono- to trisubstituted by methyl, ethyl, n-propyl, i-propyl, n-butyl, i-butyl, s-butyl, t-butyl, $CF_3$, methoxy, ethoxy, F, Cl, Br,
$R^2$ represents $COOR^{26}$ or CN,
in which
$R^{26}$ represents hydrogen or straight-chain or branched alkyl having up to 4 carbon atoms;
X represents straight-chain or branched alkylene having up to 4 carbon atoms, which may contain a group selected from O, $S(O)_r$, $NR^{30}$, or a three- to six-membered saturated or unsaturated carbocycle having optionally one or more straight-chain or branched alkyl radicals having 1 to 4 carbon atoms and having optionally one or two heteroatoms from the group consisting of $S(O)_r$, $NR^{32}$ and O,
in which
r represents 0, 1 or 2,
$R^{30}$ represents hydrogen, straight-chain or branched alkyl having up to 6 carbon atoms, phenyl or benzyl,
$R^{32}$ represents hydrogen, straight-chain or branched alkyl having up to 6 carbon atoms, cycloalkyl having 3 to 6 carbon atoms or phenyl,
$R^1$ represents CN or $COOR^{35}$,
in which
$R^{35}$ represents hydrogen or straight-chain or branched alkyl having up to 6 carbon atoms.
Very particular preference according to the invention is given to compounds of the formula (I) in which $R^1$ and $R^2$ each represent COOH.
Especially preferred here are compounds in which B represents phenyl, $R^3$ represents H, W represents $CH_2CH_2$ or $CH=CH$, X represents $(CH_2)_4$, U represents $CH_2$, A represents phenyl and $R^1$ and $R^2$ represent COOH, where V, Q, Y and r are as defined above.

The compounds of the general formula (I) according to the invention may also be present in the form of their salts. In general, salts with organic or inorganic bases or acids may be mentioned here.
In the context of the present invention, preference is given to physiologically acceptable salts. Physiologically acceptable salts of the compounds according to the invention may be salts of the substances according to the invention with mineral acids, carboxylic acids or sulfonic acids. Particular preference is given, for example, to salts with hydrochloric acid, hydrobromic acid, sulfuric acid, phosphoric acid, methanesulfonic acid, ethanesulfonic acid, p-toluenesulfonic acid, benzenesulfonic acid, naphthalenedisulfonic acid, acetic acid, propionic acid, lactic acid, tartaric acid, citric acid, fumaric acid, maleic acid or benzoic acid.
Physiologically acceptable salts may also be the metal or ammonium salts of the compounds according to the invention which have a free carboxyl group. Particular preference is given, for example, to sodium, potassium, magnesium or calcium salts, and to ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.
The compounds according to the invention may exist in stereoisomeric forms which are either like image and mirror image (enantiomers) or which are not like image and mirror image (diastereomers). The invention relates both to the enantiomers or diastereomers and to their respective mixtures. The racemates, like the diastereomers, can be separated into stereoisomerically uniform components in a known manner, for example by optical resolution or chromatographic separation. Any double bonds present in the compounds according to the invention can be present in the cis or trans configuration (Z or E form).
In the context of the present invention, the substituents generally have, unless indicated otherwise, the following meanings:
Alkyl generally represents a straight-chain or branched hydrocarbon radical having 1 to 20 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl, nonyl, decyl, dodecyl, eicosyl.
Alkylene generally represents a straight-chain or branched hydrocarbon bridge having 1 to 20 carbon atoms. Examples which may be mentioned are methylene, ethylene, propylene, α-methylethylene, β-methylethylene, α-ethylethylene, β-ethylethylene, butylene, α-methylpropylene, β-methylpropylene, γ-methylpropylene, α-ethylpropylene, β-ethylpropylene, γ-ethylpropylene, pentylene, hexylene, heptylene, octylene, nonylene, decylene, dodecylene and eicosylene.
Alkenyl generally represents a straight-chain or branched hydrocarbon radical having 2 to 20 carbon atoms and one or more, preferably one or two, double bonds. Examples which may be mentioned are allyl, propenyl, isopropenyl, butenyl, isobutenyl, pentenyl, isopentenyl, hexenyl, isohexenyl, heptenyl, isoheptenyl, octenyl, isooctenyl.
Alkinyl generally represents a straight-chain or branched hydrocarbon radical having 2 to 20 carbon atoms and one or more, preferably one or two, triple bonds. Examples which may be mentioned are ethinyl, 2-butinyl, 2-pentinyl and 2-hexinyl.
Alkenediyl generally represents a straight-chain or branched hydrocarbon bridge having 2 to 20 carbon atoms and one or more, preferably one or two, double bonds. Examples which may be mentioned are ethene-1,2-diyl, propene-1,3-diyl, propene-1,2-diyl, 1-butene-1,4-diyl, 1-butene-1,3-diyl, 1-butene-1,2-diyl, 2-butene-1,4-diyl, 2-butene-1,3-diyl, 2-butene-2,3-diyl.

Alkinediyl generally represents a straight-chain or branched hydrocarbon bridge having 2 to 20 carbon atoms and one or more, preferably one or two, triple bonds. Examples which may be mentioned are ethine-1,2-diyl, propine-1,3-diyl, 1-butine-1,4-diyl, 1-butine-1,3-diyl, 2-butene-1,4-diyl.

Acyl generally represents straight-chain or branched lower alkyl having 1 to 9 carbon atoms which is attached via a carbonyl group. Examples which may be mentioned are: acetyl, ethylcarbonyl, propylcarbonyl, isopropylcarbonyl, butylcarbonyl and isobutylcarbonyl.

Alkoxy generally represents a straight-chain or branched hydrocarbon radical having 1 to 14 carbon atoms which is attached via an oxygen atom. Examples which may be mentioned are methoxy, ethoxy, propoxy, isopropoxy, butoxy, isobutoxy, pentoxy isopentoxy, hexoxy, isohexoxy, heptoxy, isoheptoxy, octoxy or isooctoxy. The terms "alkoxy" and "alkyloxy" are used synonymously.

Alkoxyalkyl generally represents an alkyl radical having up to 8 carbon atoms which is substituted by an alkoxy radical having up to 8 carbon atoms.

Alkoxycarbonyl can be depicted, for example, by the formula

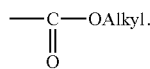

Alkyl here generally represents a straight-chain or branched hydrocarbon radical having 1 to 13 carbon atoms. The following alkoxycarbonyl radicals may be mentioned as examples: methoxycarbonyl, ethoxycarbonyl, propoxycarbonyl, isopropoxycarbonyl, butoxycarbonyl or isobutoxycarbonyl.

Cycloalkyl generally represents a cyclic hydrocarbon radical having 3 to 8 carbon atoms. Preference is given to cyclopropyl, cyclopentyl and cyclohexyl. Examples which may be mentioned are cyclopentyl, cyclohexyl, cycloheptyl and cyclooctyl.

Cycloalkoxy represents, in the context of the invention, an alkoxy radical whose hydrocarbon radical is a cycloalkyl radical. The cycloalkyl radical generally has up to 8 carbon atoms. Examples which may be mentioned are: cyclopropyloxy and cyclohexyloxy. The terms "cycloalkoxy" and "cycloalkyloxy" are used synonymously.

Aryl generally represents an aromatic radical having 6 to 10 carbon atoms. Preferred aryl radicals are phenyl and naphthyl.

Halogen represents, in the context of the invention, fluorine, chlorine, bromine and iodine.

Heterocycle generally represents, in the context of the invention, a saturated, unsaturated or aromatic 3- to 10-membered, for example 5- or 6-membered, heterocycle which may contain up to 3 heteroatoms from the group consisting of S, N and O and which, in the case of a nitrogen atom, may also be attached via this nitrogen atom. Examples which may be mentioned are: oxadiazolyl, thiadiazolyl, pyrazolyl, pyridyl, pyrimidinyl, pyridazinyl, pyrazinyl, thienyl, furyl, pyrrolyl, pyrrolidinyl, piperazinyl, tetrahydropyranyl, tetrahydrofuranyl, 1,2,3-triazolyl, thiazolyl, oxazolyl, imidazolyl, morpholinyl or piperidyl. Preference is given to thiazolyl, furyl, oxazolyl, pyrazolyl, triazolyl, pyridyl, pyrimidinyl, pyridazinyl and tetrahydropyranyl. The term "heteroaryl" (or "hetaryl") represents an aromatic heterocyclic radical. In the heterocycle structures shown in the present application, in each case only one bond to the adjacent group is indicated, for example in the heterocycle structures suitable for Y the bond to the unit Q. However, as indicated, these heterocycle structures may, independently of this, carry further substituents.

The present invention furthermore relates to a process for preparing the compounds of the formula (I)

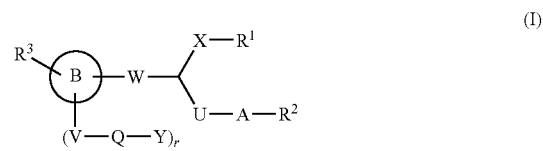

comprising

[A] the reaction of aldehydes of the general formula (II)

in which $R^1$, $R^2$, A, U and X have the meaning given above, with the proviso that $R^1$ and $R^2$ may not represent free carboxylic acid groups, with phosphorus compounds of the general formula (III)

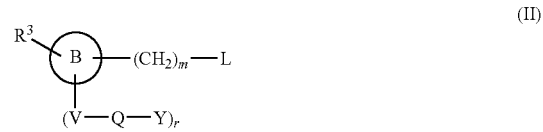

in which $R^3$, B, V, Q, Y and r have the meanings given above, m represents an integer from 1 to 5, and L represents a radical of the formula

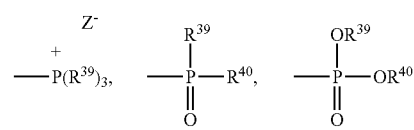

in which $R^{39}$ and $R^{40}$ independently of one another represent straight-chain or branched alkyl having up to 12 carbon atoms or phenyl, and Z represents a halide anion or tosylate anion, in inert solvents in the presence of a base, and, if appropriate, the subsequent partial or complete hydrolysis of the radicals $R^1$ and $R^2$ to free carboxylic acid groups;

or

[B] compounds of the formula (IV),

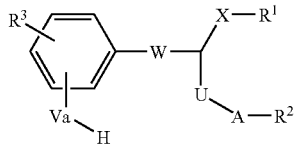

in which
Va represents O or S
$R^1, R^2, R^3, U, W, A, X$ have the meaning given above
are reacted with compounds of the formula (V)

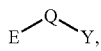

in which
Q, Y have the same meanings as defined above,
E represents either a leaving group which is substituted in the presence of a base or an optionally activated hydroxyl function;

or

[C] compounds of the formula (VI),

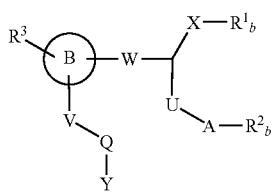

in which
$R^3, V, Q, Y, W, U, A, B$ have the same meanings as defined above,
$R^1_b$ and $R^2_b$ each independently represent CN or COOAlk, where Alk represents a straight-chain or branched alkyl radical having up to 6 carbon atoms,
are converted with aqueous solutions of strong acids or strong bases into the corresponding free carboxylic acids.

or

[D] compounds of the formula (VII)

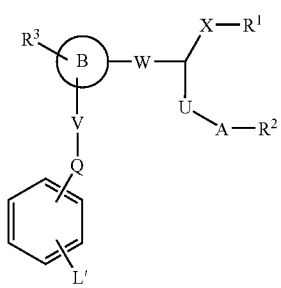

in which
$R^1, R^2, R^3, V, Q, X, W, U, A, B$ have the same meanings as defined above, L' represents Br, I or the group $CF_3SO_2$—O,
are reacted with compounds of the formula (VIII)

in which
M represents an aryl or heteroaryl radical, a straight-chain or branched alkyl, alkenyl or alkinyl radical or cycloalkyl radical or represents an arylalkyl, an arylalkenyl or arylalkinyl radical,
Z' represents the groupings —B(OH)$_2$, —CH≡CH, —CH=CH$_2$ or —Sn(nBu)$_3$
in the presence of a palladium compound, if appropriate additionally in the presence of a reducing agent and further additives and in the presence of a base;

or

[E] compounds of the formula (VII)

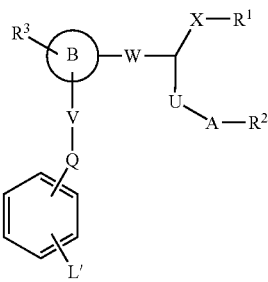

in which
$R^1, R^2, R^3, V, Q, X, W, U, A, B$ have the same meanings as defined above,
L' represents Br, I or the group $CF_3SO_2$—O,
are reacted with compounds of the formula (IX)

in which
$R^a$ and $R^b$ independently of one another represent hydrogen or a straight-chain or branched alkyl radical having up to 8 carbon atoms or together with the nitrogen atom to which they are attached may form an an aromatic heterocycle having 1 to 9 carbon atoms and up to 3 heteroatoms from the group consisting of S, N and O,
in the presence of a palladium compound, if appropriate additionally in the presence of a reducing agent and further additives and in the presence of a base;

or

[F] compounds of the formula (IV),

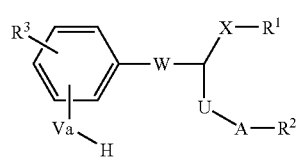

in which
Va represents O or S
$R^1, R^2, R^3, U, W, A, X$ have the meaning given above
are reacted with compounds of the formula (X)

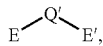
(X)

in which
Q' has the same meaning as Q or represents phenyl,
E and E' in each case independently of one another represent either a leaving group which is substituted in the presence of a base or an optionally activated hydroxyl function or a radical containing such a group;
and the resulting compounds of the formula (XI)

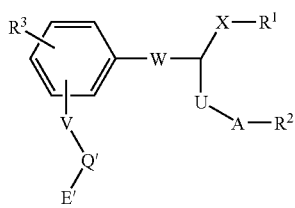
(XI)

in which
$R^1$, $R^2$, $R^3$, A, U, V, W, X and E' have the meanings given above,
Q' has the same meaning as Q or represents 1,4-$CH_2$—Ph—$CH_2$—,
are reacted with amines of the formula (XII)

$NHR^aR^b$ (XII)

in which
$R^a$ and $R^b$ independently of one another represent hydrogen or a straight-chain or branched alkyl radical having up to 8 carbon atoms or together with the nitrogen atom to which they are attached may form an an aromatic heterocycle having 1 to 9 carbon atoms and up to 3 heteroatoms from the group consisting of S, N and O, or

[G] compounds of the formula (XIII)

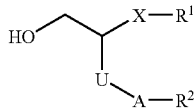
(XIII)

in which
$R^1$, $R^2$, A, U, X have the meanings given above,
are reacted with compounds of the formula (XIV)

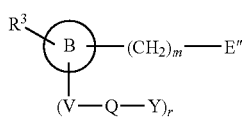
(XIV)

in which
$R^3$, V, Q, Y, r and B have the meanings given above,
m represents an integer from 1 to 5, and E" represents either a leaving group which is substituted in the presence of a base or an optionally activated hydroxyl function.

or

[H] compounds of the formula (XV)

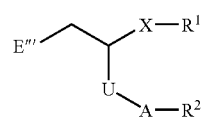
(XV)

in which
$R^1$, $R^2$, A, U, X have the meanings given above,
E''' represents either a leaving group which is substituted in the presence of a base or an optionally activated hydroxyl function;
are reacted with compounds of the formula (XVI)

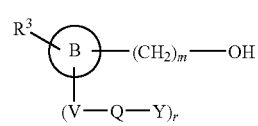
(XVI)

in which
$R^3$, V, Q, Y, r and B have the meanings given above,
m represents an integer from 1 to 5, or

[I] compounds of the formula (XVII)

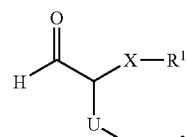
(XVII)

in which
$R^1$, $R^2$, A, U, X have the meanings given above,
are reacted with compounds of the formula (XVIII)

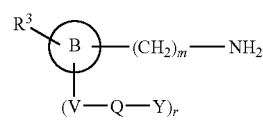
(XVIII)

in which
$R^3$, V, Q, Y, r and B have the meanings given above,
m represents an integer from 0 to 5,
giving initially a Schiff's base, which is then reduced with customary reducing agents or reacted directly under the conditions of a reductive alkylation in the presence of a reducing agent;

or

[J] compounds of the formula (XIX)

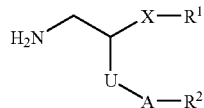  (XIX)

in which
$R^1$, $R^2$, A, U, X have the meanings given above,
are reacted with compounds of the formula (XX)

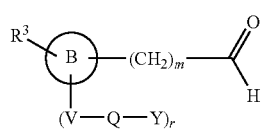  (XX)

in which
$R^3$ V, Q, Y, r and B have the meanings given above,
m represents an integer from 0 to 5,
giving initially a Schiff's base, which is then reduced with customary reducing agents or reacted directly under the conditions of a reductive alkylation in the presence of a reducing agent, or

[K] aldehydes of the formula (XXI)

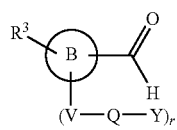  (XXI)

in which
$R^3$, V, Q, Y, r and B have the meanings given above,
are reacted with phosphorus compounds of the formula (XXII)

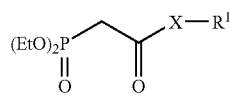  (XXII)

in which
X and $R^1$ have the meanings given above.
to give compounds of the formula (XXIII)

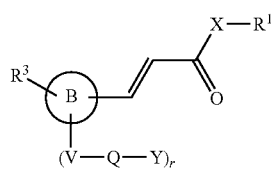  (XXIII)

in which
$R^3$, V, Q, Y, r, B, X and $R^1$ have the meanings given above,
and subsequently, by successive reduction of the alkene group and the carbonyl group and subsequent substitution of the hydroxyl group generated by reduction of the carbonyl group or by reaction of the halogen radical generated from the hydroxyl group using halogenating agents with alcohols, primary amines or thiols and, if appropriate, subsequent oxidation to the corresponding sulfoxide or sulfone compounds, converted into compounds of the formula (XXIV),

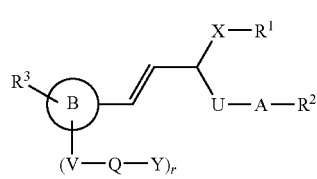  (XXIV)

in which
$R^3$, V, Q, Y, r, B, X, A, $R^2$ and $R^1$ have the meanings riven above,
U represents O, NH or S.

According to the present invention, in process [A], Z preferably represents a halide anion, particularly preferably chloride, bromide or iodide.

According to the present invention, the partial or complete hydrolysis to the corresponding free carboxylic acid groups, which is to be carried out in process [A], if appropriate, is preferably carried out using strong acids, such as, for example, HCl, or using strong bases, such as, for example, NaOH or LiOH, which are present in aqueous solution or in solvent mixtures of water with alcohols, such as, for example, methanol, or ethers.

Preferred inert solvents for the process [A] according to the invention are customary organic solvents which do not change under the reaction conditions. For the process [A] according to the invention, preference is given to using ethers, such as diethyl ether, butyl methyl ester, dioxane, tetrahydrofuran, glycol dimethyl ether or diethylene glycol dimethyl ether, or hydrocarbons, such as benzene, toluene, xylene or petroleum ether, or amides, such as dimethylformamide or hexamethylphosphoric triamide, or 1,3-dimethyl-imidazolidin-2-one, 1,3-dimethyl-tetrahydropyrimidin-2-one or dimethyl sulfoxide. It is, of course, also possible to use mixtures of the solvents mentioned above.

Bases which are preferred for the process [A] according to the invention include basic compounds which are customarily used for basic reactions. Preference is given to using alkali metal hydrides, such as, for example, sodium hydride or potassium hydride, or alkali metal alkoxides, such as sodium methoxide, sodium ethoxide, potassium methoxide, potassium ethoxide or potassium t.-butoxide, or amides, such as sodium amide or lithium diusopropylamide, or sodium hexamethyidisilazane, or organolithium compounds, such as phenyllithium, butyllithium or methyllithium. To optimize the reaction, in the process [A] according to the invention a customary crown ether such as 18-crown-6 may be added, if appropriate.

The selection of the solvent or base depends on the stability, sensitivity to hydrolysis or the CH activity of the corresponding phosphorus compound. Solvents that are particularly preferably used are ethers, such as diethyl ether, tetrahydrofuran, dimethoxyethane or dioxane, together with a cosolvent, such as dimethylformamide or 1,3-dimethyltetrahydropyridin-2-one or 1,3-dimethylimidazolidin-2-one. Alkali metal alkoxides, such as potassium t.-butoxide, or organolithium compounds, such as phenyllithium or butyllithium, or sodium hydride are bases which are particularly preferably used.

The reaction can generally be carried out in a temperature range of from −80° C. to +70° C., preferably from −80° C. to +20° C.

The reaction can be carried out at atmospheric pressure, elevated or reduced pressure (for example in a range of from 0.5 to 5 bar). In general, the reaction is carried out at atmospheric pressure.

When carrying out the reaction, the phosphorus compounds are generally employed in an amount of 1-2 mol, based on 1 mol of aldehyde. The bases are generally employed in an amount of 1-5 mol, preferably 1-2 mol, based on 1 mol of phosphorus compound.

The process [A] according to the invention can be carried out, for example, by adding the base and then the aldehyde, if appropriate in a solvent, to the phosphorus compound which is suspended or dissolved in a solvent, and subsequently, if appropriate, heating the mixture. Work-up is carried out in a customary manner, by extraction, chromatography and/or crystallization.

When carrying out the process [A] according to the invention, it is also possible to use, instead of the phosphonium salts mentioned above, the corresponding phosphoranes (U equals —P(R$^{12}$)$_3$═CHR) which are prepared beforehand in a separate reaction from the corresponding phosphonium salts in basic medium. However, it has been found to be advantageous to carry out the reaction with the phosphorus compounds in the presence of bases as a one-pot process.

The phosphorus compounds of the general formula (III) can be prepared by the following different routes.

Process I—1st Variant

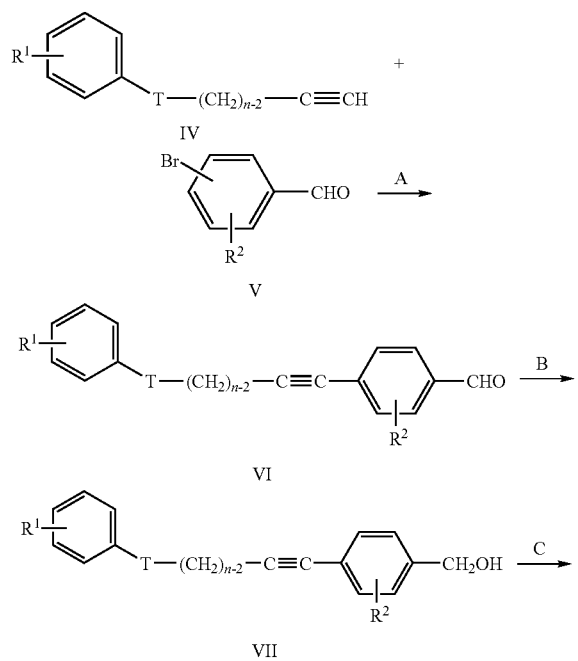

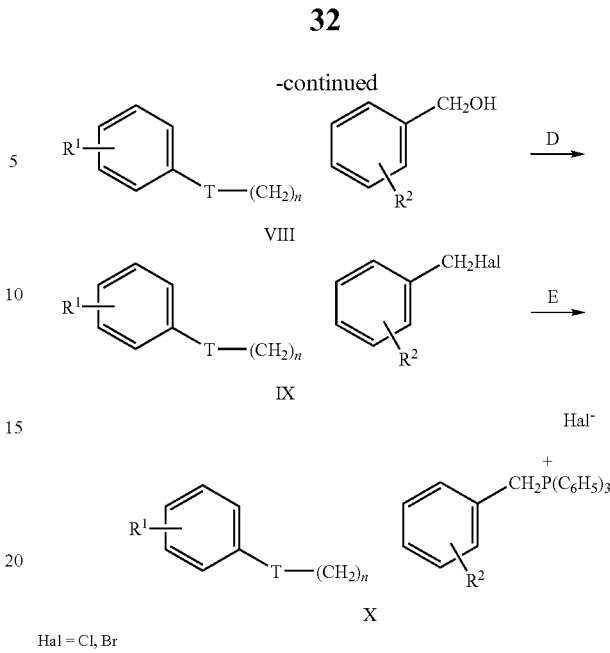

Hal = Cl, Br where the process is not limited to the compounds shown here by way of example in which Y and B represent phenyl, Q represents an alkylene chain and V is absent, but can be carried out in principle with compounds having any radicals V, Q, Y and B.

In the first reaction step A of this variant, the acetylene compounds (IVa) are reacted with the bromobenzaldehydes (Va) in solvents such as triethylamine, acetonitrile, pyridine or mixtures thereof, preferably in triethylamine, in the presence of copper(I) salts and palladium(0) compounds, preferably in the presence of copper(I) halides, such as, for example, copper iodide, and bis-(triphenylphosphine)-palladium(II) chloride, in a temperature range of from −40° C. to +80° C., preferably from 0° C. to +40° C.

In the second reaction step B, the formyl compound (VIa) is reduced in solvents such as alcohols, for example methanol, ethanol, propanol or isopropanol, or ethers, such as diethyl ether, tetrahydrofuran or dioxane, or in basic solvents, such as triethylamine, pyridine or dimethylformamide, or in water or in mixtures of the abovementioned solvents, using complex hydrides, such as, for example, borohydrides or aluminum hydrides, preferably sodium borohydride or lithium D aluminum hydride, as reducing agents, in a temperature range of from −40° C. to +60° C., preferably from 0° C. to +40° C., to give the hydroxyl compounds (VIIa).

In the third reaction step C, the compounds (VIIa) are hydrogenated in inert solvents such as alcohols, for example methanol, ethanol, propanol or isopropanol, or hydrocarbons, such as benzene, toluene or xylene, or in ethers, such as diethyl ether or tetrahydrofuran, or in ethyl acetate, particularly preferably in methanol, in the presence of noble metal catalysts, such as palladium or platinum, in a temperature range of from −30° C. to +80° C., preferably from 0° C. to +40° C., under a pressure of from 1 bar to 50 bar, preferably from 1 bar to 20 bar.

Steps B and C can also be carried out in reverse order.

In the fourth step D, the hydrogenated compounds VIIIa are brominated by reaction with brominating agents, such as, for example, phosphorus tribromide, sulfonyl bromide, hydrogen bromide or carbon tetrabromide/triphenylphosphine, in inert solvents, such as ethers, for example diethyl ether or tetrahydrofuran, or hydrocarbons, such as benzene or toluene, or, particularly preferably, chlorinated hydrocarbons, such as methylene chloride or chloroform, in a temperature range of from −20° C. to +60° C., preferably from 0° C. to +40° C. However, it is also possible to use the corresponding chlorine compounds which are obtainable, for example, by reacting the compounds VIIIa with SOCl$_2$.

In the fifth reaction step E, the brominated or chlorinated compounds (IXa) are reacted with triphenylphosphine in inert solvents such as acetonitrile or hydrocarbons, such as benzene, toluene or xylene, or benzonitrile or dimethyl-formamide or dimethyl sulfoxide or in an alcohol, such as methanol, ethanol, propanol, butanol or isopropanol or in the absence of a solvent, in a temperature range of from 0° C. to +200° C., preferably from +20° C. to +180° C., with formation of the phosphonium salts Xa.

Using this process, it is possible to obtain the compounds of the formula (I) according to the invention in which V is absent. In the compounds of the formulae (IVa) to (Xa), the radical $R^3$ has the same meaning as defined above.

The acetylene compounds of the formula (IVa) can be obtained, for example, by reacting corresponding amines or cyclic substrates with a nucleophilic group, for example phenol derivatives, aniline derivatives or carbanionic derivatives, such as Grignard reagents, with ω-halogenoalkines in the presence of bases, in a known manner. Particular preference is given here to ω-chloroalkines such as, for example, 5-chloro-1-pentine. Suitable for use as bases are, for example, metal hydrides, such as sodium hydride. The conversion into the acetylene compounds of the formula (IVa) can be carried out in organic solvents, such as, for example, ethers, in particular tetrahydrofuran, at temperatures of from +20° C. to +80° C., under an atmosphere of inert gas, for example argon. In some cases, it may be advantageous to add complexing agents, such as hexaphosphoric triamide. Alternatively, the acetylene compounds (IVa) can be obtained by reacting corresponding substrates having a group which is nucleophilically substitutable, for example ω-halogenoalkylphenyl compounds, preferably ω-chloroalkylphenyl compounds, with acetylides, such as, for example, sodium acetylide or lithium acetylide, under conditions known to the person skilled in the art (cf., for example, J. March, Advanced Organic Chemistry, 3. edition, Wiley, p. 429).

Process I—2nd Variant

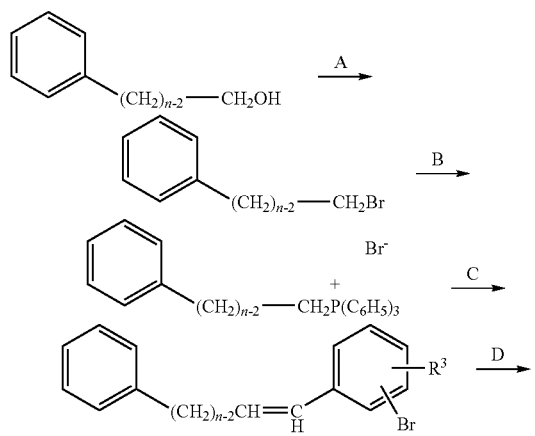

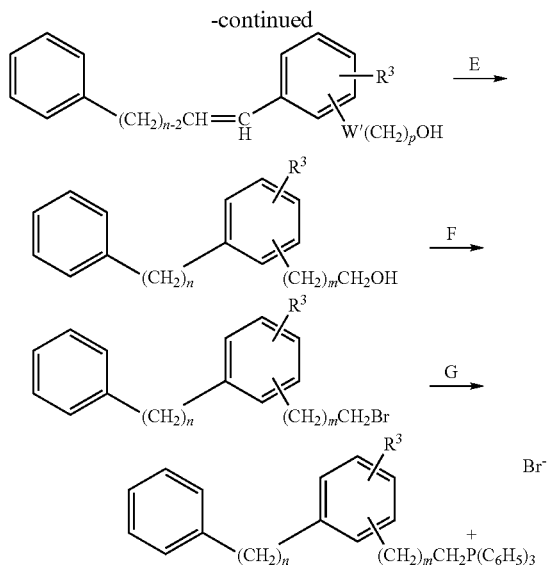

where the process is not limited to the compounds shown here by way of example in which Y and B represent phenyl, Q represents an alkylene chain and V is absent, but can be carried out in principle with compounds having any radicals V, Q, Y and B.

In the first reaction step, the alcohols used as starting materials are brominated, suitable brominating agents being, for example, the compounds listed in step D of the 1st variant of process I.

The resulting bromides are reacted with triphenylphosphine as in step E of the 1st variant of process I.

In the next reaction step, the reactive ylide is generated as illustrated above, and this is then reacted with a bromobenzaldehyde having the desired substitution pattern.

From the resulting compound, it is possible to obtain, by reaction with a base, preferably t-butyllithium, in an inert solvent (tetrahydrofuran), at low temperatures and subsequent addition of an appropriate electrophile, such as paraformaldehyde or ethylene oxide, the corresponding primary alcohols (W' is a direct bond). Alternatively, the resulting compounds can be converted using an optionally protected hydroxyalkine such as the tetrahydropyranyl ether of propargyl alcohol, under the same conditions as in process step I of the 1st variant of process I (W' is C≡C), followed by a hydrogenation, which can be carried out analogously to step C of the 1st variant of process I, into the primary alcohols. The resulting primary alcohols are, analogously to the 1st variant of process I, converted into the corresponding phosphonium salts.

Using this process, it is possible to obtain the compounds of the formula (I) according to the invention in which V is absent.

The alcohols used as starting materials in this process, for example hydroxyalkyl-oxyphenyl compounds or hydroxyalkylphenyl compounds, are either commercially available or can be prepared by customary reactions known to the person skilled in the art.

In the compounds shown in the diagram above, the radical $R^3$ has the same meaning as defined above.

Process II—1st Variant

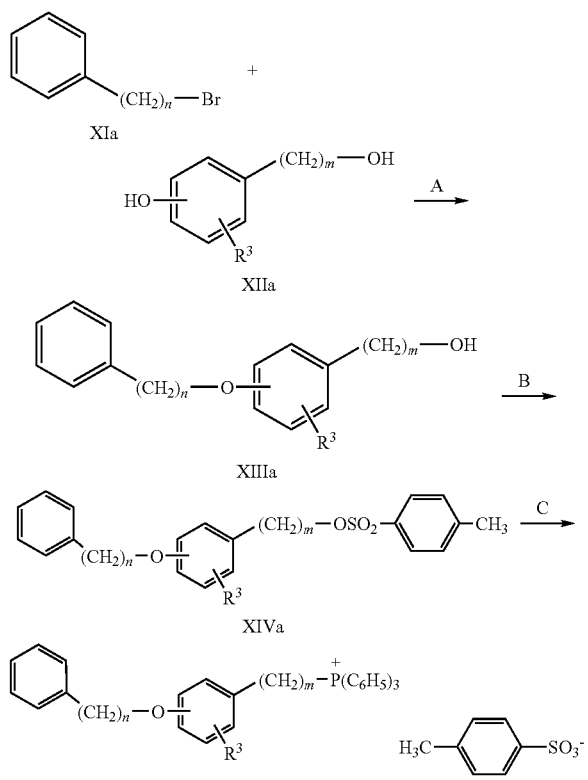

where the process is not limited to the compounds shown here by way of example in which Y and B represent phenyl, Q represents an alkylene chain and V represents O, but can be carried out in principle with compounds having any radicals V, Q, Y and B.

In the first reaction step of this variant, the bromine compounds (XIa) are reacted with the phenols (XIIa) in preferred solvents such as water or alcohols, such as, for example, methanol, ethanol, propanol or isopropanol, or ethers, such as diethyl ether, tetrahydrofuran, dioxane or dimethyloxymethane, or dimethylformamide or dimethyl sulfoxide, or acetonitrile or ketones, such as, for example, acetone, particularly preferably in isopropanol, in the presence of bases, such as alkali metal hydroxides, carbonates or alkoxides, such as, for example, sodium carbonate, potassium carbonate, cesium carbonate, sodium hydroxide, potassium hydroxide, sodium ethoxide or potassium t-butoxide, in a temperature range of from 0° C. to 200° C., preferably from +20° C. to +180° C.

In the second step B, the phenyl ethers (XIIIa) are reacted with tosyl chloride in inert solvents such as ethers, for example diethyl ether, tetrahydrofuran or dioxane, or hydrocarbons, such as benzene or toluene, or chlorinated hydrocarbons, such as chloroform or methylene chloride, or in ethyl acetate, acetone or acetonitrile, preferably in methylene chloride, in the presence of bases, such as triethylamine, pyridine or dimethylaminopyridine, preferably in the presence of pyridine, in a temperature range of from −30° C. to +50° C., preferably from −10° C. to +30° C.

In the third reaction step C, the tosyl compounds (XIVa) are reacted with triphenyl-phosphine in preferred solvents such as hydrocarbons, for example benzene or toluene, benzonitrile, acetonitrile, dimethylformamide or dimethyl sulfoxide, or in the absence of a solvent, particularly preferably in acetonitrile, in a temperature range of from 0° C. to +200° C., preferably from +20° C. to +180° C., giving the phosphonium salts (XVa).

In steps B and C, the hydroxyl compound XIIIa can also, analogously to steps D and E of the first variant of process A, be initially converted into the bromide and then into the phosphonium salt.

Using this process, it is possible to obtain the compounds of the formula (I) according to the invention in which V is O.

If B represents a heterocycle, the process can also be carried out by reacting, instead of the bromide (XIa), the corresponding alcohol with a compound (XIIa) which, instead of the hydroxyl group located directly on the heterocycle, has a suitable leaving group, such as, for example, a halogen radical, a tosyl, mesyl or triflate group, and furthermore, instead of the radical (CH$_2$)$_m$OH, has an ester group. By subsequent reduction of the ester group with customary reducing agents, such as, for example LiAlH$_4$, it is possible to obtain the compound of the formula (XIIIa).

Process II—2nd Variant

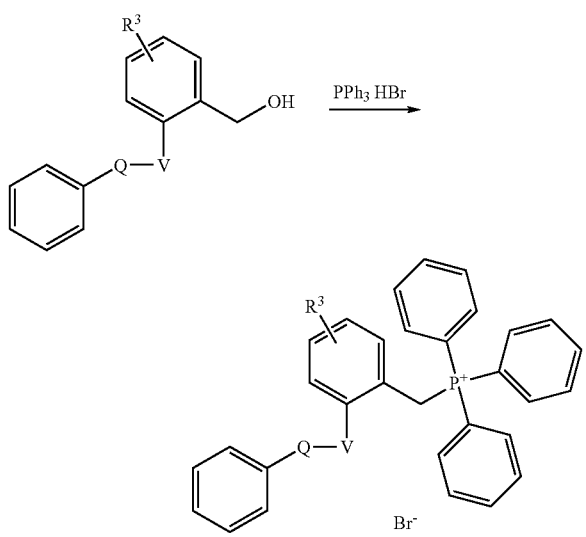

where the process is not limited to the compounds shown here in an exemplary manner, where Y and B represent phenyl, but can, in principle, also be carried out using compounds having any radicals Y and B.

In this variant, the corresponding alcohols, for example hydroxyalkylphenyl compounds, are reacted with triphenylphosphonium hydrobromide in an organic solvent, such as, for example, acetonitrile, at a temperature of from +30° C. to +100° C., preferably from +50° C. to +90° C. The starting materials can be obtained in a customary manner. For example, in the case that V is O, by reacting a corresponding halogen compound, for example a halogenoalkylphenyl compound, preferably a chloro- or bromoalkylphenyl compound, such as, for example, benzyl bromide, with a corresponding alcohol, for example a phenol compound, such as, for example, 2-hydroxybenzyl alcohol, in an organic solvent, such as an alcohol, preferably isopropanol, in the presence of a base, such as, for example, potassium carbonate, at a temperature from +30 to 100° C., preferably from +50 to 90° C. reacted.

In the compounds shown in the above diagrams of process II, the radical $R^3$ has the same meaning as defined above. The radical V may represent O or be absent.

Process II—3rd Variant

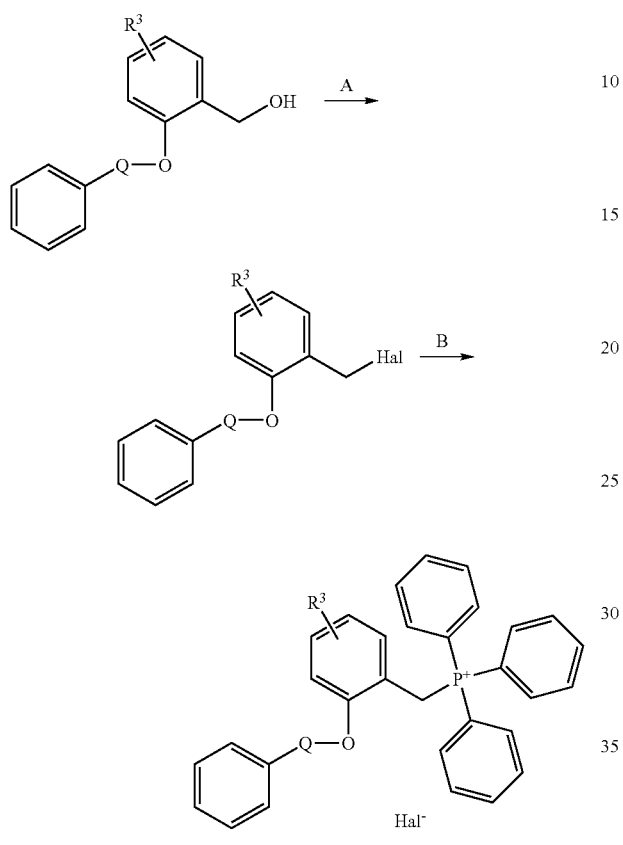

Hal = Cl, Br where the process is not limited to the compounds shown here in an exemplary manner, in which Y and B represent phenyl, but can, in principle, be carried out with compounds having any radicals Y and B.

In this variant, the alcohol is initially, according to step D of process I, variant 1, converted into a halide, which can then, analogously to step E of process I, variant 1, be converted into the desired phosphonium salt.

In this variant, Q and $R^3$ have the meanings given above.

Depending on the meanings of the different radicals, the aldehydes of the general formula (II) can be prepared, for example, by the process below.

Process III

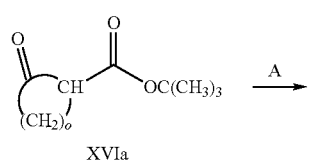

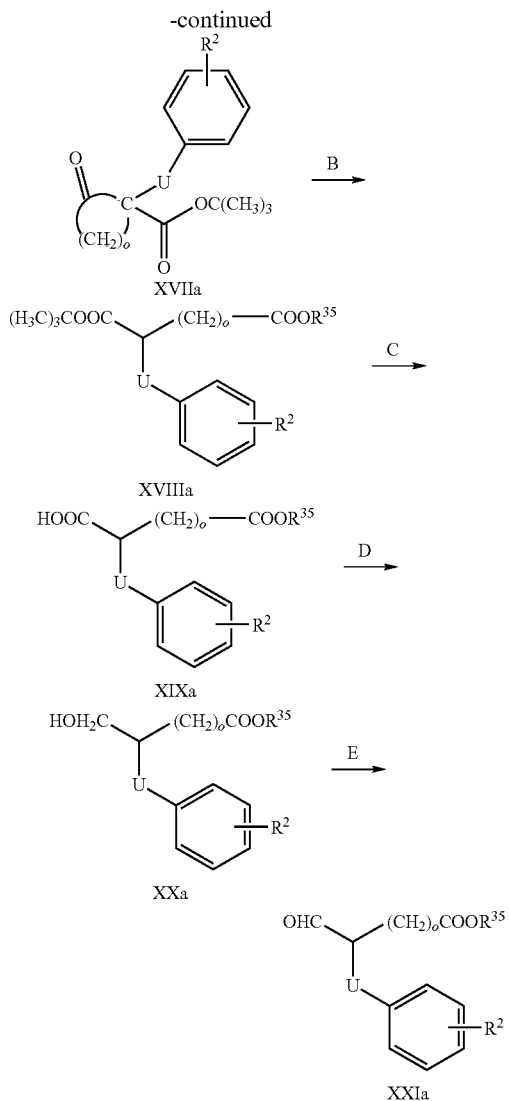

In the first reaction step A of this variant, the ketone XVIa (where o is 3, 4 or 5) is reacted with 4-halogenomethylbenzoic acid esters or 4-halogenosulfenylbenzoic acid esters, where the halogen radical is preferably chlorine or bromine, or the corresponding nitrites, in inert solvents, such as an ether, for example diethyl ether, tetrahydrofuran or dioxane, or dimethylformamide, or dimethyl sulfoxide, or in mixtures thereof, particularly preferably in dimethylformamide, in the presence of bases, such as alkali metal hydrides, amides or alkoxides, such as sodium hydride, potassium hydride, lithium diisopropylamide, potassium ethoxide, sodium ethoxide, potassium methoxide or potassium t-butoxide, particularly preferably in the presence of sodium hydride, in a temperature range of from −40° C. to +60° C., particularly preferably from −20° C. to +30° C.

In the second reaction step B, the ketones XVIIa are reacted in solvents such as dimethylformamide or alcohols, for example methanol, ethanol, propanol or isopropanol, or in water or mixtures thereof, particularly preferably in dimethylformamide or ethanol, in the presence of bases, such as alkali metal hydroxides, alkali metal carbonates or alkali metal alkoxides, such as sodium hydroxide, potassium hydroxide, sodium carbonate, sodium methoxide, sodium ethoxide, potassium ethoxide or potassium t-butoxide, particularly preferably in the presence of potassium t-butoxide, in a temperature range of from 0° C. to +150° C., particularly preferably from +20° C. to +100° C., giving the compounds XVIIIa.

In the third reaction step C, the compounds XVIIIa are hydrolyzed in solvents such as alcohols, for example methanol, ethanol, propanol or isopropanol, or in ethers, for example methyl ether, tetrahydrofuran or dioxane, or in chlorinated hydrocarbons, such as methylene chloride or chloroform, or carboxylic acids, such as acetic acid or trifluoroacetic acid, or in mixtures thereof, particularly preferably in trifluoroacetic acid, in the presence of acids, such as mineral acids, for example hydrochloric acid, hydrobromic acid or sulfuric acid, or carboxylic acids, for example acetic acid or trifluoroacetic acid, particularly preferably in the presence of acetic acid, especially preferably in the presence of trifluoroacetic acid, both as solvent and as acid, in a temperature range of from −20° C. to +60° C., particularly preferably from 0° C. to +30° C., giving the carboxylic acids XIXa.

In the fourth step D, the carboxylic acids XIXa are reduced in solvents such as ethers, for example diethyl ether, tetrahydrofuran or dioxane, or in chlorinated hydrocarbons such as methylene chloride or chloroform, or in mixtures thereof, particularly preferably in tetrahydrofuran, using boron compounds as reducing agents, for example borane or borane-dimethyl sulfide complex, in a temperature range of from −40° C. to +60° C., particularly preferably from −20° C. to +30° C., giving the hydroxyl compounds XXa.

In the fifth reaction step E, the hydroxyl compounds XXa are oxidized in solvents such as ethers, for example diethyl ether, dioxane or tetrahydrofuran, or in chlorinated hydrocarbons, such as methylene chloride or chloroform, or in dimethyl sulfoxide or in mixtures thereof, particularly preferably in dichloromethane, using oxidizing agents such as pyridinium chlorochromate, chromium(VI) salts, dimethyl sulfoxide/pyridine/SO$_3$, catalytic amounts of tetraalkylammonium perruthenate in the presence of N-methylmorpholine oxide and molecular sieve, dimethyl sulfoxide/oxalyl chloride/triethylamine, particularly preferably using pyridinium chlorochromate, catalytic amounts of tetraalkylammonium perruthenate in the presence of N-methylmorpholine and molecular sieve or dimethyl sulfoxide/oxalyl chloride/triethylamine, if appropriate in the presence of bases, such as triethylamine, diisopropylamine, pyridine or dimethylaminopyridine, particularly preferably in the presence of triethylamine, in a temperature range of from −20° C. to +60° C., particularly preferably from 0° C. to +30° C., giving the aldehydes XXIa.

The cyclic ketones XVIa are either commercially available or preparable by customary routes known to the person skilled in the art, for example by Dieckmann condensation of the corresponding carboxylic acid diesters.

The 4-chloromethylbenzoic acid esters or 4-chlorosulfenylbenzoic acid esters to be reacted with the ketones XVIa, or the corresponding nitriles, are either commercially available or can be prepared by customary routes known to the person skilled in the art.

In the compounds shown in the above diagram of process III, the radicals $R^2$, $R^{35}$ and U have the same meanings as defined above, and o represents an integer from 1 to 12.

Using the process III, it is possible to prepare aldehydes (II) in which X represents an alkylene chain, U represents —CH$_2$—, $R^1$ represents COOR$^{35}$ and $R^2$ represents CN or COOR$^{26}$.

Process IV

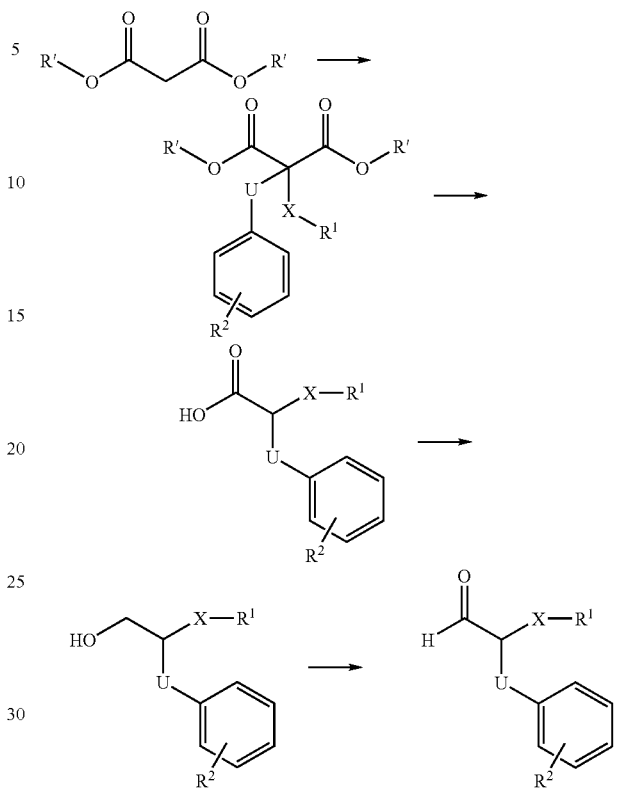

In this process, a malonic acid diester (where the alcoholic component R' used can be an allyl radical or lower alkyl radicals, such as methyl, ethyl, t-Bu or a benzyl radical) is converted by two successive reactions with corresponding electrophiles into a 2,2-disubstituted malonic acid diester. The malonic acid diester used as starting material can, for example, initially be reacted in the presence of a base, such as, for example, sodium hydride, triethylamine, potassium carbonate, sodium hydroxide, DABCO, potassium hydroxide, lithium diisopropylamide or sodium amide, preferably sodium hydride, with a corresponding electrophile, such as a corresponding halide, tosylate, mesylate or triflate, for example a halide such as ω-chloro- or ω-bromocarboxylic acid ester, for example methyl bromoacetate, in a solvent such as dioxane, at temperatures of from 0 to 50° C. In a second step, the resulting monosubstituted malonic acid diester derivative can be reacted by reaction with a corresponding electrophile, such as a corresponding halide, tosylate, mesylate or triflate, for example a 2-halogenobenzyl derivative, such as methyl 2-(bromomethyl)benzoate, in the presence of a base, such as, for example, sodium hydride, triethylamine, potassium carbonate, sodium hydroxide, DABCO, potassium hydroxide, lithium diisopropylamide or sodium amide, preferably sodium hydride, in a solvent such as dimethylformamide, at temperatures of from 0 to 50° C. However, it is also possible to carry out the reactions with the two electrophiles in reverse order.

The resulting 2,2-disubstituted malonic acid diester derivative can be converted by reaction with an acid such as, for example, hydrochloric acid, sulfuric acid or trifluoroacetic acid, or by reaction with a base such as potassium hydroxide, sodium hydroxide or lithium hydroxide, or by a palladium-catalyzed reaction, such as, for example, with formic acid in the presence of a Pd catalyst, preferably a Pd(II) catalyst, such as palladium(II) acetate, and a phosphine, such as triphenylphosphine, and a base, such as an amine, preferably triethylamine, in a solvent such as dioxane, at temperatures of from 20 to 120° C. by ester cleavage and subsequent decarboxylation at elevated temperatures into the corresponding carboxylic acid derivatives.

These carboxylic acid derivatives can in turn be converted by reduction with customary reducing agents such as, for example, diisobutylaluminum hydride (DIBAL), lithium aluminum hydride or borohydrides, such as borane, in tetrahydrofuran, into the corresponding alcohols.

These alcohols can then be oxidized using customary mild oxidizing agents such as Cr(VI) compounds, such as PDC or PCC, potassium permanganate, dimethyl sulfoxide/oxalyl chloride/triethalmine (Swern oxidation) or tetrapropylammonium perruthenate (TPAP) in the presence of a base such as N-methylmorpholine oxide and molecular sieve, or by Dess-Martin oxidation, to give the corresponding aldehydes.

In the compounds shown in the above diagram of process IV, the radicals $R^1$, $R^2$, U, X have the same meanings as defined above; however, X may not represent O and $R^1$ and $R^2$ may not represent free carboxyl functions.

Process V

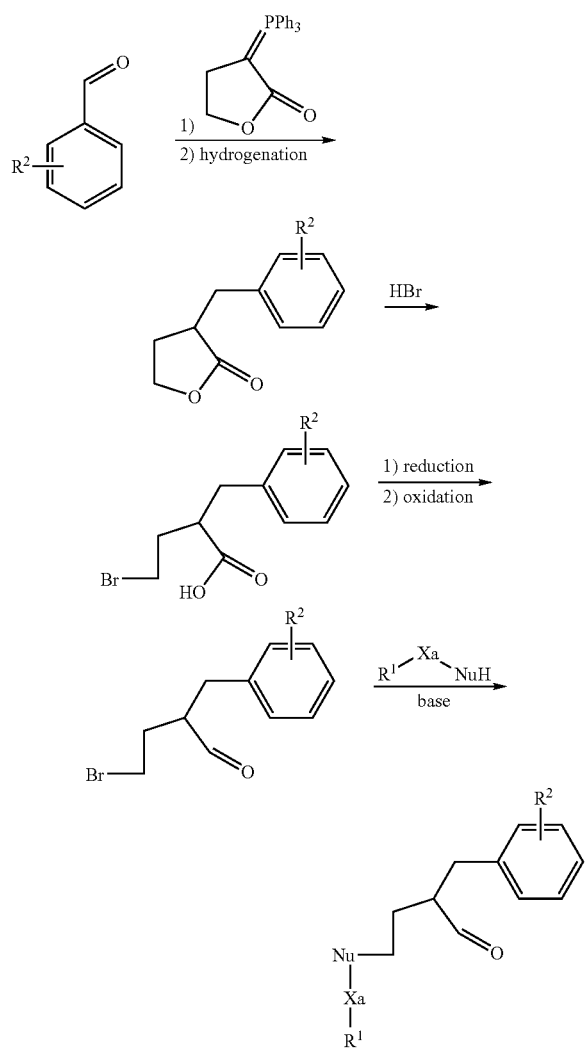

In this variant, a benzaldehyde derivative is initially reacted with a tetrahydofuranonephosphorane in an organic solvent such as dimethyl sulfoxide, with heating. The resulting alkene is then reacted with customary reducing agents such as Pd/H$_2$/C to give the corresponding 3-benzoylmethyltetrahydrofuranone derivative. This is then converted by ring-opening with addition of an acid such as HBr with heating into butyric acid derivative. The subsequent reduction with reducing agents which are customarily used for this purpose, such as borane in an organic solvent such as tetrahydrofuran, gives initially the corresponding alcohol which can then be oxidized using a customary reducing agent, such as pyridinium dichromate (PDC), to give the aldehyde. By reaction with a compound $R^1$—Xa-Nu in the presence of a customary base such as, for example, NaHCO$_3$, the side-chain can be modified appropriately. However, it is also possible to carry out this side-chain variation only after the reaction of the aldehyde with a phosphonium salt according to process A.

In the compounds shown in the scheme above, $R^1$ and $R^2$ have the meanings given above. Xa has the meaning of X given above, but additionally carries a nucleophilic group Nu such as, for example, an amino group, and is shorter by the number of carbon atoms which are already present in the molecule in the side-chain.

Process VI

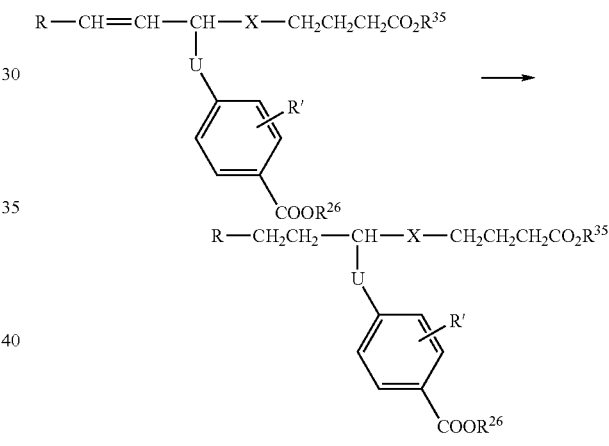

In this process, an alkene derivative is reacted in solvents such as alcohols, water, benzene, toluene, ethers, such as dimethyl ether, tetrahydrofuran, dioxane, esters, such as ethyl acetate, or in hydrocarbons, such as hexane, or in amines, such as triethylamine, or in ammonia, with a reducing agent such as hydrogen in the presence of a metal catalyst, such as the oxides or soluble complexes of palladium, platinum, ruthenium or nickel, or with a metal such as lithium or sodium, or with hydrazine or arylaralkoxy-substituted hydrazines. The product of this reaction is an alkane derivative in which W in the general formula (I) represents —CH$_2$CH$_2$— or —CH$_2$CH$_2$CH$_2$—. The usual temperature range for this process is from −20° C. to +30° C.

In the compounds shown in the above diagram of process VI, the radicals $R^{26}$, $R^{35}$, U and X have the same meanings as defined in claim 1. R' represents one of the substituents which, according to claim 1, may be present on U. R represents the radical of the compounds of the general formula (I), where R may contain an aryl radical, but no double bond.

The process B according to the invention can preferably be carried out in acetonitrile by reacting the compounds (IV) and (V) in the presence of a base, such as sodium carbonate, Et$_3$N, DABCO, $K_2CO_3$, KOH, NaOH, $Cs_2CO_3$, using, if appropriate, NaI as catalyst or NaH. The reaction can generally be carried out in a temperature range of from −20° C. to +90° C., preferably from 0° C. to +90° C. The reaction can be carried out at atmospheric pressure, elevated or reduced pressure (for example in a ranae from 0.5 to 5 bar). In general, the reaction is carried out at atmospheric pressure.

In the process B according to the invention, a compound of the formula (I) is prepared by nucleophilic substitution of a leaving croup E in the compound of the formula (V) by the hydroxyl or thiol function of the compound of the formula (IV). Suitable leaving groups E are here, for example: halogen, for example Cl, Br, I, tosylate, mesylate, or a hydroxyl function activated by reagents such as diisopropyl azodicarboxylate/$PPh_3$ (Mitsonobu reaction).

The compound of the formula (IV) used as starting material can be prepared by reacting a corresponding, phosphonium compound, such as, for example, 2-hydroxybenzyltriphenylphosphonium bromide, with a corresponding aldehyde(II), analogously to process A. The compounds of the formula (V) are commercially available or obtainable by a customary manner known to the person skilled in the art.

In the process C according to the invention, a compound of the formula (I), in which $R^1$ and $R^2$ each represent a free carboxyl function, is obtained by converting ester and/or nitrile functions of the compound (VI) into the corresponding free carboxyl functions. This reaction can be effected, for example, by addition of aqueous solutions of strong, acids, such as, for example, HCl or $H_2SO_4$, or of strong bases, such as, for example, NaOH, KOR or LiOH. The reaction can preferably be carried out in a customary organic solvent which does not change under the reaction conditions, or in water. For the process C according to the invention, preference is given to using ethers, such as diethyl ether, butyl methyl ester, dioxane, tetrahydrofuran, glycol dimethyl ether or diethylene glycol dimethyl ether, or hydrocarbons, such as benzene, toluene, xylene or petroleum ether, or amides, such as dimethylformamide or hexamethylphosphoric triamide, or 1,3-dimethyl-imidazolidin-2-one, 1,3-dimethyl-tetrahydropyrimidin-2-one, acetonitrile, ethyl acetate or dimethyl sulfoxide. It is, of course, also possible to use mixtures of the solvents mentioned above.

Preference according to the invention is given, for example, to carrying out the reaction in a mixture of water and methanol. In general, the reaction can be carried out in a temperature range of from −20° C. to +90° C., preferably from 0° C. to +90° C. The reaction can be carried out at atmospheric pressure, elevated or reduced pressure (for example in a range of from 0.5 to 5 bar). In general, the reaction is carried out at atmospheric pressure.

The compounds of the formula (VI) used as starting materials can be prepared by one of the routes, described in the present application, for preparing the compounds of the formula (I), for example according to process A.

In the process D according to the invention, a compound of the formula (I) is prepared by reacting a compound of the formula (VII), which contains a substitutable group L', with a compound of group (VII) in the presence of a palladium compound and, if appropriate, a reducing agent and further additives, in basic medium. Formally, the reaction is a reductive coupling of the compounds of the formulae (VII) and (VIII) as described, for example, in L. S. Hegedus, Organometallics in Synthesis, M. Schlosser, Ed., Wiley & Sons, 1994.

Suitable for use as substitutable group L' in the compounds of the formula (VII) is, for example, a halogen radical such as Br or I or a customary leaving group such as, for example, a triflate radical.

The compounds of the formula (VIII) contain a reactive group Z' which can be selected from the group consisting of —$B(OH)_2$, —CH≡CH, —CH=$CH_2$ and —$Sn(nBu)_3$.

Suitable for use as palladium compound is a palladium(II) compound, such as, for example, $Cl_2Pd(PPh_3)_2$ or $Pd(OAc)_2$, or a palladium(0) compound, such as, for example, $Pd(PPh_3)_4$ or $Pd_2(dba)_3$. If required, it is possible to additionally add to the reaction mixture a reducing agent, such as, for example, triphenylphosphine, BINAP or other additives, such as, for example, Cu(I)Br, $NBu_4NCl$, LiCl or $Ag_3PO_4$ (cf. in this context T Jeffery, Tetrahedron lett. 1985, 26, 2667-2670; T. Jeffery, J. Chem. Soc., Chem. Commun. 1984, 1287-1289; S. Bräse, A. deMejiere in "Metal-catalyzied cross-coupling reactions", Ed. F. Diederich, P. J. Stang, Wiley-VCH, Weinheim 1998, 99-166).

The reaction is carried out in the presence of a customary base, such as, for example, $Na_2CO_3$, NaOH or triethylamine. Suitable solvents are the organic solvents mentioned above in process C, particular preference being given to ethers, such as, for example, dimethoxyethane. In general, the reaction can be carried out in a temperature range of from −20° C. to +90° C., preferably from 0° C. to +90° C. The reaction can be carried out at atmospheric pressure, elevated or reduced pressure (for example in a range of from 0.5 to 5 bar). In general, the reaction is carried out at atmospheric pressure.

The compounds of the formula (VII) used as starting materials can be prepared by one of the routes, described in the present application, for preparing the compounds of the formula (I), for example according to process A. The compounds of the formula (VIII) are commercially available or can be prepared in a customary manner known to the person skilled in the art.

In the process E according to the invention, a compound of the formula (I) is prepared by reacting a compound of the formula (VII), which contains a substitutable group L', with a compound of the group (IX) in the presence of a palladium compound and, if appropriate, a reducing agent and further additives, in basic medium. Formally, the reaction is a reductive coupling of the compounds of the formulae (VII) and (IX), as described, for example, by J. F. Hartwig, Angew. Chem. 1998, 10, 2154.

Suitable for use as substitutable group L', in the compounds of the formula (VII) is, for example, a halogen radical, such as Br or I, or a customary leaving group, such as, for example, a triflate radical.

Suitable for use as palladium compound is a palladium(II) compound, such as, for example, $Cl_2Pd(PPh_3)_2$ $Pd_2(dba)_3$ (dba=dibenzylideneacetone) or $Pd(OAc)_2$, or a palladium(0) compound, such as, for example, $Pd(PPh_3)_4$. If required, a reducing agent such as, for example, triphenylphosphine or tributylphosphine, or other additives such as, for example, Cu(I)I, may be additionally added to the reaction mixture.

The reaction is carried out in the presence of a customary base such as, for example, $Na_2CO_3$, NaOH, NaOt-Bu or triethylamine. Suitable solvents are the organic solvents mentioned above under process C, with particular preference being given to ethers, such as, for example, dimethoxyethane. In general, the reaction can be carried out in a temperature range of from −20° C. to +90° C., preferably from 0° C. to +90° C. The reaction can be carried out at atmospheric pressure, elevated or reduced pressure (for example in a range of from 0.5 to 5 bar). In general, the reaction is carried out at atmospheric pressure.

The compounds of the formula (VII) used as starting materials can be prepared by one of the routes, described in the present application, for preparing the compounds of the formula (I), for example according to process A. The compounds of the formula (IX) are commercially available or can be prepared in a customary manner known to the person skilled in the art.

In the process F according to the invention, initially a compound of the formula (IV) is reacted analogously to process B with a compound of the formula (X). The compound of the formula (X) has two leaving groups E and E' which, independently of one another, may represent, for example, halogen, for example Cl, Br, I, tosylate, mesylate or a hydroxyl function activated by reagents such as diisopropyl azodicarboxylate/PPh$_3$ (Mitsonobu reaction), or radicals containing such groups, such as, for example, halogenoalkyl radicals, such as chloromethyl. However, the leaving groups E and E' have to be selected such that they can react selectively and independently of one another. However, it is also possible to use, in the reaction with the compound of the formula (IV), an excess of the compound of the formula (X). In this case, the leaving groups E and E' can also be identical.

The resulting compound of the formula (XI) is then reacted with an amine of the formula (XII) in the presence of a base. The reaction is carried out in the presence of a customary base such as, for example, Na$_2$CO$_3$, K$_2$CO$_3$, NaOH, NaOt-Bu or triethyl-amine. Suitable solvents are the organic solvents mentioned above under process C, with acetonitrile being particularly preferred. The reaction can generally be carried out in a temperature range of from −20° C. to +90° C., preferably from 0° C. to +90° C. The reaction can be carried out at atmospheric pressure, elevated or reduced pressure (for example in a range of from 0.5 to 5 bar). In general, the reaction is carried out at atmospheric pressure. If appropriate, a catalytic amount of potassium iodide may be added to the reaction solution.

The compounds of the formula (X) and (XI) are commercially available or can be prepared in a customary manner known to the person skilled in the art.

In the processes G and H according to the invention, in each case an alcohol (XIII) or (XVI) is reacted with a compound having a customary leaving group (XIV) or (XV), according to a nucleophilic substitution reaction.

Suitable leaving groups E" and E''' in the compounds of the formulae (XIV) and (XV) are: halogen, for example Cl, Br, I, tosylate, mesylate, or a hydroxyl function activated by reagents such as diisopropyl azodicarboxylate/PPh$_3$ (Mitsonobu reaction).

Suitable bases are, for example, sodium carbonate, Et$_3$N, DABCO, K$_2$CO$_3$, Cs$_2$CO$_3$, KOH, NaOH, NaH or silver oxide/molecular sieve. In general, the reaction can be carried out in a temperature range of from −20° C. to +90° C., preferably from 0° C. to +90° C. The reaction can be carried out at atmospheric pressure, elevated or reduced pressure (for example in a range of from 0.5 to 5 bar). In general, the reaction is carried out at atmospheric pressure. Suitable solvents are the organic solvents mentioned above under process C, with benzene being particularly preferred.

The compounds of the formulae (XIII) to (XVI) used as starting materials can be prepared by one of the processes I to IV, where they are described as intermediates. Furthermore, the compound XV can be prepared, for example, by bromination using PBr$_3$ or CBr$_4$/PPh$_3$ from a compound of the formula XIII.

In the processes I and J according to the invention, an amine of the formula (XVIII) or (XIX) is reacted with a carbonyl compound of the formula (XVII) or (XX). This can take place either with formation of a Schiff's base and subsequent reduction of the same or directly under conditions of a reductive alkylation.

In the first variant, the reactants are reacted with one another under customary conditions (cf. J. March, Advanced organic Chemistry, Wiley, 3$^{rd}$ ed., p. 796 f.). The resulting Schiff's base is then reduced with a reducing agent to give the desired amino compound. Suitable for use as reducing agents are the reducing agents customarily used for this purpose, such as, for example, NaBR$_4$, H$_2$/Pd/C, NaBH(OAc)$_3$ or NaCNBH$_3$.

In the second variant, the reactants are reacted with each other under customary conditions (cf. J. March, Advanced organic Chemistry, Wiley, 3$^{rd}$ ed., p. 798 f.) in the presence of a reducing agent. Suitable for use as reducing agents are the reducing agents which are customarily used for this purpose, such as, for example, H$_2$/Pd/C, NaCNBH$_3$ or NaBH(OAc)$_3$.

The compounds of the formula (XVII) used as starting materials can be prepared according to one of the processes III or IV. The compounds of the formula (XVIII) or (XX) used as starting materials can be prepared, for example, from one of the intermediates obtained in process I or II, by customary processes. Thus, the amines (XVIII) are obtainable, for example, in a known manner by reacting the corresponding halides or tosylates with phthalimide (Gabriel synthesis), and the aldehydes (XX) by oxidation of the corresponding alcohols. The compounds of the formula (XIX) used as starting materials can be prepared from one of the intermediates obtained in process III or IV, for example by reacting a tosylate obtained from a corresponding alcohol with benzylamine and subsequent hydrogenolytic removal of the benzyl group, or by reacting the compound of the formula (XVII) with benzylamine according to process [J] and subsequent hydrogenolytic removal of the benzyl group.

The compounds of the formula (I) according to the invention in which U represents O, NH, S, SO or SO$_2$ can be prepared by the process [K] according to the invention. Here, aldehydes of the formula (XXI)

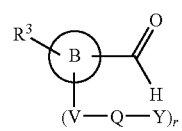

(XXI)

in which
R$^3$, V, Q, Y, r and B have the meanings given above,
are reacted with phosphorus compounds of the formula (XXII)

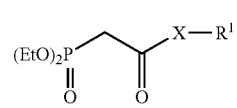

(XXII)

in which
X and R$^1$ have the meanings given above,
to give compounds of the formula (XXIII)

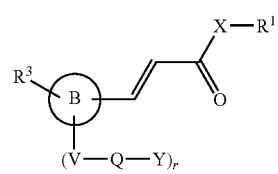

(XXIII)

in which
R$^3$, V, Q, Y, r, B, X and R$^1$ have the meanings given above, and subsequently, by successive reduction of the alkene group and the carbonyl group and subsequent substitution of the hydroxyl group generated by reduction of the carbonyl group or by reaction of the halogen radical generated from the hydroxyl group using halogenating agents with alcohols, primary amines or thiols and, if appropriate, subsequent oxidation to the corresponding sulfoxide or sulfone compounds, converted into compounds of the formula (XXIV),

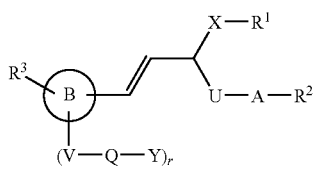

(XXIV)

in which $R^3$, V, Q, Y, r, B, X, U, A, $R^2$ and $R^1$ have the meanings given above.

The aldehydes of the formula (XXI) can be obtained, for example, from the alcohols used in processes I and II as intermediates, by customary oxidation reactions known to the person skilled in the art (cf., for example, J. March, Advanced organic Chemistry, $3^{rd}$ ed., p. 1057 ff., Wiley).

The phosphorus compounds of the formula (XXII) can be prepared, for example, by reacting alkanedicarboxylic acid derivatives, for example the corresponding monoesters, with phosphonoacetic acid derivatives, for example the corresponding diesters. However, it is also possible to synthesize these compounds from phosphites such as, for example, triethyl phosphite, using the corresponding ox-halogenoketone derivatives (Arbuzov reaction, cf., for example, J. March, Advanced organic Chemistry, $3^{rd}$ ed., p. 848 ff., Wiley).

The reaction of the compounds of the formula (XXI) with compounds of the formula (XXII) is carried out in the presence of bases such as alkali metal hydrides, for example sodium hydride, alkali metal alkoxides, for example potassium t-butoxide, or in the presence of salts such as, for example, $MgCl_2$, and bases, such as amines, for example triethylamine, or Hünig base. The reaction is preferably carried out in organic solvents, particularly preferably in tetrahydrofuran, at room temperature or with gentle heating.

The resulting carbonyl compounds of the formula (XXIII) are reduced according to customary processes known to the person skilled in the art to the corresponding alcohols (cf., for example, J. March, Advanced organic Chemistry. $3^{rd}$ ed., p. 809 ff., Wiley). The use of complex metal hydrides such as diisobutyl, aluminum hydride (DIBAL), $NaBH_4$ or $NaBH_4$/$CeCl.7 H_2O$ is particularly preferred. The reaction is preferably carried out in organic solvents such as, for example, alcohols, such as methanol, with cooling.

The olefinic double bond of the resulting hydroxyl compounds can be hydrogenated by customary processes known to the person skilled in the art (cf., for example, J. March, Advanced organic Chemistry, $3^{rd}$ ed., p. 691 ff., Wiley). Preference is given to hydrogenation with hydrogen in the presence of a metal catalyst such as Pd/C or Raney nickel in an organic solvent such as, for example, ethyl acetate.

The radical U-A-$R^2$ can be introduced by several routes. It is possible, for example, to react the hydroxyl compound under Mitsunobu conditions (cf., O. Mitsunobu, Synthesis, 1981, 1-28) with corresponding alcohols, phenols, primary amines or thiols. However, it is also possible to initially convert the hydroxyl group into a leaving group which can then be substituted by corresponding alcohols, phenols, primary amines or thiols in the presence of a base such as, for example, DABCO, triethylamine, NaH, NaOH, KOH, LDA, sodium amide or, particularly preferably, potassium carbonate. Leaving groups which are preferred according to the invention are halogen radicals, such as Cl, Br or I, which can be introduced by reacting the hydroxyl compound with, for example, $SOCl_2$, $SOBr_2$, $POCl_3$, $PCl_3$, $PCl_5$, $PBr_3$, etc., the tosylate radical, which can be introduced, for example, by reaction with tosyl chloride, the mesylate radical, which can be introduced, for example, by reaction with MsCl, or the triflate radical which can be introduced by reaction with, for example, $Tf_2O$ or TfCl.

The compounds according to the invention, in particular the compounds of the general formula (I), have an unforeseeable useful pharmacological activity spectrum.

The compounds according to the invention, in particular the compounds of the general formula (I), effect a relaxation of the vessels, inhibit platelet aggregation and lower the blood pressure, and also increase coronary blood flow. These effects are mediated via direct stimulation of soluble guanylate cyclase and intracellular cGMP increase.

They can therefore be employed in medicaments for the treatment of cardiovascular disorders, such as, for example, for the treatment of hypertension and cardiac insufficiency, stable and unstable angina pectoris, peripheral and cardiac vascular disorders, arrhythmias, for the treatment of thromboembolic disorders and ischemias, such as myocardial infarct, stroke, transitory and ischemic attacks, peripheral circulatory disorders, prevention of restenoses such as after thrombolysis therapy, percutaneous transluminal angioplasty (PTA), percutaneous transluminal coronary angioplasty (PTCA), bypass and also for the treatment of arteriosclerosis, fibrotic disorders, such as hepatic fibrosis or pulmonary fibrosis, asthmatic disorders and disorders of the urogenital system, such as, for example, prostate hypertrophy, erectile dysfunction, female sexual dysfunction and incontinence, and also for the treatment of glaucoma.

The compounds described in the present invention, in particular the compounds of the general formula (I), are also active compounds for controlling disorders in the central nervous system which are characterized by disturbances of the NO/cGMP system. In particular, they are suitable for eliminating cognitive deficits, for improving learning and memory performance and for treating Alzheimer's disease. They are also suitable for the treatment of disorders of the central nervous system, such as states of anxiety, tension and depression, sleeping disorders and sexual dysfunction caused by the central nervous system, and for regulating pathological eating disorders or disorders associated with the use of stimulants and drugs.

Furthermore, the active compounds are also suitable for regulating cerebral circulation, and they are therefore effective agents for controlling migraine.

They are also suitable for the prophylaxis and control of sequelae of cerebral infarcts (Apoplexia cerebri) such as stroke, cerebral ischemias and skull-brain trauma. The compounds according to the invention, in particular the compounds of the general formula (I), can also be employed for controlling pain.

Additionally, the compounds according to the invention have antiinflammatory action and can therefore be employed as antiinflammatories.

Vasorelaxant Action In Vitro

Rabbits are anesthetized by intravenous injection of thiopental sodium or killed (about 50 mg/kg) and exsanguinated.

The arteria saphena is removed and divided into 3 mm wide rings. The rings are individually mounted on in each case one triangular pair of hooks, open at the end, made of 0.3 mm strong special wire (Remanium®). Under a pretension, each ring is transferred into 5 ml organ baths containing a warm, carbogen-aerated Krebs-Henseleit solution at 37° C. having the following composition (mM): NaCl: 119; KCl: 4.8; $CaCl_2 \times 2\ H_2O$: 1; $MgSO_4 \times 7\ H_2O$: 1.4; $KH_2PO_4$: 1.2; $NaHCO_3$: 25; glucose: 10; bovine serum albumin: 0.001%. The contractility is detected using Statham UC2 cells, amplified and digitalized by means of A/D converters (DAS-1802 HC, Keithley Instruments Munich), and recorded in parallel on linear recorders. Contractions are induced by addition of phenylephrine.

After several (in general 4) control cycles, the substance to be investigated is added in each further passage in increasing dosage, and the height of the contraction achieved under the influence of the test substance is compared with the height of the contraction achieved in the last preliminary passage. From this, the concentration which is necessary in order to reduce the contraction achieved in the preliminary control to 50% ($IC_{50}$) is calculated. The standard administration volume is 5 μl. The proportion of DMSO in the bath solution corresponds to 0.1%.

The results are shown in Table 1:

TABLE 1

| vasorelaxant action in vitro | |
|---|---|
| Example | $IC_{50}$ (nM) |
| 26 | 1.9 |
| 29 | 2.5 |
| 30 | 3500 |
| 34 | 170 |
| 72 | 0.2 |
| 76 | 5.2 |
| 78 | 5.8 |
| 81 | 3.9 |
| 93 | 0.2 |
| 116 | 190 |
| 132 | 220 |
| 150 | 30 |
| 164 | 580 |

Stimulation of Recombinant Soluble Guanylate Cyclase (sGC) In Vitro

The investigations on the stimulation of recombinant soluble guanylate cyclase (sGC) and the compounds according to the invention with and without sodium nitroprusside and with and without the heme-dependent sGC inhibitor 1H-1,2,4-oxadiazole-(4,3a)-quinoxalin-1-one (ODQ) were carried out by the method described in detail in the following literature reference: M. Hoenicka, E. M. Becker, H. Apeler, T. Sirichoke, H. Schroeder, R. Gerzer and J.-P. Stasch: Purified soluble guanylyl cyclase expressed in a baculovirus/Sf9 system: stimulation by YC-1, nitric oxide, and carbon oxide. J. Mol. Med. 77 (1999): 14-23.

Heme-free guanylate cyclase was obtained by adding Tween 20 to the sample buffer (final concentration 0.5%).

Activation of sGC by a test substance is stated as n-fold stimulation of basal activity.

The results are shown in Table 2.

TABLE 2

| | Stimulation of recombinant soluble guanylate cyclase (sGC) in vitro | | | | |
|---|---|---|---|---|---|
| | Stimulation (n-fold) | | | | |
| Ex. 93 | Heme-containing sGC | | | Heme-free sGC | |
| concentration (μM) | Basal | +SNP (0.1 μM) | +ODQ (10 μM) | Basal | +ODQ (10 μM) |
| 0 | 1 | 15 | 1 | 1 | 1 |
| 0.1 | 17 | 45 | 84 | 436 | 392 |
| 1.0 | 23 | 44 | 151 | 476 | 435 |
| 10 | 33 | 54 | 178 | 541 | 500 |

It can be seen from Table 2 that stimulation both of the heme-containing and of the heme-free enzyme is achieved. Furthermore, a combination of sGC stimulator and sodium nitroprusside (SNP), an NO donor, does not show any synergistic effect, i.e. the effect of SNP is not potentiated, as would be expected for an sGC stimulator acting via a heme-dependent mechanism. In addition, the effect of the sGC stimulator according to the invention is not blocked by the heme-dependent inhibitor of soluble guanylate cyclase, ODQ. Thus, the results in Table 2 demonstrate the novel mechanism of action of the stimulators according to the invention of soluble guanylate cyclase.

The present invention includes pharmaceutical preparations which, in addition to non-toxic, inert, pharmaceutically acceptable excipients, contains the compounds according to the invention, in particular the compounds of the general formula (I), and also processes for the production of these preparations.

The active compounds can optionally be present in one or more of the excipients indicated above and also in microencapsulated form.

The therapeutically active compounds, in particular the compounds of the general formula (I), should be present in the abovementioned pharmaceutical preparations in a concentration of from approximately 0.1 to 99.5, preferably from approximately 0.5 to 95,% by weight of the total mix.

In addition to the compounds according to the invention, in particular the compounds of the general formula (I), the abovementioned pharmaceutical preparations can also contain other pharmaceutically active compounds.

In general, it has proved advantageous both in human and in veterinary medicine to administer the active compound(s) according to the invention in total amounts of from approximately 0.5 to approximately 500, preferably 5 to 100, mg/kg of bodyweight every 24 hours, if appropriate in the form of several individual doses, to achieve the desired results. An individual dose contains the active compound(s) according to the invention preferably in amounts from approximately 1 to approximately 80, in particular 3 to 30, mg/kg of bodyweight.

Below, the present invention is illustrated in more detail using non-limiting, preferred examples. Unless indicated otherwise, all amounts given refer to percent by weight.

EXAMPLES

Abbreviations:
RT: room temperature
EA: ethyl acetate
BABA: n-butyl acetate/n-butanol/glacial acetic acid/phosphate buffer pH 6 (50:9:25:15; org. phase)
Mobile Phases for Thin-Layer Chromatography:
T1 E1: toluene/ethyl acetate (1:1)
T1 EtOH1: toluene/methanol (1:1)

C1 E1: cyclohexane/ethyl acetate (1:1)
C1 E2: cyclohexanelethyl acetate (1:2)
Starting Materials
Preparation of the Phosphonium Compounds Ia: 2-(5-Phenylpentyloxy)nicotinic acid

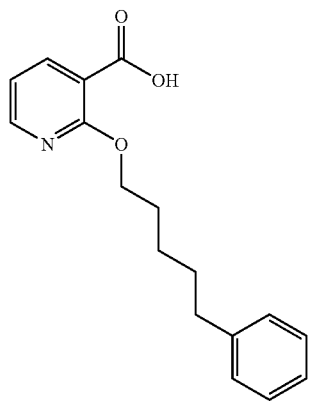

At 0° C., 1.00 g (6.35 mmol) of 2-chloronicotinic acid is slowly added to a suspension of 635 mg (15.9 mmol) of 60% sodium hydride in 25 ml of DMF, and the mixture is then stirred at 0° C. for 30 min. 1.15 g (6.98 mmol) of 5-phenyl-1-pentanol are dissolved in 5 ml of DMF and slowly added dropwise to the above reaction solution. The solution is stirred at room temperature for 3.5 hours. It is then heated at 75° C. and stirred overnight. The substance is taken up in water, ethyl acetate is then added and the aqueous phase is acidified using 1M HCl. The mixture is then extracted with ethyl acetate and the extract is washed with water, dried over magnesium sulfate and concentrated under reduced pressure.
The crude product is reacted further.

Ib: 2-(5-Benzyloxy)nicotinic acid

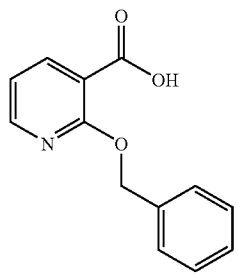

The preparation was carried out analogously to example Ia using 4.00 g (25.4 mmol) of benzyl alcohol as alcoholic component.

Yield: 5.02 g (86.4% of theory)

$^1$H-NMR (200 MHz, CDCl$_3$): 8.50 (m, 2H), 7.40 (m, 5H), 7.10 (m, 1H), 5.60 (s, 2H).

IIa) 2-(5-Phenylpentoxy)-3-pyridinylmethanol

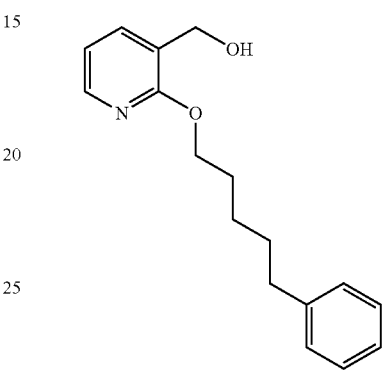

At 0° C., 500 mg (1.75 mmol) of the acid from Ex. Ia were dissolved in 20 ml of tetrahydrofuran (THF) under argon. 3.5 ml (3.5 mmol) of an LiAlH$_4$ solution (1M in THF) were then added slowly. The mixture was boiled at reflux for 3 hours. The solution was cooled to 0° C. and 1 ml of water, 1 ml of 1N aqueous sodium hydroxide solution and 3 ml of water were added slowly. At room temperature, another about 50 ml of water were added. The mixture was then extracted with ethyl acetate and the extract was washed with water, dried over magnesium sulfate and concentrated under reduced pressure.

Yield: 410 mg (86.4% of theory)

$^1$H-NMR (200 MHz, CDCl$_3$): 8.00 (m, 1H), 7.50 (m, 1H), 7.20 (m, 5H), 6.80 (m, 1H), 4.60 (s, 2H), 4.40 (t, 2H), 3.60 (t, 1H), 2.60 (m, 2H), 1.90-1.20 (m, 6H).

The following compound was prepared analogously:

| Ex. | Formula | Yield (%) | Spectroscopical data |
|---|---|---|---|
| IIb (from Ex. Ib) |  | 94.2 | $^1$H-NMR (200 MHz, CDCl$_3$): 8.00 (m, 1H), 7.60 (m, 1H), 7.20 (m, 5H), 6.90 (m, 1H), 5.50 (s, 2H), 4.70 (bs, 2H), 2.20 (bs, 1H) |

IIc: 3-(5-Phenylpentoxy)-2-pyridinylmethanol

IId) 2-Butyloxybenzyl alcohol

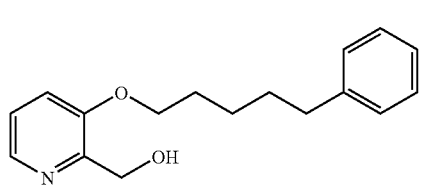

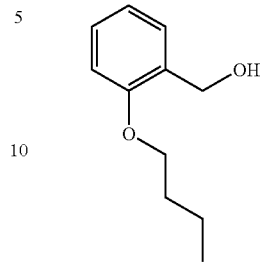

1.9 g (6.01 mmol) of phenylpentyl bromide, 1.00 g (8.00 mmol) of 2-hydroxymethyl-3-pyridinol and 1.2 g (8.8 mmol) of potassium carbonate are heated at reflux overnight. The mixture is taken up in ethyl acetate, washed with water, 2N aqueous sodium hydroxide solution and water, dried and concentrated under reduced pressure.

Yield: 853 mg (52.3% of theory)

$^1$H-NMR (200 MHz, CDCl$_3$): 8.10 (m, 1H), 7.40-7.10 (m, 7H), 4.80 (d, 2H), 4.40 (t, 1H), 4.00 (t, 2H), 2.60 (m, 2H), 1.90-1.20 (m, 6H)

12.4 g (90.5 mmol) of butyl bromide, 11.2 g (90.5 mmol) of 2-hydroxybenzyl alcohol and 12.5 g (90.5 mmol) of potassium carbonate in 270 ml of 2-propanol are heated at reflux overnight. The suspension is cooled, taken up in ethyl acetate and washed with 1N aqueous sodium hydroxide solution and water, dried over magnesium sulfate and concentrated under reduced pressure.

Yield: 12.8 g (78.3% of theory).

$R_f$(SiO$_2$, C4E1): 0.14

The following compounds were prepared analogously:

| Example | Formula | Yield (%) | $R_f$-value |
|---|---|---|---|
| IIe (from heptyl iodide) | | 96.3 | 0.57 (C1E1) |
| IIf (from 4-phenylbenzyl bromide) | | 90.8 | 0.53 (C1E1) |

-continued

| Example | Formula | Yield (%) | R_f value |
|---|---|---|---|
| IIg (from CH$_3$(CH$_2$)$_{15}$Br) | (2-hexadecyloxyphenyl)methanol | 88.9 | 0.56 (C1E1) |
| IIh (from octyl bromide) | (2-octyloxyphenyl)methanol | 82.9 | 0.63 (C1E1) |
| IIi (from hexyl bromide) | (2-hexyloxyphenyl)methanol | 74.5 | 0.69 (C1E1) |

IIIa: 3-(Bromomethyl)-2-(5-phenylpentoxy)pyridine

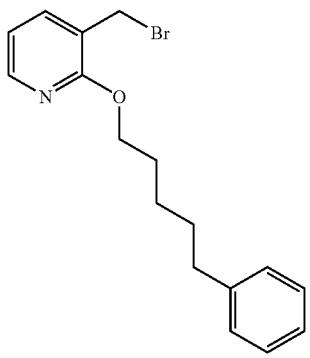

410 mg (1.51 mmol) of the alcohol from Ex. IIa are dissolved in toluene/dichloromethane 2:1. 820 mg (3.03 mmol) of phosphorus tribromide are then added and the mixture is stirred at room temperature for 1 hour. The substance is taken up in saturated $NaHCO_3$ solution and extracted with ethyl acetate, and the extract is washed with water, dried over magnesium sulfate, concentrated and purified by column chromatography.

Yield: 321 mg (63.8% of theory)

$^1$H-NMR (200 MHz, $CDCl_3$): 8.10 (m, 1H), 7.60 (m, 1H), 7.20 (m, 5H), 6.80 (m, 1H), 4.50 (s, 2H), 4.40 (t, 2H), 2.60 (m, 2H), 1.90-1.20 (m, 6H).

IIIb: 2-Benzyloxy-3-chloromethylpyridine

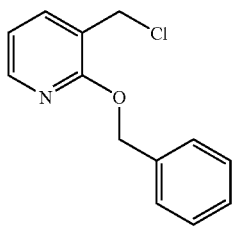

1.48 g (6.88 mmol) of the alcohol from Ex. IIb are dissolved in dichloromethane and treated with 5 ml (68.8 mmol) of thionyl chloride. The solution is stirred at room temperature for 2 h and the solvent is then evaporated under reduced pressure. The product precipitates out as hydrochloride. It is taken up in water and ethyl acetate, washed with aqueous sodium hydroxide solution, dried and concentrated under reduced pressure.

Yield: 769 mg (47.9% of theory)

$^1$H-NMR (400 MHz, $CDCl_3$): 8.00 (m, 1H), 7.60 (m, 1H), 7.20 (m, 5H), 6.80 (m, 1H), 5.40 (s, 2H), 4.60 (s, 2H).

The following compound was prepared analogously:

IVa: (2-(5-Phenylpentoxy)-3-pyridinyl)methyltriphenylphosphonium bromide

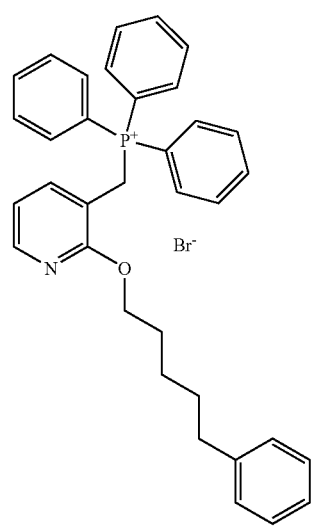

321 mg (0.96 mmol) of the bromide from Ex. IIIa and 264 mg (1.00 mmol) of triphenylphosphine in 20 ml of toluene are heated at reflux for 4 hours. The solvent is evaporated under reduced pressure and the residue is comminuted with ethyl ether, filtered and dried.

Yield: 322 mg (56.3% of theory)

$^1$H-NMR (400 MHz, $CDCl_3$): 7.80-7.10 (m, 21H), 6.80 (m, 2H), 5.45 (d, J=15 Hz, 2H), 3.70 (t, 2H), 2.60 (m, 2H), 1.60-1.30 (m, 6H).

The following compounds were prepared analogously:

| Ex. | Formula | Yield (%) | Spectroscopical data |
|---|---|---|---|
| IIIc (from IIc) | | 88.1 | $^1$H-NMR (400 MHz, $CDCl_3$): 8.20 (m, 1H), 7.70-7.20 (m, 7H), 4.70 (s, 2H), 4.10 (t, 2H), 2.60 (t, 2H), 1.90-1.50 (m, 6H) |

| Ex. | Formula | Yield (%) | Spectroscopical data |
|---|---|---|---|
| IVb (from IIIb) | | 86.6 | $^1$H-NMR (400 MHz, d$^6$-DMSO): 8.10 (m, 1H), 7.90-7.20 (m, 21H), 6.90 (m, 1H), 5.00 (d, J = 15Hz, 2H), 4.90 (s, 2H) |
| IVc (from IIIc) | | 48.9 | $^1$H-NMR (400 MHz, d$^6$-DMSO): 7.80-7.10 (m, 23H), 5.30 (d, J = 15Hz, 2H), 3.80 (m, 2H), 2.60 (m, 2H), 1.60-1.30 (m, 6H) |

IVd: 2-(butyloxy)benzyltriphenylphosphonium bromide

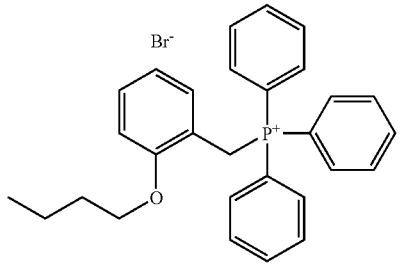

8.2 g (45.5 mmol) of the benzyl alcohol IId and 15.6 g (45.5 mmol) of triphenyl-phosphonium hydrobromide in 100 ml of acetonitrile are heated at reflux for 5 hours. The solvent is evaporated under reduced pressure, and diethyl ether is then added. The solid is filtered and dried under reduced pressure. The crude product is reacted further.

$^1$H-NMR (400 MHz, d$^6$-DMSO): 7.80-6.70 (m, 19H), 4.90 (d, J=15 Hz, 2H), 3.40 (t, 2H), 1.30 (m, 4H), 0.90 (t, 3H).

The following compounds were prepared analogously:

| Ex. | Formula | Yield (%) | Spectroscopical data |
|---|---|---|---|
| IVe (from IIe) | | 91.2 | $^1$H-NMR (200 MHz, d$^6$-DMSO): 7.80-6.70 (m, 19H), 4.90 (d, J = 15Hz, 2H), 3.40 (m, 2H), 1.30 (m, 10H), 0.90 (t, 3H) |

-continued

| Ex. | Formula | Yield (%) | Spectroscopical data |
|---|---|---|---|
| IVf (from IIf) | | 88.3 | $^1$H-NMR (200 MHz, d$^6$-DMSO): 7.80-6.70 (m, 28H), 5.00 (d, J = 15Hz, 2H), 4.70 (s, 2H) |
| IVg (from IIg) | | 69.1 | $^1$H-NMR (200 MHz, d$^6$-DMSO): 7.80-6.70 (m, 19H), 4.90 (d, J = 15Hz, 2H), 3.40 (m, 2H), 1.30 (bs, 28H), 0.90 (t, 3H) |
| IVh (from IIh) | | 95.2 | $^1$H-NMR (200 MHz, d$^6$-DMSO): 7.90-6.70 (m, 19H), 4.90 (d, J = 15Hz, 2H), 3.40 (m, 2H), 1.30 (m, 12H), 0.90 (t, 3H) |
| IVi (from IIi) | | 97.6 | $^1$H-NMR (200 MHz, d$^6$-DMSO): 7.90-6.70 (m, 19H), 4.90 (d, J = 15Hz, 2H), 3.40 (m, 2H), 1.30 (m, 8H), 0.90 (t, 3H) |
| IVj (from 2-methoxy-benzyl alcohol) | | 87.2 | $^1$H-NMR (200 MHz, CDCl$_3$): 7.80-7.20 (m, 17H), 6.80 (d, 1H), 6.60 (s, 1H), 5.20 (d, J = 15Hz, 2H), 3.20 (s, 3H) |

-continued

| Ex. | Formula | Yield (%) | Spectroscopical data |
|---|---|---|---|
| IVk (from 2-allyloxy-benzyl alcohol) | | 85.7 | $^1$H-NMR (200 MHz, CDCl$_3$): 7.80-7.20 (m, 17H), 6.80 (t, 1H), 6.60 (d, 1H), 5.60 (m, 1H), 5.20 (d, J = 15Hz, 2H), 5.10 (m, 2H), 3.90 (m, 2H) |
| IVl (from 2,5-dimethoxy-benzyl alcohol) | | 77.6 | $^1$H-NMR (200 MHz, CDCl$_3$): 7.80-7.50 (m, 15H), 7.00 (m, 1H), 6.80 (m, 1H), 6.50 (d, 1H), 6.20 (d, J = 15Hz, 2H), 3.60 (s, 3H), 3.10 (s, 3H) |
| IVm (from 2,3-dimethoxy-benzyl alcohol) | | crude | $^1$H-NMR (200 MHz, CDCl$_3$): 7.90-7.50 (m, 15H), 7.00 (m, 1H), 6.85 (t, 1H), 6.40 (m, 1H), 5.00 (d, J = 15Hz, 2H), 3.70 (s, 3H), 3.40 (s, 3H) |
| IVn (from 2-phenoxy-benzyl alcohol) | | 99.8 | $^1$H-NMR (200 MHz, CDCl$_3$): 7.80-7.00 (m, 20H), 6.90 (t, 1H), 6.50 (t, 3H), 5.00 (d, J = 15Hz, 2H) |
| IVo (from 2-(5-phenyl-pentyl-sulfanyl-benzyl alcohol) | | 98.7 | $^1$H-NMR (200 MHz, d$^6$-DMSO): 7.80-6.70 (m, 24H), 5.60 (d, J = 15Hz, 2H), 2.60 (m, 4H), 1.60-1.30 (m, 6H) |

| Ex. | Formula | Yield (%) | Spectroscopical data |
|---|---|---|---|
| IVp (from 2-benzyl-sulfanyl-benzyl alcohol) | 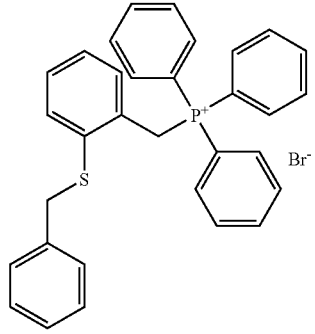 | 90.9 | $^1$H-NMR (200 MHz, d$^6$-DMSO): 8.00-7.00 (m, 24H), 5.00 (d, J = 15Hz, 2H), 3.90 (s, 2H) |
| IVq (from 2-benzyl-amino-benzyl alcohol) | 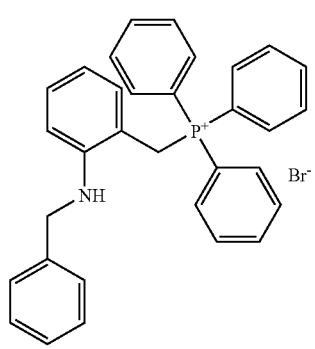 | 100 | $^1$H-NMR (200 MHz, d$^6$-DMSO): 7.80-6.30 (m, 24H), 6.05 (m, 1H), 5.00 (d, J = 15Hz, 2H), 3.90 (d, 2H) |
| IVr (from 4-bromo-benzyl bromide and 2-hydroxy-benzyl alcohol) | 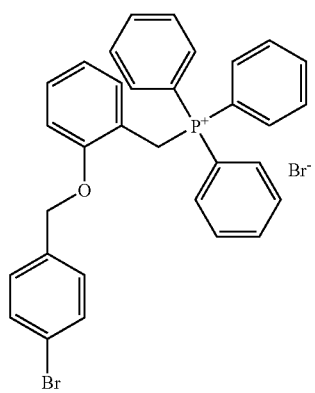 | | |

V: Methyl 4-{[2-oxodihydro-3(2H)-furanylidene]methyl}benzoate

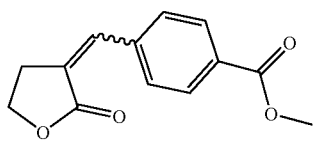

A mixture of 40.00 g (0.12 mol) of 3-(triphenylphosphoranylidene)dihydro-2(3H)-furanone and 20.85 g (0.13 mol) of methyl 4-formylbenzoate in 240 ml of dimethyl sulfoxide is stirred at 80° C. for 18 hours. After cooling, 400 ml of chloroform are added, and the mixture is extracted five times with 200 ml of water. The organic phase is dried over magnesium sulfate and the solvent is distilled off under reduced pressure. The residue is stirred with diethyl ether and dried under reduced pressure at 40° C.

Yield: 17.82 g (66.4% of theory)

$^1$H-NMR (300 MHz, d$^6$-DMSO): δ=3.30 (m, 2H), 3.990 (s, 3H), 4.45 (t, 2H), 7.25 (d, 2H), 8.03 (d, 2H).

VI: Methyl 4-[(2-oxotetrahydro-3-furanyl)methyl]benzoate

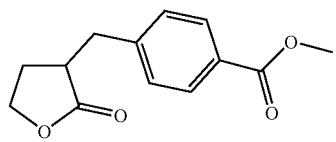

20.00 g (0.09 mol) of methyl 4-([2-oxodihydro-3(2H)-furanylidene]methyl)benzoate from Ex. V are suspended in 240 ml of glacial acetic acid, 2.00 g of 10% palladium-carbon are added and the mixture is hydrogenated at atmospheric pressure for 4 hours. The reaction mixture is filtered through kieselguhr and the solvent is distilled off under reduced pressure.

Yield: 19.00 g (92.4% of theory)

$^1$H-NMR (300 MHz, d$^6$-DMSO): δ=1.9 (m, 1H) 2.15 (m, 1H), 2.8 (m, 1H), 3.0 (m, 1H), 3.1 (m, 1H), 3.85 (s, 3H), 4.1 (m, 1H), 4.2 (m, 1H), 7.25 (d, 2H), 8.03 (d, 2H).

VII: 4-Bromo-2-[4-(methoxycarbonyl)benzyl]butanoic acid

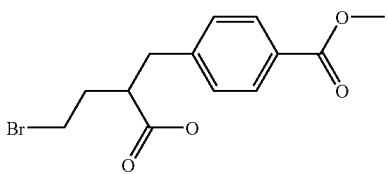

9.00 g (38.42 mmol) of methyl 4-[(2-oxotetrahydro-3-furanyl)methyl]benzoate from Ex. VI are suspended in 54 ml of a 33 percent strength HBr solution in glacial acetic acid, and the mixture is stirred at 80° C. for 40 min. The reaction solution is poured into ice-water and the resulting precipitate is filtered off with suction, washed with water and dried under reduced pressure at 40° C.

Yield: 11.01 g (90.9% of theory).

$^1$H-NMR (300 MHz, d$^6$-DMSO): δ=1.90 (m, 1H), 2.10 (m, 1H), 2.70 (m, 1H), 2.90 (m, 2H), 3.53 (m, 2H), 3.83 (s, 3H), 7.35 (d, 2H), 7.92 (d, 2H).

VIII: Methyl 4-(4-bromo-2-formylbutyl)benzoate

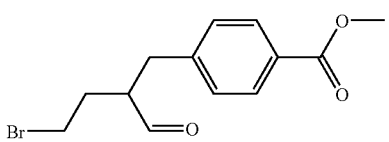

At 0° C., 10.7 g (33.95 mmol) of 4-bromo-2-[4-(methoxycarbonyl)benzyl]butanoic acid from Ex. VII in 200 ml of THF are treated with 40.74 ml (40.74 mmol) of a 1M solution of borane in THF, and the mixture is stirred with warming to room temperature for 2 hours. Excess borane is destroyed by addition of water. The mixture is extracted with ether and the organic phase is then dried over magnesium sulfate and the solvent is distilled off under reduced pressure. 10.23 g (33.92 mmol) of the highly unstable methyl 4-[4-bromo-2-(hydroxymethyl)butyl]benzoate remain, and this residue is immediately dissolved in 100 ml of methylene chloride and added dropwise to a suspension of 10.98 g (50.92 mmol) of pyridinium chlorochromate in 200 ml of methylene chloride. After 3.5 hours, the solution is filtered through silica gel which is washed thoroughly with ether, and the solvent is distilled off. The crude product is purified by flash chromatography on silica gel (0.04-0.063 nm) using methylene chloride/methanol 3/1 as mobile phase.

Yield: 7.08 g (69.7% of theory)

$^1$H-NMR (300 MHz, d$^6$-DMSO): δ=1.85 (m, 1H), 2.15 (m, 1H), 2.85 (m, 2H), 3.10 (m, 1H), 3.53 (m, 2H), 3.85 (s, 3H)7.38 (d, 2H), 7.90 (d, 2H), 9.70 (s, 1H).

IX: Methyl 4-((E/Z)-2-(2-bromoethyl)-4-{2-[(5-phenylpentyl)oxy]phenyl}-3-butenyl)benzoate

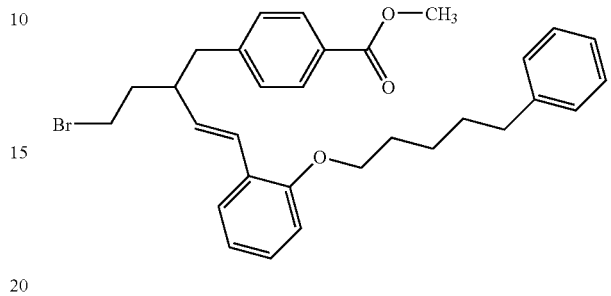

5.97 g (10.03 mmol) of triphenyl{2-[(5-phenylpentyl)oxy]benzyl}phosphonium bromide (preparable analogously to Exs IId to IVd using 5-phenylpentyl bromide instead of butyl bromide) are suspended in 80 ml of THF and, at 0° C., treated with 7.52 ml of a 1.6M solution of n-butyllithium. The mixture is stirred for 30 minutes and then cooled to −20° C., and 3.00 g (10.03 mmol) of methyl 4-(4-bromo-2-formyl-butyl)benzoate from Ex. VIII, dissolved in 20 ml of THF, are then added. After a further 30 min at −20° C., water is added and the mixture is extracted with ethyl acetate. The organic phase is washed with saturated sodium chloride solution and dried over magnesium sulfate, and the solvent is distilled off under reduced pressure. The crude product is purified by flash chromatography on silica gel (0.04-0.063 nm) using cyclohexane/methylene chloride 1/1 as mobile phase.

Yield: 2.53 g (46.5% of theory) of the E/Z isomer mixture in a ratio of 15:85

$^1$H-NMR (300 MHz, d$^6$-DMSO): δ=1.40 (m, 1H), 1.65 (m, 4H9, 1.95 (m, 2H), 2.55 (t, 2H), 2.85 (m, 2H), 3.45 (m, 2H), 3.80 (s, 3H), 3.90 (t, 2H), 6.00 (m, 1H), 6.45 (m, 1H), 6.90 (m, 2H), 7.1-7.4 (m, 10H), 7.85 (d, 2H).

X: Methyl 4-((E/Z)-2-(2-iodoethyl)-4-{2-[(5-phenylphentyl)oxy]phenyl}-3-butenyl)benzoate

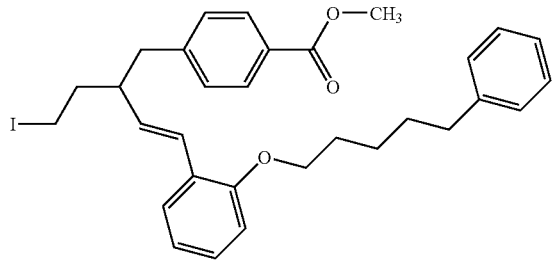

500.0 mg (0.930 mmol) of methyl 4-((E/Z)-2-(2-bromoethyl)-4-{2-[(5-phenyl-phenyl)oxy]phenyl}-3-butenyl)benzoate from Ex. IX and 153.95 mg (1.03 mmol) of sodium iodide in 2 ml of acetone are heated at reflux for 18 hours. The solid is filtered off and the filtrate is admixed with water and extracted with methylene chloride. The organic phase is washed with saturated sodium chloride solution and dried over magnesium sulfate, and the solvent is distilled off under reduced pressure.

Yield: 550.3 mg (97% of theory)

XI: Methyl 4-{4-[(2-ethoxy-2-oxoethyl)(methyl)amino]-2-formylbutyl}benzoate

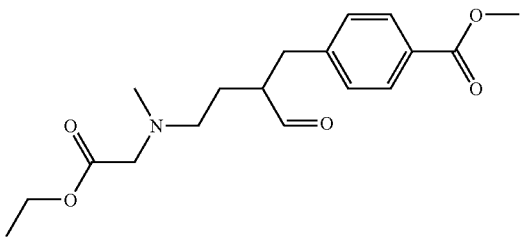

0.500 g (1.67 mmol) of methyl-4-(4-bromo-2-formylbutyl)benzoate from Ex. VIII, 0.257 g (1.67 mmol) of ethyl sarcosinate hydrochloride and 0.309 g (3.68 mmol) of sodium bicarbonate in 10 ml of acetonitrile are heated at reflux for 1 hour. The reaction mixture is cooled, 50 ml of water are added and the mixture is extracted repeatedly with ethyl acetate. The combined organic phases are washed with saturated sodium chloride solution and dried over magnesium sulfate, and the solvent is distilled off under reduced pressure. The crude product is purified by chromatography on silica gel (0.04-0.063 nm) using methylene chloride/methanol 100:3 as mobile phase.

Yield: 0.479 g (85.4% of theory)

XII: Methyl 8-(2-hydroxyphenyl)-6-(4-methoxycarbonylphenoxy)-octanoate

XIIa: 2-{[tert-Butyl(dimethyl)silyl]oxy}benzaldehyde

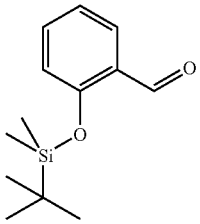

13.58 g (90.07 mmol) of t-butyidimethylsilyl chloride (TBDMSCl) were added to a solution of 10.00 g (81.89 mmol) of salicylaldehyde and 6.13 g (90.07 mmol) of imidazole in 82 ml of DMF. The mixture was stirred at room temperature and the reaction was monitored by thin-layer chromatography (cyclohexane/EA 10:1). 1 N NaOH was added, and the mixture was extracted with petroleum ether. The combined organic phases were dried over $Na_2SO_4$, the solvent was removed and the product was purified chromatographically (silica gel, cyclohexane/EA 10:1). This gave 16.94 g (87.5%) of a clear liquid.

$^1$H-NMR (300 MHz, $CDCl_3$): δ=0.18 (s, 6H), 0.92 (s, 9H), 6.78 (d, J=8.3 Hz, 1H), 6.93 (t, J=7.7 Hz, 1H), 7.36 (dt, J=8.1 Hz, J=1.9 Hz, 1H), 7.71 (dd, J=9.3 Hz, J=1.5 Hz, 1H), 10.37 (s, 1H).

XIIb: Methyl 7-(diethoxyphosphoryl)-6-oxoheptanoate

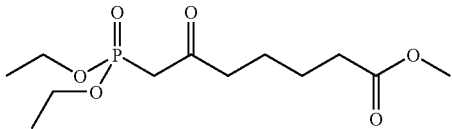

At 0° C., 30.34 g (299.79 mmol) of triethylamine and 12.21 g (112.42 mmol) of trimethylchlorosilane were added dropwise to a solution of 15.00 g (74.95 mmol) of diethyl phosphonoacetate in 400 ml of toluene. The mixture was stirred at room temperature for 1 h, and 7.14 g (74.95 mmol) of magnesium chloride were added. The mixture was stirred for one hour, and 16.56 g (89.94 mmol) of monomethyl adipoyl chloride were added dropwise. The mixture was stirred at room temperature for 24 h. Water was added. The mixture was extracted with diethyl ether, the organic phases were dried over $Na_2SO_4$ and the solvent was removed. The product was purified chromatographically (silica gel, ethyl acetate). This gave 7.83 g (35.5%) of a clear liquid.

$^1$H NMR (300 MHz, $CDCl_3$): δ=1.34 (t, J=6.9 Hz, 6H), 1.59-1.66 (m, 4H), 2.25-2.40 (m, 2H), 2.59-2.70 (m, 2H), 3.07 (d, J=22.9 Hz, 2H), 3.66 (s, 3H), 4.14 (quint, J=7.2 Hz, 4H).

XIIc: Methyl(E)-8-(2-{[tert-butyl(dimethyl)silyl]oxy}phenyl)-6-oxo-7-octenoate

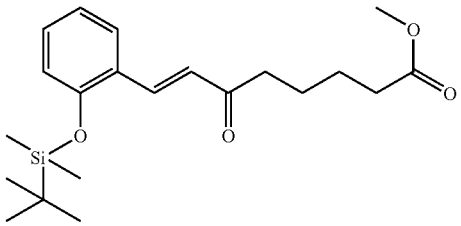

Under argon, 0.26 g (10.87 mmol) of sodium hydride was added to a solution of 3.20 g (10.87 mmol) of methyl 7-(diethoxyphosphoryl)-6-oxoheptanoate from Ex. XIIb in 53 ml of THF. The mixture was stirred at room temperature for 30 min, a solution of 9.06 mmol of 2-{[tert-butyl(dimethyl)silyl]oxy}benzaldehyde from Ex. XIIa in 20 ml of THF was added and the mixture was stirred at room temperature for 18 h. Water was added, the mixture was extracted with ethyl acetate, the combined organic phases were dried over $Na_2SO_4$ and the solvent was removed. The product was purified chromatographically (silica gel, cyclohexane/EA 10:1). This gave 2.51 g (67.8%) of a colorless liquid.

$^1$H-NMR (300 MHz, $CDCl_3$): δ=0.24 (s, 6H), 1.05 (s, 9H), 1.62-1.77 (m, 4H), 2.29-2.41 (m, 2H), 2.62-2.73 (m, 2H), 3.66 (s, 3H), 6.67 (d, J=16.6 Hz, 1H), 6.84 ($m_c$=1H), 6.96 (t, J=7.6 Hz, 1H), 7.20-7.30 (m, 1H), 7.56 (d, J=7.7 Hz, 1H), 7.96 (d, J=16.6 Hz, 1H).

XIId: Methyl (E)-8-(2-{[tert-butyl(dimethyl)silyl]oxy}phenyl)-6-hydroxy-7-octenoate

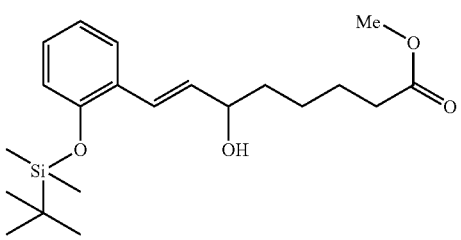

At 0° C., 0.146 g (3.86 mmol) of sodium borohydride was added to a solution of 1.436 g (3.86 mmol) of $CeCl_3.7H_2O$ and 3.67 mmol of methyl (E)-8-(2-{[tert-butyl(dimethyl)silyl]oxy}phenyl)-6-oxo-7-octenoate from Ex. XIIc in 30 ml of methanol. The mixture was stirred at 0° C. and the progress of the reaction was monitored by thin-layer chromatography. Saturated NH$_4$Cl solution was added, the mixture was extracted with ethyl acetate and the combined organic phases were dried over Na$_2$SO$_4$. The product was purified chromatographically (silica gel, cyclohexane/EA 10:2). This gave 1.38 g (91.5%) of a colorless liquid.

$^1$H NMR (400 MHz, CDCl$_3$): δ=0.01 (s, 6H), 0.80 (s, 9H), 1.13-1.54 (m, 7H), 2.11 (t J=7.3 Hz, 2H), 3.44 (s, 3H), 3.99-4.11 (m, 1H), 5.93 (dd, J=15.9 Hz, J=6.9 Hz, 1H), 6.57 (dd, J=8.0 Hz, J=1.0 Hz, 1H), 6.63-6.73 (m, 2H), 6.90 (dt, J=8.0 Hz, J=1.7 Hz, 1H), 7.23 (dd, J=7.8 Hz, J=1.7 Hz, 1H).

XIIe: Methyl 8-(2-{[tert-butyl(dimethyl)silyl]oxy}phenyl)-6-hydroxyoctanoate

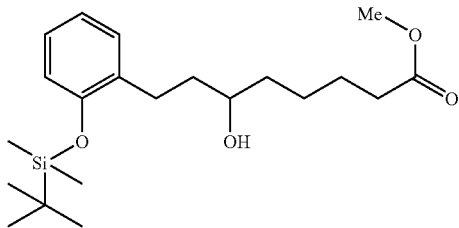

30 mg of palladium-on-carbon (10%) were added to a solution of 4.38 mmol of the compound from Ex. XIId in 22.5 ml of ethyl acetate. The mixture was stirred under an atmosphere of hydrogen until no more absorption could be observed and filtered through Celite, and the solvent was removed.

Yield: 82.2%

$^1$H NMR (300 MHz, CDCl$_3$): δ=0.25 (s, 3H), 0.26 (s, 3H), 1.03 (s, 9H), 1.20-1.84 (m, 9H), 2.26-2.38 (m, 2H), 2.66-2.78 (m, 2H), 3.49-3.62 (m, 1H), 3.67 (s, 3H), 6.75-6.84 (m, 1H), 6.85-6.94 (m, 1H), 7.02-7.19 (m, 2H).

XIIf: Methyl 8-(2-{[tert-butyl(dimethyl)silyl]oxy}phenyl)-6-(4-methoxycarboyl-phenoxy)-octanoate

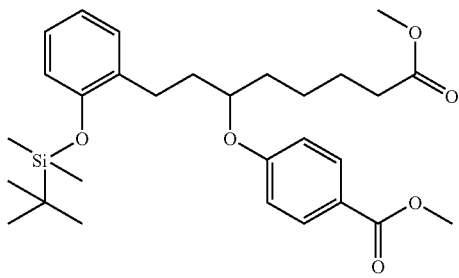

Over a period of 2 h, a solution of 0.24 mmol of the compound from Ex. XIIe and 63.32 mg (0.36 mmol) of DEAD in 2.5 ml of THF was added dropwise to a solution of 55.32 mg (0.36 mmol) of methyl 4-hydroxybenzoate and 95.36 mg (0.36 mmol) of triphenylphosphine in 2.5 ml of THF. The mixture was stirred at room temperature for 18 h, 40 ml of diethyl ether were added, the mixture was filtered and the solvent was removed. The product was purified chromatographically (silica gel, cyclohexane/EA 10:1).

Yield: 64.3%

$^1$H NMR (400 MHz, CDCl$_3$): δ=0.20 (s, 3H), 0.21 (s, 3H), 0.98 (s, 9H), 1.31-1.77 (m, 6H), 1.84-2.07 (m, 2H), 2.28 (t, J=7.3 Hz, 2H), 2.54-2.68 (m, 1H), 2.70-2.81 (m, 1H), 3.64 (s, 3H), 3.87 (s, 3H), 4.25-4.38 (m, 1H), 6.74-6.88 (m, 4H), 7.01-7.10 (m, 2H), 7.93 (d, J=8.8 Hz, 2H).

XII: Methyl 8-(2-hydroxphenyl)-6-(4-methoxycarbonylphenoxy)-octanoate

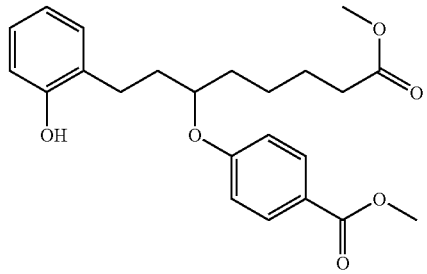

A solution of 1.30 g (2.53 mmol) of the compound from Ex. XIIf was treated with 2.78 ml (2.78 mmol) of tetrabutylammonium fluoride (TBAF) (1 M in THF). The mixture was stirred at room temperature and the progress of the reaction was monitored by TLC (silica gel, cyclohexane/EA 10:1, KMnO$_4$). After the reaction had ended, water was added, the mixture was extracted with diethyl ether, the combined organic phases were dried over Na$_2$SO$_4$ and the solvent was removed. The product was purified chromatographically, giving 0.85 g (84.24%) of a clear liquid.

$^1$H NMR (400 MHz, CDCl$_3$): δ=1.32-1.78 (m, 6H), 1.90-2.04 (m, 2H), 2.30 (t, J=6.6 Hz, 2H), 2.60-2.72 (m, 1H), 2.72-2.83 (m, 1H), 3.65 (s, 3H), 3.87 (s, 3H), 4.33 (quint, J=5.9 Hz, 1H), 5.31 (bs, 1H), 6.71-6.88 (m, 4H), 7.01-7.14 (m, 2H), 7.93 (d, J=9.0 Hz, 2H).

XIII: Methyl (7E)-8-{2-[(4-cyclohexylbenzyl)oxy]phenyl}-6-oxo-7-octenoate

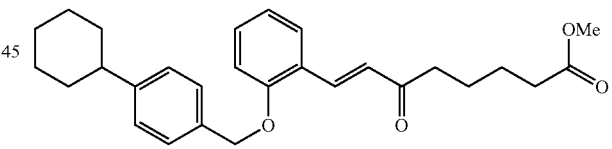

Under argon, a solution of 3.00 g (10.19 mmol) of methyl 7-(diethoxyphosphoryl)-6-oxo-heptanoate XIIb in 10 ml of THF was added dropwise to a suspension of 0.25 g (10.19 mmol) of sodium hydride in 20 ml of THF. After 30 min, a solution of 2.50 g (8.49 mmol) of 2-[(4-cyclohexylbenzyl)oxy]benzaldehyde (obtainable from salicylaldehyde and 4-cyclohexylbenzyl chloride in 10 ml of THF was added dropwise. The mixture was stirred at room temperature for 2 days. Water was added, the mixture was extracted with ethyl acetate and the combined organic phases were dried over Na$_2$SO$_4$. The product was purified chromatographically (silica gel, cyclo-hexane/ethyl acetate 10:1).

Yield: 2.82 g (76.41%).

$^1$H NMR (200 MHz, CDCl$_3$): δ=1.10-1.98 (m, 14H), 2.23-2.74 (m, 5H), 3.66 (s, 3H), 5.12 (s, 2H), 6.80 (d, J=16.4 Hz, 1H), 6.88-7.08 (m, 2H), 7.15-7.43 (m, 5H), 7.47-7.63 (m, 1H), 7.95 (d, J=16.4 Hz, 1H).

XIV: Methyl 8-{2-[(4-cyclohexylbenzyl)oxy]phenyl}-6-oxooctanoate

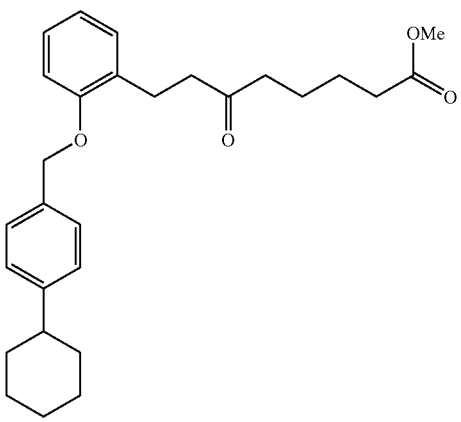

XV: Methyl (7E)-8-{2-[(4-cyclohexylbenzyl)oxy]phenyl}-6-hydroxy-7-octenoate

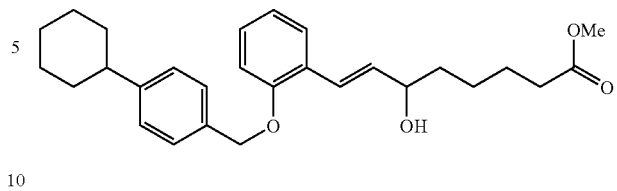

Methyl (7E)-8-{2-[(4-cyclohexylbenzyl)oxy]phenyl}-6-oxo-7-octenoate from Ex. XIII was converted analogously to Ex. XIId using sodium borohydride into the corresponding alcohol. The yield was 92.2%.

$^1$H NMR (300 MHz, CDCl$_3$): δ=1.19-1.94 (m, 17H), 2.31 (t, J=7.7 Hz, 2H), 2.42-2.60 (m, 1H), 3.65 (s, 3H), 4.26 (q, J=6.6 Hz, 1H), 5.05 (s, 2H), 6.22 (dd, J=16.1 Hz, J=7.0 Hz, 1H), 6.87-6.97 (m, 3H), 7.13-7.26 (m, 3H), 7.30-7.37 (m, 2H), 7.40-7.48 (m, 1H).

The following compound was prepared analogously:

| Ex. | Formula | Yield (%) | Spectroscopical data |
|---|---|---|---|
| XVI (from XIV) | 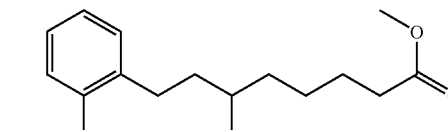 | 83.6 | $^1$H NMR (400 MHz, CDCl$_3$): δ = 1.17-1.94 (m, 19H), 2.28 (t, J = 7.6Hz, 2H), 2.45-2.56 (m, 1H), 2.66-2.88 (m, 2H), 3.51 (bs, 1H), 3.65 (s, 3H), 5.04 (s, 2H), 6.87-6.96 (m, 2H), 7.12-7.19 (m, 2H), 7.22 (d, J = 8.1Hz, 2H), 7.34 (d, J = 8.1Hz, 2H). |

A suspension of 2.80 g (6.44 mmol) of methyl (7E)-8-{2-[(4-cyclohexylbenzyl)-oxy]phenyl}-6-oxo-7-octenoate XIII and 0.06 g of Pd/C (10% Pd) in 30 ml of ethyl acetate was stirred under an atmosphere of hydrogen for 3 h. The catalyst was removed by filtration through Celite, and the product was purified chromatographically (silica gel, cyclohexane/ethyl acetate 20:1).

Yield: 2.30 g (81.7%)

$^1$H NMR (300 MHz, CDCl$_3$): δ=1.15-1.62 (m, 9H), 1.69-1.96 (m, 5H), 2.20-2.39 (m, 4H), 2.51 (m, 1H), 2.70 (t, J=7.0 Hz, 2H), 2.93 (t, J=7.6 Hz, 2H), 3.65 (s, 3H), 5.04 (s, 2H), 6.82-6.94 (m, 2H), 7.06-7.27 (m, 4H), 7.33 (d, J=7.93 Hz, 2H).

XVII: Methyl 6-bromo-8-{2-[(4-cyclohexylbenzyl)oxy]phenyl}octanoate

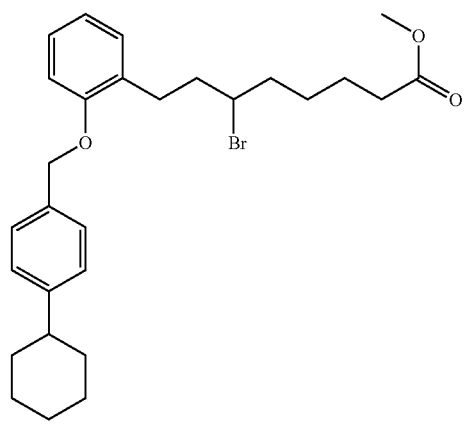

At 0° C., 140 mg (0.51 mmol) of phosphorus tribromide were added to a solution of 500 mg (1.14 mmol) of methyl 8-{2-[(4-cyclohexylbenzyl)oxy]phenyl}-6-hydroxyoctanoate XVI in 5 ml of diethyl ether. The mixture was stirred at 0° C. for 1 h and at room temperature for another 16 h. Water was added, the mixture was extracted with cyclohexane and the combined organic phases were dried over Na$_2$SO$_4$. The product was purified chromatographically (silica gel, cyclohexane(ethyl acetate 10:1).

Yield: 290 mg (50.7%).

$^1$H NMR (300 MHz, CDCl$_3$): δ=1.17-1.94 (m, 16H), 2.05-2.17 (m, 2H), 2.28 (t, J=7.2 Hz, 2H), 2.44-2.58 (m, 1H), 2.68-2.81 (m, 1H), 2.88-3.01 (m, 1H), 3.65 (s, 3H), 3.98 (quint, J=6.5 Hz, 1H), 5.04 (s, 2H), 6.83-6.94 (m, 2H), 7.11-7.37 (m, 6H).

XVIII: Dimethyl 6-[2-(2-hydroxyphenyl)ethyl]undecanedioate

XVIIIa: 1,1-Diallyl 5-methyl 1,1,5-pentanetricarboxylate

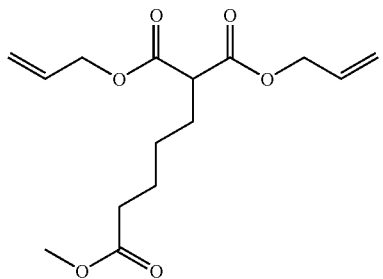

1.50 g (52.22 mmol) of sodium hydride were added carefully to a solution of 2.00 g (69.62 mmol) of diallyl malonate in 700 ml of dioxane. After the evolution of gas had ended, the mixture was stirred at room temperature for 20 min, and a solution of 7.00 g (34.81 mmol) of methyl 5-bromovalerate in 120 ml of dioxane was added dropwise. The solution was stirred at 110° C. for 16 h. The resulting precipitate was filtered off, the solvent was removed and the residue was taken up in water. The mixture was extracted with diethyl ether, the combined organic phases were dried over Na$_2$SO$_4$ and the solvent was removed. The product was purified chromato-graphically (silica gel, cylcohexane/ethyl acetate 10:1).

Yield: 4.16 g (40.1%)

$^1$H NMR (300 MHz, CDCl$_3$): δ=1.37-1.49 (m, 2H), 1.58-1.78 (m, 2H), 1.87-2.03 (m, 2H), 2.33 (t, J=5.5 Hz, 2H), 3.41 (t, J=8.0 Hz, 1H), 3.68 (s, 3H), 4.60-4.68 (m, 4H)5.21-5.40 (m, 4H), 5.79-6.02 (m, 2H).

XVIIIb: 5,5-Diallyl 1,9-dimethyl 1,5,5,9-nonanetetracarboxylate

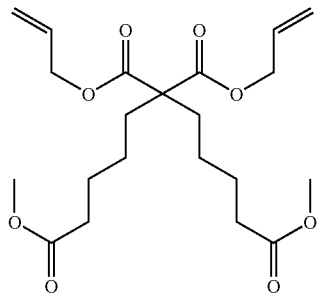

0.182 g (7.37 mmol) of sodium hydride was added carefully to a solution of 2.00 g (6.70 mmol) of XVIIIa in 20 ml of dimethylformamide (DMF). After the evolution of gas had ended, a solution of 1.75 g (8.71 mmol) of methyl 5-bromovalerate was added, and the mixture was stirred at room temperature for 16 h. Water was added, the mixture was extracted with diethyl ether, the combined organic phases were dried over Na$_2$SO$_4$ and the solvent was removed. The product was purified chromato-graphically (silica gel, cyclohexane/ethyl acetate 10:1)

Yield: 2.39 g (86.4%)

$^1$H NMR (300 MHz, CDCl$_3$): δ=1.34-1.45 (m 2H), 1.60-1.71 (m, 2H), 1.82-1.93 (m, 2H), 2.32 (t, J=7.4 Hz, 2H), 3.52 (s, 2H), 3.67 (s, 3H), 4.56-4.70 (m, 4H), 5.21-5.34 (m, 4H), 5.79-5.94 (m, 2H), 7.25-7.66 (m, 4H).

XVIIIc: 7-Methoxy-2-(5-methoxy-5-oxopentyl)-7-oxoheptaptanoic acid

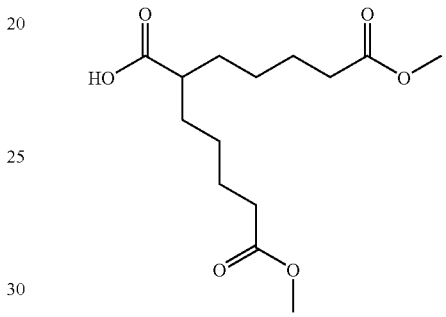

0.51 g (1.94 mmol) of triphenylphosphine and 0.11 g (0.48 mmol) of palladium acetate were added to a solution of 10.00 g (24.24 mmol) of XVIIIb in 85 mmol of dioxane. The mixture was treated with a solution of 3.28 g (60.61 mmol) of formic acid and 8.10 g (80.00 mmol) of triethylamine in 255 ml of dioxane. The solution was heated at reflux for 3 h. The solvent was removed and the product was purified chromatographically (silica gel, ethyl acetate, then MeOH).

Yield: 5.84 g (83.5%)

$^1$H NMR (300 MHz, CDCl$_3$): δ=1.20-1.42 (m, 4H), 1.50-1.67 (m, 4H), 1.76-1.91 (m, 4H), 2.18-2.34 (m, 5H), 3.62 (s, 6H).

XVIIId: Dimethyl 6-(hydroxymethyl)undecanedioate

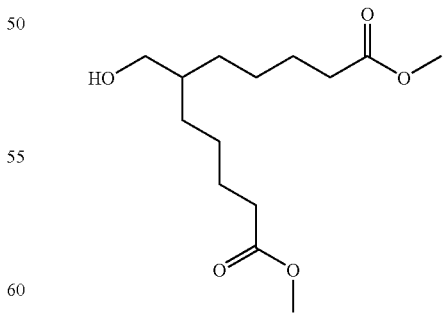

At −10° C., 8.49 ml of 1 M BH$_3$ in THF were added dropwise to a solution of 1.90 g (6.59 mmol) of XVIIIc. The reaction mixture was allowed to warm to room temperature and, after the reaction had ended, was admixed with water. The mixture was extracted with ethyl acetate, the combined organic phases were dried over Na$_2$SO$_4$ and the solvent was removed. The crude product was reacted further.

XVIIIe: Dimethyl 6-formylundecanedioate

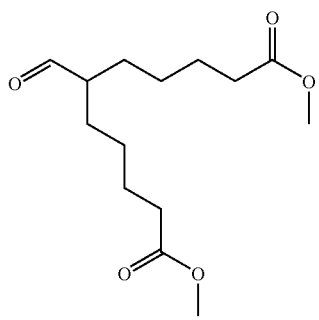

Compound XVIIId is converted under the conditions of the Swern oxidation (cf., for example, J. March, Advanced Organic Chemistry, 3$^{rd}$ ed., Wiley 1985, 1082) into the aldehyde. The crude product is reacted further.

XVIIIf: Dimethyl 6-[(E)-2-(2-hydroxyphenyl)ethenyl]undecanedioate

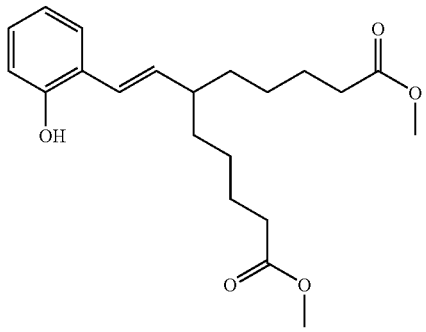

At −78° C., 8.15 ml of n-butyllithium (1.6 M in hexane) were added dropwise to a suspension of 3.03 g (6.61 mmol) of (2-hydroxybenzyl)triphenylphosphonium bromide in 10 ml of tetrahydrofuran (THF). The mixture was stirred at −78° C. for 30 min, the cooling bath was removed and the reaction mixture was allowed to warm to room temperature. The mixture was once more cooled to −78° C., and a solution of 1.50 g (5.51 mmol) of XVIIIe was added. The reaction mixture was allowed to warm to room temperature and stirred overnight. Water was added, the mixture was extracted with ethyl acetate and the combined organic phases were dried over Na$_2$SO$_4$. The product was purified chromatographically (silica gel, cyclohexane/ethyl acetate 5:1).

Yield: 0.80 g (40.3%)

$^1$H NMR (200 MHz, CDCl$_3$): δ=1.06-1.81 (m, 12H), 2.06-2.41 (m, 5H), 3.65 (s, 6H), 5.60 (s, 1H), 5.77 (dd, J=15.9 Hz, J=9.2 Hz, 1H), 6.56 (d, J=15.8 Hz, 1H), 6.76-6.94 (m, 2H), 7.05-7.17 (m, 1H), 7.21-7.38 (m, 1H).

XVIII: Dimethyl 6-[2-(2-hydroxyphenyl)ethyl]undecanedioate

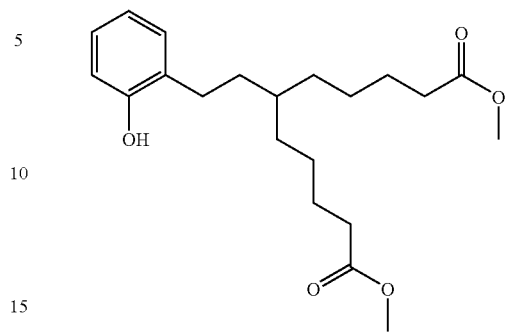

A solution of 770 mg (2.14 mmol) of XVIIIf in 15 ml of ethyl acetate was admixed with 20 mg of (Pd/C (10% Pd). The mixture was stirred overnight under an atmosphere of hydrogen. The mixture was filtered off with suction through Celite, and the solvent was removed.

Yield: 766 mg (98.8%)

$^1$H NMR (400 MHz, CDCl$_3$): δ=1.17-1.68 (m, 12H), 2.02-2.16 (m, 4H), 2.27-2.36 (m, 4H), 2.53-2.60 (m, 2H), 3.67 (s, 6H), 6.73-6.77 (m, 1H), 6.79-6.91 (m, 1H), 7.02-7.13 (m, 2H).

Synthesis Examples

Ex. 1

Methyl 6-(4-methoxycarbonylbenzyl)-8-(2-methoxyphenyl)-7-octenoate

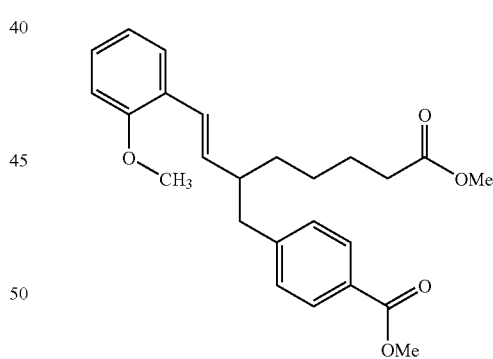

At 0° C., 77.4 mg (0.17 mmol) of 2-methoxybenzyltriphenylphosphonium bromide from Ex. IVj are suspended under argon in 20 ml of THF, and 0.115 ml of buthyl-lithium (0.18 mmol, 1.6 M solution in hexane) are added. The deep-orange solution is stirred at 0° C. for 30 min. At this temperature, a solution of 51.2 mg (0.17 mmol) of methyl 6-formyl-7-(4-methoxycarbonylphenyl)heptanoate (synthesis analogously to EP-A-0 341 551, p. 32, Ex. 44) in 15 ml of THF is added dropwise. The mixture is stirred at 0° C. for 30 min. At 0° C., water is added and the mixture is warmed to room temperature and extracted with ethyl acetate. The organic phase is washed with sodium chloride solution, dried with magnesium sulfate and concentrated under reduced pressure. For purification, the substance is chromatographed on silica gel 60 (particle size 0.040-0.063 mm) using cyclohexane/ethyl acetate 9:1 to 1:1 as mobile phase.

Yield: 17.7 mg (25.8% of theory)

$^1$H-NMR (400 MHz, CDCl$_3$): 7.95 (m, 2H), 7.40-6.70 (m, 6H), 6.50 (d, J=16 Hz, 1H), 6.00 (dd, J=16 Hz, J=8 Hz, 1H), 3.90 (s, 3H), 3.80 (s, 3H), 3.60 (s, 3H), 2.80-2.50 (m, 3H), 2.30 (m, 2H), 1.80-1.20 (m, 6H)

The following compounds were prepared analogously:

| Ex. | Formula | Yield (%) | Spectroscopical data |
|---|---|---|---|
| 2 (from 3-trifluoro-benzyl alcohol) | | 10.6 | 70% (E), 30% (Z) $^1$H-NMR (200 MHz, CDCl$_3$): 7.95 (m, 2H), 7.55-7.00 (m, 6H), 6.45 (d, 0.3H, J = 9Hz), 6.20 (d, 0.7H, J = 16Hz), 6.05 (dd, 0.7H, J = 16Hz, J = 8Hz), 5.50 (t, 0.3H, J = 9Hz), 3.90 (s, 3H), 3.60 (s, 3H), 2.75 (m, 2H), 2.50 (m, 1H), 2.30 (m, 2H), 1.70-1.10 m, 6H) |
| 3 (from 2-phenyl-benzyl alcohol) | | 21.7 | 70% (E), 30% (Z) $^1$H-NMR (300 MHz, CDCl$_3$): 7.95 (m, 2H), 7.55-7.00 (m, 11H), 6.25 (d, 0.3H, J = 9Hz), 6.10 (d, 0.7H, J = 16Hz), 5.80 (dd, 0.7H, J = 16Hz, J = 8Hz), 5.30 (t, 0.3H, 9Hz), 3.90 (s, 3H), 3.60 (s, 3H), 2.90-2.60 (m, 2H), 2.40 (m, 1H), 2.30 (m, 2H), 1.70-1.20 (m, 6H) |
| 4 (from 2-trifluoro-benzyl alcohol) | | 19.2 | 66% (E), 34% (Z) $^1$H-NMR (300 MHz, CDCl$_3$): 7.95 (m, 2H), 7.55-7.10 (m, 6H), 6.65 (m, 1H), 5.90 (dd, 0.7H, J = 16Hz, J = 8Hz), 5.50 (t, 0.3H, J = 9Hz), 3.90 (m, 3H), 3.60 (m, 3H), 2.75-2.50 (m, 3H), 2.30 (m, 2H), 1.70-1.00 (m, 6H) |
| 5 (from IVl) | | 25.6 | 70% (E), 30% (Z) $^1$H-NMR (400 MHz, CDCl$_3$): 7.90-6.70 (m, 7H), 6.50 (d, J = 16Hz, 0.7H), 6.40 (d, J = 9Hz, 0.3H), 6.10 (dd, J = 16Hz, J = 8Hz, 0.7H), 5.40 (t, J = 9Hz, 0.3H), 3.90 (m, 3H), 3.70 (m, 6H), 3.60 (m, 3H), 2.75-2.50 (m, 3H), 2.30 (m, 2H), 1.70-1.10 (m, 6H) |

-continued

| Ex. | Formula | Yield (%) | Spectroscopical data |
|---|---|---|---|
| 6 (from IVm) | | 19.6 | 70% (E), 30% (Z)<br>$^1$H-NMR (400 MHz, CDCl$_3$):<br>7.80-6.70 (m, 7H), 6.50 (m, 1H), 5.95 (dd, J = 16Hz, J = 8Hz, 0.7H), 5.40 (t, J = 9Hz, 0.3H), 3.90 (s, 3H), 3.8 (s, 3H), 3.60 (m, 6H), 2.75-2.50 (m, 3H), 2.30 (t, 2H), 1.70-1.10 (m, 6H) |
| 7 (from Ive using the base NaH) | | 31.6 | 90% (E), 10% (Z)<br>$^1$H-NMR (300 MHz, CDCl$_3$):<br>7.95 (m, 2H), 7.30-6.70 (m, 6H), 6.55 (d, J = 16Hz, 0.9H), 6.47 (d, J = 9Hz, 0.1H), 6.00 (dd, J = 16Hz, J = 8Hz, 0.9H), 5.40 (t, J = 9Hz, 0.1H), 4.85 (q, J = 6Hz, 2H), 4.10 (q, J = 6Hz, 2H), 3.90 (m, 2H), 2.75 (m, 2H), 2.55 (m, 1H), 2.30 (m, 2H), 1.80-1.20(m, 22H), 0.90 (m, 3H) |
| 8 (from IVf using the base NaH) | | 43.8 | 85% (E), 15% (Z)<br>$^1$H-NMR (300 MHz, CDCl$_3$): 7.95 (m, 2H), 7.70-6.90 (m, 15H), 6.60 (d, J = 16Hz, 0.8H), 6.55 (d, J = 9Hz, 0.2H), 6.00 (dd, J = 16Hz, J = 8Hz, 0.8H), 5.40 (t, J = 9Hz, 0.2H), 5.10 (s, 1.6H), 5.00 (m, 0.4H), 4.80 (q, J = 6Hz, 2H), 4.10 (q, J = 6Hz, 2H), 2.80 (m, 2H), 2.55 (m, 1H), 2.30 (m, 2H), 1.70-1.25 (m, 12H) |
| 9 (from IVo) | | 5.3 | 85% (E), 15% (Z)<br>$^1$H-NMR (300 MHz, CDCl$_3$); 7.95 (m, 2H), 7.40-7.10 (m, 11H), 6.70 (d, J = 16Hz, 0.8H), 6.50 (d, J = 9Hz, 0.2H), 5.85 (dd, J = 16Hz, J = 8Hz, 0.8H), 5.30 (t, J = 9Hz, 0.2H), 4.35 (q, J = 6Hz, 2H), 4.10 (q, J = 6Hz, 2H), 2.90-2.50 (m, 7H), 2.30 (t, 2H), 1.70-1.25 (m, 18H) |

-continued

| Ex. | Formula | Yield (%) | Spectroscopical data |
|---|---|---|---|
| 10 (from IVp) | | 49.0 | 70% (E), 30% (Z) $^1$H-NMR (300 MHz, CDCl$_3$): 7.95 (m, 2H), 7.40-7.00 (m, 11H), 6.70 (d, J = 16Hz, 0.7H), 6.50 (d, J = 9Hz, 0.3H), 5.90 (dd, J = 16Hz, J = 8Hz, 0.7H), 5.45 (t, J = 9Hz, 0.3H), 4.35 (q, J = 6Hz, 2H), 4.10 (q, J = 6Hz, 2H), 4.00 (s, 0.6H), 3.80 (m, 1.4H), 2.90-2.50 (m, 3H), 2.30 (m, 2H), 1.70-1.25 (m, 12H) |
| 11 (from IVh) | | 43.6 | 70% (E), 30% (Z) $^1$H-NMR (300 MHz, CDCl$_3$): 7.90 (m, 2H), 7.30-6.70 (m, 6H), 6.55 (d, J = 16Hz, 0.7H), 6.40 (d, J = 9Hz, 0.3H), 6.00 (dd, J = 16Hz, J = 8Hz, 0.7H), 5.35 (t, J = 9Hz, 0.3H), 4.35 (q, J = 6Hz, 2H), 4.10 (q, J = 6Hz, 2H), 3.90 (m, 2H). 2.75 (m, 2H), 2.55 (m, 1H), 2.30 (m, 2H), 1.80-1.20 (m, 24H), 0.90 (m, 3H) |
| 12 (from IVq) | | 19.0 | MS: 514 (M + H)$^+$ |
| 13 (from IVi) | | 66.2 | 70% (E), 30% (Z) $^1$H-NMR (300 MHz, CDCl$_3$): 7.90 (m, 2H), 7.30-6.70 (m, 6H), 6.50 (d, J = 16Hz, 0.7H), 6.45 (d, J = 9Hz, 0.3H), 6.00 (dd, J = 16Hz, J = 8Hz, 0.7H), 5.40 (t, J = 9Hz, 0.3H), 4.35 (q, J = 6Hz, 2H), 4.10 (q, J = 6Hz, 2H), 3.95 (m, 2H), 2.80 (m, 2H), 2.55 (m, 1H), 2.25 (m, 2H), 1.80-1.20 (m, 20H), 0.90 (m, 3H) |

| Ex. | Formula | Yield (%) | Spectroscopical data |
|---|---|---|---|
| 14 (from 4-butoxy-benzyl alcohol) | 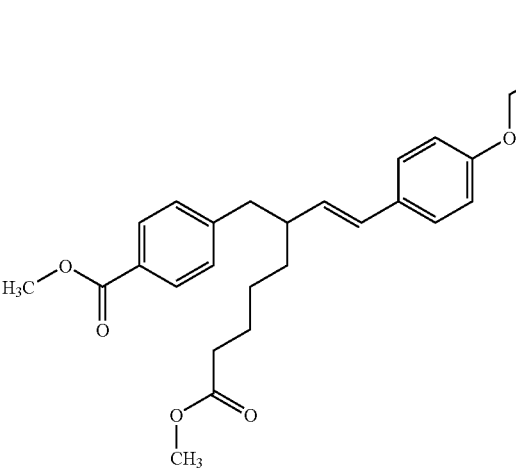 | 34.9 | $^1$H-NMR (400 MHz, CDCl$_3$): 7.90 (m, 2H), 7.30-6.70 (m, 6H), 6.10 (d, J = 16Hz, 1H), 5.80 (dd, J = 16Hz, J = 8Hz, 1H), 3.90 (m, 5H), 3.60 (s, 3H), 2.75-2.50 (m, 3H), 2.30 (m, 2H), 1.80-1.20 (m, 10H), 0.90 (t, J = 6Hz, 3H) |
| 15 (from N-((2-hy-droxy-methyl)-phenyl)-N'-phenyl-urea) | 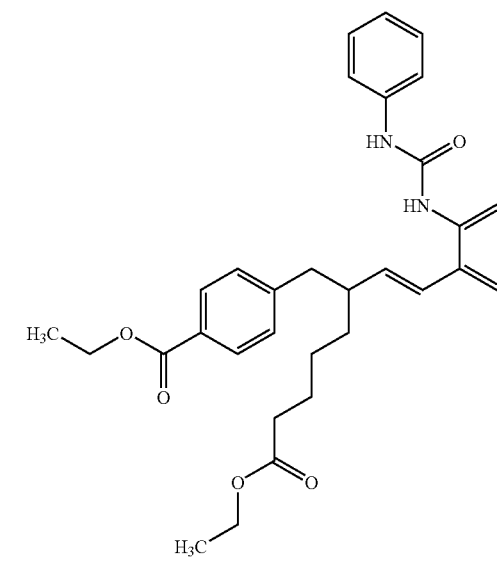 | 15.2 | MS: 543 (M + H)$^+$ |
| 16 (from IVa) | 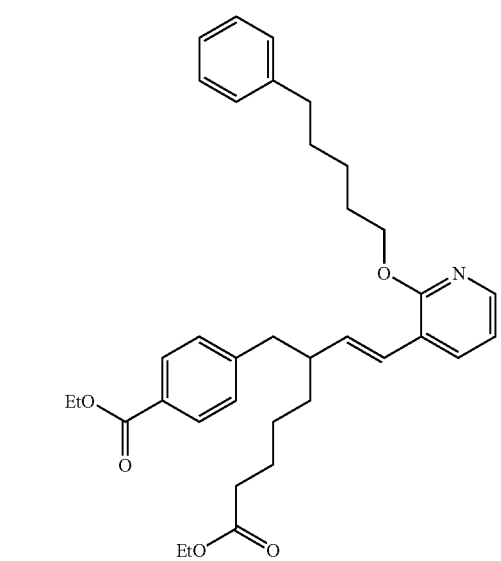 | 20.1 | 50% (E), 50% (Z) $^1$H-NMR (400 MHz, CDCl$_3$): 7.90 (m, 4H), 7.40-6.60 (m, 8H), 6.40 (m, 1H), 6.00 (d, J = 12Hz, 0.5H), 5.40 (t, J = 10Hz, 0.5Hz), 4.30 (m, 4H), 4.10 (q, J = 6Hz, 2H), 2.70 (m, 5H), 2.20 (m, 2H), 2.10-1.20 (m, 18H) |

| Ex. | Formula | Yield (%) | Spectroscopical data |
|---|---|---|---|
| 17 (from IV b) | 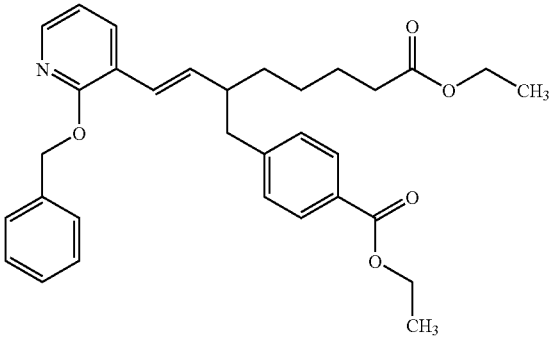 | | 60% (E), 40% (Z)<br>¹H-NMR (400 MHz. CDCl₃): 8.00-7.70 (m, 3H), 7.40-6.70 (m, 9H), 6.40 (m, 1H), 6.05 (dd, J = 16Hz. J = 8Hz, 0.6H), 5.30 (m, 2.4H), 4.30 (m, 2H), 4.10 (q, J = 6Hz, 2H), 2.80-2.50 (m, 3H), 2.20 (m, 2H), 1.60-1.20 (m, 12H) |
| 18 (from IV c) | 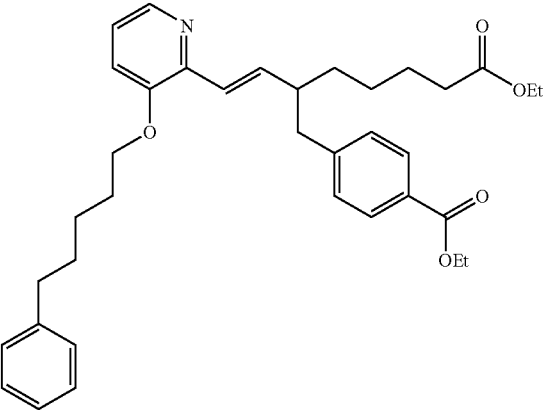 | 9.0 | 572 (M + H) |
| 18a (from IVr) | 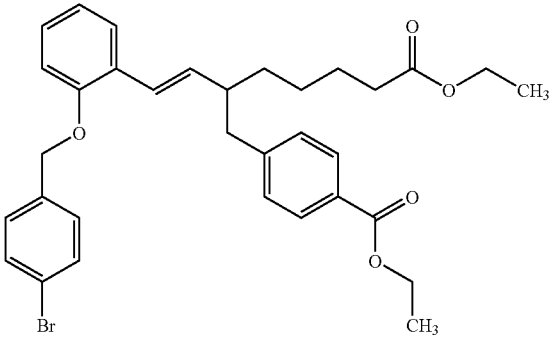 | | ¹H-NMR (200 MHz, (CDCl₃): 7.95 (d, 2H, J = 10Hz, 7.40-7.10 (m, 8H), 6.90 (m, 2H), 6.52 (d, 1H, J = 16Hz), 5.95 (dd, 1H, J = 16Hz, J = 9Hz), 5.00 (m, 2H), 4.35 (q, J = 6Hz, 2H), 4.10 (q, J = 6Hz, 2H), 2.75 (m, 2H), 2.45 (m, 1H), 2.30 (m, 2H), 1.80-1.10 (m, 12H) |

19

6-(4-Carboxybenzyl)-8-(2-methoxyphenyl)oct-7-enioic acid

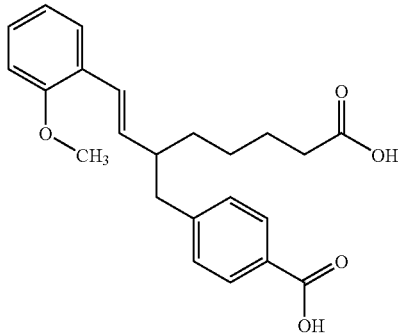

16.0 mg (0.04 mmol) of the diester from Example 1 are dissolved in 1 methanol and, at 0° C., treated with 0.5 ml of 45% strength aqueous sodium hydroxide solution. At room temperature, 0.2 ml of dichloromethane is added. The solution is stirred at room temperature for 16 hours, some water is added and the mixture is extracted with ethyl ether. The aqueous phase is adjusted to pH 2-3 using 10% strength sulfuric acid and extracted twice with ethyl acetate, and the extract is dried with magnesium sulfate and concentrated under reduced pressure.

Yield: 7.0 mg (47.0% of theory) as a mixture: 70.0% trans/ 30.0% cis.

$^1$H-NMR (400 MHz, CD$_3$COCD$_3$): 7.95 (m, 2H), 7.80-7.10 (m, 6H), 6.60 (d, J=16 Hz, 0.3H), 6.40 (d, J=9 Hz, 0.7H), 6.25 (dd, J=16 Hz, J=8 Hz, 0.7H), 5.50 (t, J=9 Hz, 0.3H), 3.10-2.50 (m, 3H), 2.30 (m, 5H), 1.80-1.20 (m, 6H).

The following compounds were prepared analogously:

| Ex. | Formula | Yield (%) | Spectroscopical data |
|---|---|---|---|
| 20 (from 2) | | 42.4 | 70% (E), 30% (Z) $^1$H-NMR (200 MHz, CDCl$_3$): 7.95 (m, 2H), 7.55-7.00 (m, 6H), 6.45 (d, J = 9Hz, 0.3H) 6.30 (d, J = 16Hz, 0.7H), 6.05 (dd, J = 16Hz, J = 8Hz, 0.7H), 5.50 (t, J = 9Hz, 0.3H), 2.75 (m, 2H), 2.50 (m, 1H), 2.30 (m, 2H), 1.70-1.10 (m, 6H) |
| 21 (from 3) | | 52.0 | 70% (E), 30% (Z) $^1$H-NMR (400 MHz, CDCOCD$_3$): 7.95 (m, 2H), 7.55-7.00 (m, 11H), 6.20 (d, J = 9Hz, 0.3H), 6.00 (d, J = 16Hz, 0.7H), 5.95 (dd, J = 16Hz, J = 8Hz, 0.7H), 5.40 (t, J = 9Hz, 0.3H), 2.90-2.60 (m, 2H), 2.40 (m, 1H), 2.30 (m, 2H), 1.70-1.20 (m, 6H) |
| 22 (from 4) | | 53.3 | 70% (E), 30% (Z) $^1$H-NMR (200 MHz, CDCl$_3$): 7.95 (m, 2H), 7.55-7.10 (m, 6H), 6.65 (m, 1H). 5.90 (dd, J = 16Hz, J = 8Hz, 0.7H), 5.55 (t, J = 9Hz, 0.3H), 2.75-2.50 (m, 3H), 2.30 (m, 2H), 1.70-1.10 (m, 6H) |

| Ex. | Formula | Yield (%) | Spectroscopical data |
|---|---|---|---|
| 23 (from 5) | | 53.4 | 90% (E), 10% (Z) <br> $^1$H-NMR (400 MHz, CDCl$_3$): 7.90-6.70 (m, 7H), 6.50 (d, J = 16Hz, 0.7H), 6.40 (d, J = 9Hz, 0.3H), 6.10 (dd, J = 16Hz, J = 8Hz, 0.7H), 5.40 (t, J = 9Hz, 0.3H), 3.70 (m, 6H), 2.75-2.50 (m, 3H), 2.30 (m, 2H), 1.70-1.10 (m, 6H) |
| 24 (from 6) | | 91.2 | $^1$H-NMR (400 MHz, CDCl$_3$): 10.60 (bs, 2H), 7.80-6.70 (m, 7H), 6.40 (d, J = 16Hz, 1H), 5.90 (dd, J = 16Hz, J = 8Hz, 1H), 3.70 (s, 3H), 3.40 (s, 3H), 2.75-2.50 (m, 3H), 2.30 (t, 2H), 1.70-1.10 (m, 6H) |
| 25 (from 7) | | crude | 90% (E), 10% (Z) <br> $^1$H-NMR (400 MHz, CD$_2$Cl$_2$): 7.95 (m, 2H), 7.30 (m, 3H), 7.10 (m, 1H), 6.80 (m, 2H), 6.55 (d, J = 16Hz, 0.9H), 6.47 (d, J = 9Hz, 0.1H), 6.00 (dd, J = 16Hz, J = 8Hz, 0.9H), 5.40 (t, J = 9Hz, 0.1H), 3.90 (m, 2H), 2.75 (m, 2H), 2.55 (m, 1H), 2.30 (m, 2H), 1.80-1.20 (m, 16H), 0.90 (t, J = 6Hz, 3H) |
| 26 (from 8) | | 62.6 | 85% (E), 15% (Z) <br> $^1$H-NMR (400 MHz, CD$_2$Cl$_2$): 7.95 (m, 2H), 7.70 (m, 4H), 7.50-7.10 (m, 9H), 6.90 (m, 2H), 6.60 (d, J = 16Hz, 0.8H), 6.55 (d, J = 9Hz, 0.2H), 6.00 (dd, J = 16Hz, J = 8Hz, 0.8H), 5.45 (t, J = 9Hz, 0.2H), 5.10 (s, 1.6H), 5.00 (m, 0.4H), 2.80 (m, 2H), 2.55 (m, 1H), 2.30 (m, 2H), 1.70-1.25 (m, 6H) |

-continued

| Ex. | Formula | Yield (%) | Spectroscopical data |
|---|---|---|---|
| 27 (from 9) | | crude | 85% (E), 15% (Z)<br>$^1$H-NMR (400 MHz, CD$_3$COCD$_3$): 7.95 (m, 2H), 7.40-7.10 (m, 11H), 6.70 (d, J = 16Hz, 0.8H), 6.50 (d, J = 9Hz, 0.2H), 6.00 (dd, J = 16Hz, J = 8Hz, 0.8H), 5.50 (t, J = 9Hz, 0.2H), 2.90-2.50 (m, 7H), 2.30 (t, 2H), 1.70-1.25 (m, 12H) |
| 28 (from 10) | | 68.6 | 70% (E), 30% (Z)<br>$^1$H-NMR (400 MHz, CD$_3$COCD$_3$): 10.70 (bs, 2H), 7.95 (m, 2H), 7.40-7.00 (m, 11H), 6.70 (d, J = 16Hz, 0.7H), 6.40 (d, J = 9Hz, 0.3H), 6.00 (dd, J = 16Hz, J = 8Hz, 0.7H), 5.50 (t, J = 9Hz, 0.3H), 4.10 (s, 0.6H), 3.90 (s, 1.4H), 3.00-2.50 (m, 3H), 2.30 (m, 2H), 1.70-1.25 (m, 6H) |
| 29 (from 11) | | 53.6 | 70% (E), 30% (Z)<br>$^1$H-NMR (400 MHz, CD$_2$Cl$_2$): 10.60 (bs, 2H), 7.90 (m, 2H), 7.30-6.70 (m, 6H), 6.55 (d, J = 16Hz, 0.7H), 6.40 (d, J = 9Hz, 0.3H), 6.10 (dd, J = 16Hz, J = 8Hz, 0.7H), 5.40 (t, J = 9Hz, 0.3H), 3.90 (m, 2H), 2.75 (m, 2H), 2.55 (m, 1H), 2.30 (m, 2H), 1.80-1.20 (m, 18H), 0.90 (t, J = 6Hz, 3H) |
| 30 (from 12) | | 57.7 | $^1$H-NMR (400 MHz, CD$_3$COCD$_3$): 10.70 (bs, 2H), 7.95 (m, 2H), 7.40-6.80 (m, 10H), 6.40 (m, 2H), 5.80 (dd, J = 16Hz, J = 8Hz, 0.7H), 4.30 (s, 0.6H), 3.00-2.50 (m, 3H), 2.30 (m, 2H), 1.70-1.25 (m, 6H) |

-continued

| Ex. | Formula | Yield (%) | Spectroscopical data |
|---|---|---|---|
| 31 (from 13) | | 49.0 | 70% (E), 30% (Z) <br> $^1$H-NMR (400 MHz, CD$_2$Cl$_2$): 10.60 (bs, 2H), 7.90 (m, 2H), 7.30-6.70 (m, 6H), 6.50 (d, J = 16Hz, 0.7H), 6.45 (d, J = 9Hz, 0.3H), 6.10 (dd, J = 16Hz, J = 8Hz, 0.7H), 5.40 (t, J = 9Hz, 0.3H), 3.90 (m, 2H), 2.80 (m, 2H), 2.55 (m, 1H), 2.25 (m, 2H), 1.80-1.20 (m, 14H), 0.90 (t, J = 6Hz, 3H) |
| 32 (from 14) | | 70.6 | 70% (E), 30% (Z) <br> $^1$H-NMR (400 MHz, CD$_3$COCD$_3$): 7.90 (m, 2H), 7.30-6.70 (m, 6H), 6.35 (d, J = 9Hz, 0.3H), 6.15 (d, J = 16Hz, 0.7H), 5.90 (dd, J = 16Hz, J = 8Hz, 0.7H), 5.30 (t, J = 9Hz, 0.3H), 3.95 (m, 2H), 2.80 (m, 2H), 2.55 (m, 1H), 2.25 (m, 2H), 1.80-1.20 (m, 10H), 0.9 (m, 3H) |
| 33 (from 15) | | 22.3 | MS: 487 (M + H)$^+$ |

| Ex. | Formula | Yield (%) | Spectroscopical data |
|---|---|---|---|
| 34 (from 16) | | crude | 50% (E), 50% (Z) 516.5 (M + H) $^1$H-NMR (400 MHz, CD$_3$COCD$_3$): 10.0 (bs, 2H), 8.20 (m, 2H), 7.95 (m, 2H), 7.40-7.10 (m, 8H), 6.40 (m, 1H), 6.30 (d, J = 12Hz, 0.5H), 5.70 (t, J = 10Hz, 0.5H), 4.50 (m, 2H), 2.90-2.50 (m, 5H), 2.30-1.20 (m, 14H) |
| 35 (from 17) | | | 60% (E), 40% (Z) $^1$H-NMR (400 MHz, CD$_3$COCD$_3$): 10.7 (bs, 2H), 8.00-7.70 (m, 3H), 7.40-7.10 (m, 8H), 6.70 (m, 1H), 6.40 (m, 1H), 6.20 (dd, J = 16Hz, J = 8Hz, 0.6H), 5.50 (t, J = 9Hz, 0.4H), 5.35 (s, 1.2H), 5.30 (dd, 0.8H), 2.90-2.50 (m, 3H), 2.20 (m, 2H), 1.60-1.20 (m, 6H) |
| 36 (from 18) | | 61.0 | 516.5 (M + H) $^1$H-NMR (400 MHz, CD$_3$COCD$_3$): 10.0 (bs, 2H), 8.10-7.10 (m, 13H), 6.70 (m, 1H), 4.150 (m, 2H), 2.90-1.20 (m, 19H) |

37

6-(4-Carboxybenzyl)-8-(2-phenyloxyphenyl)-7-octeinoic acid

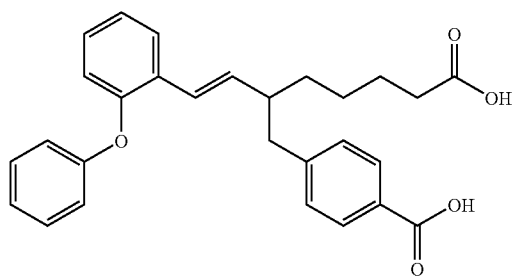

At 0° C. and under argon, 294.5 mg (0.56 mmol) of 2-benzylbenzyltriphenyl-phosphonium bromide (prepared from Ex. IVn) are suspended in 20 ml of THF, and 0.42 ml of buthyllithium (0.72 mmol, 1.6M solution in hexane) is added. The deep-orange solution is stirred at 0° C. for 30 min. At this temperature, a solution of 125 mg (0.37 mmol) of ethyl 6-formyl-7-(4-ethoxycarbonylphenyl)heptanoate (cf. EP-A-0 341 551) in 15 ml of THF is added dropwise. The mixture is stirred at 0° C. for 30 min. At 0° C., water is added and the mixture is warmed to room temperature and extracted with ethyl acetate. The organic phase is washed with sodium chloride solution, dried with magnesium sulfate and evaporated to dryness. The crude product is dissolved in 5 ml of methanol and, at 0° C., treated with 1.5 ml of 45% strength sodium hydroxide solution. At room temperature, 0.2 ml of dichloromethane is added. The solution is stirred at room temperature for 16 hours, some water is added and the mixture is extracted with ethyl ether. The aqueous phase is adjusted to pH 2-3 using 10% strength sulfuric acid and extracted twice with ethyl acetate, and the extracts are dried with magnesium sulfate and concentrated under reduced pressure.

Yield: 175 mg, (crude) as a mixture: 70.0% trans/30.0% cis.

$^1$H-NMR (400 MHz, CD$_2$Cl$_2$): 9.70 (bs, 2H), 7.95 (m, 2H), 7.70-7.00 (m, 9H), 6.80 (m, 2H), 6.40 (m, 1H), 6.00 (dd, J=16 Hz, J=8 Hz, 0.7H), 5.45 (t, J=9 Hz, 0.3H), 3.90 (m, 2H), 2.75 (m, 2H), 2.50-2.20 (m, 3H), 1.80-1.20 (m, 6H)

The following compounds were prepared analogously:

| Ex. | Formula | Yield (%) | Spectroscopical data |
|---|---|---|---|
| 38 (from IV k) | | 52.4 | 77% (E), 23% (Z) $^1$H-NMR (200 MHz, CDCl$_3$): 10.70 (bs, 2H), 7.95 (m, 2H), 7.55-7.10 (m, 6H), 6.60 (d, 0.8H, J = 16Hz), 6.50 (d, 0.2H, J = 9Hz), 6.10 (m, 1.8H), 5.50 (t, 0.2H, J = 9Hz), 5.40 (m, 1H), 5.20 (m, 1H), 4.53 (m, 1.6H), 4.47 (m, 0.4H), 2.75 (m, 2H), 2.60 (m, 1H), 2.30 (m, 2H), 1.70-1.10 (m, 6H) |
| 39 (from IVd) | | 100 | LC/MS Rf = 4.7 min, 424 (M+) |
| 40 (from IV g) | | 72.5 | 75% (E), 25% (Z) $^1$H-NMR (400 MHz, CD$_2$Cl$_2$): 7.95 (m, 2H), 7.75-7.10 (m, 4H), 6.80 (m, 2H), 6.55 (d, J = 16Hz, 0.8H), 6.47 (d, J = 9Hz, 0.2H), 6.00 (dd, J = 16Hz, J = 8Hz, 0.8H), 5.40 (t, J = 9Hz, 0.2H), 3.90 (m, 2H), 2.75 (m, 2H), 2.55 (m, 1H), 2.30 (m, 2H), 1.80-1.20 (m, 32H), 0.90 (m, 3H) |

-continued

| Ex. | Formula | Yield (%) | Spectroscopical data |
|---|---|---|---|
| 41 (from 1,3-bis(chloromethyl)-benzene) | | 27.4 | 70% (E), 30% (Z) ¹H-NMR (400 MHz, CD₃COCD₃): 7.95 (m, 2H), 7.75-7.00 (m, 6H), 6.40 (d, J = 9Hz, 0.3H), 6.25 (d, J = 16Hz, 0.7H), 6.10 (dd, J = 16Hz, J = 8Hz, 0.7H), 5.45 (t, J = 9Hz, 0.3H), 4.35 (m, 2H), 2.75-2.50 (m, 3H), 2.30 (m, 2H), 1.80-1.20 (m, 6H) |
| 42 (from 4-trifluoromethoxy-benzyl alcohol) | | 30.8 | 65% (E), 35% (Z) ¹H-NMR (400 MHz, CD₃COCD₃): 7.95 (m, 2H), 7.75-6.90 (m, 6H), 6.40 (d, J = 9Hz, 0.3H), 6.20 (d, J = 16Hz, 0.7H), 6.00 (dd, J = 16Hz, J = 8Hz, 0.7H), 5.40 (t, J = 9Hz, 0.3H), 2.75-2.50 (m, 3H), 2.30 (m, 2H), 1.80-1.20 (m, 6H) |
| 43 (from 3-phenoxy-benzyl alcohol) | | 61.6 | 70% (E), 30% (Z) ¹H-NMR (400 MHz, CD₂Cl₂): 7.95 (m, 2H), 7.75-6.90 (m, 11H), 6.40 (d, J = 9Hz, 0.3H), 6.20 (d, J = 16Hz, 0.7H), 6.00 (dd, J = 16Hz, J = 8Hz, 0.7H), 5.40 (t, J = 9Hz, 0.3H), 2.75-2.50 (m, 3H), 2.30 (m, 2H), 1.80-1.20 (m, 6H) |

LC/MS conditions: column: Symmetry C18 2.1×50 mm; mobile phase: acetonitrile/water; gradient: 10% acetoizitrile to 90% acetonitrile; flow rate: 0.5 ml/min; detector: UV 210 nm.

44

Ethyl 6-(4-ethoxycarbonylbenzyl)-8-(2-hydroxyphenyl)-7(E)-octenoate

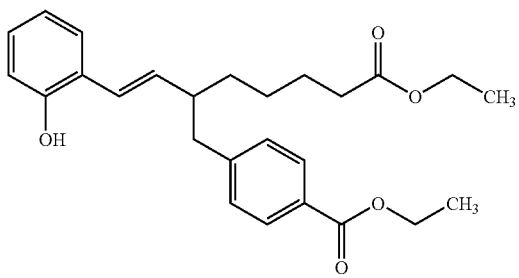

At 0° C. and under argon, 645.2 mg (1.44 mmol) of 2-hydroxy-benzyltriphenylphosphonium bromide are suspended in 25 ml of THF, and 2.2 ml of buthyllithium (3.53 mmol, 1.6M solution in hexane) are added. The deep-orange solution is stirred at 0° C. for 30 min. At this temperature, a solution of 437 mg (1.31 mmol) of ethyl 6-formyl-7-(4-ethoxycarbonylphenyl)heptanoate (cf. EP-A-0 341 551) in 2 ml of THF is added dropwise. The mixture is stirred at 0° C. for 30 min. At 0° C., water and dichloromethane are added and the mixture is warmed to room temperature and adjusted to pH 2 using hydrochloric acid. The mixture is filtered through Extrelut and concentrated under reduced pressure. The crude material is chromatographed.

Yield 184 mg (33.2% of theory)

$^1$H-NMR (200 MHz, CDCl$_3$): 7.95 (d, 2H, J=10 Hz), 7.25 (d, 2H), 7.10 (m, 2H), 6.80 (m, 2H), 6.40 (d, 1H, J=16 Hz), 5.85 (dd, 1H, J=16 Hz, J=9 Hz), 5.10 (s, 1H), 4.35 (q, J=6 Hz, 2H), 4.10 (m, 2H), 2.75 (m, 2H), 2.50 (m, 1H), 2.30 (m, 2H), 1.80-1.10 (m, 12H).

45

6-(4-Carbonbenzyl)-8-(2-hydroxyphenyl)-7(E)-octenoic acid

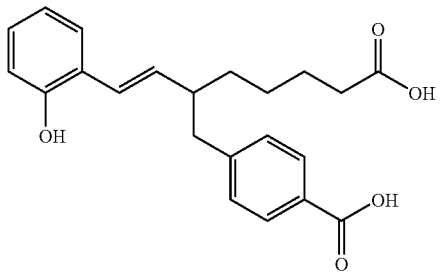

The diester from Ex. 44 is dissolved in 50 times the amount of methanol and, at 0° C., treated dropwise with 12 times the amount of aqueous sodium hydroxide solution. The mixture is allowed to warm to room temperature and methylene chloride (about 0.2 ml) is added until the solution becomes clear. After five hours, a little water is added, the mixture is covered with ether, the ether layer is removed and the aqueous phase is adjusted to pH 2-3 using 10% strength sulfuric acid, extracted twice with ethyl acetate, dried and concentrated using a rotary evaporator.

$^1$H-NMR (200 MHz, CDCl$_3$): 7.90 (d, 2H), 7.75-7.30 (m, 4H) 6.80 (m, 2H), 6.55 (d, 1H, J=16 Hz), 6.10 (dd, 1H, J=16 Hz, J=9 Hz), 4.70 (s, 1H), 2.75 (m, 2H), 2.50 (m, 1H), 2.30 (m, 1H), 1.80-1.10 (m, 6H).

46

Ethyl 6-(4-ethoxycarbonlbenzyl)-8-(2-hydroxyphenyl)octanoate

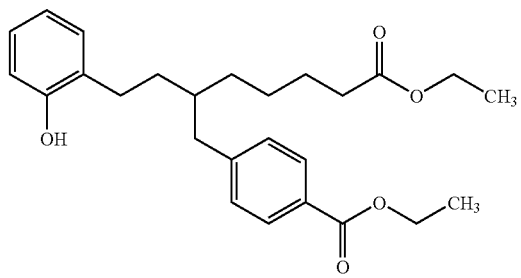

510.2 mg (1.44 mmol) of ethyl 6-(4-ethoxycarbonylbenzyl-8-(2-hydroxyphenyl)-7(E)-octenoate from Ex. 44 and 250 mg of palladium/activated carbon, 10%, are added to 20 ml of ethyl acetate, and the mixture is hydrogenated at room temperature under atmospheric pressure using hydrogen. After five hours, the mixture is filtered through Celite and concentrated under reduced pressure.

Yield 507.9 mg (99.1% of theory)

$^1$H-NMR (400 MHz, CDCl$_3$): 7.95 (d, 2H, J=10 Hz), 7.20 (d, 2H), 7.00 (m, 2H), 6.80 (m, 2H), 4.90 (s, 1H), 4.35 (q, J=6 Hz, 2H), 4.10 (m, 2H), 2.65 (m, 4H), 2.30 (m, 2H), 1.80-1.10 (m, 15H)

47

Ethyl 6-(4-ethoxycarbonylbenzyl)-8-(2-((2-phenyl)-benzyloxy)phenyl)-7(E)-octenoate

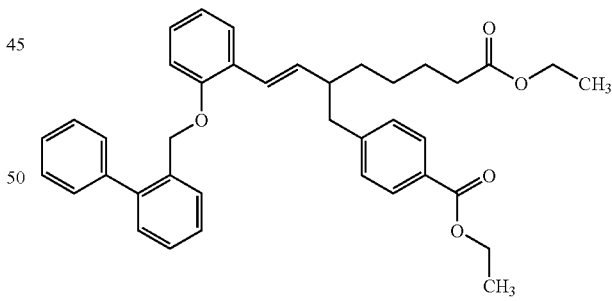

97 mg (0.23 mmol) of the phenol from Example 44, 67.9 mg (0.27 mmol) of 2-phenylbenzyl bromide and 47.5 mg (0.34 mmol) of potassium carbonate are added to 5 ml of acetonitrile, and the mixture is heated at reflux. The mixture is cooled, filtered, concentrated under reduced pressure and chromatographed.

Yield: 79 mg (58.4% of theory)

$^1$H-NMR (400 MHz, CD$_2$Cl$_2$): 7.90 (d, 2H), 7.50-6.70 (m, 15H), 6.55 (d, J=16 Hz, 1H), 6.00 (dd, J=16 Hz, J=8 Hz, 1H), 4.90 (s, 2H), 4.35 (q, J=6 Hz, 2H), 4.05 (q, J=6 Hz, 2H), 2.75 (m, 2H), 2.50 (m, 1H), 2.30 (m, 2H), 1.70-1.20 (m, 12H).

The following compounds were synthesized analogously:

| Ex. | Formula | Yield (%) | Spectroscopical data |
|---|---|---|---|
| 48 (from 4-cyclo-hexylbenzyl chloride and 44) | 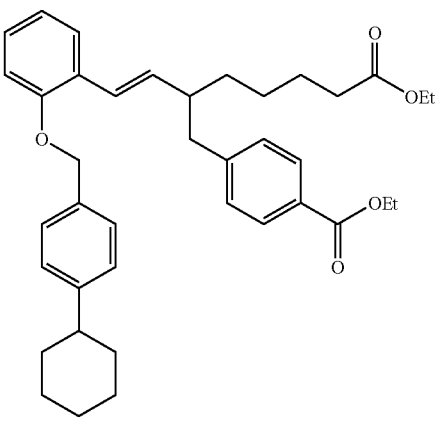 | 42.8 | $^1$H-NMR (200 MHz, CDCl$_3$): 7.90 (d, 2H), 7.50-6.80 (m, 10H), 6.55 (d, J = 16Hz, 1H), 6.00 (dd, J = 16Hz, J = 8Hz, 1H), 5.00 (s, 2H), 4.35 (q, J = 6Hz, 2H), 4.10 (q, J = 6Hz, 2H), 2.80-2.40 (m, 4H), 2.25 (m, 2H), 1.85-1.30 (m, 22H) |
| 49 (from 4-chloro-methyl2-phenylthiazole and 44) | 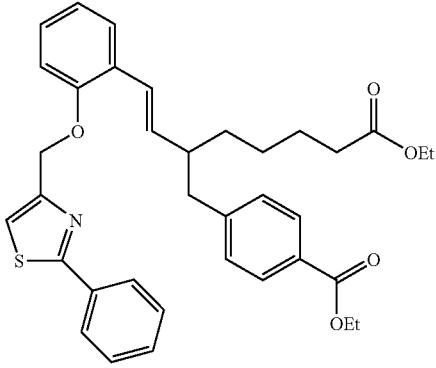 | 18.4 | $^1$H-NMR (200 MHz, CDCl$_3$): 7.90 (m, 2H), 7.50-6.90 (m, 12H), 6.55 (d, J = 16Hz, 1H), 6.00 (dd, J = 16Hz, J = 8Hz, 1H), 525 (s, 2H), 4.35 (q, J = 6Hz, 2H), 4.05 (q, J = 6Hz, 2H), 2.80-2.40 (m, 3H), 2.25 (m, 2H), 1.85-1.30 (m, 12H) |
| 50 (from 3-chloro-methyl-5-(4-meth-oxy)-phenyloxa-diazole and 44) | 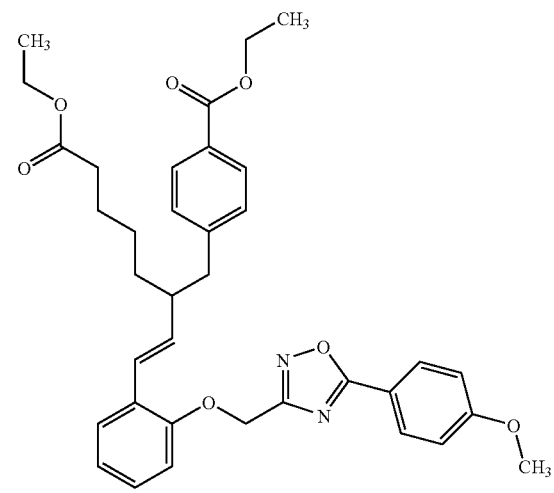 | 35.3 | $^1$H-NMR (200 MHz, CDCl$_3$): 7.90 (m, 2H), 7.50-6.90 (m, 10H), 6.55 (d, J = 16Hz, 1H), 6.05 (dd, J = 16Hz, J = 8Hz, 1H), 4.60 (s, 2H), 4.35 (q, J = 6Hz, 2H), 4.10 (q, J = 6Hz, 2H), 3.90 (s, 3H), 2.80-2.40 (m, 3H), 2.25 (m, 2H), 1.85-1.30 (m, 12H) |

-continued

| Ex. | Formula | Yield (%) | Spectroscopical data |
|---|---|---|---|
| 51 (from 4-bromo-methyl3-(2,6-dichlorophenyl-5-methyl-iso-oxazole and 44) | | 27.6 | $^1$H-NMR (200 MHz, CDCl$_3$): 7.90 (m, 2H), 7.50-6.70 (m, 9H), 6.45 (d, J = 16Hz, 1H), 5.90 (dd, J = 16Hz, J = 8Hz, 1H), 4.65 (s, 2H), 4.35 (q, J = 6Hz, 2H), 4.10 (q, J = 6Hz, 2H), 2.80-2.50 (m, 3H), 2.40 (s, 3H), 2.25 (m, 2H), 1.85-1.30 (m, 12H) |
| 52 (from 3-chloro-methyl1-(2,6-dichlorophenyl-5-methyl-1H-pyrazole and 44) | | 20.3 | $^1$H-NMR (200 MHz, CDCl$_3$): 7.90 (m, 2H), 7.50-6.80 (m, 9H), 6.55 (d, J = 16Hz, 1H), 6.00 (dd, J = 16Hz, J = 8Hz, 1H), 5.05 (s, 2H), 4.35 (q, J = 6Hz, 2H), 4.10 (q, J = 6Hz, 2H), 2.80 (m, 2H), 2.50 (m, 1H), 2.40 (s, 3H), 2.25 (m, 2H), 1.85-1.30 (m, 12H) |
| 53 (from 1,5-dibromopentane and 44) | | 60.5 | $^1$H-NMR (200 MHz, CDCl$_3$): 7.90 (d, 2H), 7.50-6.80 (m, 6H), 6.50 (d, J = 16Hz, 1H), 6.00 (dd, J = 16Hz, J = 8Hz, 1H), 4.35 (q, J = 6Hz, 2H), 4.10 (q, J = 6Hz, 2H), 3.90 (m, 2H), 3.40 (m, 2H), 2.80-2.40 (m, 3H), 2.25 (m, 2H), 1.85-1.30 (m, 18H) |

-continued

| Ex. | Formula | Yield (%) | Spectroscopical data |
|---|---|---|---|
| 54 (from 2-bromo-methylbenzo-thiophene and 44) | | 25.0 | ¹H-NMR (200 MHz, CDCl₃): 7.90-7.70 (m, 4H), 7.40-7.10 (m, 7H), 6.90 (m, 2H), 6.60 (d, J = 16 Hz, 1H), 6.00 (dd, J = 16Hz, J = 8Hz, 1H), 5.30 (s, 2H), 4.35 (q, J = 6Hz, 2H), 4.10 (q, J = 6 Hz, 2H), 2.80-2.40 (m, 3H), 2.25 (m, 2H), 1.85-1.30 (m, 12H) |
| 55 (from 2-(5-bromopentyl)-furan and 44) | | 63.7 | ¹H-NMR (200 MHz, CDCl₃): 7.90 (m, 2H), 7.40-6.70 (m, 7H), 6.50 (d, J = 16Hz, 1H), 6.25 (m, 1H), 6.00 (m, 2H), 4.35 (q, J = 6 Hz, 2H), 4.10 (q, J = 6Hz, 2H), 3.95 (m, 2H), 3.40 (m, 2H), 2.80-2.40 (m, 3H), 2.25 (m, 2H), 1.85-1.30 (m, 18H) |

-continued

| Ex. | Formula | Yield (%) | Spectroscopical data |
|---|---|---|---|
| 56 (from 1-bromo-methylnaphtha-lene and 44) | | 40.4 | $^1$H-NMR (400 MHz, CDCl$_3$): 7.90-7.70 (m, 4H), 7.40-6.90 (m, 11H), 6.50 (d, J = 16Hz, 1H), 5.90 (dd, J = 16Hz, J = 8Hz, 1H), 5.50 (s, 2H), 4.35 (q, J = 6Hz, 2H), 4.10 (q, J = 6Hz, 2H), 2.60 (m, 2H), 2.50 (m, 1H), 2.20 (m, 2H), 1.85-1.30 (m, 12H) |
| 57 (from 4-(4-bromomethyl)-phenyl-(2-trifluoro-methyl-thiazole and 44) | | 39.2 | $^1$H-NMR (200 MHz, CDCl$_3$): 8.00-6.80 (m, 13H), 6.60 (d, J = 16Hz, 1H), 5.90 (dd, J = 16Hz, J = 8Hz, 1H), 5.10 (s, 2H), 4.35 (q, J = 6Hz, 2H), 4.10 (q, J = 6 Hz, 2H), 2.60 (m, 2H), 2.50 (m, 1H), 2.20 (m, 2H), 1.85-1.30 (m, 12H) |

-continued

| Ex. | Formula | Yield (%) | Spectroscopical data |
|---|---|---|---|
| 58 (from 2-(5-bromopentyl)-thiophene and 44) | | 15.8 | ¹H-NMR (400 MHz, CDCl₃): 7.90 (d, 2H), 7.40-6.80 (m, 9H), 6.50 (d, J = 16Hz, 1H), 6.00 (dd, J = 16Hz, J = 8Hz, 1H), 4.35 (m, 2H), 4.10 (m, 2H), 3.90 (m, 2H), 2.90 (m, 2H), 2.80 (m, 2H), 2.50 (m, 1H), 2.30 (m, 2H), 2.00-1.40 (m, 18H) |
| 59 (from 4-phenyl-ethenyl-benzyl chloride and 44) | | 86.0 | ¹H-NMR (400 MHz, CDCl₃): 7.90 (d, 2H), 7.50 (d, 4H), 7.40-7.10 (m, 11H), 6.90 (m, 2H), 6.60 (d, J = 16Hz, 1H), 6.00 (dd, J = 16Hz, J = 8Hz, 1H), 5.00 (s, 2H), 4.35 (q, J = 6Hz, 2H), 4.10 (q, J = 6Hz, 2H), 2.80 (m, 2H), 2.50 (m, 1H), 2.30 (t, 2H), 1.50-1.20 (m, 12H) |
| 60 (from 4-acet-amido-benzyl chloride and 44) | | 65.3 | ¹H-NMR (300 MHz, CDCl₃): 7.90 (d, 2H), 7.65 (d, 1H), 7.55 (d, 1H), 7.50-7.30 (m, 5H), 7.15 (m, 1H), 7.00 (d, 1H), 6.85 (t, 1H), 6.55 (d, J = 16Hz, 1H), 6.10 (dd, J = 16Hz, J = 8Hz, 1H), 5.00 (s, 2H), 4.60 (d, 1H), 4.35 (q, J = 6Hz, 2H), 4.10 (q, J = 6Hz, 2H), 2.90-2.50 (m, 3H), 2.20 (m, 5H), 1.60-1.20 (m, 12H) |

| Ex. | Formula | Yield (%) | Spectroscopical data |
|---|---|---|---|
| 61 (from 2-(4-(chloromethyl)-phenyl)5-methyl-1,3-benzoxazole and 44) | | 97.3 | $^1$H-NMR (400 MHz, CDCl$_3$): 8.25 (d, 2H), 7.90 (d, 2H), 7.65-6.90 (m, 11H), 6.60 (d, J = 16Hz, 1H), 6.05 (dd, J = 16Hz, J = 8Hz, 1H), 5.10 (s, 2H), 4.35 (q, J = 6 Hz, 2H), 4.10 (q, J = 6Hz, 2H), 2.90 (m, 2H), 2.50 (m, 4H), 2.25 (t, 2H), 1.60-1.20 (m, 12H) |
| 62 (from 6-bromo-hexyl)acetate and 44) | | 85.4 | $^1$H-NMR (400 MHz, CDCl$_3$): 7.90 (d, 2H), 7.40-7.10 (m, 4H), 6.85 (m, 2H), 6.60 (d, J = 16Hz, 1H), 6.00 (dd, J = 16Hz, J = 8Hz, 1H), 4.35 (q, J = 6Hz, 2H), 4.10 (m, 4H), 3.40 (m, 2H), 2.80 (m, 2H), 2.50 (m, 1H), 2.25 (m, 2H), 2.10 (s, 3H), 1.80-1.20 (m, 20H) |
| 63 (from N-(3-bromopropyl-mercapto-carbonyl)-pyr-rolidine and 44) | | crude | $^1$H-NMR (300 MHz, CDCl$_3$): 7.90 (d, 2H), 7.40-6.70 (m, 6H), 6.60 (d, J = 16Hz, 1H), 6.00 (dd, J = 16Hz, J = 8Hz, 1H), 4.35 (q, J = 6Hz, 2H), 4.00 (m, 4H), 3.50 (m, 2H), 3.40 (m, 4H), 2.90-2.50 (m, 3H), 2.25 (m, 2H), 2.00-1.30 (m, 18H) |

-continued

| Ex. | Formula | Yield (%) | Spectroscopical data |
|---|---|---|---|
| 64 (from 4-bromo-butyl benzyl ether and 44) | 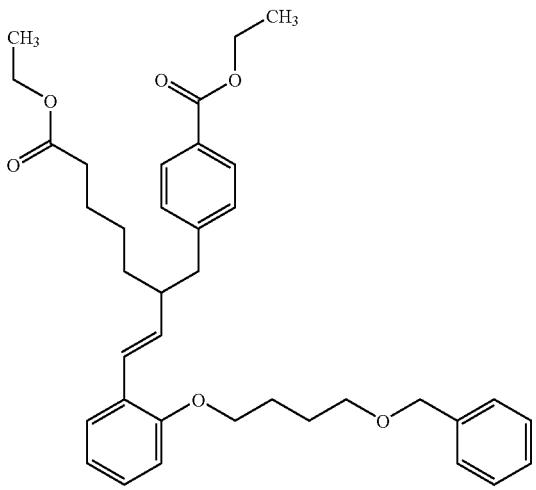 | crude | ¹H-NMR (400 MHz, CDCl₃): 7.90 (d, 2H), 7.40-7.00 (m, 9H), 6.90 (m, 2H), 6.60 (d, J = 16Hz, 1H), 6.00 (dd, J = 16Hz, J = 8Hz, 1H), 4.50 (s, 2H), 4.35 (q, J = 6 Hz, 2H), 4.10 (q, J = 6Hz, 2H), 4.00 (m, 2H), 3.50 (t, 2H), 2.90-2.50 (m, 3H), 2.25 (t, 2H), 1.90-1.30 (m, 16H) |
| 65 (from 5-chloro-methyl3-phenyl-12,4-oxadiazole and 44) | 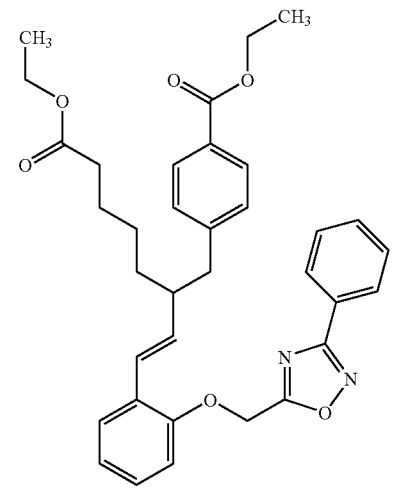 | crude | ¹H-NMR (300 MHz, CDCl₃): 8.10 (d, 2H), 7.90 (d, 2H), 7.60-7.30 (m, 5H), 7.20-6.70 (m, 4H), 6.60 (d, J = 16Hz, 1H), 6.10 (dd, J = 16Hz, J = 8Hz, 1H), 5.30 (s, 2H), 4.35 (q, J = 6Hz, 2H), 4.10 (q, J = 6Hz, 2H), 2.80 (m, 2H), 2.50 (m, 1H), 2.25 (m, 2H), 1.70-1.20 (m, 12H) |
| 66 (from N-(2-chloroethyl)-morpholine and 44) | 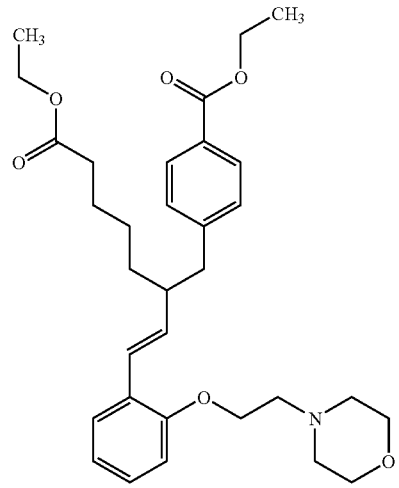 | 81.3 | ¹H-NMR (300 MHz, CDCl₃): 7.90 (d, 2H), 7.40-6.70 (m, 6H), 6.60 (d, J = 16Hz, 1H), 6.00 (dd, J = 16Hz, J = 8Hz, 1H), 4.35 (q, J = 6Hz, 2H), 4.10 (m, 4H), 3.70 (m, 4H), 2.80 (m, 4H), 2.50 (m, 5H), 2.25 (t, 2H), 1.70-1.20 (m, 12H) |

-continued

| Ex. | Formula | Yield (%) | Spectroscopical data |
|---|---|---|---|
| 67 (from 5-(3-bromopropyl)-2-aminopyrimidine and 44) | 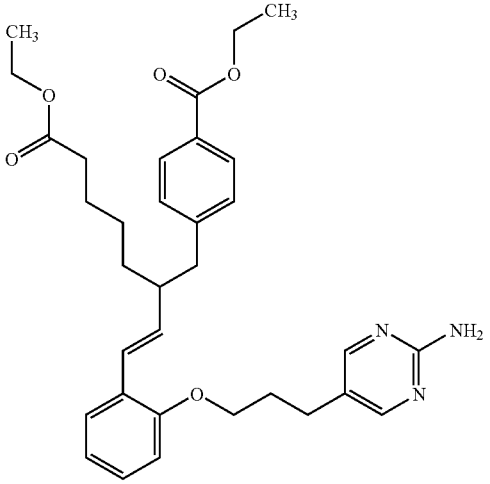 | 73.1 | $^1$H-NMR (300 MHz, CDCl$_3$): 8.10 (s, 2H), 7.90 (d, 2H), 7.40-6.70 (m, 6H), 6.50 (d, J = 16Hz, 1H), 5.90 (dd, J = 16Hz, J = 8Hz, 1H), 4.95 (bs, 2H), 4.35 (q, J = 6 Hz, 2H), 4.10 (m, 2H), 3.90 (m, 2H), 2.80-2.50 (m, 5H), 2.25 (t, 2H), 2.00 (m, 2H), 1.70-1.20 (m, 12H) |
| 68 (from 4-chloro-methyl-N-phenyl-benz-amide and 44) | 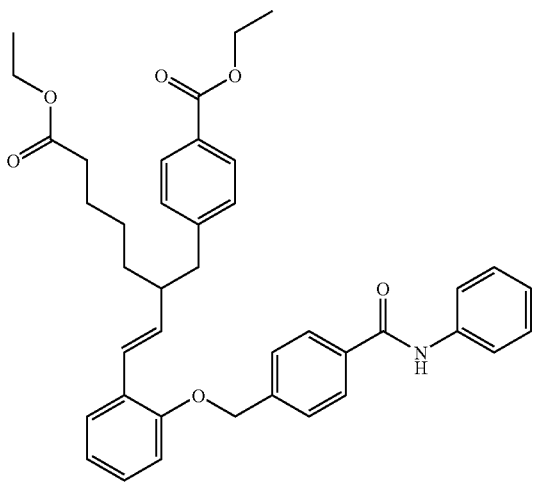 | crude | $^1$H-NMR (300 MHz, CDCl$_3$): 8.60 (bs, 1H), 7.90-6.80 (m, 17H), 6.50 (d, J = 16Hz, 1H), 5.90 (dd, J = 16Hz, J = 8Hz, 1H), 4.95 (s, 2H), 4.35 (q, J = 6Hz, 2H), 4.10 (m, 2H), 2.90-2.50 (m, 3H), 2.25 (t, 2H), 1.70-1.20 (m, 12H) |
| 69 (from 4-cyclohexylbenzyl chloride and 46) | 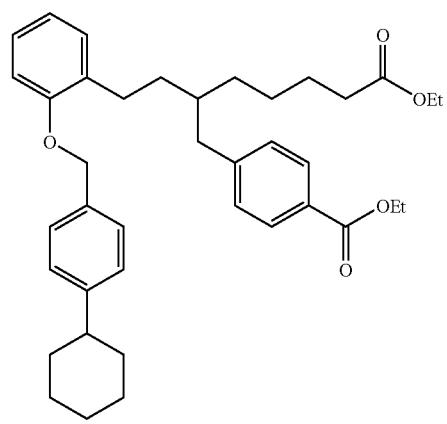 | 52.0 | $^1$H-NMR (400 MHz, CDCl$_3$): 7.90 (d, 2H), 7.50-7.10 (m, 8H), 6.85 (m, 2H), 5.00 (s, 2H), 4.35 (q, J = 6Hz, 2H), 4.10 (q, J = 6 Hz, 2H), 2.80-2.40 (m, 5H), 2.25 (m, 2H), 1.85-1.30 (m, 25H) |

-continued

| Ex. | Formula | Yield (%) | Spectroscopical data |
|---|---|---|---|
| 70 (from 4-phenyl-ethylbenzyl chloride and 46) | | 25.8 | $^1$H-NMR (400 MHz, CDCl$_3$): 7.90 (d, 2H), 7.40-7.00 (m, 13H), 6.90 (m, 2H), 5.00 (s, 2H), 4.35 (q, J = 6Hz, 2H), 4.10 (q, J = 6 Hz, 2H), 2.90 (m, 6H), 2.60 (m, 2H), 2.20 (t, 2H), 1.60-0.80 (m, 15H) |
| 70a (from 4-bromo-benzyl bromide and 46) | | | $^1$H-NMR (200 MHz, CDCl$_3$): 7.95 (d, 2H, J = 10Hz), 7.40 (d, 2H), 7.20-6.80 (m, 8H), 5.00 (m, 2H), 4.35 (q, J = 6Hz, 2H), 4.10 (q, J = 6Hz, 2H), 2.65 (m, 4H), 2.30 (t, 2H), 1.70 (m, 1H), 1.60-1.20 (m, 14H) |
| 70b (from 46 and 1,3-dibromo-propane) | | | $^1$H-NMR (400 MHz, CDCl$_3$): 7.90 (d, 2H), 7.50-6.80 (m, 6H), 4.35 (q, J = 6Hz, 2H), 4.10 (q, J = 6Hz, 2H), 4.00 (t, 2H), 3.50 (t, 2H), 2.80-2.40 (m, 4H), 2.25 (m, 4H), 1.85-1.30 (m, 15H) |
| 70c (from 46 and 1,5-dibromo-pentane) | | | $^1$H-NMR (200 MHz, CDCl$_3$): 7.90 (d, 2H), 7.50-6.80 (m, 6H), 4.35 (q, J = 6Hz, 2H), 4.10 (q, J = 6Hz, 2H), 3.90 (t, 2H), 3.40 (t, 2H), 2.80-2.40 (m, 4H), 2.25 (t, 2H), 2.00-1.30 (m, 21H) |

| Ex. | Formula | Yield (%) | Spectroscopical data |
|---|---|---|---|
| 70d (from 46 and 1,4-dibromo-butane) | | | ¹H-NMR (400 MHz, CDCl₃): 7.90 (d, 2H), 7.50-6.80 (m, 6H), 4.35 (q, J = 6Hz, 2H), 4.10 (q, J = 6Hz, 2H), 4.00 (t, 2H), 3.40 (t, 2H), 2.80-2.40 (m, 4H), 2.25 (t, 2H), 2.00 (m, 2H), 1.90 (m, 2H), 1.70 (m, 1H), 1.85-1.30 (m, 14H) |
| 70e (from 46 and 1,2-dibromo-ethane) | | | ¹H-NMR (400 MHz, CDCl₃): 7.90 (d, 2H), 7.50-6.80 (m, 6H), 4.35 (q, J = 6Hz, 2H), 4.25 (t, 2H), 4.10 (q, J = 6Hz, 2H), 3.50 (t, 2H), 2.80-2.40 (m, 4H), 2.25 (m, 2H), 1.85-1.30 (m, 15H) |
| 70f (from 46 and 1,4-(dichloro-methyl)benzene | | | ¹H-NMR (200 MHz, CDCl₃): 7.90 (d, 2H), 7.50-6.80 (m, 10H), 5.30 (s, 2H), 5.00 (s, 2H), 4.35 (q, J = 6Hz, 2H), 4.10 (q, J = 6 Hz, 2H), 2.80-2.40 (m, 4H), 2.25 (m, 2H), 1.85-1.30 (m, 15H) |

71

6-(4-Carboxybenzyl-8-(2-(2-phenylbenzyloxy)phenyl)-7(E)-octenoic acid 70 mg (0.12 mmol) of the diethyl ester from Ex. 47 are dissolved in 5 ml of methanol, and 0.5 ml of 45% strength aqueous sodium hydroxide solution are added. The reaction is exothermic. The mixture is allowed to warm to room temperature, and 0.3 ml of dichloromethane are added. After 20 hours at room temperature, the reaction solution is washed once with ether, acidified using 10% strength sulfuric acid and extracted twice with ethyl acetate, and the combined organic phases are filtered through Extrelut and concentrated.

Yield: 15 mg (20.0% of theory)

LC/MS: Rf: 5.1 min, 535 (M+1)

The following substances are synthesized analogously:
| Ex. | Formula | Yield (% of theory) | Spectroscopical data |
|---|---|---|---|
| 72 (from 48) | 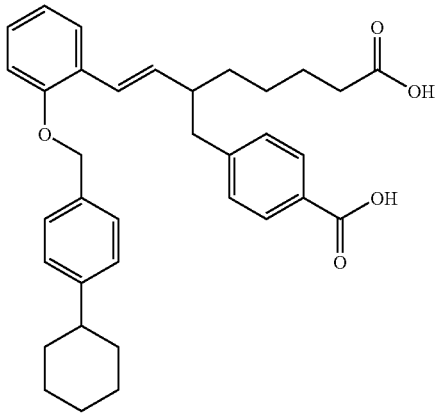 | 4.1 | ¹H-NMR (400 MHz, CD$_3$COCD$_3$): 10.70 (bs, 2H), 7.90 (d, 2H), 7.50-6.80 (m, 10H), 6.55 (d, J = 16Hz, 1H), 6.10 (dd, J = 16Hz, J = 8Hz, 1H), 5.00 (s, 2H), 2.80-2.40 (m, 4H), 2.25 (m, 2H), 1.85-1.30 (m, 6H) |
| 73 (from 49) | 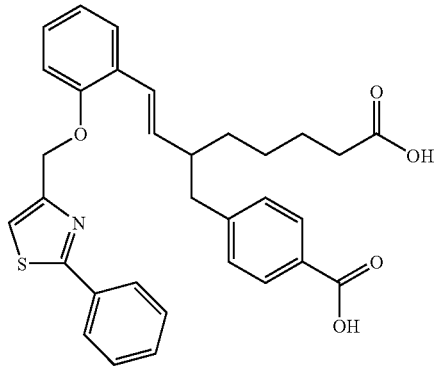 | 13.1 | LC/MS: 542 (M + 1), R$_f$ 4.9 min |
| 74 (from 50) | 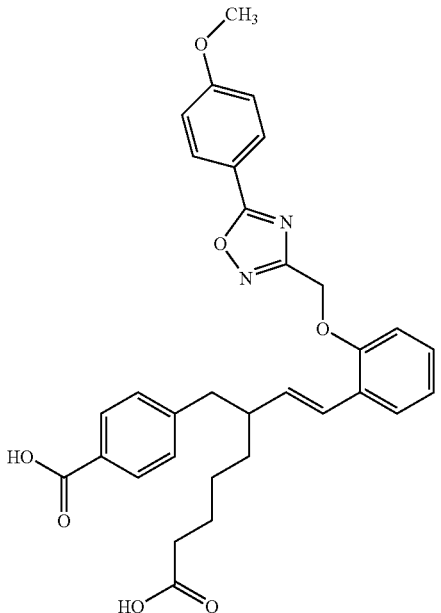 | 9.7 | LC/MS: 557 (M + 1), R$_f$ 4.7 min |

-continued

| Ex. | Formula | Yield (% of theory) | Spectroscopical data |
|---|---|---|---|
| 75 (from 51) | | 14.0 | LC/MS: 608 (M + 1), R$_f$ 4.8 min |
| 76 (from 52) | | 27.9 | LC/MS: 607 (M + 1), R$_f$ 5.2 min |
| 77 (from 53) | | 20.9 | LC/MS: 517 (M + 1), R$_f$ 4.9 min |

-continued

| Ex. | Formula | Yield (% of theory) | Spectroscopical data |
|---|---|---|---|
| 78 (from 54) | | 37.6 | LC/MS: 515 (M + 1), $R_f$ 4.9 min |
| 79 (from 55) | | 23.7 | LC/MS: 505 (M + 1), $R_f$ 5.0 min |
| 80 (from 56) | | 42.9 | LC/MS: 509 (M + 1), $R_f$ 4.9 min |
| 81 (from 57) | | 40.1 | $^1$H-NMR (400 MHz, CD$_3$COCD$_3$): 10.70 (bs. 2H), 8.10 (m, 2H), 7.90 (d, 2H), 7.60-6.80 (m, 9H), 6.60 (d, J = 16Hz, 1H), 6.10 (dd, J = 16 Hz, J = 8Hz, 1H), 5.15 (s, 2H), 2.80-2.40 (m, 3H), 2.25 (m, 2H), 1.75-1.30 (m, 6H) |

| Ex. | Formula | Yield (% of theory) | Spectroscopical data |
|---|---|---|---|
| 82 (from 58) | | crude | $^1$H-NMR (400 MHz, CD$_3$COCD$_3$): 10.60 (bs, 2H), 7.90 (d, 2H), 7.40-6.80 (m, 9H), 6.50 (d, J = 16Hz, 1H), 6.10 (dd, J = 16Hz, J = 8Hz, 1H), 3.90 (m, 2H), 2.90-2.40 (m, 5H), 2.30 (m, 2H), 2.10-1.40 (m, 12H) |
| 83 (from 59) | | 69.3 | $^1$H-NMR (400 MHz, CD$_3$COCD$_3$): 7.90 (m, 2H), 7.60 (m, 4H), 7.50-7.20 (m, 10H), 7.10 (t, 1H), 7.00 (d, 1H), 6.90 (t, 1H), 6.60 (d, J = 16 Hz, 1H), 6.00 (dd, J = 16Hz, J = 8Hz, 1H), 5.00 (s, 2H), 2.80-2.40 (m, 3H), 2.10 (m, 2H), 1.50-1.30 (m, 6H) |
| 84 (from 60) | | 97.7 | $^1$H-NMR (400 MHz, CD$_3$COCD$_3$): 10.70 (bs, 2H), 7.90 (d, 2H), 7.65 (d, 1H), 7.55 (d, 1H), 7.50-7.30 (m, 5H), 7.15 (m, 1H), 7.00 (d, 1H), 6.85 (t, 1H), 6.55 (d, J = 16Hz 1H), 6.10 (dd, J = 16Hz, J = 8Hz, 1H), 5.00 (s, 2H), 4.60 (d, 1H), 2.90-2.50 (m, 3H), 2.20 (m, 5H), 1.60-1.20 (m, 6H) |

-continued

| Ex. | Formula | Yield (% of theory) | Spectroscopical data |
| --- | --- | --- | --- |
| 85 (from 61) | | crude | $^1$H-NMR (400 MHz, CD$_3$COCD$_3$): 8.25 (d, 2H), 7.90 (d, 2H), 7.65-6.90 (m, 11H), 6.60 (d, J = 16Hz, 1H), 6.10 (dd, J = 16Hz, J = 8Hz, 1H), 5.20 (s, 2H), 2.90-2.50 (m, 3H), 2.45 (s, 3H), 2.25 (t, 2H), 1.60-1.20 (m, 6H) |
| 86 (from 62) | | 65.6 | $^1$H-NMR (400 MHz, CD$_3$COCD$_3$): 7.90 (d, 2H), 7.40 (m, 3H), 7.10 (m, 1H), 6.85 (m, 2H), 6.60 (d, J = 16Hz, 1H), 6.10 (dd, J = 16Hz, J = 8Hz, 1H), 3.90 (m, 2H), 3.60 (m, 2H), 2.90-2.50 (m, 3H), 2.25 (m, 2H), 1.80-1.20 (m, 14H) |
| 87 (from 63) | | crude | $^1$H-NMR (400 MHz, CD$_3$COCD$_3$): 7.90 (d, 2H), 7.40 (m, 2H), 7.15-6.70 (m, 4H), 6.60 (d, J = 16Hz, 1H), 6.10 (dd, J = 16Hz, J = 8Hz, 1H), 4.00 (m, 2H), 3.30 (m, 6H), 2.90-2.50 (m, 3H), 2.25 (m, 2H), 2.00-1.30 (m, 12H) |

-continued

| Ex. | Formula | Yield (% of theory) | Spectroscopical data |
|---|---|---|---|
| 88 (from 64) | | crude | ¹H-NMR (400 MHz, CD₃COCD₃): 7.90 (d, 2H), 7.40-7.20 (m, 8H), 7.10 (m, 1H), 6.85 (m, 2H), 6.50 (d, J = 16Hz, 1H), 6.10 (dd, J = 16 Hz, J = 8Hz, 1H), 4.50 (s, 2H), 4.00 (m, 2H), 3.50 (t, 2H), 2.90-2.50 (m, 3H), 2.25 (t, 2H), 1.90-1.30 (m, 10H) |
| 89 (from 65) | | crude | ¹H-NMR (400 MHz, CD₃COCD₃): 10.80 (bs, 2H), 8.10 (d, 2H), 7.90 (d, 2H), 7.60-7.30 (m, 5H), 7.20-6.70 (m, 4H), 6.60 (d, J = 16Hz, 1H), 6.20 (dd, J = 16Hz, J = 8Hz, 1H), 5.50 (s, 2H), 2.90-2.50 (m, 3H), 2.25 (m, 2H), 1.70-1.30 (m, 6H) |
| 90 (from 66) | | 69.0 | LC-MS: 482 (M + 1), R$_f$ 3.1 min |

-continued

| Ex. | Formula | Yield (% of theory) | Spectroscopical data |
|---|---|---|---|
| 91 (from 67) | | | LC-MS: 504 (M + 1), R$_f$ 3.74 min |
| 92 (from 68) | | 21.9 | $^1$H-NMR (400 MHz, CDCOCD$_3$): 10.90 (bs, 2H), 9.50 (bs, 1H), 7.90-6.80 (m, 17H), 6.60 (d, J = 16 Hz, 1H), 6.10 (dd, J = 16Hz, J = 8Hz, 1H), 5.15 (s, 2H), 2.90-2.50 (m, 3H), 2.25 (t, 2H), 1.70-1.20 (m, 6H) |
| 93* (from 69) | | 90.0 | $^1$H-NMR (400 MHz, CDCOCD$_3$): 10.60 (bs, 2H), 7.90 (d, 2H), 7.40 (d, 2H), 7.25 (m, 4H), 7.10 (d, 2H), 7.00 (d, 1H), 6.80 (t, 1H), 5.00 (s, 2H), 2.80-2.50 (m, 5H), 2.25 (t, 2H), 1.85-1.30 (m, 19H) |

-continued
| Ex. | Formula | Yield (% of theory) | Spectroscopical data |
|---|---|---|---|
| 94 (from 70) | 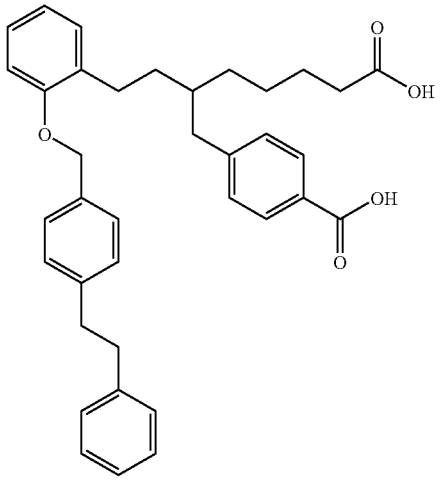 | 82.6 | ¹H-NMR (400 MHz, CDCOCD$_3$): 7.90 (d, 2H), 7.20-7.00 (m, 13H), 6.90 (m, 1H), 6.70 (m, 1H), 4.90 (s, 2H), 2.90 (m, 6H), 2.60 (m, 2H), 2.20 (t, 2H), 1.60-0.80 (m, 9H) |
| 94a (from 46 and 4-(chloromethyl)-4'-(trifluoromethoxy)-1,1'-biphenyl and hydrolysis analogously to Ex. 19) | 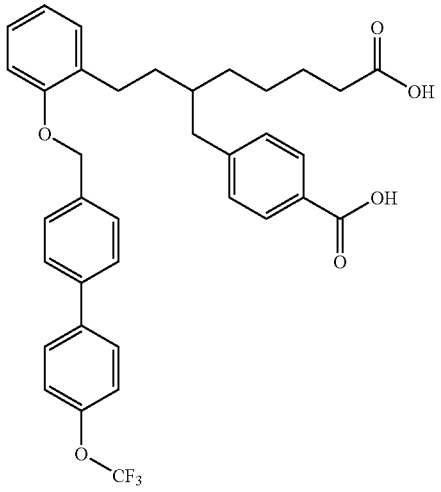 | (M + 1), Rt = 5.41 | |
| 94b from Ex. 46 and 4-(chloromethyl)-4'-ethyl-1,1'-biphenyl and hydrolysis analogously to 19 | 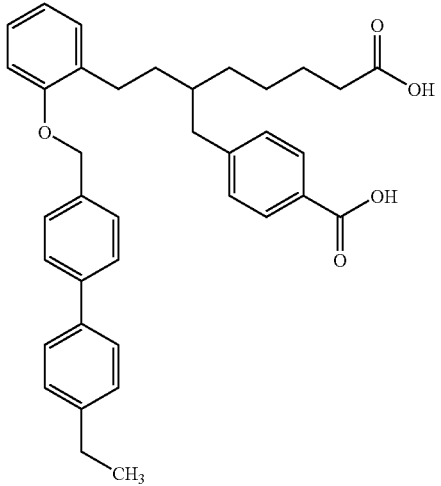 | 565 (M + 1), Rt = 5.43 | |

| Ex. | Formula | Yield (% of theory) | Spectroscopical data |
|---|---|---|---|
| 94c from Ex. 46 and 4-(chloro-methyl)-4'-propyl-1,1'-biphenyl and hydrolysis analogously to 19 | | | 579 (M + 1), Rt = 5.61 |

*prepared as pure (−)-enantiomer from enantiomerically pure Ex. 44 via Ex. 46 and 69. The separation of the enantiomers of the compound from Ex. 44 was carried out by chromatography on a chiral stationary polyamide-silica gel phase based on the monomer N-methacryloyl-L-isoleucine-3-pentylamide which, after free-radical polymerization, is covalently attached to a modified silica gel. Phases of this type are described in EP-A-0 379 917.

LC/MS conditions: column: Symmetry C18 2.1×50 mm; mobile phase: aceto-nitrile/water; gradient: 10% acetonitrile to 90% acetonitrile; flow rate: 0.5 ml/min; detector: UV 210 nm.

95

6-(4-Carboxybenzyl)-8-(2-heptoxyphenyl)octanoic acid

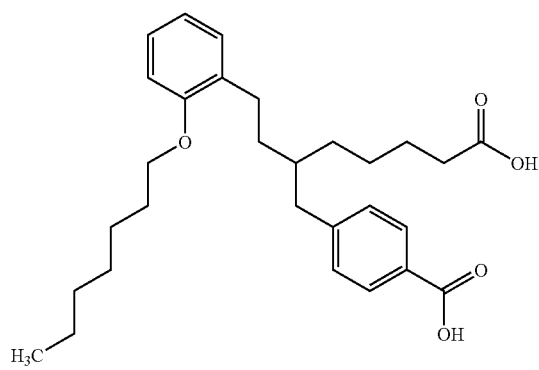

31.6 mg (0.07 mmol) of 6-(4-carboxybenzyl)-8-(2-heptox-yphenyl)-7-octenoic acid from Ex. 25 and 20 mg of palladium/activated carbon (10%) are added to 5 ml of ethyl acetate and, at room temperature and under atmospheric pressure, hydrogenated with hydrogen. After two hours, the mixture is filtered through Celite and concentrated under reduced pressure.

Yield: 15.6 mg (80.7 of theory)

$^1$H-NMR (400 MHz, CD$_2$Cl$_2$): 7.90 (d, 2H), 7.60-7.00 (m, 4H), 6.80 (d, 2H), 3.90 (t, 2H), 2.80-2.50 (m, 4H), 2.30 (m, 2H), 1.70-1.25 (m, 19H), 0.90 (t, 3H)

The following compound was prepared analogously:

| Ex. | Formula | Yield (%) | Spectroscopical data |
|---|---|---|---|
| 96 (from 26) | | 63.5 | ¹H-NMR (400 MHz, CD$_2$Cl$_2$): 7.95 (m, 2H), 7.70-6.70 (m, 15H), 5.30 (s, 2H), 2.80-2.50 (m, 4H), 2.30 (m, 2H), 1.70-1.25 (m, 9H) |

97

Ethyl 6-(4-ethoxycarbonylbenzyl)-8-(2-(5-N-morpholinopentyloxy)phenyl)-7-(E)-octenoate 50 mg (0.09 mmol) of the bromide from Ex. 53, 15.2 mg (0.17 mmol) of morpholine, 13.2 mg (0.1 mmol) of potassium carbonate and a catalytic amount of potassium iodide in 5 ml of acetonitrile are heated at reflux overnight. 0.5 ml of water is added and the solution is taken up in dichloromethane, filtered through Extrelut and concentrated under reduced pressure.

Yield: 50.0 mg (98.9% of theory)

¹H-NMR (300 MHz, CDCl$_3$): 7.90 (d, 2H), 7.40-7.10 (m, 4H), 6.80 (m, 2H), 6.55 (d, J=16 Hz, 1H), 6.00 (dd, J=16 Hz, J=8 Hz, 1H), 4.35 (q, J=6 Hz, 2H), 4.10 (q, J=6 Hz, 2H), 3.90 (m, 2H), 3.70 (m, 4H), 2.80 (m, 2H), 2.50 (m, 7H), 2.25 (t, 2H), 1.70-1.20 (m, 18H).

The following compounds were prepared analogously:

| Ex. | Formula | Yield (%) | Spectroscopical data |
|---|---|---|---|
| 98 (from aniline) | | crude | $^1$H-NMR (200 MHz, CDCl$_3$): 7.90 (d, 2H), 7.40-6.70 (m, 11H), 6.55 (d, J = 16 Hz, 1H), 6.00 (dd, J = 16Hz, J = 8Hz, 1H), 4.35 (q, J = 6Hz, 2H), 4.10 (q, J = 6Hz, 2H), 4.00 (m, 2H), 3.70 (bs, 1H), 3.15 (t, 2H), 2.80 (m, 2H), 2.50 (m, 1H), 2.25 (t, 2H), 1.70-1.20 (m, 18H) |
| 99 (from 4-aminocarbonyl-piperidine) | | 81.2 | $^1$H-NMR (200 MHz, CDCl$_3$): 7.90 (d, 2H), 7.40-6.70 (m, 6H), 6.55 (d, J = 16 Hz, 1H), 6.00 (dd, J = 16Hz, J = 8Hz, 1H), 5.50 (2bs, 2H), 4.35 (q, J = 6Hz, 2H), 4.10 (q, J = 6Hz, 2H), 4.00 (m, 2H), 3.15 (m, 6H), 2.80 (m, 2H), 2.50 (m, 1H), 2.25-1.20 (m, 23H) |

-continued

| Ex. | Formula | Yield (%) | Spectroscopical data |
|---|---|---|---|
| 100 (from bis-(methoxy-ethyl)-amine) | | 95.6 | $^1$H-NMR (200 MHz, CDCl$_3$): 7.90 (d, 2H), 7.40-7.10 (m, 4H), 6.80 (m, 2H), 6.55 (d, J = 16Hz, 1H), 6.00 (dd, J = 16 Hz, J = 8Hz, 1H), 4.35 (q, J = 6Hz, 2H), 4.10 (q, J = 6Hz, 2H), 3.90 (m, 2H), 3.50 (m, 4H), 3.30 (s, 6H), 2.80-2.50 (m, 9H), 2.30 (m, 2H), 1.90-1.20 (m, 18H) |
| 101 (from di-methyl-amine) | | 97.9 | $^1$H-NMR (200 MHz, CDCl$_3$): 7.90 (d, 2H), 7.40-7.10 (m, 4H), 6.80 (m, 2H), 6.55 (d, J = 16Hz, 1H), 6.00 (dd, J = 16 Hz, J = 8Hz, 1H), 4.35 (q, J = 6Hz, 2H), 4.10 (q, J = 6Hz, 2H), 3.90 (m, 2H), 2.80 (m, 8H), 2.50 (m, 5H), 2.30 (m, 2H), 1.90-1.20 (m, 18H) |

| Ex. | Formula | Yield (%) | Spectroscopical data |
|---|---|---|---|
| 102 (from N-acetyl-piperazine) | | crude | ¹H-NMR (200 MHz, CDCl₃): 7.90 (d, 2H), 7.40-7.10 (m, 4H), 6.80 (m, 2H), 6.55 (d, J = 16Hz, 1H), 6.00 (dd, J = 16 Hz, J = 8Hz, 1H), 4.35 (q, J = 6Hz, 2H), 4.10 (q, J = 6Hz, 2H), 4.00 (m, 2H), 3.50 (m, 4H), 2.90 (m, 8H), 2.50 (m, 4H), 2.20 (m, 2H), 1.90-1.20 (m, 18H) |
| 103 (from N-benzyl-piperazine) | | crude | LC-MS: 669 (M + 1). Rf 4.01 min |

-continued
| Ex. | Formula | Yield (%) | Spectroscopical data |
|---|---|---|---|
| 104 (from pyrrol- idine) | 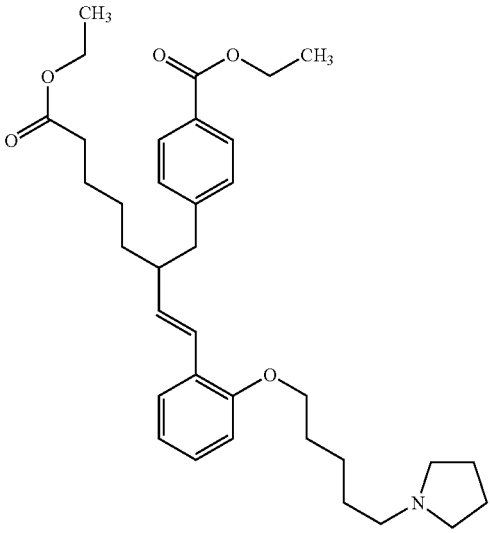 | 100 | ¹H-NMR (200 MHz, CDCl$_3$): 7.90 (d, 2H), 7.40-7.10 (m, 4H), 6.80 (m, 2H), 6.55 (d, J = 16Hz, 1H), 6.00 (dd, J = 16 Hz, J = 8Hz, 1H), 4.35 (q, J = 6Hz, 2H), 4.10 (q, J = 6Hz, 2H), 3.90 (m, 2H), 2.70 (m, 8H), 2.50 (m, 5H), 2.30 (m, 2H), 1.90-1.20 (m, 22H) |
| 105 (from N- phenyl- piper- azine) | 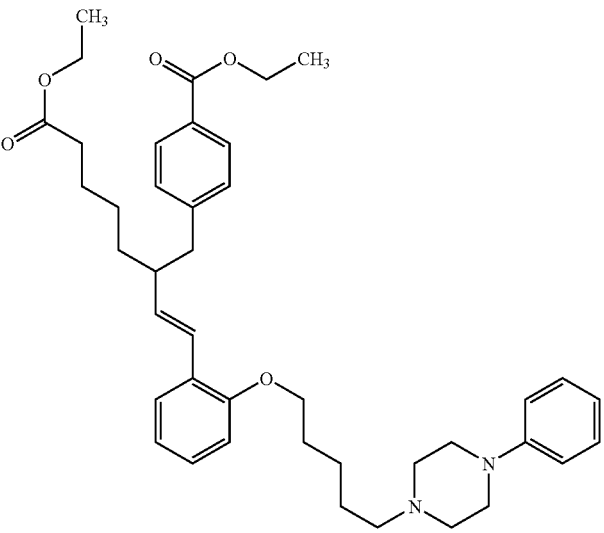 | crude | LC-MS: 655 (M + 1). Rf 4.07 min |

-continued

| Ex. | Formula | Yield (%) | Spectroscopical data |
|---|---|---|---|
| 106 (from N-methyl-piperazine) | | 97.0 | $^1$H-NMR (200 MHz, CDCl$_3$): 7.90 (d, 2H), 7.40-7.10 (m, 4H), 6.80 (m, 2H), 6.55 (d, J = 16Hz, 1H), 6.00 (dd, J = 16 Hz, J = 8Hz, 1H), 4.35 (q, J = 6Hz, 2H), 4.10 (q, J = 6Hz, 2H), 3.90 (m, 2H), 3.10 (m, 4H), 2.50 (m, 14H), 1.90-1.20 (m, 18H) |
| 107 (from piperidine) | | 96.5 | $^1$H-NMR (200 MHz, CDCl$_3$): 7.90 (d, 2H), 7.40-7.10 (m, 4H), 6.80 (m, 2H), 6.55 (d, J = 16Hz, 1H), 6.00 (dd, J = 16 Hz, J = 8Hz, 1H), 4.35 (q, J = 6Hz, 2H), 4.10 (q, J = 6Hz, 2H), 3.90 (m, 2H), 2.80 (m, 2H), 2.50 (m, 7H), 2.20 (t, 2H), 1.90-1.20 (m, 24H) |
| 108 (from pyrrole using the base KOH) | | 94.6 | $^1$H-NMR (400 MHz, d$^6$-DMSO): 7.80 (d, 2H), 7.40-6.80 (m, 6H), 6.65 (m, 2H), 6.30 (d, J = 16Hz, 1H), 6.00 (m, 3H), 4.35 (q, J = 6Hz, 2H), 4.10 (q, J = 6Hz, 2H), 3.90 (m, 4H), 2.80 (m, 2H), 2.50 (m, 1H), 2.20 (t, 2H), 1.90-1.20 (m, 18H) |

LC/MS conditions: column: symmetry C18 2.1×50 mm; mobile phase: aceto-nitrile/water; gradient: 10% acetonitrile to 90% acetonitrile; flow rate: 0.5 ml/min; detector: UV 210 nm.

109

6-(4-Carboxybenzyl)-8-(2-(5-N-morpholinopentyloxy)-7-(E)-octenoic acid

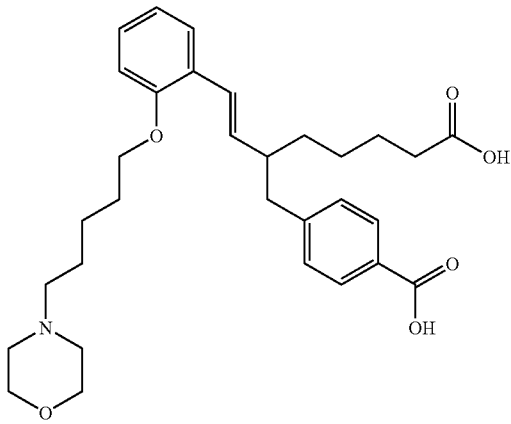

50 mg (0.09 mmol) of the diethyl ester from Ex. 97 are dissolved in 5 ml of methanol, and 0.5 ml of 45% strength aqueous sodium hydroxide solution is added. The reaction is exothermic. The mixture is allowed to warm to room temperature, and 0.3 ml of dichloromethane is added. After 20 hours at room temperature, the reaction solution is washed once with water, adjusted to pH=4 using 10% strength sulfuric acid and extracted twice with ethyl acetate, and the combined organic phases are dried over magnesium sulfate, filtered and concentrated.

Yield: 39.1 mg (86.6% of theory)

$^1$H-NMR (400 MHz, D$_2$O): 7.90 (d, 2H), 7.40-7.10 (m, 6H), 6.40 (d, J=16 Hz, 1H), 6.20 (dd, J=16 Hz, J=8 Hz, 1H), 3.90 (m, 2H), 3.70 (m, 4H), 2.90 (m, 1H), 2.80 (m, 1H), 2.50 (m, 5H), 2.30 (m, 2H), 2.25 (t, 2H), 1.70-1.20 (m, 12H)

The following compounds were prepared analogously:

| Ex. | Formula | Yield (%) | Spectroscopical data |
|---|---|---|---|
| 110 (from 98) | ![structure] | 53.8 | $^1$H-NMR (400 MHz, d$^6$-DMSO): 12.30 (bs, 2H), 7.90 (d, 2H), 7.30-6.80 (m, 9H), 6.55 (m, 2H), 6.40 (d, J = 16Hz, 1H), 6.00 (dd, J = 16Hz, J = 8Hz, 1H), 3.90 (m, 2H), 3.70 (bs, 1H), 3.00 (t, 2H), 2.70 (m, 2H), 2.50 (m, 1H), 2.15 (t, 2H), 1.70-1.20 (m, 12H) |

-continued

| Ex. | Formula | Yield (%) | Spectroscopical data |
|---|---|---|---|
| 111 (from 99) | | 33.3 | $^1$H-NMR (400 MHz, d$^6$-DMSO): 12.50 (bs, 2H), 7.90 (d, 2H), 7.40-6.60 (m, 6H), 6.45 (d, J = 16Hz, 1H), 6.00 (dd, J = 16Hz, J = 8Hz, 1H), 4.00 (m, 2H), 2.80-1.20 (m, 23H) |
| 112 (from 100) | | 68.3 | $^1$H-NMR (400 MHz, d$^6$-DMSO): 7.80 (d, 2H), 7.40-7.10 (m, 4H), 6.80 (m, 2H), 6.35 (d, J = 16Hz, 1H), 6.00 (dd, J = 16Hz, J = 8Hz, 1H), 3.90 (m, 2H), 3.40 (m, 4H), 3.20 (s, 6H), 2.90-2.40 (m, 9H), 2.20 (m, 2H), 1.80-1.20 (m, 12H) |
| 113 (from 101) | | | $^1$H-NMR (200 MHz, d$^6$-DMSO): 7.80 (d, 2H), 7.40-7.10 (m, 4H), 6.80 (m, 2H), 6.45 (d, J = 16Hz, 1H), 6.00 (dd, J = 16Hz, J = 8Hz, 1H), 3.90 (m, 2H), 2.80-1.20 (m, 25H) |

-continued
| Ex. | Formula | Yield (%) | Spectroscopical data |
|---|---|---|---|
| 114 (from 102) | 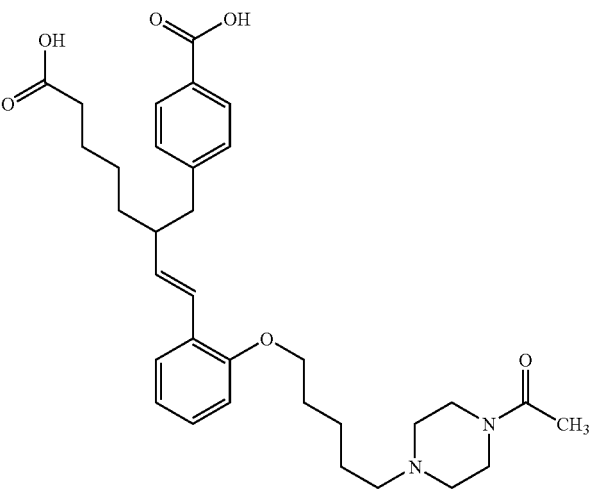 | 25.8 | $^1$H-NMR (200 MHz, d$^6$-DMSO): 7.80 (d, 2H), 7.40-6.50 (m, 6H), 6.45 (d, J = 16Hz, 1H), 6.00 (dd, J = 16Hz, J = 8Hz, 1H), 3.90 (m, 2H), 3.50-1.20 (m, 30H) <br> LC-MS: 565 (M + 1), Rf 3.20 min |
| 115 (from 103) | 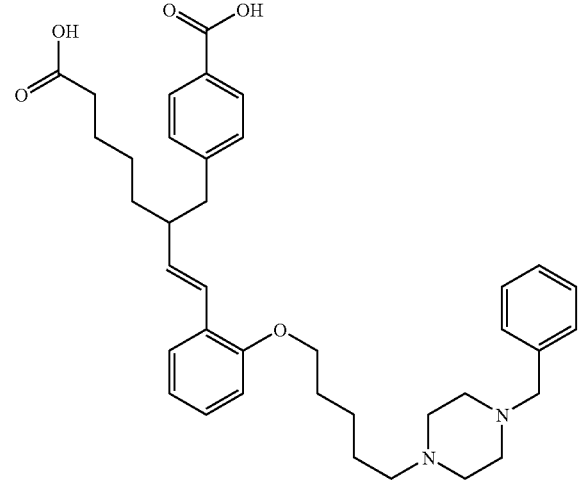 | 13.7 | LC-MS: 613 (M + 1), Rf 3.33 min |
| 116 (from 104) | 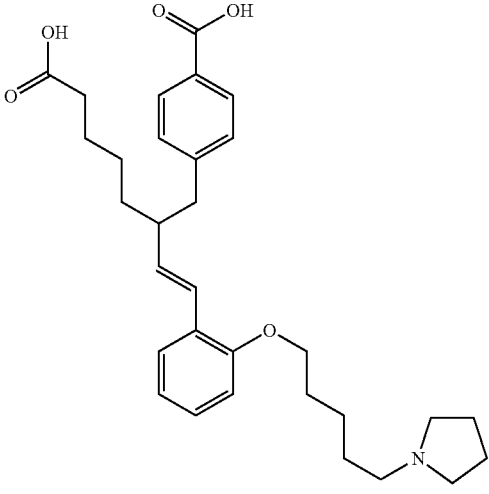 | 70.2 | LC-MS: 508 (M + 1), Rf 3.27 min <br> $^1$H-NMR (400 MHz, d$^6$-DMSO): 7.70 (d, 2H), 7.40-7.10 (m, 4H), 6.80 (m, 2H), 6.30 (d, J = 16Hz, 1H), 6.00 (dd, J = 16Hz, J = 8Hz, 1H), 3.90 (m, 2H), 3.40-1.20 (m, 27H) |

-continued
| Ex. | Formula | Yield (%) | Spectroscopical data |
|---|---|---|---|
| 117 (from 105) | 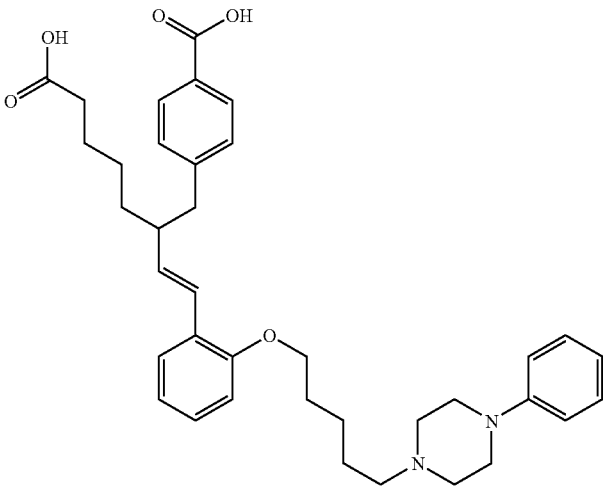 | 33.8 | LC-MS: 599 (M + 1), Rf 4.07 min $^1$H-NMR (400 MHz, d$^6$-DMSO): 7.70 (d, 2H), 7.40-6.70 (m, 11H), 6.30 (d, J = 16Hz, 1H), 6.00 (dd, J = 16Hz, J = 8Hz, 1H), 3.90 (m, 2H), 3.50-1.20 (m, 27H) |
| 118 (from 107) | 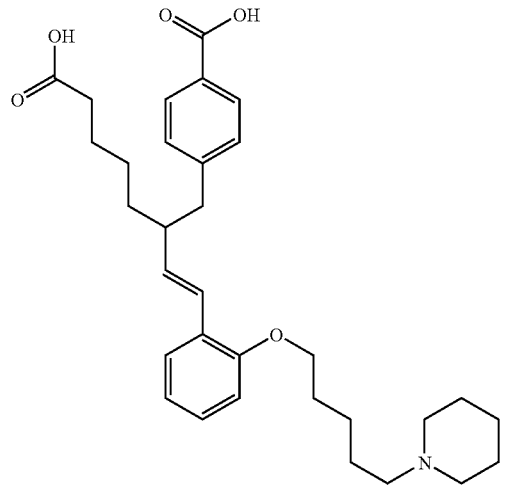 | 79.8 | LC-MS: 522 (M + 1), Rf 3.25 min $^1$H-NMR (200 MHz, d$^6$-DMSO): 7.80 (d, 2H), 7.40-7.10 (m, 4H), 6.80 (m, 2H), 6.40 (d, J = 16Hz, 1H), 6.00 (dd, J = 16Hz, J = 8Hz, 1H), 3.90 (m, 2H), 3.00 (m, 2H), 2.80 (m, 2H), 2.50-1.20 (m, 25H) |
| 119 (from 106) | 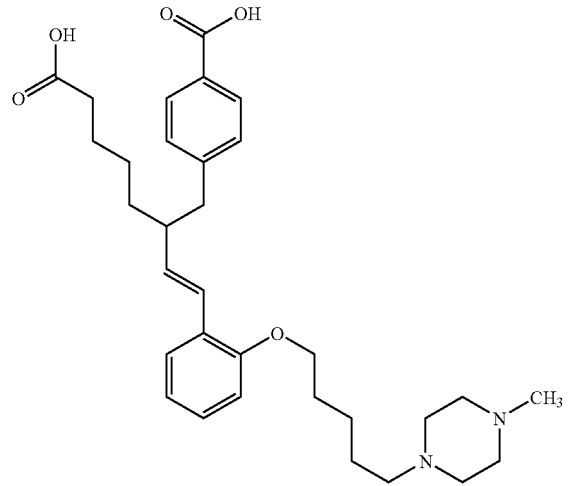 | 60.8 | $^1$H-NMR (400 MHz, d$^6$-DMSO): 7.90 (d, 2H), 7.40-7.10 (m, 4H), 6.80 (m, 2H), 6.40 (d, J = 16Hz, 1H), 6.00 (dd, J = 16Hz, J = 8Hz, 1H), 3.80 (m, 2H), 3.10-1.20 (m, 30H) |

-continued
| Ex. | Formula | Yield (%) | Spectroscopical data |
|---|---|---|---|
| 120 (from 108) | 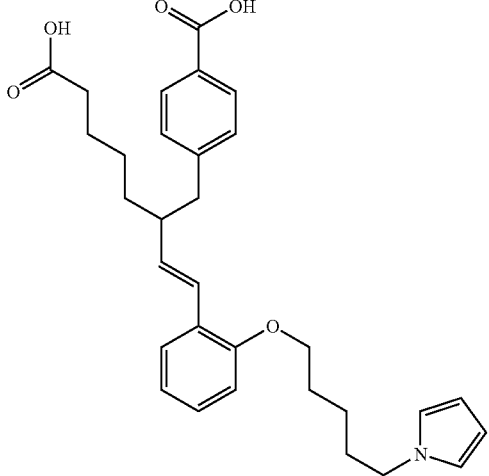 | crude | $^1$H-NMR (400 MHz, d$^6$-DMSO): 7.80 (d, 2H), 7.40-6.80 (m, 6H), 6.65 (m, 2H), 6.30 (d, J = 16Hz, 1H), 6.00 (m, 3H), 3.90 (m, 4H), 2.90-1.20 (m, 17H) |
| 120a (from 53 and 3-azabicyclo-[3.2.1]-octane) | 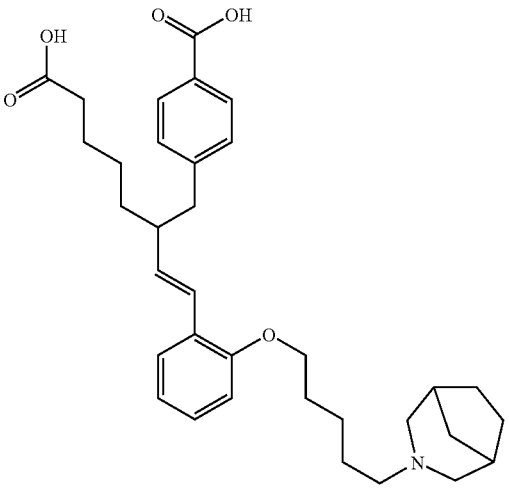 | | 548 (M + 1), Rt = 3.27 |
| 120b (from 53 and 4-methyl-piperidine) | 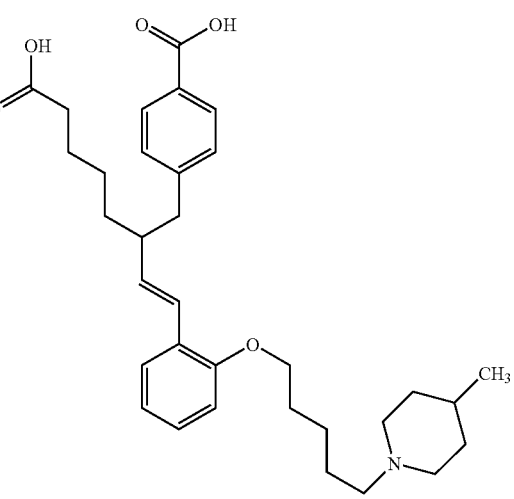 | | 536 (M + 1), Rt = 3.27 |

-continued
| Ex. | Formula | Yield (%) | Spectroscopical data |
|---|---|---|---|
| 120c from 53 and dibutyl-amine | 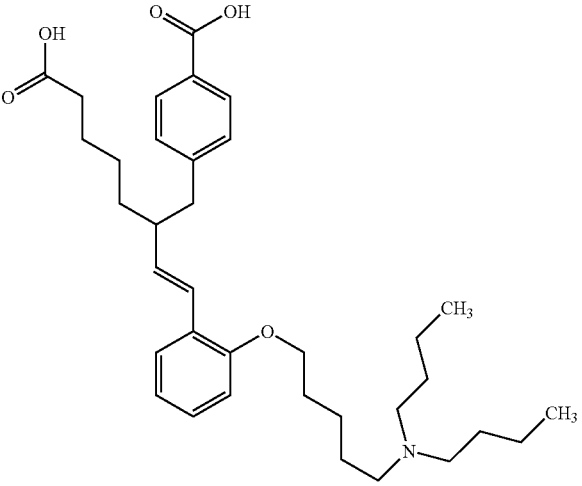 | | 566 (M + 1), Rt = 3.44 |
| 120d from 53 and thio-morpholine | 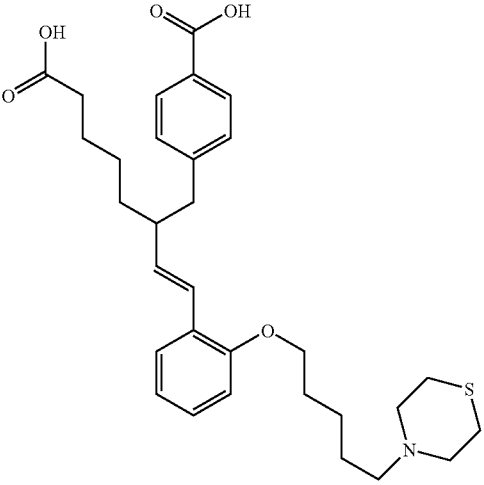 | | 540 (M + 1), Rt = 3.20 |
| 120e from 53 and benzyl-methyl-amine | 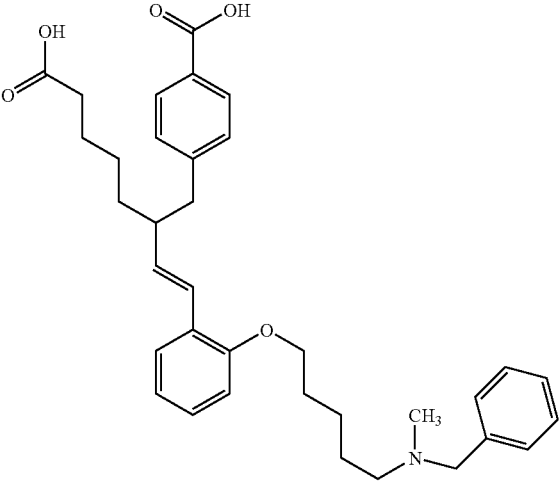 | | 558 (M + 1), Rt = 3.31 |

-continued

| Ex. | Formula | Yield (%) | Spectroscopical data |
|---|---|---|---|
| 120f from 53 and 4-cyclo-pentyl-piperazine | | | 591 (M + 1), Rt = 3.02 |
| 120g from 53 and 4-(3-methyl-phenyl)-piperazine | | | 613 (M + 1), Rt = 3.44 |
| 120h from 53 and 4-(3-methyl-phenyl)-piperazine | | | 613 (M + 1), Rt = 3.47 |

-continued

| Ex. | Formula | Yield (%) | Spectroscopical data |
|---|---|---|---|
| 120i from 53 and 4-(2,4-difluorophenyl)-piperazine | | | 635 (M + 1), Rt = 3.44 |
| 120j from 53 and 4-(4-fluorophenyl)-piperazine | | | 617 (M + 1), Rt = 3.42 |
| 120k from 53 and 4-(2-methoxyphenyl)-piperazine | | | 629 (M + 1), Rt = 3.38 |

-continued
| Ex. | Formula | Yield (%) | Spectroscopical data |
|---|---|---|---|
| 120l from 53 and 1-(2-pyridinyl)piperazine | 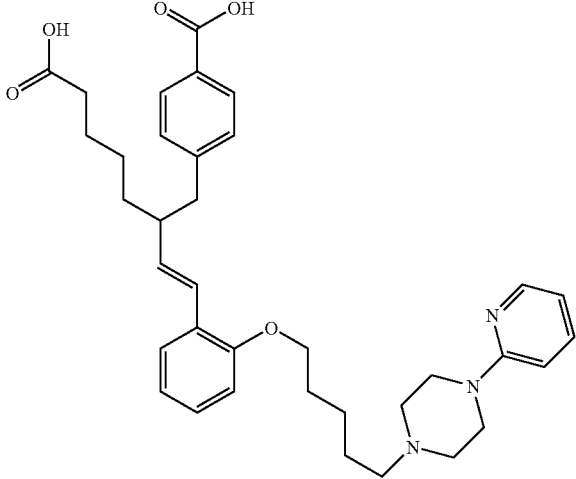 | | 600 (M + 1), Rt = 3.15 |
| 120m from 53 and N-methyl-N-(4-pyridinylmethyl)-amine | 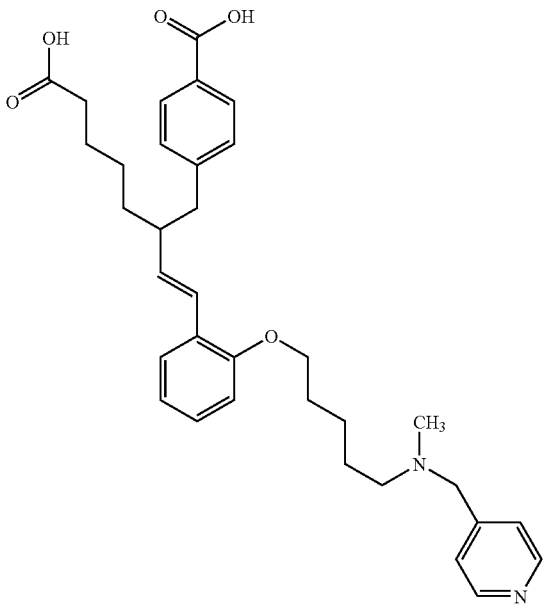 | | 559 (M + 1), Rt = 3.09 |
| 120n from 53 and 4-(3-trifluoromethylphenyl)-piperazine | 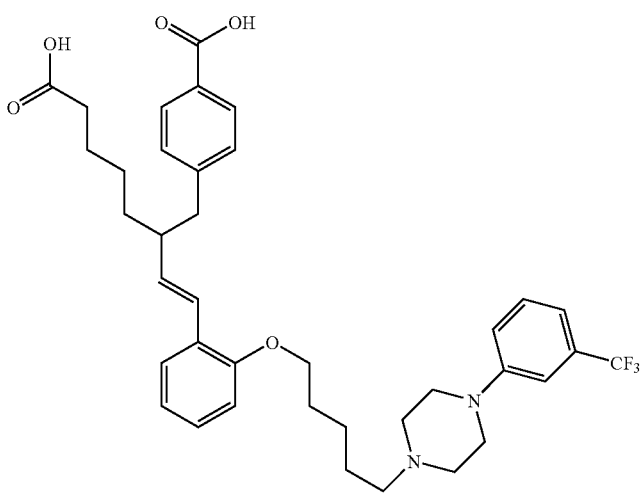 | | 667 (M + 1), Rt = 3.54 |

-continued
| Ex. | Formula | Yield (%) | Spectroscopical data |
|---|---|---|---|
| 120o from 53 and 1-(4-pyridinyl)piperazine | 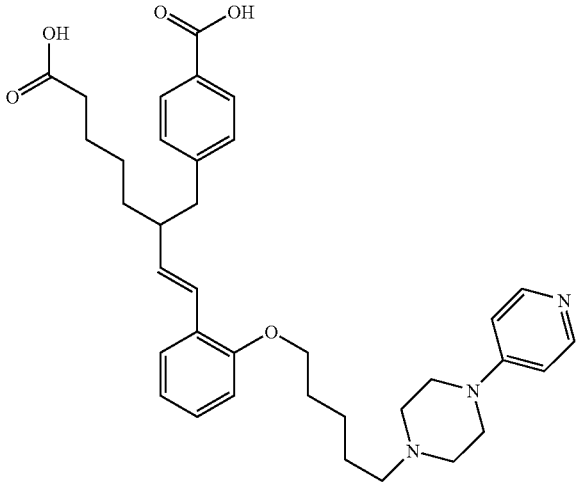 | | 600 (M + 1), Rt = 2.82 |
| 120p from 53 and 4-(4-chlorophenyl)-3-methylpiperazine | 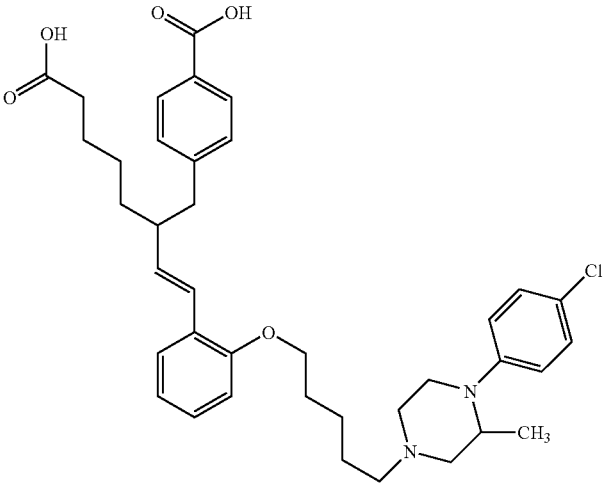 | | 647 (M + 1), Rt = 3.51 |
| 120q from 53 and azepane | 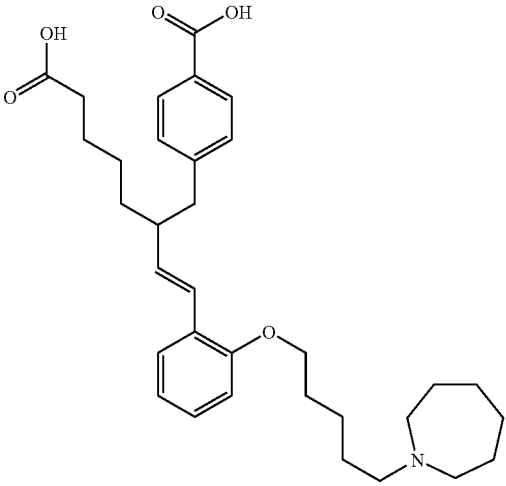 | | 536 (M + 1), Rt = 3.27 |

-continued

| Ex. | Formula | Yield (%) | Spectroscopical data |
|---|---|---|---|
| 120r from 53 and 4-(4-methoxyphenyl)-piperazine | | | 629 (M + 1), Rt = 3.38 |
| 120s from 53 and N,N-di-propylamine | | | 538 (M + 1), Rt = 3.33 |
| 120t from 53 and L-proline amide | | | 551 (M + 1), Rt = 3.15 |

| Ex. | Formula | Yield (%) | Spectroscopical data |
|---|---|---|---|
| 120u from 53 and 2-(1-piperazinyl)-pyrimidine | 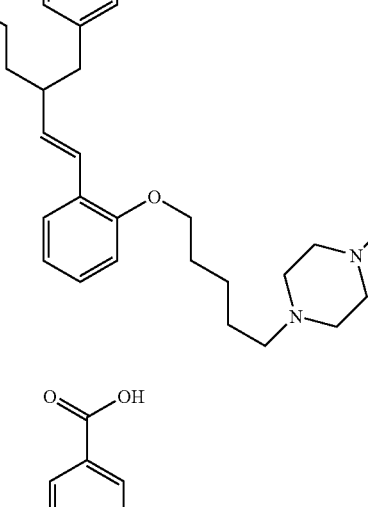 | | 601 (M + 1), Rt = 3.26 |
| 120v from 53 and benzylamine | 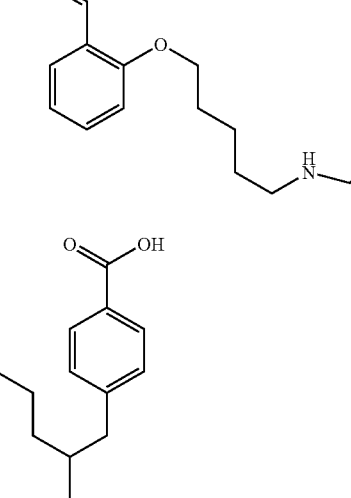 | | 544 (M + 1), Rt = 3.31 |
| 120w from 53 and cyclopentylamine | 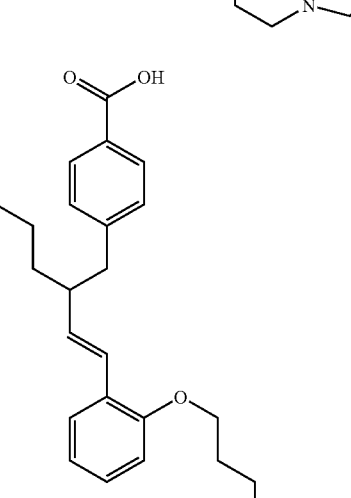 | | 522 (M + 1), Rt = 3.27 |

-continued
| Ex. | Formula | Yield (%) | Spectroscopical data |
| --- | --- | --- | --- |
| 120x from 53 and 4-trifluoro-methyl-aniline | 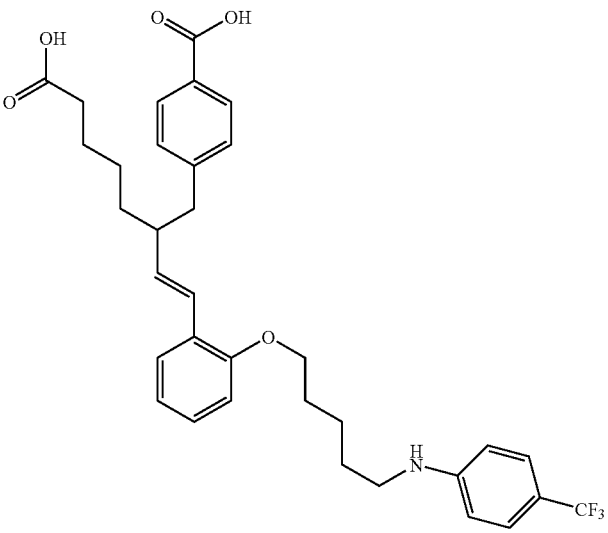 | | 598 (M + 1), Rt = 3.11 |
| 120y from 53 and 4-methoxy-aniline | 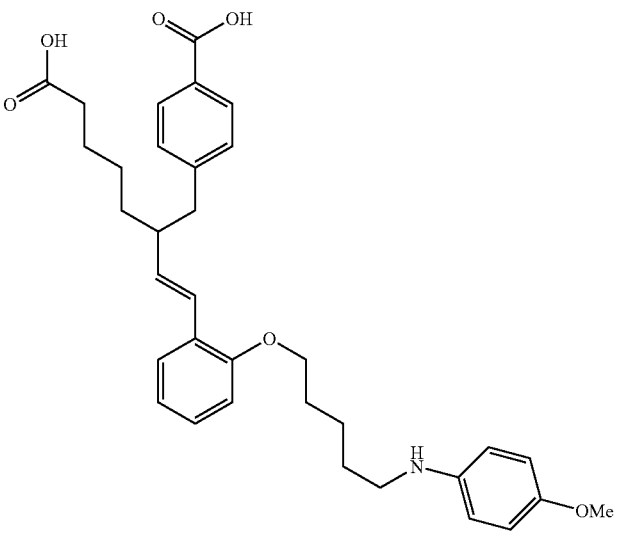 | | 560 (M + 1), Rt = 3.54 |
| 120z from 53 and 4-cyclo-heptyl-piperazine | 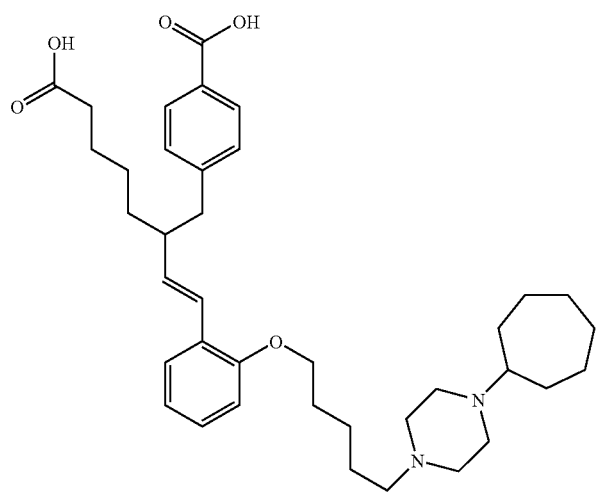 | | 619 (M + 1), Rt = 3.15 |

-continued

| Ex. | Formula | Yield (%) | Spectroscopical data |
|---|---|---|---|
| 120α from 53 and 3,5-dimethyl-morpholine | | | 552 (M + 1), Rt = 3.22 |
| 120β from 53 and N-methoxy-ethyl-N-methyl-amine | | | 526 (M + 1), Rt = 3.22 |
| 120γ from 53 and 4-dimethyl-amino-aniline | | | 573 (M + 1), Rt = 3.22 |

-continued

| Ex. | Formula | Yield (%) | Spectroscopical data |
|---|---|---|---|
| 120δ from 53 and N-methyl-N-(3-pyridinyl-methyl)-amine | | | 559 (M + 1), Rt = 3.13 |

LC/MS conditions: column: Symmetry C18 2.1 × 50 mm; mobile phase: acetonitrile/water; gradient: 10% acetonitrile to 90% acetonitrile; flow rate: 0.5 ml/min; detector: UV 210 nm.

The following examples were obtained in an analogous manner, using various halogen derivatives:

| Ex. | Formula | Yield (%) | Spectroscopical data |
|---|---|---|---|
| 120-I from 70b and morpholine | | | 498 (M + 1), Rt = 2.93 |

-continued

| Ex. | Formula | Yield (%) | Spectroscopical data |
|---|---|---|---|
| 120-II from 70b and 4-(3-methylphenyl)-piperazine | | | 587 (M + 1), Rt = 3.26[1] |
| 120-III from 70b and 4-(2-methylphenyl)-piperazine | | | 587 (M + 1), Rt = 3.28[1] |
| 120-IV from 70b and 4-(4-fluorophenyl)-piperazine | | | 591 (M + 1), Rt = 3.21[1] |

-continued
| Ex. | Formula | Yield (%) | Spectroscopical data |
|---|---|---|---|
| 120-V from 70b and 4-(2-methoxy-phenyl)-piperazine | 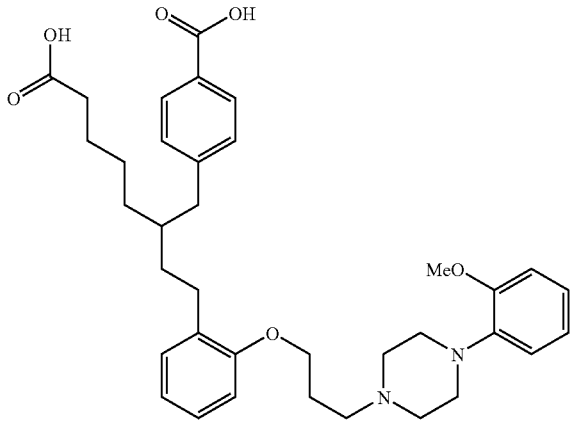 | | 603 (M + 1), Rt = 3.18[1)] |
| 120-VI from 70b and 4-(4-chloro-phenyl)-3-methylpiperazine | 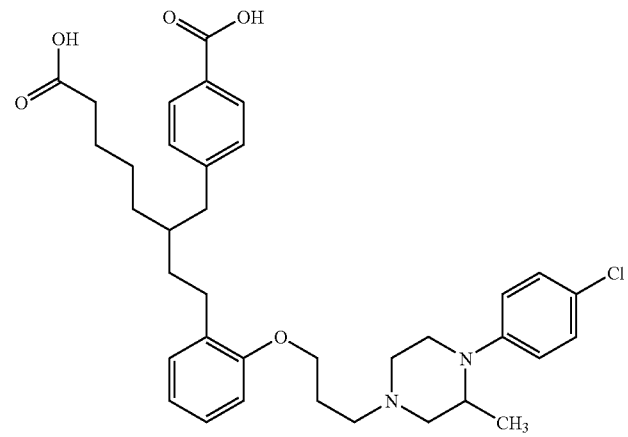 | | 621 (M + 1), Rt = 3.36[1)] |
| 120-VII from 70b and 2-(1-piperazin-yl)pyrimidine | 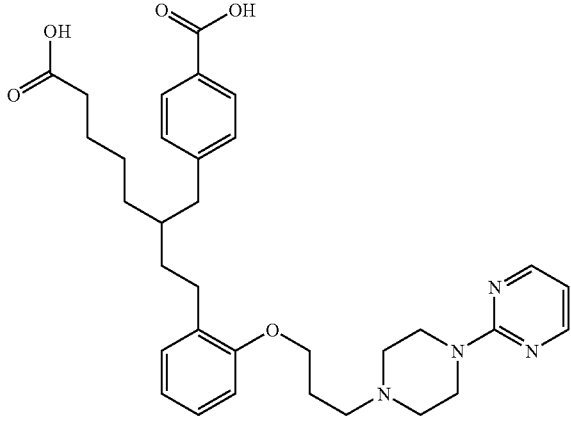 | | 575 (M + 1), Rt = 3.05[1)] |

-continued

| Ex. | Formula | Yield (%) | Spectroscopical data |
|---|---|---|---|
| 120-VIII from 70b and 3,5-dimethyl-morpholine | | | 526 (M + 1), Rt = 3.02[1] |
| 120-IX from 70d and morpholine | | | 512 (M + 1), Rt = 3.00[1] |
| 120-X from 70d and 4-(3-methyl-phenyl)-piperazine | | | 601 (M + 1), Rt = 3.31[1] |

-continued

| Ex. | Formula | Yield (%) | Spectroscopical data |
|---|---|---|---|
| 120-XI from 70d and 4-(2-methylphenyl)-piperazine | | | 601 (M + 1), Rt = 3.33[1) |
| 120-XII from 70d and 4-(4-fluorophenyl)-piperazine | | | 605 (M + 1), Rt = 3.27[1) |
| 120-XIII from 70d and 4-(2-methoxyphenyl)-piperazine | | | 617 (M + 1), Rt = 3.24[1) |

-continued

| Ex. | Formula | Yield (%) | Spectroscopical data |
|---|---|---|---|
| 120-XIV from 70d and 2-(1-piperazinyl)-pyrimidine | | | 589 (M + 1), Rt = 3.09[1)] |
| 120-XV from 70d and 4-(4-chlorophenyl)-3-methylpiperazine | | | 635 (M + 1), Rt = 3.33[1)] |
| 120-XVI from 70d and 3,5-dimethyl-morpholine | | | 539 (M + 1), Rt = 3.10[1)] |

| Ex. | Formula | Yield (%) | Spectroscopical data |
|---|---|---|---|
| 120-XVII from 70c and 4-(2,4-difluorophenyl)-piperazine | | | ¹H-NMR (400 MHz, CD3COCD3): 7.90 (d, 2H), 7.50-6.80 (m, 9H), 3.90 (t, 2H), 3.00 (m, 8H), 2.80-1.30 (m, 21H) |
| 120-XVIII from 70c and 4-(4-fluorophenyl)-piperazine | | | ¹H-NMR (400 MHz, DMSO): 7.90 (d, 2H), 7.50-6.80 (m, 10H), 3.90 (t, 2H), 3.00-1.30 (m) |
| 120-XIX from 70c and 4-phenylpiperazine | | | 601 (M + 1) |

-continued
| Ex. | Formula | Yield (%) | Spectroscopical data |
|---|---|---|---|
| 120-XX from 70b* and 4-(4-fluorophenyl)-piperazine | 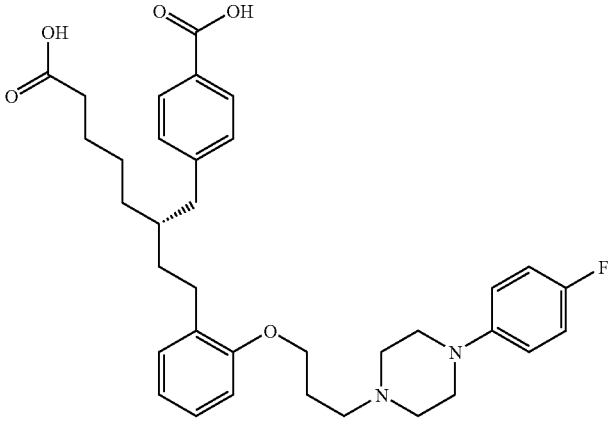 | | 591 (M + 1), Rt = 4.0 min (C18, 0.75 mL/min, ACN/H2O + H3PO4 [α] = +7.4° (c = 0.367) |
| 120-XXI from 70b* and 4-(4-trifluoro-methylphenyl)-piperazine | 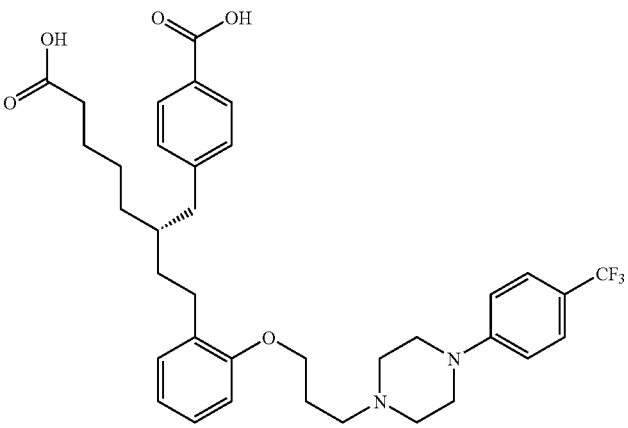 | | 641 (M + 1), Rt = 3.38[1)] |
| 120-XXII from 70b* and 4-phenylpiperazine | 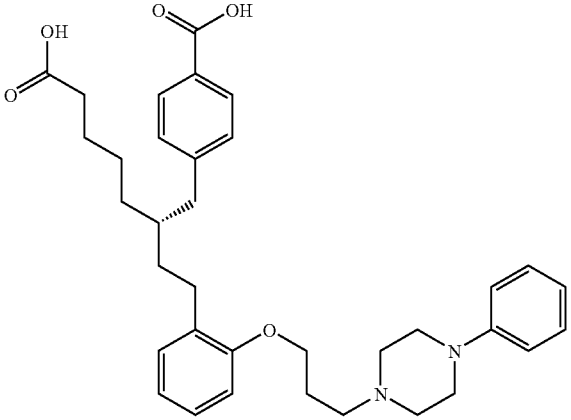 | | 573 (M + 1), Rt = 3.2[1)] |

-continued
| Ex. | Formula | Yield (%) | Spectroscopical data |
|---|---|---|---|
| 120-XXIII from 70b* and 4-(2,4-difluoro-phenylpiperazine | 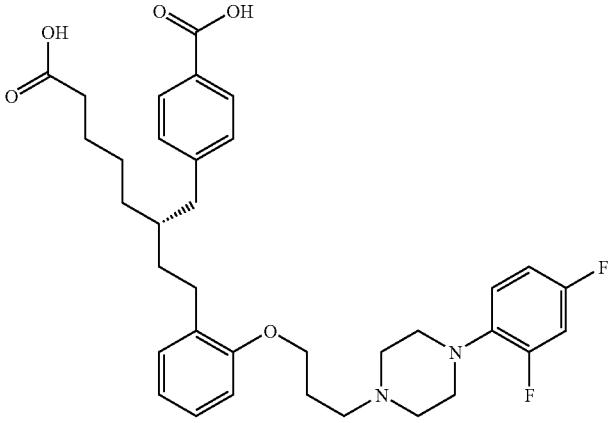 | | 609 (M + 1), Rt = 3.2[1)] |
| 120-XXIV from 70b* and 4-(4-methylphen-yl)piperazine | 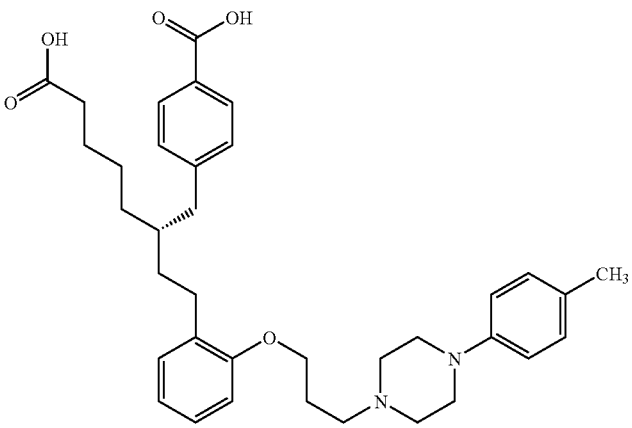 | | 587 (M + 1), Rt = 3.3[1)] |
| 120-XXV from 70e and 4-(2,4-difluoro-phenylpiperazine | 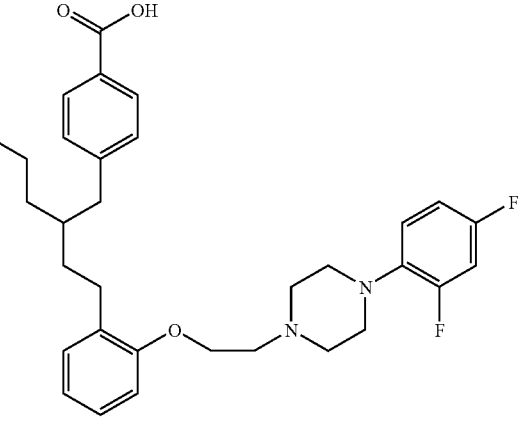 | | 595 (M + 1), Rt = 3.40[2)] |

| Ex. | Formula | Yield (%) | Spectroscopical data |
|---|---|---|---|
| 120-XXVI from 70e and 4-(4-trifluoro-methylphenyl-piperazine | 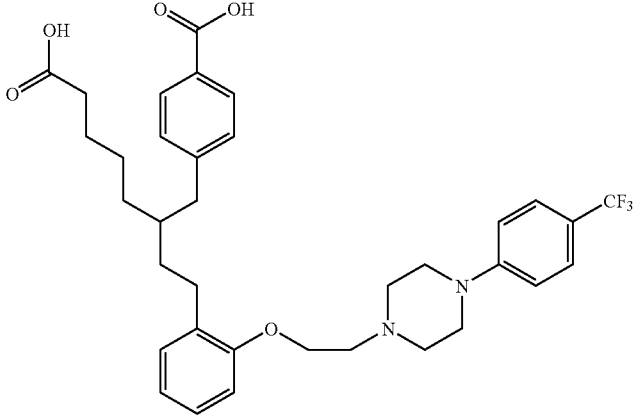 | | 627 (M + 1), Rt = 3.54[2)] |
| 120-XXVII from 70f and pyrrolidine | 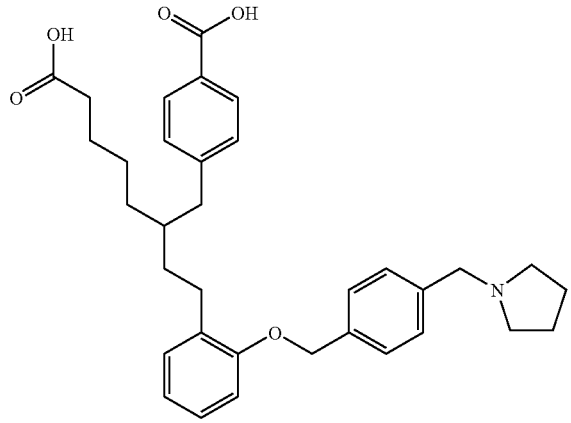 | | 544 (M + 1), Rt = 3.15[2)] |
| 120-XXVIII from 70f and morpholine | 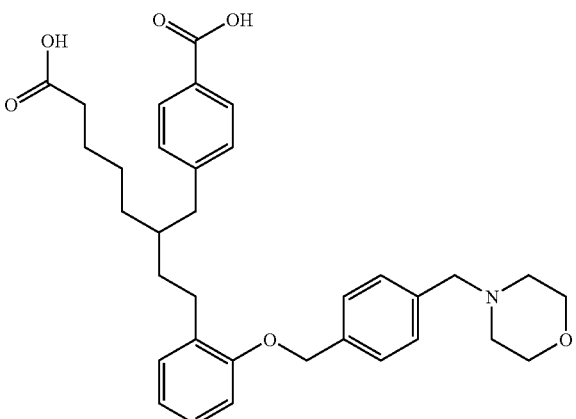 | | 560 (M + 1), Rt = 3.15[2)] |

-continued

| Ex. | Formula | Yield (%) | Spectroscopical data |
|---|---|---|---|
| 120-XXIX from 70f and piperidine | 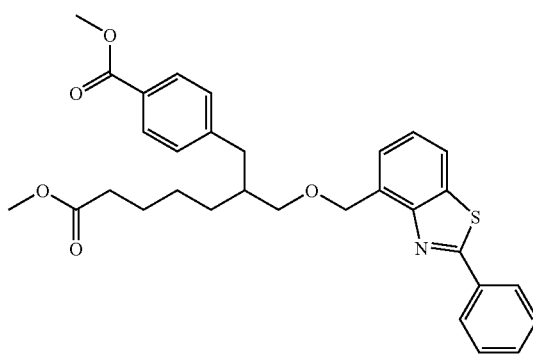 | | 558 (M + 1), Rt = 3.20[2) |

*prepared as pure enantiomer from enantiomerically pure Ex. 44 (see also the notes for Ex. 93)
[1)]LC/MS conditions: column: Symmetry C18 2.1*50 mm; mobile phase: acetonitrile/H2O (0.1% formic acid); gradient: 10% acetonitrile to 90% acetonitrile; flow rate: 0.5 ml/min; detector: UV 210 nm
[2)]LC/MS conditions: column: Symmetry C18 2.1*150 mm; mobile phase: acetonitrile + 0.6 g of 30% strength HCl/1 L H2O; gradient: 10% acetonitrile to 90% acetonitrile; flow rate: 0.6 ml/min; detector: UV 210 nm

121

Methyl 7-{[2-(3-fluorophenyl)-1,3-benzothiazol-4-yl]methoxy}-6-[4-(methoxycarbonyl)benzyl]heptanoate Under argon, 102.8 mg (0.32 mmol) of 4-bromomethyl-2-(3-fluorophenyl)-benzothiazole and 300 mg of MS3A are dissolved in 5 ml of benzene. At room temperature, 82 mg (0.27 mmol) of methyl 6-hydroxymethyl-7-(4-methoxycarbonyl-phenyl)heptanoate (synthesis cf. EP-A-0 341 551, p. 31, Ex. 42) and 92 mg (0.40 mmol) of silver oxide are added. The mixture is stirred at room temperature for 6 days. About 0.2 ml of water is added, the mixture is filtered through Extrelut, which is washed with toluene, and the filtrate is concentrated under reduced pressure and chromatographed.

Yield: 64 mg (43.8% of theory)

$^1$H-NMR (200 MHz, CDCl$_3$): 8.00-7.10 (m, 11H), 5.10 (s, 2H), 3.90 (s, 3H), 3.70 (s, 3H), 3.50 (m, 2H), 2.70 (m, 2H), 2.30 (m, 2H), 1.80 (m, 1H), 1.70-1.20 (m, 6H)

The following substances were synthesized analogously:

| Ex. | Formula | Yield (%) | Spectroscopical data |
|---|---|---|---|
| 122 (from benzyl bromide) | | 43.3 | $^1$H-NMR (200 MHz, CDCl$_3$): 7.95 (m, 2H), 7.40-6.80 (m, 7H), 4.50 (s, 2H), 3.90 (s, 3H), 3.70 (s, 3H), 3.30 (d, 2H), 2.80 (m, 2H), 2.30 (m, 2H), 1.90-1.30 (m, 7H) |

-continued

| Ex. | Formula | Yield (%) | Spectroscopical data |
|---|---|---|---|
| 123 (from 3-(2-fluorophenoxy)benzyl bromide) | 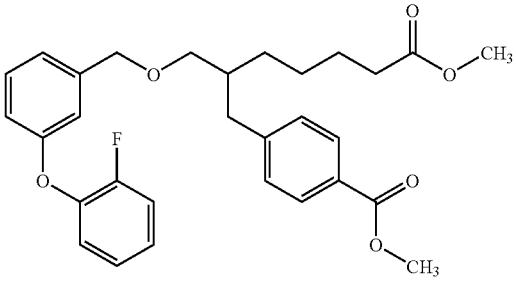 | crude | $^1$H-NMR (200 MHz, CDCl$_3$): 7.95 (m, 2H), 7.40-6.80 (m, 10H), 4.40 (s, 2H), 3.90 (s, 3H), 3.70 (s, 3H), 3.30 (d, 2H), 2.80 (m, 2H), 2.30 (m, 2H), 1.90 (m, 1H), 1.70-1.00 (m, 6H) |
| 124 (from 4-fluoro-1-bromomethyl-naphthalene) | 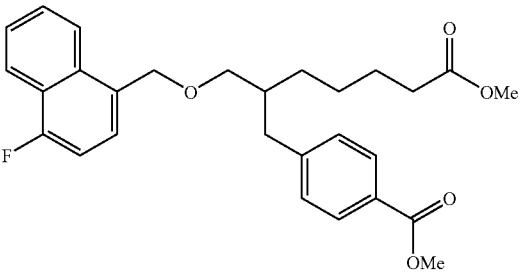 | 96.7 | $^1$H-NMR (200 MHz, CDCl$_3$): 8.10-6.80 (m, 10H), 4.80 (s, 2H), 3.90 (s, 3H), 3.70 (s, 3H), 3.30 (d, 2H), 2.70 (m, 2H), 2.30 (m, 2H), 1.90 (m, 1H), 1.70-1.30 (m, 6H) |
| 125 (from 4-t-butylbenzyl bromide) | 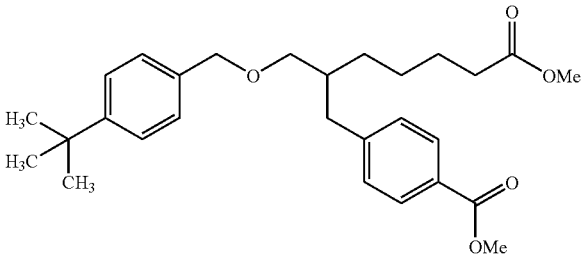 | 38.1 | $^1$H-NMR (200 MHz, CDCl$_3$): 7.95 (m, 2H), 7.40-6.80 (m, 6H), 4.40 (s, 2H), 3.90 (s, 3H), 3.70 (s, 3H), 3.40 (m, 2H), 2.70 (m, 2H), 2.30 (m, 2H), 1.90 (m, 1H), 1.70-1.30 (m, 15H) |
| 126 (from 2-bromomethyl-biphenyl) | 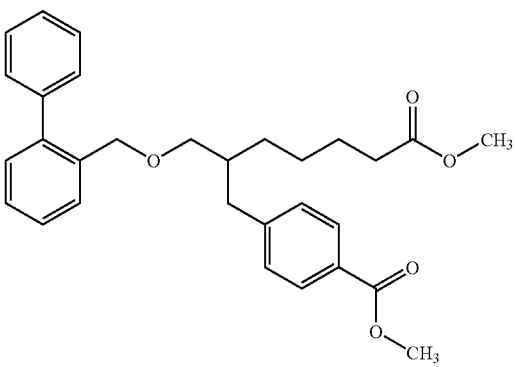 | 57.1 | $^1$H-NMR (200 MHz, CDCl$_3$): 7.95 (m, 2H), 7.40-6.80 (m, 11H), 4.40 (s, 2H), 3.90 (s, 3H), 3.70 (s, 3H), 3.20 (m, 2H), 2.60 (m, 2H), 2.30 (m, 2H), 1.90 (m, 1H), 1.70-1.30 (m, 6H) |
| 127 (from 2-difluoromethoxy-benzyl bromide) | 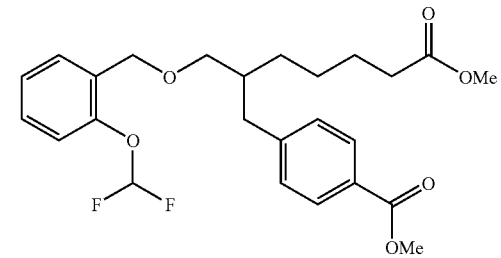 | 51.0 | $^1$H-NMR (200 MHz, CDCl$_3$): 7.95 (m, 2H), 7.40-7.00 (m, 6H), 6.40 (dt, 1H), 4.50 (s, 2H), 3.90 (s, 3H), 3.70 (s, 3H), 3.30 (d, 2H), 2.60 (m, 2H), 2.30 (m, 2H), 1.90 (m, 1H), 1.70-1.30 (m, 6H) |

| Ex. | Formula | Yield (%) | Spectroscopical data |
|---|---|---|---|
| 128 (from 2-chloro-6-methoxy-benzyl bromide) | | 63.9 | $^1$H-NMR (200 MHz, CDCl$_3$): 7.95 (m, 2H), 7.40-6.80 (m, 5H), 4.60 (s, 2H), 4.00 (m, 2H), 3.90 (s, 3H), 3.70 (s, 3H), 3.30 (m, 2H), 2.60 (m, 2H), 2.30 (m, 2H), 1.90 (m, 1H), 1.70-1.30 (m, 9H) |
| 129 (from 3-fluorobenzyl bromide) | | crude | $^1$H-NMR (200 MHz, CDCl$_3$): 7.95 (m, 2H), 7.40-6.80 (m, 6H), 4.40 (s, 2H), 3.90 (s, 3H), 3.70 (s, 3H), 3.30 (d, 2H), 2.60 (m, 2H), 2.30 (m, 2H), 1.90 (m, 1H), 1.70-1.30 (m, 6H) |

130

6-(4-Carboxybenzyl)-7-{[2-(3-fluorophenyl)-1,3-benzothiazol-4-yl]methoxy}-heptanoic acid

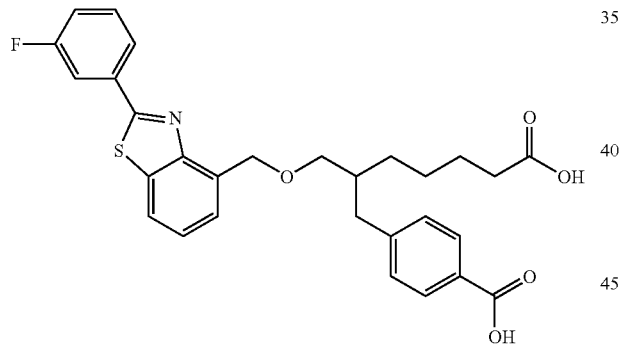

The diester from Ex. 121 is dissolved in 5 ml of methanol, and 0.8 ml of 45% strength aqueous sodium hydroxide solution is added. At room temperature, 0.3 ml of dichloromethane is added. After 20 hours at room temperature, the reaction solution is washed once with ether, acidified with 10% strength sulfuric acid and extracted twice with ethyl acetate, the combined organic phases are filtered through Extrelut and the solvent is evaporated under reduced pressure.

Yield: 39.5 mg (38.5% of theory)

LC/MS: 522 (M+1), Rt=4.98 min

The following substances are synthesized analogously:

| Ex. | Formula | Yield (%) | Spectroscopical data |
|---|---|---|---|
| 131 (from 122) | | 56.9 | $^1$H-NMR (200 MHz, CDCl$_3$): 9.90 (bs, 2H), 7.95 (m, 2H), 7.40-6.80 (m, 7H), 4.50 (s, 2H), 3.20 (d, 2H), 2.80 (m, 2H), 2.30 (m, 2H), 1.90-1.30 (m, 7H) |

-continued

| Ex. | Formula | Yield (%) | Spectroscopical data |
|---|---|---|---|
| 132 (from 123) | | 24.8 | 481 (M + 1), Rt = 4.53 min |
| 133 (from 124) | | 43.7 | 439 (M + 1), Rt = 4.51 min |
| 134 (from 125) | | 27.9 | 427 (M + 1), Rt = 4.77 min |
| 135 (from 126) | | 25.1 | 447 (M + 1), Rt = 4.71 min |
| 136 (from 127) | | 21.1 | 437 (M + 1), Rt = 4.32 min |

-continued

| Ex. | Formula | Yield (%) | Spectroscopical data |
|---|---|---|---|
| 137 (from 128) | | 24.5 | 449 (M + 1), Rt = 4.57 min |
| 138 (from 129) | | 50.9 | 389 (M + 1), Rt = 4.28 min |

LC/MS conditions: column: Symmetry C18 2.1 × 50 mm; mobile phase: acetonitrile/water; gradient: 10% acetonitrile to 90% acetonitrile; flow rate: 0.5 ml/min; detector: UV 210 nm.

139

6-(4-Carboxbenzyl)-7-(4-methoxphenoxy)heptanoic acid

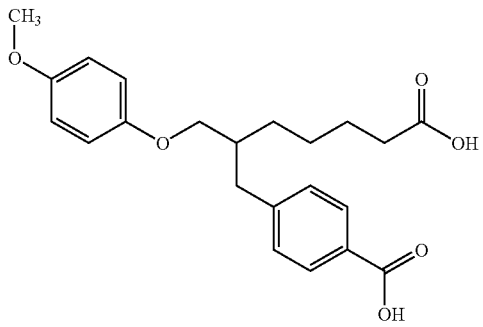

Under argon, 16.8 mg (0.14 mmol) of 4-methoxyphenol are dissolved in dimethylformamide, and 7.5 mg (0.19 mmol) of sodium hydride (60% oily suspension) are added at room temperature. The mixture is stirred at this temperature for 30 minutes, and a solution of 41.6 mg (0.10 mmol) of ethyl 7-bromo-6-(4-ethoxycarbonylbenzyl)heptanoate (preparable from methyl 6-hydroxymethyl-7-(4-methoxycarbonylphenyl)heptanoate (synthesis cf. EP-A-0 341 551, p. 31, Ex. 42) by reaction with brominating agents such as $PBr_3$) in DMF is added at this temperature. The reaction mixture is heated at 60° C. After 18 hours, another 20 mg of sodium hydride are added, and the mixture is heated at 100° C. After 20 hours, the mixture is cooled, admixed with water and washed with ethyl acetate. The aqueous phase is adjusted to pH 2 using 1N hydrochloric acid and extracted twice with ethyl acetate. The organic phase is dried with magnesium sulfate and concentrated under reduced pressure.

Yield: 24 mg (59.6% of theory)

$^1$H-NMR (200 MHz, $CDCl_3$): 7.90 (m, 4H), 7.30 (m. 4H), 3.70 (s, 3H), 3.40 (m, 2H), 2.60 (m, 2H), 2.30 (m, 2H), 1.70-1.30 (m, 7H).

The following compounds were prepared analogously:

| Ex. | Formula | Yield (%) | Spectroscopical data |
|---|---|---|---|
| 140 (from 3-trifluoro-methyl-phenol) | | 86.3 | $^1$H-NMR (200 MHz, $CDCl_3$): 12.50 (bs, 2H), 7.90-7.00 (m, 8H), 3.70 (d, 2H), 2.80 (m, 2H), 2.30 (m, 2H), 1.70-1.30 (m, 7H) |

| Ex. | Formula | Yield (%) | Spectroscopical data |
|---|---|---|---|
| 141 (from 2-benzyl-oxy-phenol) | | 89.3 | ¹H-NMR (200 MHz, CDCl₃): 11.10 (bs, 2H), 7.90-6.70 (m, 13H), 5.10 (s, 2H), 3.00 (m, 2H), 2.80-1.30 (m, 13H) |
| 142 (from 5-phenyl-pentyl-oxy-phenol) | | 55.2 | ¹H-NMR (200 MHz, CDCl₃): 7.90-6.70 (m, 13H), 4.10 (m, 2H), 3.80 (d, 2H), 5.10 (s, 2H), 2.80-1.30 (m, 19H) |

143

Methyl 7-anilino-6-(4-methoxycarbonylbenzyl)heptanoate

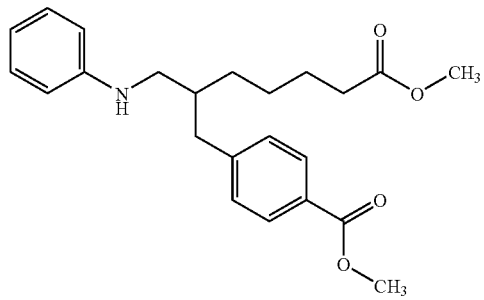

30.0 mg (0.33 mmol) of aniline are dissolved in dichloromethane and 0.02 ml of acetic acid and a solution of 90.6 mg (0.30 mmol) of ethyl 6-formyl-7-(4-methoxy-carbonylphenyl)heptanoate (synthesis cf. EP-A-0 341 551, p. 32, Ex. 44) in dichloromethane are added. After 30 minutes at room temperature, the solution is cooled to 0° C., and 87.7 mg (0.41 mmol) of sodium triacetoxyborohydride are added. The reaction mixture is stirred at room temperature for 18 hours, 0.2 ml of water are added and the mixture is filtered through Extrelut. For purification, the substance is chromatographed on 10 g of silica gel 60 (particle size 0.040-0.063 mm) using the mobile phase cyclohexane/ethyl acetate 3:1 to 1:1.

Yield: 52 mg (45.9% of theory)

¹H-NMR (200 MHz, CDCl₃): 7.95 (m, 2H), 7.20 (m, 4H), 6.70 (m, 2H), 6.50 (d, 1H), 3.90 (s, 3H), 3.70 (s, 3H), 3.60 (bs, 1H), 3.00 (m, 2H), 2.70 (d, 2H), 2.30 (m, 2H), 2.00 (m, 1H), 1.70-1.30 (m, 6H).

The following compounds were prepared analogously:

| Ex. | Formula | Yield (%) | Spectroscopical data |
|---|---|---|---|
| 144 (from benzylamine) | | 17.4 | ¹H-NMR (200 MHz, CDCl₃): 7.95 (m, 2H), 7.30 (m, 7H), 4.35 (q, J = 6Hz, 2H), 4.10 (q, J = 6Hz, 2H), 3.70 (s, 2H), 2.70 (m, 4H), 2.50 (m, 2H), 2.30 (t, 2H), 1.80 (m, 1H), 1.70-1.20 (m, 12H) |
| 145 (from 2-(5-phenyl-pentyloxy)-aniline) | | 93.4 | ¹H-NMR (200 MHz, CDCl₃): 7.95 (m, 2H), 7.20 (m, 7H), 6.70 (m, 2H), 6.50 (m, 2H), 4.35 (q, J = 6Hz, 2H), 4.20 (bs, 1H), 4.10 (q, J = 6Hz, 2H), 3.90 (t, 2H), 3.10 (m, 2H), 2.70 (m, 4H), 2.30 (m, 2H), 2.00 (m, 1H), 1.90-1.40 (m, 18H) |
| 146 (from 2-benzyloxy-aniline) | | 47.7 | ¹H-NMR (200 MHz, CDCl₃): 7.95 (m, 2H), 7.50-7.20 (m, 7H), 6.80-6.50 (m, 4H), 5.00 (s, 2H), 4.35 (q, J = 6Hz, 2H), 4.10 (q, J = 6Hz, 2H), 3.30 (bs, 1H), 3.10 (m, 2H), 2.70 (m, 2H), 2.30 (m, 2H), 2.00 (m, 1H), 1.60-1.40 (m, 12H) |
| 147 (from 2-butylaniline) | | 58.5 | ¹H-NMR (200 MHz, CDCl₃): 7.95 (m, 2H), 7.30 (m, 2H), 6.90 (m, 2H), 6.50 (m, 2H), 4.35 (q, J = 6Hz, 2H), 4.10 (q, J = 6Hz, 2H), 3.70 (bs, 1H), 3.10 (m, 2H), 2.70 (m, 2H), 2.50 (m, 2H), 2.30 (m, 2H), 2.00 (m, 1H), 1.60-1.30 (m, 16H), 0.90 (t, 3H) |

148

7-Anilino-6-(4-carboxybenzyl)heptanoic acid

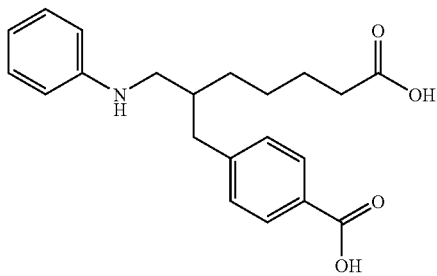

This substance is prepared analogously to Example 130 by hydrolysis of the ester from Ex. 143.

Yield: 30.5 mg (74.8 of theory)

LC/MS: 356 (M+1), R 3.9 min

The following compounds were prepared analogously:

| Ex. | Formula | Yield (%) | Spectroscopical data |
|---|---|---|---|
| 149 (from 144) | | 17.4 | $^1$H-NMR (400 MHz, d$^6$-DMSO): 7.95 (m, 2H), 7.20 (m, 7H), 3.60 (bs, 1H), 3.20 (m, 4H), 2.70-1.20 (m, 15H) |
| 150 (from 145) | | 59.9 | $^1$H-NMR (200 MHz, CDCOCD$_3$): 10.80 (bs, 2H), 7.95 (m, 2H), 7.30 (m, 2H), 7.10 (m, 5H), 6.70 (m, 2H), 6.50 (m, 2H), 3.90 (t, 2H), 3.10 (m, 2H), 2.80 (m, 3H), 2.60 (m, 2H), 2.30 (m, 2H), 2.00 (m, 1H), 1.90-1.40 (m, 12H) |
| 151 (from 146) | | 83.3 | $^1$H-NMR (200 MHz, CDCOCD$_3$): 10.60 (bs, 2H), 7.95 (m, 2H), 7.50-7.20 (m, 7H), 6.80 (m, 2H), 6.50 (m, 2H), 5.10 (s, 2H), 3.10 (m, 2H), 2.80 (m, 3H), 2.30 (m, 2H), 2.00 (m, 1H), 1.60-1.40 (m, 6H) |

| Ex. | Formula | Yield (%) | Spectroscopical data |
|---|---|---|---|
| 152 (from 147) | 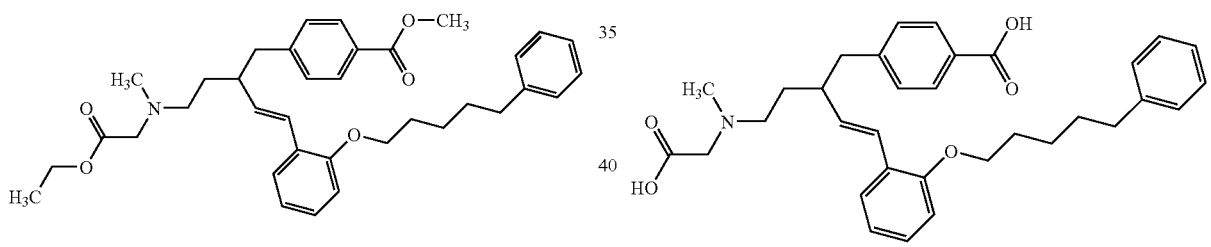 | 71.4 | ¹H-NMR (200 MHz, CDCOCD₃): 10.60 (bs, 2H), 7.95 (m, 2H), 7.30 (m, 2H), 6.90 (m, 2H), 6.50 (m, 2H), 3.10 (m, 2H), 2.80 (m, 3H), 2.50 (m, 2H), 2.30 (m, 2H), 2.00 (m, 1H), 1.60-1.30 (m, 10H), 0.90 (t, 3H) |

153

Methyl 4-((E/Z)-2-{2-[(2-ethoxy-2-oxoethyl)(methyl)amino]ethyl}-4-{2-[(5phenylpentyl)oxy]phenyl}-3-butenyl)benzoate 0.532 g (0.89 mmol) of triphenyl{2-[(5-phenylpentyl)oxy]benzyl}phosphonium bromide (preparable analogously to Exs IId to IVd using 5-phenylpentyl bromide instead of butyl bromide) is suspended in 10 ml of THF and, at −20° C., treated with 0.671 ml of a 1.6 M solution of n-butyllithium in n-hexane. The mixture is stirred at −20° C. for 30 minutes, and 0.300 g (0.89 mmol) of methyl 4-{4-[(2-ethoxy-2-oxoethyl)(methyl)amino]-2-formylbutyl}benzoate from Ex.XI, dissolved in 3 ml of THF, is then added. The mixture is stirred at −20° C. for another hour, 20 ml of water are added and the mixture is extracted repeatedly with ethyl acetate. The combined organic phases are washed with saturated sodium chloride solution and dried over magnesium sulfate, and the solvent is distilled off under reduced pressure.

Yield: 192.1 mg (37.1% of theory) E/Z mixture (85:15)

¹H-NMR (300 MHz, d⁶-DMSO): δ=1.15 (t), 1.2-1.7 (m), 2.20 (s), 2.55 (t), 2.70 (m), 2.85 (m) 3.20 (s), 3.80 (s), 3.90 (m), 4.05 (q), 5.75 (s), 6.05 (dd), 6.35 (d), 6.90 (dd)7.1-7.4 (m), 7.85 (d).

154

4-((E/Z)-2-{2-[(Carboxymethyl)(methyl)amino]ethyl}-4-{2-[(5-phenyl-pentyl)oxy]phenyl}-3-butenyl)benzoic acid At 0° C., 130 mg (0.230 mmol) of methyl 4-((E/Z)-2-{2-[(2-ethoxy-2-oxoethyl)-(methyl)amino]ethyl}-4-{2-[(5-phenylpentyl)oxy]phenyl}-3-butenyl)benzoate from Ex. 153 in 5 ml of methanol are treated with 1.2 ml of 45% strength aqueous sodium hydroxide solution. The mixture is warmed to 22° C., methylene chloride is added until a clear solution is obtained, and the mixture is stirred for another 18 hours. The alkaline solution is diluted with water and extracted with methylene chloride. The aqueous phase is then adjusted twice to pH 2-3 using 2N HCl and extracted repeatedly with methylene chloride. The combined organic phases are washed with saturated sodium chloride solution and dried over magnesium sulfate, and the solvent is distilled off under reduced pressure.

Yield: 55.9 mg (45.1% of theory) E/Z mixture (85:15)

¹H-NMR (300 MHz, d⁶-DMSO): δ=1.05(d), 1.40 (m), 1.65 (m), 2.55 (m), 2.80 (m), 3.0 (m), 3.20 (s), 3.85 (m), 3.50 (s), 3.90 (m), 6.03 (dd), 6.45 (d), 6.90 (dd), 7.1-7.4 (m), 7.85 (d).

155

4-((E/Z)-2-{2-[(2-methoxy-2-oxoethyl)sulfanyl]ethyl}-4-{2-[(5-phenylpentyl)-oxy]phenyl}-3-butenyl)benzoate

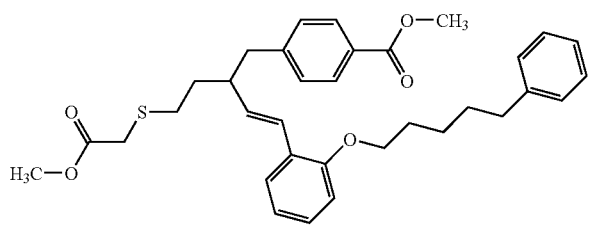

41.078 mg (1.03 mmol) of sodium hydride (80%) are initially charged in 5 ml of THF, and 104.32 mg (0.93 mmol) of methyl mercaptoacetate are added. After 10 minutes, 500.0 mg (0.930 mmol) of methyl-4-((E/Z)-2-(2-bromoethyl)-4-{2-[(5-phenylpentyl)oxy]phenyl}-3-butenyl)benzoate from Ex. IX, dissolved in 2 ml of THF, are added, and the mixture is stirred at 22° C. for 18 hours. 20 ml of water are carefully added to the reaction mixture, which is then extracted with ethyl acetate. The combined organic phases are washed with saturated sodium chloride solution and dried over magnesium sulfate, and the solvent is distilled off under reduced pressure. The purification is carried out on silica gel (0.04-0.063 nm) using the mobile phase methylene chloride.

Yield: 300.10 mg (57.3% of theory) E/Z mixture (85:15)
$^1$H-NMR (300 MHz, d$^6$-DMSO): δ=1.40 (m), 1.65 (m), 7.26 (t), 2.70 (m), 2.85 (m), 3.55 (s), 3.80 (s), 3.9 (m), 6.0 (dd), 6.45 (dd), 6.90 (dd), 7.1-7.4 (m), 7.85 (d).

156

Methyl 4-((E/Z)-2-{2-[(2-methoxy-2-oxoethyl)amino]ethyl}-4-{2-[(5-phenyl-pentyl)oxy]phenyl}-3-butenyl)benzoate

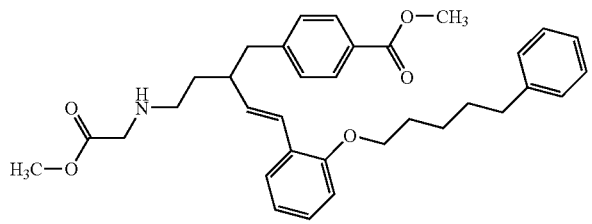

200.0 mg (0.34 mmol) of methyl 4-((E/Z)-2-(2-iodoethyl)-4-{2-[(5-phenylpentyl)-oxy]phenyl}-3-butenyl)benzoate from Ex. X, 43.107 mg (0.34 mmol) of methyl glycinate hydrochloride, 4.195 mg (0.03 mmol) of 4-dimethylaminopyridine and 0.50 ml of triethylamine in 2.0 ml of ethanol are heated at reflux for 48 hours. Water is added to the reaction mixture, which is then extracted with methylene chloride. The organic phase is washed with saturated sodium chloride solution and dried over magnesium sulfate, and the solvent is distilled off under reduced pressure. The residue is chromatographed on silica gel (0.04-0.063 nm) using methylene chloride/methanol 100:2.

Yield: 48.00 mg (25.7% of theory) E/Z mixture (85:15).
$^1$H-NMR (300 MHz, d$^6$-DMSO): δ=1.10 (t), 1.40 (m), 1.65 (m), 2.60 (m), 2.70 (m), 2.85 (m), 3.80 (s), 3.90 (m), 4.05 (q), 6.05 (dd), 6.35 (d), 6.85 (dd), 7.1-7.4 (m), 7.85 (d).

157

4-((E/Z)-2-{2-[(Carboxymethyl)amino]ethyl}-4-{2-[(5-phenylpentyl)oxy]-phenyl}-3-butenyl)benzoic acid

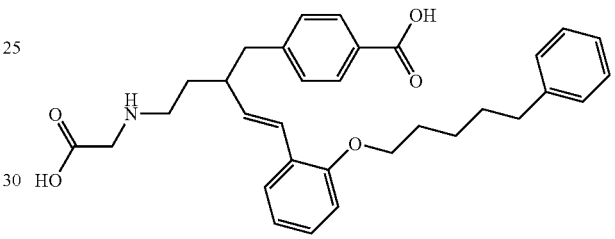

40.40 mg (0.070 mmol) of methyl 4-((E/Z)-2-{2-[(2-methoxy-2-oxoethyl)amino]-ethyl}-4-{2-[(5-phenylpentyl)oxy]phenyl}-3-butenyl)benzoate from Ex. 156 are dissolved in 1.50 ml of methylene chloride, 23.30 mg (0.16 mmol) of potassium trimethylsilanolate are added and the mixture is stirred at 22° C. for 18 hours. Water is added to the solution, the pH is adjusted to 2 using 21N HCl and the mixture is extracted with methylene chloride/methanol 2:1. The organic phase is dried over magnesium sulfate and the solvent is removed under reduced pressure.

Yield: 34.60 mg (86.3% of theory) E/Z mixture (85:15).
$^1$H-NMR (300 MHz, d$^6$-DMSO): δ=1.10 (t), 1.40 (m), 1.65 (m), 2.60 (m), 2.70 (m), 2.85 (m), 3.90 (m), 6.05 (dd), 6.35 (d), 6.85 (dd), 7.1-7.4 (m), 7.85 (d).

The following substances were obtained analogously to Examples 153 to 157:

| Ex. | Formula | $^1$H-NMR (d$^6$-DMSO, 200 MHz) |
|---|---|---|
| 161 (from IX and ethyl N-benzyl-glycinate) |  | 1.10 (t), 1.40 (m), 1.65 (m), 2.60 (m), 2.70 (m), 2.85 (m), 3.80 (s), 3.90 (m), 4.05 (q), 4.45 (s) 6.05 (dd), 6.35 (d), 6.85 (dd), 7.1-7.4 (m), 7.85 (d). |

-continued

| Ex. | Formula | $^1$H-NMR (d$^6$-DMSO, 200 MHz) |
|---|---|---|
| 162 (from IX and 2-ethoxy-carbonyl-piperidine) | | 1.12 (t), 1.3-1.8 (m), 2.60-2.90 (m), 2.85 (m), 3.80 (s), 4.00 (m), 4.05 (q), 6.00 (dd), 6.35 (d), 6.85 (dd), 7.1-7.4 (m), 7.85 (d). |
| 163 (from 161) | | 1.40 (m), 1.65 (m), 2.6-2.8 (m), 3.75 (s), 3.9 (m), 6.00 (dd), 6.35 (d), 6.85 (dd), 7.1-7.3 (m), 7.83 (d) |
| 164 (from 155) | | 1.40 (m), 1.65 (m), 2.6-2.8 (m), 3.53 (s), 3.9 (m), 6.00 (dd), 6.35 (d), 6.85 (dd), 7.1-7.3 (m), 7.83 (d), 12.5 (br.s) |
| 165 (from IX and 3-ethoxy-carbonyl-piperidine) | | 1.12 (t), 1.3-1.8 (m), 2.60-2.90 (m), 2.85 (m), 3.80 (s), 4.00 (m), 4.05 (q), 6.00 (dd), 6.35 (d), 6.85 (dd), 7.1-7.4 (m), 7.85 (d). |
| 166 (from IX and 4-methoxy-carbonyl-imidazole) | | 1.4 (m), 1.5-2.0 (m), 2.4 (m), 2.60-2.90 (m), 3.70 (s), 3.85 (s), 4.00 (m), 4.30 (m), 6.00 (dd), 6.35 (d), 6.85 (dd), 7.1-7.4 (m), 7.6-7.9 (m). |

-continued

| Ex. | Formula | $^1$H-NMR (d$^6$-DMSO, 200 MHz) |
|---|---|---|
| 167 (from 162) | | 1.3-1.8 (m), 2.60-2.90 (m), 4.00 (m), 6.00 (dd), 6.35 (d), 6.85 (dd), 7.1-7.4 (m), 7.86 (m). |
| 168 (from IX and methyl L-(−)-prolinate, followed by hydrolysis analogously to Ex. 154 | | 1.3-1.8 (m), 2.60-2.90 (m), 3.9-4.0 (m), 6.00 (dd), 6.35 (d), 6.85 (dd), 7.1-7.4 (m), 7.85 (d), 12.5 (br.s). |
| 169 (from 165) | | 1.3-1.8 (m), 2.0-2.5 (m), 2.60-2.90 (m), 3.9-4.0 (m), 6.00 (dd), 6.35 (d), 6.85 (dd), 7.1-7.4 (m), 7.85 (d), 12.5 (br.s). |
| 170 (from 166) | | 1.4 (m), 1.5-2.0 (m), 2.4 (m), 2.60-2.90 (m), 3.70 (s), 3.85 (s), 4.00 (m), 4.30 (m), 6.00 (dd), 6.35 (d), 6.85 (dd), 7.1-7.4 (m), 7.6-7.9 (m). |

Ex. 171

Methyl 6-(4-methoxycarbonylphenoxy)-8(2-(4-cyclohexylbenzyloxy)-phenyl)-octanoate

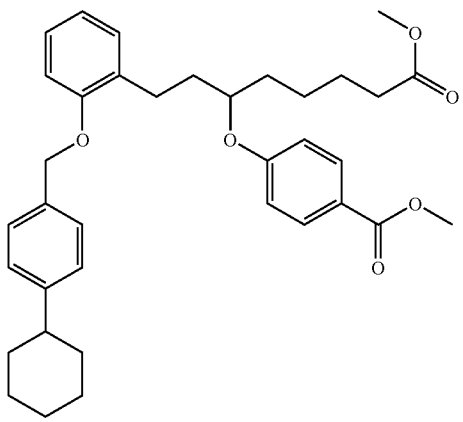

The synthesis of this compound was carried out analogously to Ex. 47 from the compound from Ex. XII and 4-cyclohexylbenzyl chloride.

Yield: 81.1%

$^1$H NMR (200 MHz, CDCl$_3$): δ=1.14-2.08 (m, 20H), 2.39-2.97 (m, 3H), 3.63 (s, 3H), 3.87 (s, 3H), 4.29 (quint, J=5.8 Hz, 1H), 5.00 (s, 2H), 6.68-6.97 (m, 4H), 7.03-7.37 (m, 6H), 7.89 (d, J=8.7 Hz, 2H).

The following compound was prepared analogously:

Ex. 173

6-(4-Carboxyphenoxy)-8(2-(4-cyclohexylbenzyloxy)phenyl)-octanoic acid

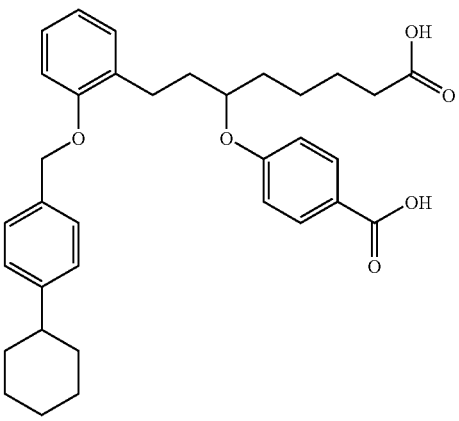

The synthesis of this compound was carried out analogously to Ex. 19 from the compound from Ex. 171.

Yield: 68.5%

$^1$H NMR (400 MHz, CDCl$_3$): δ=1.18-2.08 (m, 20H), 2.31 (t, J=7.3 Hz, 2H) 2.44-2.57 (m, 1H), 2.64-2.76 (m, 1), 2.76-2.88 (m, 1H), 4.33 (quint, J=5.8 Hz, 1H), 4.99 (s, 2H), 6.79 (d, J=8.8 Hz, 2H), 6.82-6.94 (m, 2H), 7.05-7.34 (m, 6H), 7.94 (d, J=8.8 Hz, 2H).

| Ex. | Structure | Yield (%) | $^1$H NMR (200 MHz, CDCl$_3$) |
|---|---|---|---|
| 172 (from XII and 4-(4-trifluoromethylphenoxy)-benzyl chloride) | | 73.2 | δ = 1.11-1.77 (m, 5H), 1.85-2.09 (m, 2H), 2.26 (t, J = 7.2 Hz, 2H), 2.61-2.91 (m, 2H), 3.62 (s, 3H), 3.85 (s, 3H), 4.30 (quint, J = 5.7Hz, 5.02 (s, 2H), 6.76 (d, J = 8.9Hz, 2H), 6.91 (d, J = 7.8Hz, 2H), 6.98-7.29 (m, 6H), 7.40 (d, J = 8.6Hz, 2H), 7.58 (d, J = 8.6Hz, 2H), 7.88 (d, J = 8.9Hz, 2H). |

The following compound was prepared analogously:

| Ex. | Structure | Yield (%) | $^1$H NMR (200 MHz, CDCl$_3$) |
|---|---|---|---|
| 174 (from 172) | 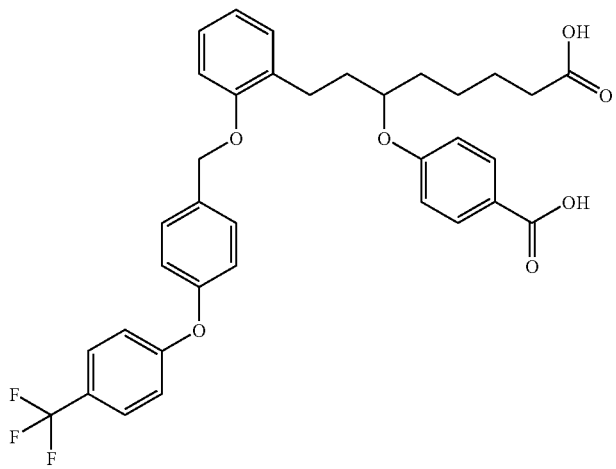 | 75.5 | $^1$H NMR (400 MHz, CDCl$_3$): δ = 1.17-2.10 (m, 10H), 2.31 (t, J = 7.1Hz, 2H), 2.68-2.89 (m, 2H), 4.33 (quint, J = 5.6Hz, 1H), 5.00 (d, J = 11.8Hz, 1H), 5.04 (d, J = 11.8Hz, 1H), 6.78 (d, J = 8.8Hz, 2H), 6.86-6.94 (m, 2H), 6.99-7.21 (m, 6H), 7.39 (d, J = 8.6Hz, 2H), 7.56 (d, J = 8.6Hz, 2H), 7.92 (d, J = 8.8Hz, 2H). |

175

Ethyl 4-[(3E)-2-(5-ethoxy-5-oxopentyl)-4-(2-{[4-(4-morpholinyl)-benzyl]oxy}phenyl)-3-butenyl]benzoate

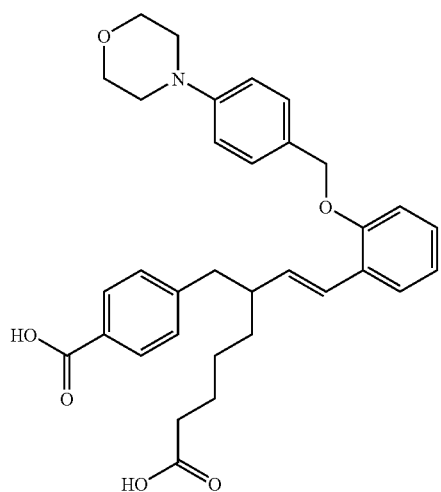

57.0 mg (0.10 mmol) of the compound 18a are initially charged in 2 ml of toluene, and 11 mg (0.12 mmol) of morpholine, 23 mg (0.24 mmol) of sodium tert-butoxide and 3 mg (0.01 mmol) of tri-tert-butylphosphine are added successively. 5.0 mg of tris(dibenzylidenacetone)dipalladium (0) are added under argon, and the mixture is then heated at 100° C. for 18 hours. The reaction solution is cooled, toluene and water are added, the mixture is filtered through Extrelut and the solvent is distilled off under reduced pressure. The crude product is chromatographed on silica gel using the mobile phase cyclohexanelethyl acetate=4:1. The resulting diester is hydrolyzed analogously to Ex. 109.

Yield: 16 mg (28%)

MS: 544 (M+1)

The following compounds were prepared analogously:

| Ex. | Structure | Yield (%) | $^1$H NMR (200 MHz, CDCl$_3$) |
|---|---|---|---|
| 176 (from 18a and 4-phenyl-piperazine) | 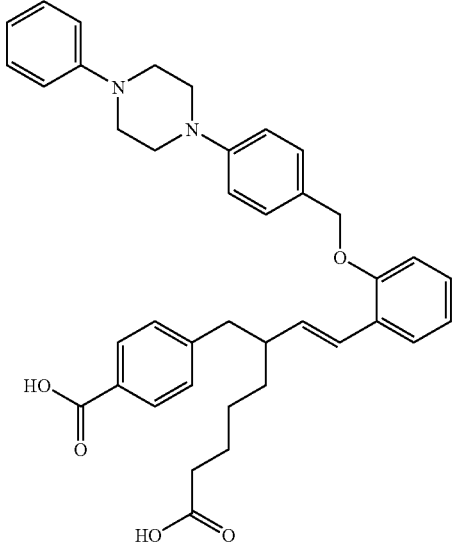 | | 619 (M + 1) |
| 177 (from 18a and 4-benzyl-piperazine) | 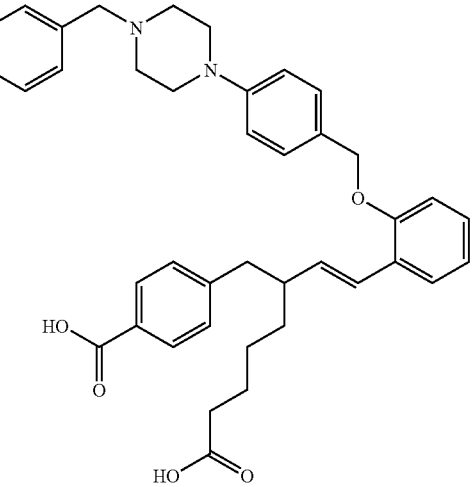 | | 633 (M + 1) |

178

4-((3E)-2-(4-carboxybutyl)-4-{2-[(4'-methyl-1,1'-biphenyl-4-yl)methoxy]-phenyl}-3-butenyl)benzoic acid

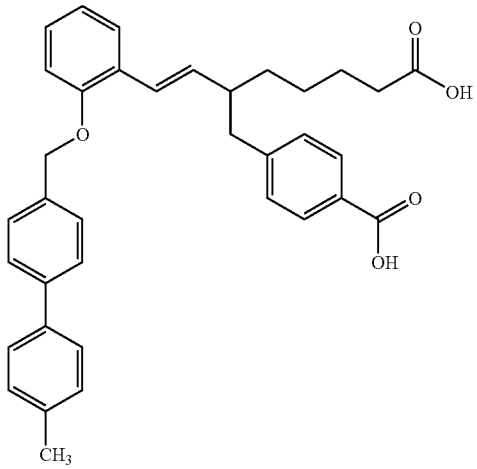

100.0 mg (0.17 mmol) of 18a are initially charged in 3 ml of dimethoxyethane, and 28 mg (0.2 mmol) of 4-methylphenylboronic acid and 0.2 ml of 2M sodium carbonate solution are added successively. 5.0 mg of dichlorobis(triphenyl-phosphine)palladium(II) are added, and the mixture is then heated at reflux temperature for 18 hours. The reaction solution is cooled, dichloromethane and water are added, the mixture is filtered through Extrelut and the solvent is distilled off under reduced pressure. The crude product is chromatographed on silica gel using the mobile phase cyclohexane/ethyl acetate=10:1. The resulting diester is hydrolyzed analogously to Ex. 19.

Yield: 80 mg (86%)

$^1$H-NMR (200 MHz, $CD_3COCD_3$): 7.95 (m, 4H), 7.40-7.10 (m, 16H), 6.52 (m, 1H), 6.05 (m, 1H), 5.00 (m, 2H), 2.75 (m, 2H), 2.45 (m, 1H), 2.30 (s, 3H), 2.25-1.10 (m)

$^1$H-NMR (200 MHz, $CD_3COCD_3$): 7.95 (m, 4H), 7.40-7.10 (m, 16H), 6.52 (m, 1H), 6.05 (m, 1H), 5.00 (m, 2H), 2.75 (m, 2H), 2.45 (m, 1H), 2.30 (s, 3H), 2.25-1.10 (m)

The following compounds are prepared analogously:

| Ex. | Structure | Yield (%) | Spectroscopical data ($^1$H-NMR or LC/MS) |
|---|---|---|---|
| 179 (from 18a and 4-ethoxyphenyl-boronic acid) | 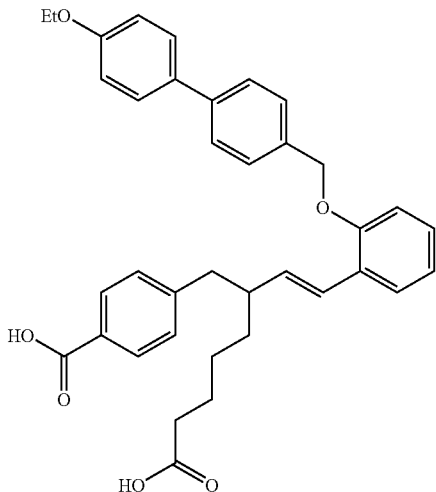 | | $^1$H-NMR (200 MHz, $CD_3COCD_3$): 7.95 (m, 4H), 7.40-7.10 (m, 16H), 6.52 (m, 1H), 6.05 (m, 1H), 5.00 (m, 2H), 4.00 q, 2H), 2.75 (m, 2H), 2.45 (m, 1H), 2.25-1.10 (m) |

| Ex. | Structure | Yield (%) | Spectroscopical data ($^1$H-NMR or LC/MS) |
|---|---|---|---|
| 180 (from 18a and 4-methoxyphenyl-boronic acid) | 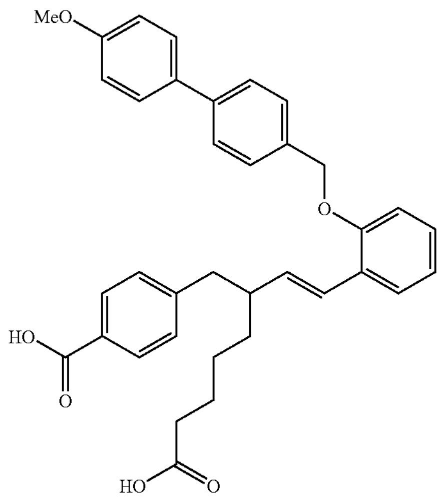 | | 582 (M + NH$_4$) |
| 181 (from 18a and 4-cyanophenyl-boronic acid) | 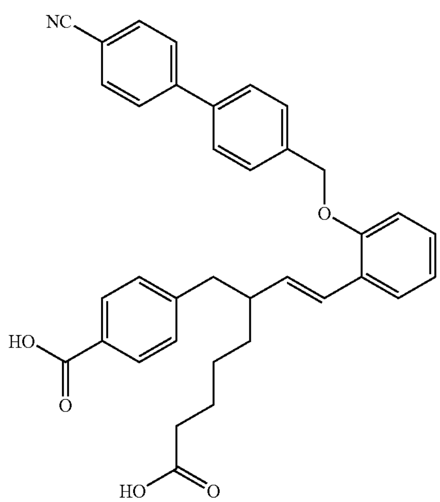 | | 577 (M + NH$_4$) |
| 182 (from 18a and 3,4-dimethoxy-phenylboronic acid) | 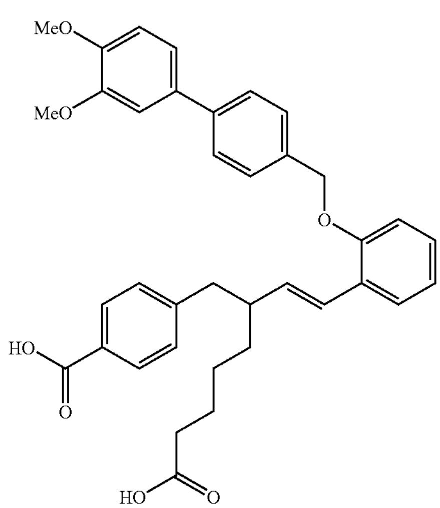 | | 612 (M + NH$_4$) |

-continued

| Ex. | Structure | Yield (%) | Spectroscopical data (¹H-NMR or LC/MS) |
|---|---|---|---|
| 183 (from 18a and 4-pyridylboronic acid) | 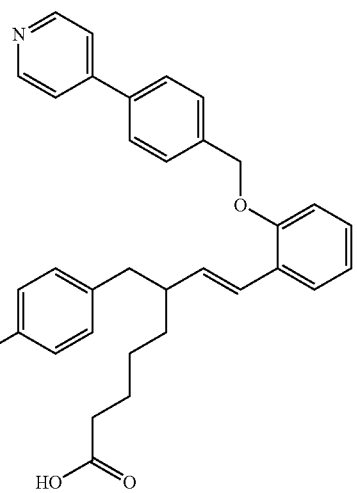 | | ¹H-NMR (200 MHz, CD₃COCD3): 7.95 (m, 2H), 7.40-7.10 (m, 14H), 6.52 (d, 1H), 6.05 (dd, 1H), 5.00 (m, 2H), 2.75 (m, 2H), 2.45 (m, 1H), 2.25-1.10 (m) |
| 184 (from 70a and 3,5-difluoro-phenylboronic acid) | 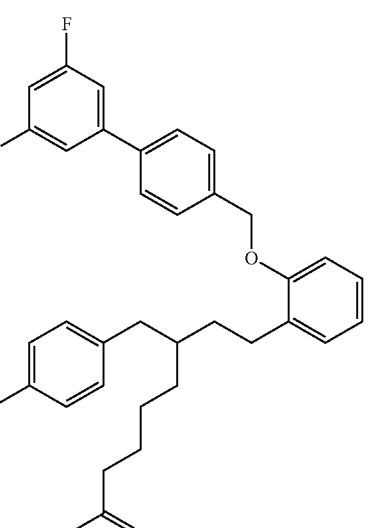 | | 573 (M + 1), $R_t$ = 5.2 min[1] |
| 185 (from 70a and 4-trifluoromethyl-phenylboronic acid) | 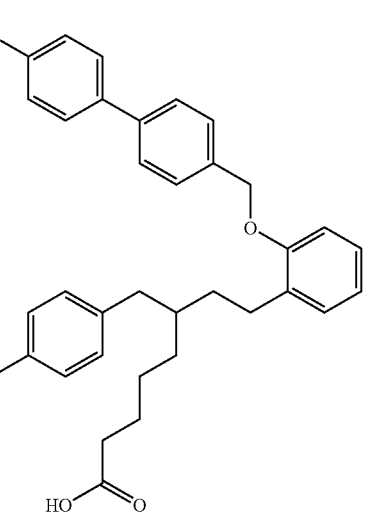 | | ¹H-NMR (200 MHz, MeOD): 7.95-7.10 (m, 16H), 4.90 (m, 2H), 2.60 (m, 4H), 2.20 (t, 2H), 2.25-1.10 (m) |

[1] LC/MS conditions: column: Symmetry C18 2.1*50 mm; mobile phase: acetonitrile/H2O (0.1% formic acid); gradient: 10% acetonitrile to 90% acetonitrile; flow rate: 0.5 ml/min; detector: UV 210 nm

186

Methyl 4-{[1-(2-{2-[(4-cyclohexylbenzyl)oxy]phenyl}ethyl)-6-methoxy-6-oxo-hexyl]amino}benzoate

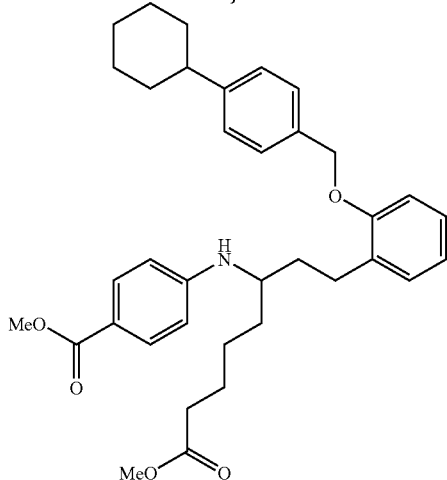

At 0° C., 217 mg (1.15 mmol) of TiCl$_4$ (1 M in CH$_2$Cl$_2$) were added to a solution of 500 mg (1.15 mmol) of methyl 8-{2-[(4-cyclohexylbenzyl)oxy]phenyl}-6-oxo-octanoate XIV and 190 mg (1.26 mmol) of methyl 4-aminobenzoate in 12.5 ml of 1,2-dichloroethane. The mixture was stirred at room temperature for 20 min, and 383 mg (1.72 mmol) of sodium triacetoxyborhydride were then added. The progress of the reaction was monitored by thin-layer chromatography, and after the reaction had ended, water was added. The mixture was extracted with ethyl acetate and the combined organic phases were dried over Na$_2$SO$_4$. The product was purified chromatographically (silica gel, gradient cyclohexane/ethyl acetate 10:1 to 0:100).

Yield: 320 mg (48.7%)

$^1$H NMR (200 MHz, CDCl$_3$): δ=1.07-2.00 (m, 16H), 2.25 (t, J=7.2 Hz, 2H), 2.41-2.68 (m, 2H), 2.72-2.91 (m, 1H), 3.10-3.28 (m, 1H), 3.32-3.51 (m, 1H), 3.63 (s, 3H), 3.73-3.93 (m, 2H), 3.83 (s, 3H), 4.98 (s, 2H), 6.28 (d, J=8.8 Hz, 2H), 6.54 (d, J=8.8 Hz, 1H), 6.81-6.97 (m, 2H), 7.05-7.39 (m, 5H), 7.76 (d, J=8.8 Hz, 2H).

187

Methyl 4-{[1-(2-{2-[(4-cyclohexylbenzyl)oxy]phenyl}ethyl-6-methoxy-6-oxo-hexyl]sulfanyl}benzoate

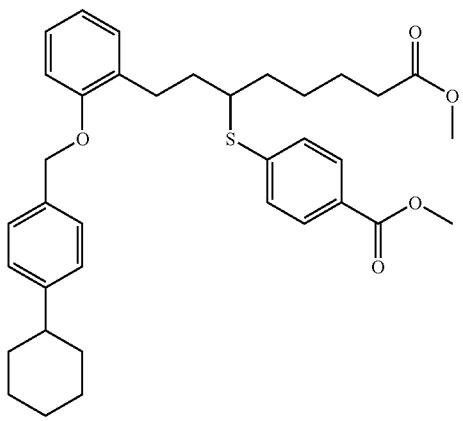

A suspension of 0.30 g (0.60 mmol) of methyl 6-bromo-8-{2-[(4-cyclohexyl-benzyl)oxy]phenyl}octanoate XVII, 0.15 g (0.90 mmol) of methyl 4-sulfanylbenzoate and 0.17 g (1.20 mmol) of potassium carbonate in 15 ml of DMF was stirred at room temperature for 2 days. 1 N NaOH was added to the mixture. The mixture was extracted with diethyl ether, the combined organic phases were dried over NaSO$_4$ and to the solvent was removed. The product was purified chromatographically (silica gel, cyclohexane/ethyl acetate 15:1).

Yield: 0.17 g (50.5%).

$^1$H NMR (300 MHz, CDCl$_3$): δ=1.20-1.98 (m, 22R), 2.23 (t, J=7.2 Hz, 2H), 2.42-2.56 (m, 1H), 2.72-2.92 (m, 2H), 3.23 (quint, J=3.2 Hz, 1H), 3.64 (s, 3H), 3.89 (s, 3H), 5.00 (s, 2H), 6.82-6.94 (m, 2H), 7.06-7.35 (m, 4H), 7.83 (d, J=8.3 Hz, 2H).

188

Methyl 4-{[1-(2-{2-[(4-cyclohexylbenzyl)oxy]phenyl}ethyl)-6-methoxy-6-oxo-hexyl]sulfinyl}benzoate

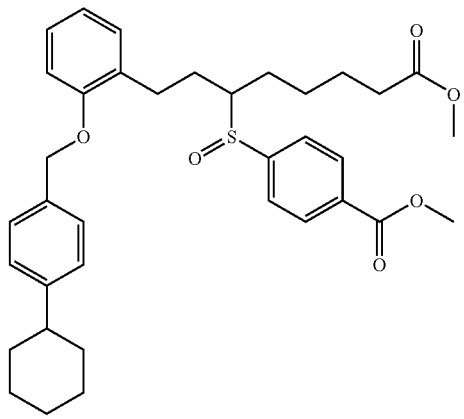

At 0° C., 47 mg (0.19 mmol) of metachloroperbenzoic acid were added to a solution of 113 mg (0.19 mmol) of methyl 4-{[1-(2-{2-[(4-cyclohexylbenzyl)oxy]phenyl}-ethyl)-6-methoxy-6-oxohexyl]sulfanyl}benzoate 187 in 25 ml of CH$_2$Cl$_2$. The mixture was stirred at 0° C. for 30 min, and the cooling bath was then removed and stirring, was continued at room temperature for 16 h. After the reaction had ended, the mixture was washed successively with saturated Na$_2$SO$_3$ solution, saturated Na$_2$CO$_3$ solution, saturated NaCl solution and water. The organic phases were dried over Na$_2$SO$_4$ and the solvent was removed. The product was purified chromatographically (silica gel, cyclohexane/ethyl acetate 2:1)

Yield: 62 mg, (53.4%).

Diastereomer mixture dr=55:45

$^1$H NMR (400 MHz, CDCl$_3$): δ=1.17-1.62 (m, 10H), 1.70-1.93 (m, 7H), 2.09 (t, J=7.3 Hz, 2H), 2.24 (t, J=7.1 Hz, 1H), 2.44-2.61 (m, 3H), 2.77-2.94 (m, 1H), 3.61 (s, 3H, Dia-1), 3.66 (s, 3H, Dia-2), 3.94 (s, 3H), 4.87 (d, J=16.1 Hz, 1H, Dia-2), 4.90 (d, J=16.3 Hz, 1H, Dia-1), 5.01 (s, 2H, Dia-2), 6.77-6.95 (m, 2H), 7.08-7.34 (m, 6H), 7.46 (d, J=8.6 Hz, 2H, Dia-2), 7.53 (d, J=8.6 Hz, 2H, Dia-1), 8.01 (d, J=8.3 Hz, 2H, Dia-2), 8.09 (d, J=8.3 Hz, 2H, Dia-1).

189

Methyl 4-{[1-(2-{2-[(4-cyclohexylbenzyl)oxy]phenyl}ethyl)-6-methoxy-6-oxo-hexyl]sulfonyl}benzoate

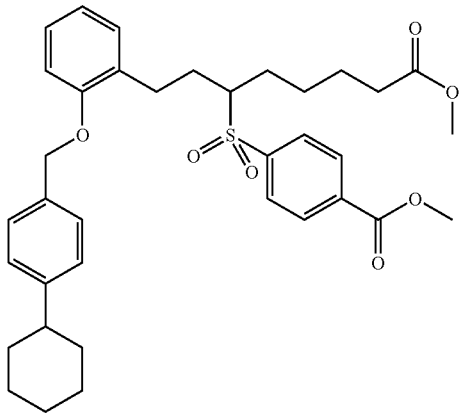

At 0° C., 149 mg (0.86 mmol) of metachloroperbenzoic acid were added to a solution of 113 mg (0.19 mmol) of methyl 4-{[1-(2-{2-[(4-cyclohexylbenzyl)oxy]phenyl}-ethyl)-6-methoxy-6-oxohexyl]sulfanyl}benzoate in 25 ml of CH$_2$Cl$_2$. The mixture was stirred at room temperature for 16 h. After the reaction had ended, the mixture was washed successively with saturated Na$_2$SO$_3$ solution, saturated Na$_2$CO$_3$ solution, saturated NaCl solution and water. The organic phases were dried over Na$_2$SO$_4$ and the solvent was removed. The product was purified chromatographically (silica gel, cyclohexane/ethyl acetate 2:1)

Yield: 110 mg (92.3%).

$^1$H NMR (400 MHz, CDCl$_3$): δ=1.17-1.66 (m, 10H), 1.71-1.93 (m, 7H), 2.02-2.12 (m, 1H), 2.15 (t, J=7.8 Hz, 2H), 2.46-2.56 (m, 1H), 2.58-2.69 (m, 1H), 2.70-2.81 (m, 1H), 2.90-2.99 (m, 1H), 3.64 (s, 3H), 3.96 (s, 3H), 4.91 (d, J=13.5 Hz, 1H), 4.94 (d, J=13.5 Hz, 1H), 6.81-6.89 (m, 2H), 6.99-7.05 (m, 1H), 7.12-7.31 (m, 5H), 7.83 (d, J=8.3 Hz, 2H), 8.10 (d, J=8.5 Hz, 2H).

190

Methyl 8-(2-(3-bromopropyloxy)-phenyl)-6-(4-(methoxycarbonylphenoxy)-octanoate

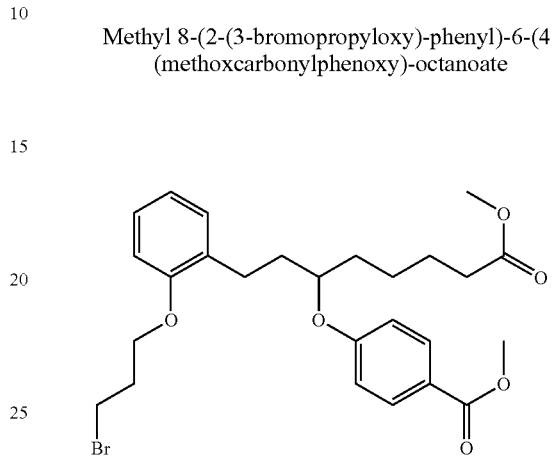

This compound was prepared analogously to the procedure of Example IId) from the compound from Example XII) and 1,3-dibromopropane.

Yield: 68.9%

$^1$H NMR (200 MHz, CDCl$_3$): δ=1.32-1.80 (m, 6H), 1.84-2.01 (m, 2H), 2.13-2.36 (m, 4H), 2.55-2.84 (m, 2H), 3.54 (t. J=6.3 Hz, 2H), 3.64 (s, 3H), 3.88 (s, 3H), 4.05 (t, J=5.6 Hz, 2H), 4.32 (quint, J=5.7 Hz, 1H), 6.74-6.91 (m, 4H), 7.00-7.22 (m, 2H), 7.94 (d, J=8.8 Hz, 2H).

The following examples were prepared from Ex. 190 and the corresponding amines, analogously to the procedure of Example 97:

| Ex. | Structure | Yield (%) | $^1$H NMR (200 MHz, CDCl$_3$) |
|---|---|---|---|
| 191 (from 4,5-diphenyl-imidazole) | 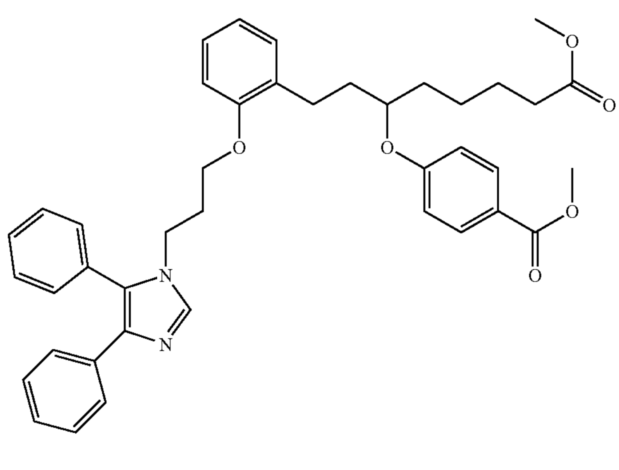 | 21.2 | $^1$H NMR (200 MHz, CDCl$_3$): δ = 1.18-1.77 (m, 6H), 1.80-2.01 (m, 4H), 2.28 (t, J = 7.4 Hz, 2H), 2.53-2.66 (m, 2H), 3.63 (s, 3H), 3.77 (t, J = 5.1Hz, 2H), 3.85 (s, 3H), 3.95 (t, J = 6.6Hz, 2H), 4.26 (quint, J = 5.9 Hz, 1H), 6.63-7.50 (m, 16H), 7.59 (s, 1H), 7.91 (d, J = 8.9 Hz, 2H). |

-continued

| Ex. | Structure | Yield (%) | $^1$H NMR (200 MHz, CDCl$_3$) |
|---|---|---|---|
| 192 (from pyrolidine) | 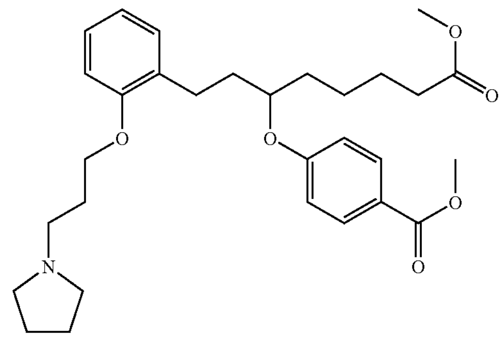 | 84.5 | $^1$H NMR (200 MHz, CDCl$_3$): δ = 1.31-2.05 (m, 13H), 2.29 (t, J = 7.5Hz, 2H), 2.41-2.77 (m, 8H), 3.64 (s, 3H), 3.87 (s, 3H), 3.98 (t, J = 6.7Hz, 2H), 4.30 (quint, J = 5.8Hz, 1H), 6.80 (d, J = 9.0Hz, 2H), 6.76-6.89 (m, 2H), 7.00-7.08 (m, 1H), 7.10-7.21 (m, 1H), 7.93 (d, J = 9.0 Hz, 2H). |
| 193 (from piperidine) | 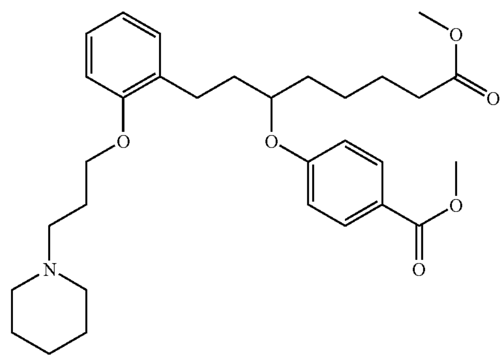 | 92.9 | $^1$H NMR (200 MHz, CDCl$_3$): δ = 1.32-1.80 (m, 12H), 1.83-2.08 (m, 4H), 2.20-2.51 (m, 8H), 2.58-2.82 (m, 2H), 3.64 (s, 3H), 3.87 (s, 3H), 3.96 (t, J = 6.0Hz, 2H), 4.30 (quint, J = 5.7 Hz, 1H), 6.80 (d, J = 8.8Hz, 2H), 6.74-6.89 (m, 2H), 7.02-7.08 (m, 1H), 7.09-7.21 (m, 1H), 7.93 (d, J = 8.9 Hz). |
| 194 (from morpholine) | 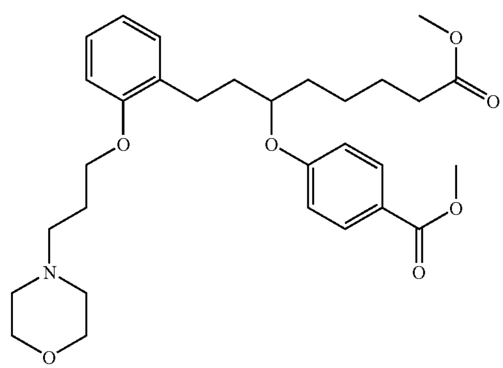 | 86.9 | $^1$H NMR (200 MHz, CDCl$_3$): δ = 1.20-1.79 (m, 6H), 1.83-2.07 (m, 4H), 2.29 (t, J = 7.7 Hz, 2H), 2.36-2.54 (m, 2H), 2.62-2.78 (m, 2H), 3.64 (s, 3H), 3.70 (t, J = 4.7Hz, 4H), 3.88 (s, 3H), 3.97 (t, J = 6.1Hz, 2H), 4.30 (quint, J = 6.1Hz, 1H), 6.73-6.91 (m, 4H), 7.01-7.09 (m, 1H), 7.10-7.22 (m, 1H), 7.93 (d, J = 8.9Hz, 2H). |
| 195 (from (3-methyl-phenyl)-piperazine) | 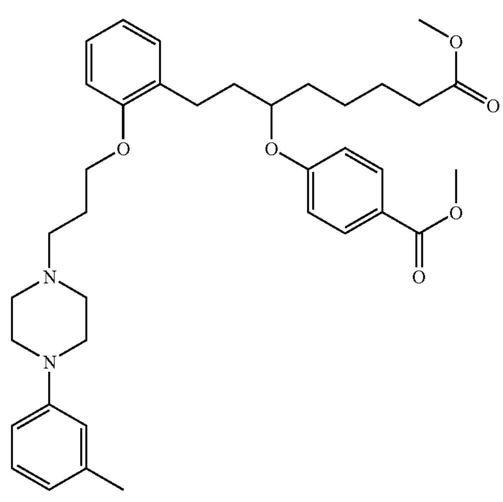 | 81.1 | $^1$H NMR (200 MHz, CDCl$_3$): δ = 1.34-1.79 (m, 6H), 1.85-2.06 (m, 4H), 2.30 (t, J = 7.6 Hz, 2H), 2.32 (s, 3H), 2.50-2.62 (m, 6H), 2.64-2.81 (m, 2H), 3.12-3.24 (m, 4H), 3.64 (s, 3H), 3.86 (s, 3H), 3.99 (t, J = 6.2Hz, 2H), 4.30 (quint, J = 5.8 Hz, 1H), 6.63-6.91 (m, 7H), 6.99-7.22 (m, 3H), 7.94 (d, J = 8.8Hz, 2H). |

-continued
| Ex. | Structure | Yield (%) | $^1$H NMR (200 MHz, CDCl$_3$) |
|---|---|---|---|
| 196 (from (2-methyl-phenyl)-piperazine) | 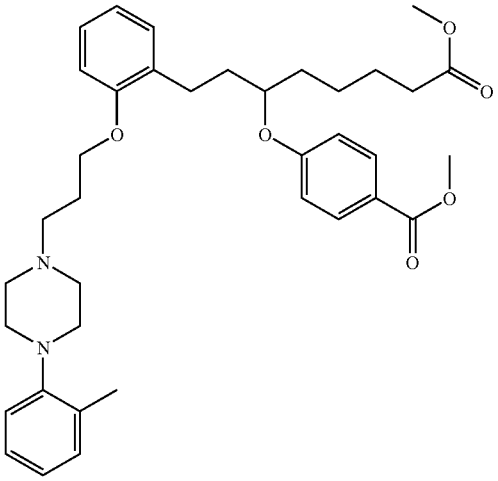 | 98.2 | $^1$H NMR (300 MHz, CDCl$_3$): δ = 1.16-1.79 (m, 7H), 1.85-2.06 (m, 6H), 2.29 (t, J = 7.4 Hz, 2H), 7.30 (s, 3H), 2.48-2.80 (m, 4H), 3.63 (s, 3H), 3.85 (s, 3H), 3.95-4.04 (m, 2H), 4.31 (quint, J = 5.7Hz, 1H), 6.81 (d, J = 9.1Hz, 2H), 6.80-6.88 (m, 2H), 6.93-7.08 (m, 3H), 7.12-7.20 (m, 3H), 7.93 (d, J = 8.9Hz, 2H). |
| 197 (from (4-fluoro-phenyl)-piperazine) | 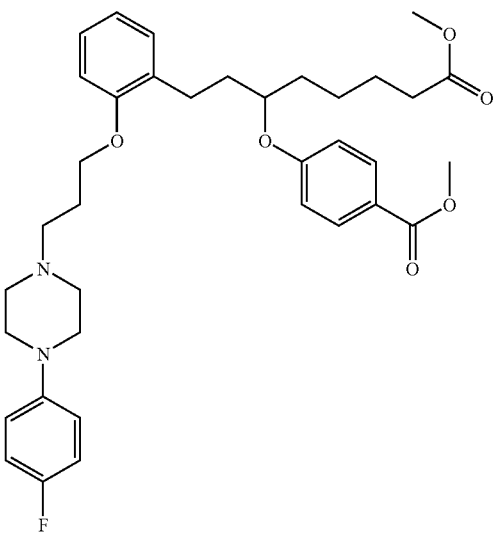 | 69.8 | $^1$H NMR (200 MHz, CDCl$_3$): δ = 1.23-2.05 (m, 10H), 2.30 (t, J = 7.6Hz, 2H), 2.47-2.79 (m, 8H), 3.03-3.16 (m, 4H), 3.64 (s, 3H), 3.86 (s, 3H), 3.99 (t, J = 6.2Hz, 2H), 4.30 (quint, J = 5.7 Hz, 1H), 6.71-7.22 (m, 10H), 7.93 (d, J = 8.8Hz, 2H). |
| 198 (from phenyl-piperazine) | 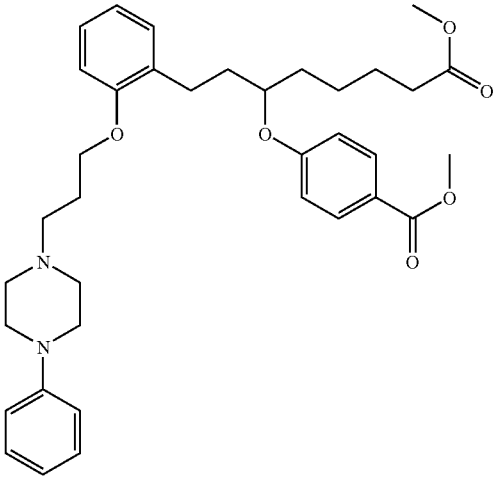 | 77.1 | $^1$H NMR (200 MHz, CDCl$_3$): δ = 1.23-1.80 (m, 6H), 1.84-2.09 (m, 4H), 2.30 (t, J = 7.5 Hz, 2H), 2.46-2.79 (m, 8H), 3.10-3.26 (m, 4H), 3.64 (s, 3H), 3.86 (s, 3H), 3.99 (t, J = 6.2Hz, 2H), 4.30 (quint, J = 5.7 Hz, 1H), 6.72-7.33 (m, 11H), 7.93 (d, J = 8.9Hz, 2H). |

The corresponding carboxylic acid derivatives are obtainable from the compounds 186 to 198, analogously to the procedure described in Ex. 109:

| Ex. | Structure | Yield (%) | ¹H NMR (200 MHz, CDCl₃) |
|---|---|---|---|
| 199 (from 189) | 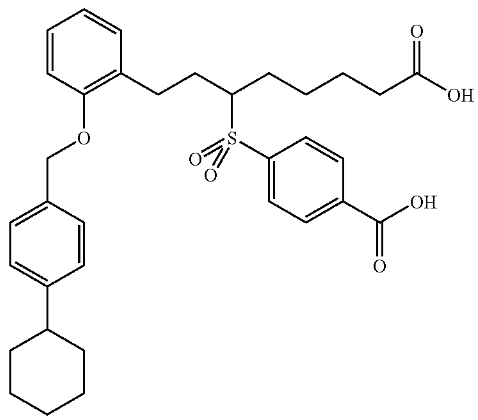 | 96.3 | $^1$H NMR (300 MHz, CDCl$_3$): δ = 1.04-2.05 (m, 18H), 2.16 (t, J = 6.8Hz, 2H), 2.21-2.39 (m, 2H), 2.45-2.58 (m, 1H), 2.67-2.88 (m, 2H), 2.88-2.98 (m, 1H), 4.97 (s, 2H), 6.85-6.93 (m, 2H), 7.08-7.36 (m, 6H), 7.91 (d, J = 8.5 Hz, 2H), 8.19 (d, J = 8.3Hz, 2H). |
| 200 (from 188) | 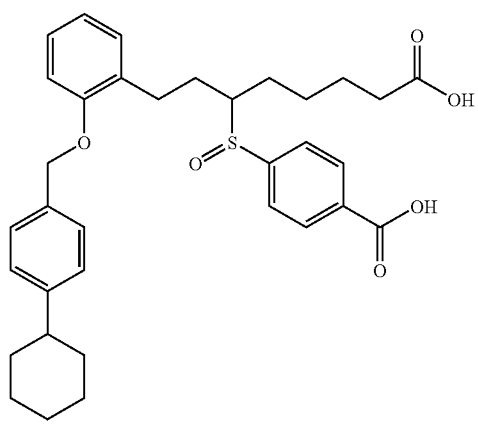 | 99.6 | dr = 57:43 $^1$H NMR (300 MHz, DMSO-d$_6$): δ = 1.09-1.51 (m, 12H), 1.53-1.82 (m, 6H), 1.91-2.02 (m, 2H), 2.09 (t, J = 7.2Hz, 2H), 2.30-2.44 (m, 2H), 2.52-2.61 (m, 1H), 2.65-2.79 (m, 1H), 4.95 (s, 2 H, dia-1), 5.03 (s, 2 H, dia-2), 6.73-7.47 (m, 10H), 7.88-7.98 (m, 2H). |
| 201 (from 187) | 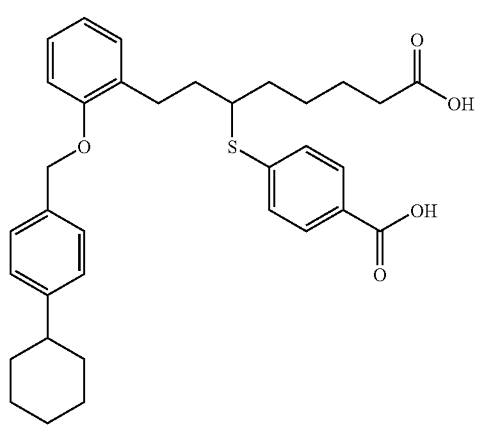 | 90.7 | LC/MS: R$_f$ = 5.50 min, 561 (M + H) |

-continued

| Ex. | Structure | Yield (%) | ¹H NMR (200 MHz, CDCl₃) |
|---|---|---|---|
| 202 (from 192) | 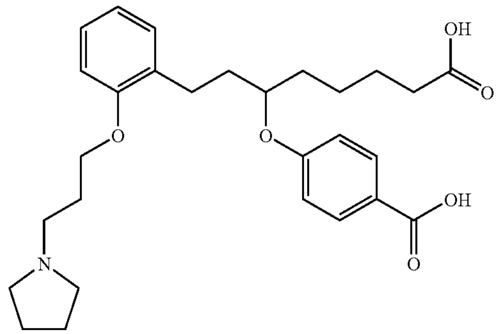 | 57.70 | LC/MS: $R_f$ = 2.86 min, 484 (M + H) |
| 203 (from 193) | 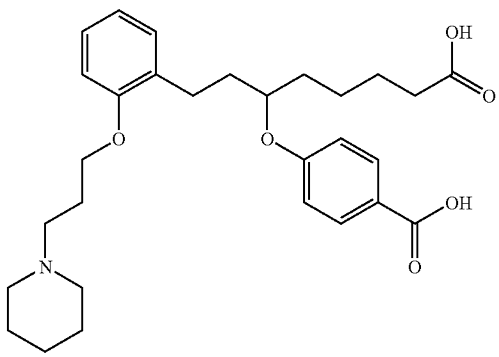 | 23.6 | LC/MS: $R_f$ = 2.88 min, 497 (M + H) |
| 204 (from 194) | 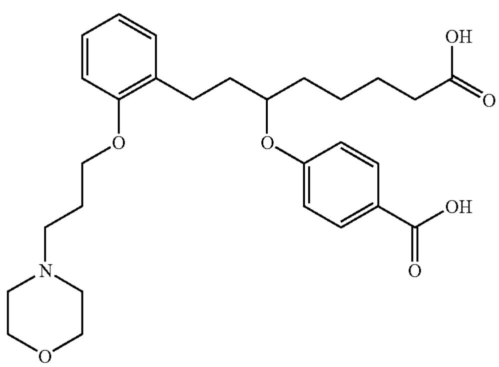 | 99.5 | LC/MS: $R_f$ = 2.84 min, 500 (M + H) |
| 205 (from 195) | 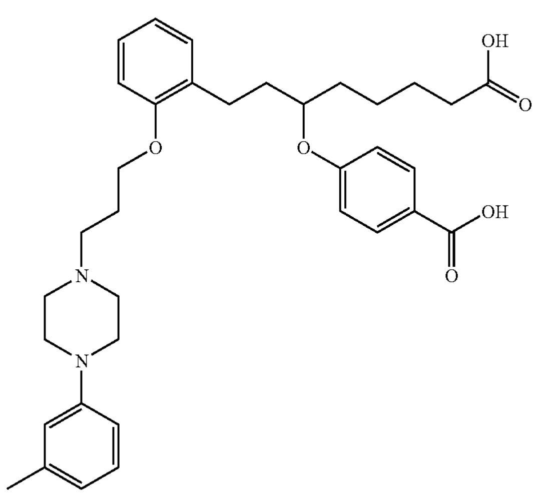 | 64.5 | LC/MS: $R_f$ = 3.17 min, 589 (M + H) |

-continued
| Ex. | Structure | Yield (%) | $^1$H NMR (200 MHz, CDCl$_3$) |
|---|---|---|---|
| 206 (from 196) | 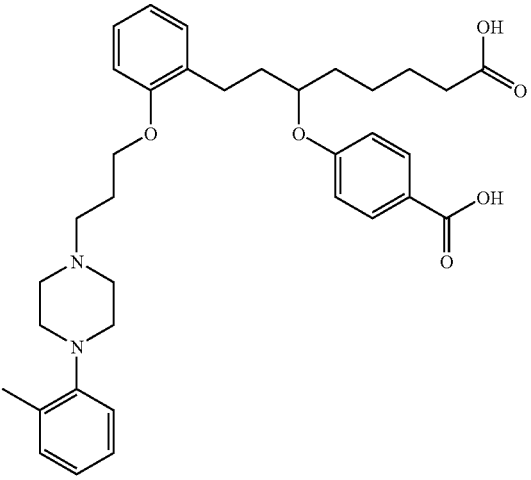 | 37.7 | LC/MS: R$_f$ = 3.18 min, 589 (M + H) |
| 207 (from 197) | 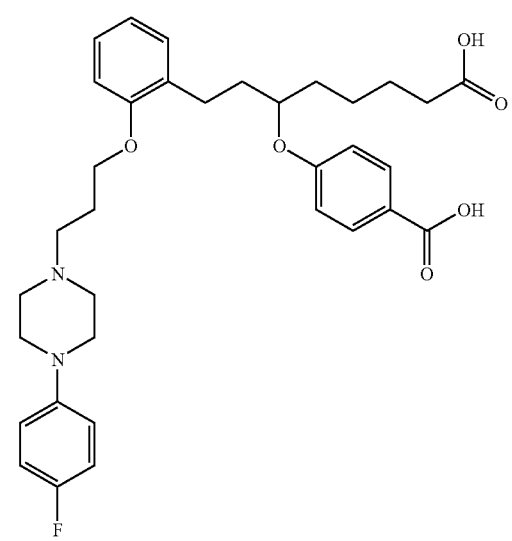 | 80.9 | LC/MS: R$_f$ = 3.10 min, 593 (M + H) |
| 208 (from 198) | 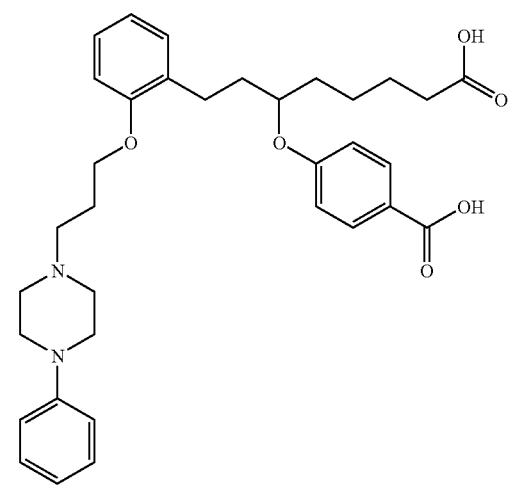 | 48.1 | LC/MS: R$_f$ = 3.07 min, 575 (M + H) |

-continued

| Ex. | Structure | Yield (%) | $^1$H NMR (200 MHz, CDCl$_3$) |
|---|---|---|---|
| 209 (from 190) | 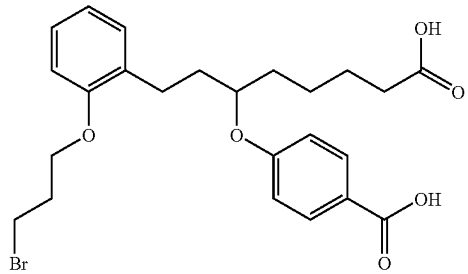 | 47.8 | LC/MS: R$_f$ = 4.45 min, 491 (M + H) |
| 210 (from 191) | 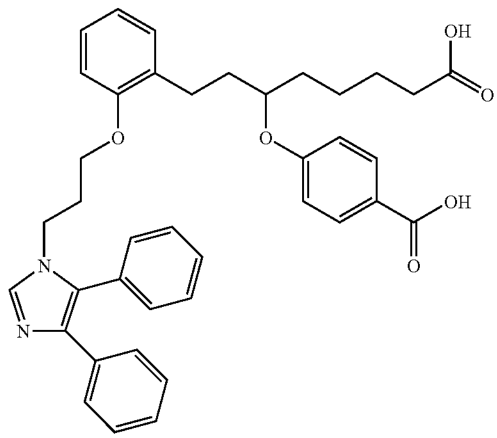 | 75.4 | LC/MS: R$_f$ = 3.46 min, 633 (M + H) |
| 211 (from 190 and (1H-imidazolo[3,4-b]-pyridine, analogously to Ex. 97 and then analogously to Ex. 109) | 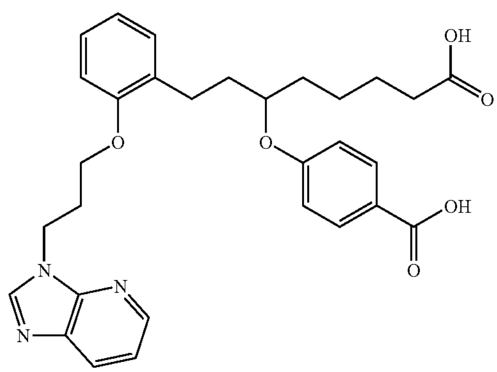 | 24.1 | LC/MS: R$_f$ = 2.88 min, 532 (M + H) |
| 212 (from 186) | 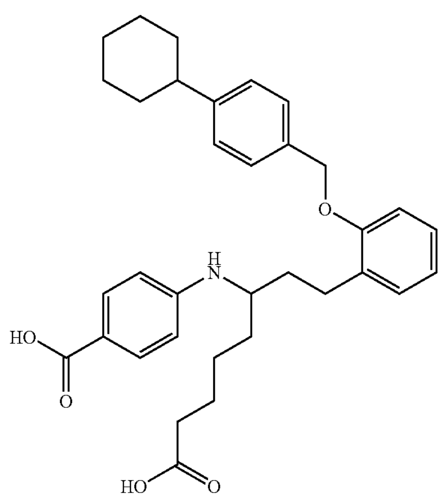 | 58.5 | LC/MS: R$_f$ = 5.72 min, 544 (M + H) |

213

8-(2-(4-Cyclohexyl)benzyloxy)-phenyl-6-(4-carboxybutyl)-octanoic acid

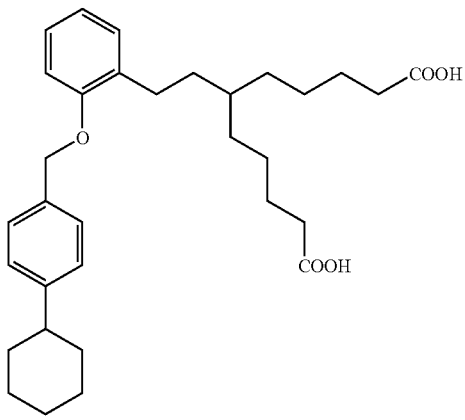

This compound was prepared analogously to the procedure of Example 47 from the phenol from Ex. XVIII, 4-cyclohexylbenzyl chloride and potassium carbonate.

Yield: 71.3%

$^1$H NMR (300 MHz, DMSO-$d_6$): δ=1.11-1.54 (m, 22H), 1.63-1.84 (m, 5H), 2.14 (t, J=7.2 Hz, 4H), 2.37-2.61 (m, 1H), 5.03 (s, 2H), 6.79-6.92 (m, 1H), 6.97-7.05 (m, 1H), 7.07-7.17 (m, 2H), 7.22 (d, J=8.1 Hz, 2H), 7.35 (d, J=7.9 Hz, 2H), 11.91 (bs, 2H).

The invention claimed is:

1. A method for treating a cardiovascular disease in a subject, the method comprising administering to the subject an effective amount of a compound capable of stimulating soluble guanylate cyclase independently of the heme group in the enzyme, wherein the compound is represented by the formula:

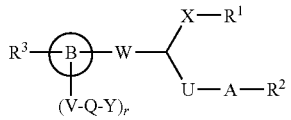

wherein
B represents aryl having from 6 to 10 carbon atoms or an aromatic heterocycle having 1 to 9 carbon atoms and up to 3 heteroatoms from the group consisting of S, N and O;
W is $CH_2CH_2$, CH=CH, $CH_2O$, $OCH_2$, $CH_2OCH_2$, $CH_2NH-$, $NHCH_2$, or $CH_2NHCH_2$;
X is $(CH_2)_4$, $CH_2CH_2SCH_2$ or $CH_2CH_2N(R')CH_2$, in which R' is H, methyl, or benzyl;
U is $CH_2$, O, NH, S, S(O), or $S(O)_2$;
A is phenyl;
$R_1$ is —COOR$^{35}$, in which R$^{35}$ represents hydrogen or straight-chain or branched alkyl having up to 6 carbon atoms;
$R_2$ is —COOR$^{26}$, in which R$^{26}$ represents hydrogen or straight-chain or branched alkyl having up to 4 carbon atoms;
$R_3$ is hydrogen, F, Cl, Br, straight-chain or branched alkyl, straight-chain or branched halogenoalkyl, straight-chain or branched alkoxy or straight-chain or branched halogenoalkoxy having in each case up to 4 carbon atoms;
r is 1;
V is absent or represents O, NH or S;
Q is absent or represents straight-chain or branched alkylene, straight-chain or branched alkenediyl having in each case up to 15 carbon atoms, which may contain one or more groups selected from O, $S(O)_p$, NR$^5$, CONR$^5$, S—CO— and OCO and which may be mono- or disubstituted by halogen or hydroxyl, or represents CONR$^5$, in which
R$^5$ represents hydrogen,
p represents 0 or 1,
Y represents hydrogen, NR$^6$R$^7$, phenyl, napthyl or a heterocycle selected from the group consisting of

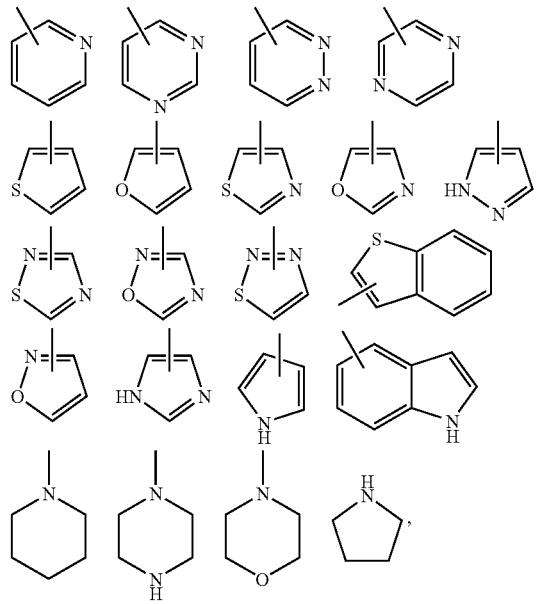

where the cyclic radicals may in each case be mono- to trisubstituted by straight-chain or branched alkyl, straight-chain or branched alkenyl, straight-chain or branched alkinyl, straight-chain or branched alkoxy, straight-chain or branched halogenoalkyl, straight-chain or branched halogenoalkoxy having in each case up to 4 carbon atoms, straight-chain or branched cycloalkyl having 3 to 7 carbon atoms, F, Cl, Br, I, NO$_2$, COR$^8$, SR$^8$, NR$^{10}$R$^{11}$NR$^9$COR$^{12}$ or CONR$^{13}$R$^{14}$,
in which
R$^6$ and R$^7$ in each case independently of one another represent hydrogen, straight-chain or branched alkyl, straight-chain or branched alkoxy or straight-chain or branched alkyloxyalkyl having in each case up to 4 carbon atoms or cycloalkyl having 3 to 8 carbon atoms or aryl having 6 to 10 carbon atoms, which is optionally mono- or polysubstituted by aryl having 6 to 10 carbon atoms or an aromatic heterocycle having 1 to 9 carbon atoms and up to 3 heteroatoms from the group consisting of S, N and O,
R$^8$ represents hydrogen, straight-chain or branched alkyl having up to 4 carbon atoms, or straight-chain or branched halogenoalkyl having up to 4 carbon atoms,
R$^9$ hydrogen, or straight-chain or branched alkyl having up to 4 carbon atoms, $R^{10}$, $R^{11}$, $R^{13}$ and $R^{14}$ independently of one another represent hydrogen, straight-chain or branched alkyl having up to 4 carbon atoms, or phenyl, where the phenyl radical may be mono- to trisubstituted by F, Cl, Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN, or two substituents $R^{10}$ and $R^{11}$ or $R^{13}$ and $R^{14}$ may be attached to one another forming a five- or six-membered ring which may be interrupted by O or N, $R^{12}$ represents hydrogen, straight-chain or branched alkyl having up to 4 carbon atoms, or phenyl, where the phenyl radical may be mono- to trisubstituted by F, Cl, Br, -hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;

and/or the cyclic radicals may in each case be mono- to trisubstituted by phenyl or a heterocycle from the group consisting of

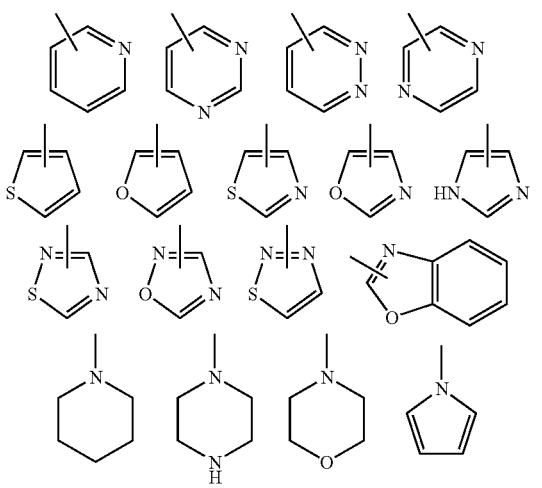

which are attached directly or via a group selected from O, S, SO, $SO_2$, $CONR^9$, $SO_2NR^9$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 4 carbon atoms and may be mono- to trisubstituted by straight-chain or branched alkyl, straight-chain or branched alkoxy, straight-chain or branched halogenoalkyl or straight-chain or branched alkenyl having in each case up to 4 carbon atoms, phenyl, benzyl, F, Cl, Br, I, CN, $NO_2$, $NR^{17}R^{18}$ or $NR^{16}COR^{19}$, in which $R^{16}$ represents hydrogen, straight-chain or branched alkyl having up to 8 carbon atoms or cycloalkyl having 3 to 8 carbon atoms, $R^{17}$, $R^{18}$ independently of one another represent hydrogen, straight-chain or branched alkyl having up to 8 carbon atoms, cycloalkyl having 3 to 8 carbon atoms, phenyl, where the phenyl radical may be mono- to trisubstituted by F, Cl, Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN or represent a radical of the formula $SO_2R^{20}$, in which $R^{20}$ represents straight-chain or branched alkyl having up to 4 carbon atoms or phenyl, and $R^{19}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by F, Cl Br, hydroxyl, methyl, ethyl, n-propyl, i-propyl, n-butyl, s-butyl, butyl, t-butyl, methoxy, ethoxy, amino, acetylamino, $NO_2$, $CF_3$, $OCF_3$ or CN;

and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O;

or a salt thereof.

2. A method for treating angina pectoris, ischemia or cardiac insufficiency in a host, comprising administering to a host in need thereof, an effective amount of at least one compound capable of stimulating soluble guanylate cyclase independently of the heme group in the enzyme, represented by the formula:

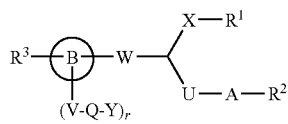

wherein

B represents aryl having from 6 to 10 carbon atoms or an aromatic heterocycle having 1 to 9 carbon atoms and up to 3 heteroatoms from the group consisting of S, N and O;

W is $CH_2CH_2$, CH=CH, $CH_2O$, $OCH_2$, $CH_2NH$—, $NHCH_2$, or $CH_2NHCH_2$;

X is $CH_2)_4$, $CH_2CH_2SCH_2$ or $CH_2CH_2N(R')CH_2$, in which R' is H, methyl, or benzyl;

U is $CH_2$, O, NH, S, S(O), or $S(O)_2$;

A is phenyl;

$R_1$ is —$COOR^{35}$, in which $R^{35}$ represents hydrogen or straight-chain or branched alkyl having up to 6 carbon atoms;

$R_2$ is —$COOR^{26}$, in which $R^{26}$ represents hydrogen or straight-chain or branched alkyl having up to 4 carbon atoms;

$R_3$ is hydrogen, F, Cl, Br, straight-chain or branched alkyl, straight-chain or branched halogenoalkyl, straight-chain or branched alkoxy or straight-chain or branched halogenoalkoxy having in each case up to 4 carbon atoms;

r is 1;

V is absent or represents O, NH or S;

Q is absent or represents straight-chain or branched alkylene, straight-chain or branched alkenediyl having in each case up to 15 carbon atoms, which may contain one or more groups selected from O, $S(O)_p$, $NR^5$, $CONR^5$, S—CO— and OCO and which may be mono- or disubstituted by halogen or hydroxyl, or represents $CONR^5$, in which $R^5$ represents hydrogen, p represents 0 or 1, Y represents hydrogen, $NR^6R^7$, phenyl, napthyl or a heterocycle selected from the group consisting of

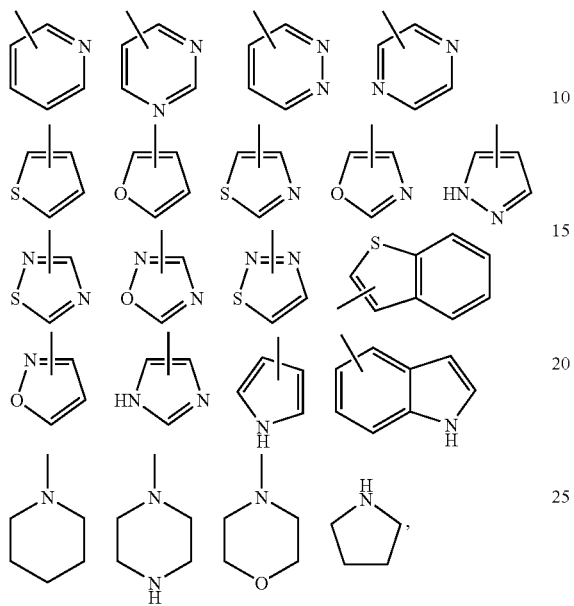

where the cyclic radicals may in each case be mono- to trisubstituted by straight-chain or branched alkyl, straight-chain or branched alkenyl, straight-chain or branched alkinyl, straight-chain or branched alkoxy, straight-chain or branched halogenoalkyl, straight-chain or branched halogenoalkoxy having in each case up to 4 carbon atoms, straight-chain or branched cycloalkyl having 3 to 7 carbon atoms, F, Cl, Br, I, $NO_2$, $COR^8$, $SR^8$, $NR^{10}R^{11}$ $NR^9COR^{12}$ or $CONR^{13}R^{14}$, in which $R^6$ and $R^7$ in each case independently of one another represent hydrogen, straight-chain or branched alkyl, straight-chain or branched alkoxy or straight-chain or branched alkyloxyalkyl having in each case up to 4 carbon atoms or cycloalkyl having 3 to 8 carbon atoms or aryl having 6 to 10 carbon atoms, which is optionally mono- or polysubstituted by aryl having 6 to 10 carbon atoms or an aromatic heterocycle having 1 to 9 carbon atoms and up to 3 heteroatoms from the group consisting of S, N and O, $R^8$ represents hydrogen, straight-chain or branched alkyl having up to 4 carbon atoms, or straight-chain or branched halogenoalkyl having up to 4 carbon atoms, $R^9$ hydrogen, or straight-chain or branched alkyl having up to 4 carbon atoms, $R^{10}$, $R^{11}$, $R^{13}$ and $R^{14}$ independently of one another represent hydrogen, straight-chain or branched alkyl having up to 4 carbon atoms, or phenyl, where the phenyl radical may be mono- to trisubstituted by F, Cl, Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN, or two substituents $R^{10}$ and $R^{11}$ or $R^{13}$ and $R^{14}$ may be attached to one another forming a five- or six-membered ring which may be interrupted by O or N, $R^{12}$ represents hydrogen, straight-chain or branched alkyl having up to 4 carbon atoms, or phenyl, where the phenyl radical may be mono- to trisubstituted by F, Cl, Br, -hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;

and/or the cyclic radicals may in each case be mono- to trisubstituted by phenyl or a heterocycle from the group consisting of

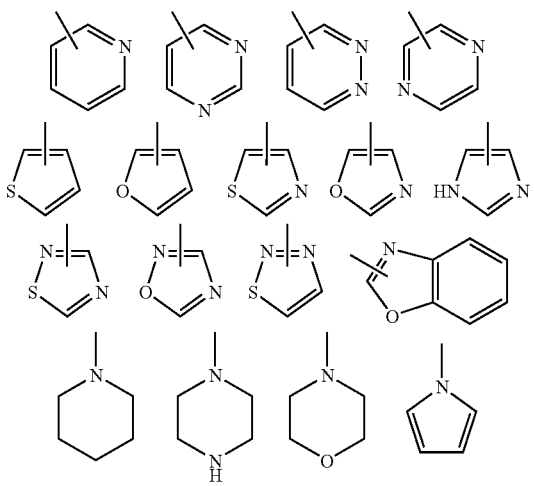

which are attached directly or via a group selected from O, S, SO, $SO_2$, $CONR^9$, $SO_2NR^9$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 4 carbon atoms and may be mono- to trisubstituted by straight-chain or branched alkyl, straight-chain or branched alkoxy, straight-chain or branched halogenoalkyl or straight-chain or branched alkenyl having in each case up to 4 carbon atoms, phenyl, benzyl, F, Cl, Br, I, CN, $NO_2$, $NR^{17}R^{18}$ or $NR^{16}COR^{19}$, in which $R^{16}$ represents hydrogen, straight-chain or branched alkyl having up to 8 carbon atoms or cycloalkyl having 3 to 8 carbon atoms, $R^{17}$, $R^{18}$ independently of one another represent hydrogen, straight-chain or branched alkyl having up to 8 carbon atoms, cycloalkyl having 3 to 8 carbon atoms, phenyl, where the phenyl radical may be mono- to trisubstituted by F, Cl, Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN or represent a radical of the formula $SO_2R^{20}$, in which $R^{20}$ represents straight-chain or branched alkyl having up to 4 carbon atoms or phenyl, and $R^{19}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by F, Cl Br, hydroxyl, methyl, ethyl, n-propyl, i-propyl, n-butyl, s-butyl, butyl, t-butyl, methoxy, ethoxy, amino, acetylamino, $NO_2$, $CF_3$, $OCF_3$ or CN;

and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O;

or a salt thereof.

3. A method for treating arteriosclerosis, hypertension, a thromboembolic disorder, a venous disorder or a fibrotic disorder in a host, comprising administering to a host in need thereof, an effective amount of at least one compound capable of stimulating soluble guanylate cyclase independently of the heme group in the enzyme, represented by the formula:

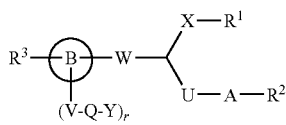

wherein

B represents aryl having from 6 to 10 carbon atoms or an aromatic heterocycle having 1 to 9 carbon atoms and up to 3 heteroatoms from the group consisting of S, N and O;

W is $CH_2CH_2$, CH=CH, $CH_2O$, $OCH_2$, $CH_2OCH_2$, $CH_2NH$—, $NHCH_2$, or $CH_2NHCH_2$;

X is $CH_2)_4$, $CH_2CH_2SCH_2$ or $CH_2CH_2N(R')CH_2$, in which R' is H, methyl, or benzyl;

U is $CH_2$, O, NH, S, S(O), or $S(O)_2$;

A is phenyl;

$R_1$ is —$COOR^{35}$, in which $R^{35}$ represents hydrogen or straight-chain or branched alkyl having up to 6 carbon atoms;

$R_2$ is $COOR^{26}$, in which $R^{26}$ represents hydrogen or straight-chain or branched alkyl having up to 4 carbon atoms;

$R_3$ is hydrogen, F, Cl, Br, straight-chain or branched alkyl, straight-chain or branched halogenoalkyl, straight-chain or branched alkoxy or straight-chain or branched halogenoalkoxy having in each case up to 4 carbon atoms;

r is 1;

V is absent or represents O, NH or S;

Q is absent or represents straight-chain or branched alkylene, straight-chain or branched alkenediyl having in each case up to 15 carbon atoms, which may contain one or more groups selected from O, $S(O)_p$, $NR^5$, $CONR^5$, S—CO— and OCO and which may be mono- or disubstituted by halogen or hydroxyl, or represents $CONR^5$, in which $R^5$ represents hydrogen, p represents 0 or 1, Y represents hydrogen, $NR^6R^7$, phenyl, napthyl or a heterocycle selected from the group consisting of

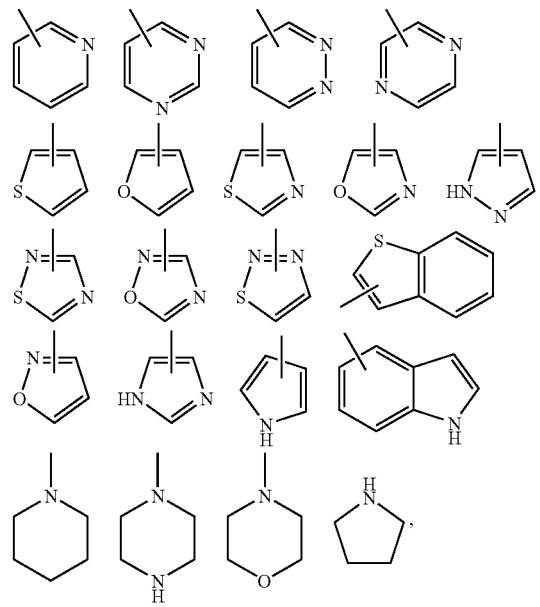

where the cyclic radicals may in each case be mono- to trisubstituted by straight-chain or branched alkyl, straight-chain or branched alkenyl, straight-chain or branched alkinyl, straight-chain or branched alkoxy, straight-chain or branched halogenoalkyl, straight-chain or branched halogenoalkoxy having in each case up to 4 carbon atoms, straight-chain or branched cycloalkyl having 3 to 7 carbon atoms, F, Cl, Br, I, $NO_2$, $COR^8$, $SR^8$, $NR^{10}R^{11}$ $NR^9COR^{12}$ or $CONR^{13}R^{14}$, in which $R^6$ and $R^7$ in each case independently of one another represent hydrogen, straight-chain or branched alkyl, straight-chain or branched alkoxy or straight-chain or branched alkyloxyalkyl having in each case up to 4 carbon atoms or cycloalkyl having 3 to 8 carbon atoms or aryl having 6 to 10 carbon atoms, which is optionally mono- or polysubstituted by aryl having 6 to 10 carbon atoms or an aromatic heterocycle having 1 to 9 carbon atoms and up to 3 heteroatoms from the group consisting of S, N and O, $R^8$ represents hydrogen, straight-chain or branched alkyl having up to 4 carbon atoms, or straight-chain or branched halogenoalkyl having up to 4 carbon atoms, $R^9$ hydrogen, or straight-chain or branched alkyl having up to 4 carbon atoms, $R^{10}$, $R^{11}$, $R^{13}$ and $R^{14}$ independently of one another represent hydrogen, straight-chain or branched alkyl having up to 4 carbon atoms, or phenyl, where the phenyl radical may be mono- to trisubstituted by F, Cl, Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN, or two substituents $R^{10}$ and $R^{11}$ or $R^{13}$ and $R^{14}$ may be attached to one another forming a five- or six-membered ring which may be interrupted by O or N, $R^{12}$ represents hydrogen, straight-chain or branched alkyl having up to 4 carbon atoms, or phenyl, where the phenyl radical may be mono- to trisubstituted by F, Cl, Br, -hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN;

and/or the cyclic radicals may in each case be mono- to trisubstituted by phenyl or a heterocycle from the group consisting of

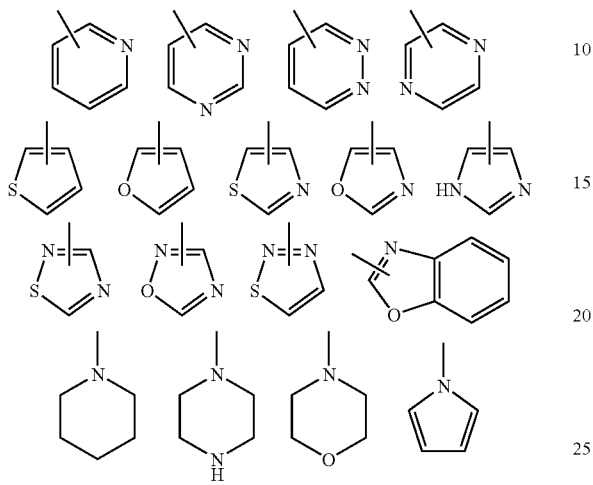

which are attached directly or via a group selected from O, S, SO, $SO_2$, $CONR^9$ $SO_2NR^9$, straight-chain or branched alkylene, straight-chain or branched alkenediyl, straight-chain or branched alkyloxy, straight-chain or branched oxyalkyloxy, straight-chain or branched sulfonylalkyl, straight-chain or branched thioalkyl having in each case up to 4 carbon atoms and may be mono- to trisubstituted by straight-chain or branched alkyl, straight-chain or branched alkoxy, straight-chain or branched halogenoalkyl or straight-chain or branched alkenyl having in each case up to 4 carbon atoms, phenyl, benzyl, F, Cl, Br, I, CN, $NO_2$, $NR^{17}R^{18}$ or $NR^{16}COR^{19}$, in which
- $R^{16}$ represents hydrogen, straight-chain or branched alkyl having up to 8 carbon atoms or cycloalkyl having 3 to 8 carbon atoms,
- $R^{17}$, $R^{18}$ independently of one another represent hydrogen, straight-chain or branched alkyl having up to 8 carbon atoms, cycloalkyl having 3 to 8 carbon atoms, phenyl, where the phenyl radical may be mono- to trisubstituted by F, Cl, Br, hydroxyl, methyl, ethyl, n-propyl, i-propyl, n-butyl, s-butyl, i-butyl, t-butyl, methoxy, ethoxy, amino, acetylamino, $NO_2$, $CF_3$, $OCF_3$ or CN or represent a radical of the formula $SO_2R^{20}$,
  in which
  - $R^{20}$ represents straight-chain or branched alkyl having up to 4 carbon atoms or phenyl,
and
- $R^{19}$ represents hydrogen, straight-chain or branched alkyl having up to 12 carbon atoms, straight-chain or branched alkenyl having up to 12 carbon atoms, aryl having 6 to 10 carbon atoms, an aromatic heterocycle having 1 to 9 carbon atoms and up to 3 heteroatoms from the group consisting of S, N and O or cycloalkyl having 3 to 8 carbon atoms, which may optionally furthermore be substituted by F, Cl Br, hydroxyl, methyl, ethyl, n-propyl, i-propyl, n-butyl, s-butyl, butyl, t-butyl, methoxy, ethoxy, amino, acetylamino, $NO_2$, $CF_3$, $OCF_3$ or CN;

and/or the cyclic radicals may be fused with an aromatic or saturated carbocycle having 1 to 10 carbon atoms or an aromatic or saturated heterocycle having 1 to 9 carbon atoms and up to 3 heteroatoms from the group consisting of S, N and O;

or a salt thereof which is capable of stimulating soluble guanylate cyclase independently of the heme group in the enzyme.

4. The method of claim 3, wherein the fibrotic disorder is hepatic fibrosis.

* * * * *